US012590292B2

(12) United States Patent
Bollard et al.

(10) Patent No.: US 12,590,292 B2
(45) Date of Patent: Mar. 31, 2026

(54) TARGETED T-CELL THERAPY FOR TREATMENT OF MULTIPLE MYELOMA

(71) Applicant: CHILDREN'S NATIONAL MEDICAL CENTER, Washington, DC (US)

(72) Inventors: Catherine Mary Bollard, Bethesda, MD (US); Conrad Russell Y. Cruz, Bethesda, MD (US); Patrick Hanley, Hyattsville, MD (US)

(73) Assignee: Children's National Medical Center, Washington, DC (US)

( * ) Notice: Subject to any disclaimer, the term of this patent is extended or adjusted under 35 U.S.C. 154(b) by 1174 days.

(21) Appl. No.: 17/421,287

(22) PCT Filed: Jan. 7, 2020

(86) PCT No.: PCT/US2020/012636
§ 371 (c)(1),
(2) Date: Jul. 7, 2021

(87) PCT Pub. No.: WO2020/146431
PCT Pub. Date: Jul. 16, 2020

(65) Prior Publication Data
US 2022/0062342 A1 Mar. 3, 2022

Related U.S. Application Data

(60) Provisional application No. 62/789,144, filed on Jan. 7, 2019.

(51) Int. Cl.
| | |
|---|---|
| *C12N 5/0783* | (2010.01) |
| *A61K 40/11* | (2025.01) |
| *A61K 40/42* | (2025.01) |
| *A61P 35/00* | (2006.01) |

(52) U.S. Cl.
CPC ............ *C12N 5/0638* (2013.01); *A61K 40/11* (2025.01); *A61K 40/4215* (2025.01); *A61K 40/4224* (2025.01); *A61K 40/424* (2025.01); *A61K 40/4242* (2025.01); *A61K 40/4243* (2025.01); *A61K 40/427* (2025.01); *A61P 35/00* (2018.01)

(58) Field of Classification Search
CPC .. C12N 5/0638; A61K 40/11; A61K 40/4215; A61K 40/4224; A61K 40/424; A61K 40/4242; A61K 40/4243; A61K 40/427; A61P 35/00; A61P 35/02; A23B 11/1332; H10D 30/6891; H10D 30/798; H10D 62/161; H10D 80/251; H10F 30/223; H10F 39/15
See application file for complete search history.

(56) References Cited

U.S. PATENT DOCUMENTS

| | | | | |
|---|---|---|---|---|
| 11,161,907 B2 * | 11/2021 | June | ..................... | C12N 15/113 |
| 2016/0176973 A1 | 6/2016 | Kufer et al. | | |
| 2016/0263155 A1 | 9/2016 | Heemskerk et al. | | |
| 2017/0037369 A1 | 2/2017 | Ramsborg et al. | | |
| 2018/0133297 A1 | 5/2018 | Bae et al. | | |
| 2021/0046119 A1 | 2/2021 | Bollard et al. | | |

OTHER PUBLICATIONS

Ali et al., T cells expressing an anti-B-cell maturation antigen chimeric antigen receptor cause remissions of multiple myeloma. Blood. Sep. 29, 2016;128(13):1688-700.
Avery et al., BAFF selectively enhances the survival of plasmablasts generated from human memory B cells. J Clin Invest. Jul. 2003;112(2):286-97.
Bae et al., A multiepitope of XBP1, CD138 and CS1 peptides induces myeloma-specific cytotoxic T lymphocytes in T cells of smoldering myeloma patients. Leukemia. Jan. 2015;29(1):218-29.
Bae et al., Identification and characterization of HLA-A24-specific XBP1, CD138 (Syndecan-1) and CS1 (SLAMF7) peptides inducing antigens-specific memory cytotoxic T lymphocytes targeting multiple myeloma. Leukemia. Mar. 2018;32(3):752-764.
Bae et al., Selective targeting of multiple myeloma by B cell maturation antigen (BCMA)-specific central memory CD8+ cytotoxic T lymphocytes: immunotherapeutic application in vaccination and adoptive immunotherapy. Leukemia. Sep. 2019;33(9):2208-2226.
Chiu et al., Hodgkin lymphoma cells express TACI and BCMA receptors and generate survival and proliferation signals in response to BAFF and APRIL. Blood. Jan. 15, 2007;109(2):729-39.
Claudio et al., A molecular compendium of genes expressed in multiple myeloma. Blood. Sep. 15, 2002;100(6):2175-86.
Ding et al., PRAME Gene Expression in Acute Leukemia and Its Clinical Significance. Cancer Biol Med. Mar. 2012;9(1):73-6.
Hobo et al., Immunogenicity of dendritic cells pulsed with MAGE3, Survivin and B-cell maturation antigen mRNA for vaccination of multiple myeloma patients. Cancer Immunol Immunother. Aug. 2013;62(8):1381-92.
Neri et al., New Strategies in Multiple Myeloma: Immunotherapy as a Novel Approach to Treat Patients with Multiple Myeloma. Clin Cancer Res. Dec. 15, 2016;22(24):5959-5965.

(Continued)

*Primary Examiner* — Tracy Vivlemore
*Assistant Examiner* — Thomas R. Amick
(74) *Attorney, Agent, or Firm* — McCarter & English, LLP; Yu Lu

(57) ABSTRACT

Provided herein are activated adoptive T-cell compositions targeting plasma cell dyscrasias such as multiple myeloma and methods of treating plasma cell dyscrasias such as multiple myeloma using such compositions. The T-cell compositions of the present disclosure are activated against a select group of antigens associated with multiple myeloma (MMAAs) and, in certain embodiments, in combination with more widely expressed tumor associated antigens (TAAs). In particular, the T-cell compositions of the present disclosure are directed to the MMAAs selected from B-cell maturation antigen (BCMA), X box Protein 1 (XBP1), CS1, and Syndecan-1 (CD138), or a combination thereof. In certain embodiments, the T-cell composition includes T-cells activated to a TAA selected from preferentially expressed antigen of melanoma (PRAME), Survivin, Wilms' Tumor 1 protein (WT1), and melanoma antigen 3 (MAGE-A3), or a combination thereof.

10 Claims, No Drawings

Specification includes a Sequence Listing.

(56) References Cited

OTHER PUBLICATIONS

O'Connor et al., BCMA is essential for the survival of long-lived bone marrow plasma cells. J Exp Med. Jan. 5, 2004;199(1):91-8.

Podar et al., Targeting the Immune Niche within the Bone Marrow Microenvironment: The Rise of Immunotherapy in Multiple Myeloma. Curr Cancer Drug Targets. 2017;17(9):782-805.

Tai et al., Role of B-cell-activating factor in adhesion and growth of human multiple myeloma cells in the bone marrow microenvironment. Cancer Res. Jul. 1, 2006;66(13):6675-82.

International Search Report and Written Opinion for Application No. PCT/US2020/012636, dated May 19, 2020, 13 pages.

International Preliminary Report on Patentability for Application No. PCT/US2020/012636, dated Jul. 22, 2021, 9 pages.

* cited by examiner

TARGETED T-CELL THERAPY FOR TREATMENT OF MULTIPLE MYELOMA

CROSS-REFERENCE TO RELATED APPLICATIONS

This application is a national stage filing under 35 U.S.C. § 371 of International Application No. PCT/US20/12636, filed Jan. 7, 2020, which claims priority to U.S. Provisional Application No. 62/789,144, filed Jan. 7, 2019, entitled "Improved Targeted T-Cell Therapy for Treatment of Multiple Myeloma," the contents of which are incorporated herein by reference in their entireties.

FIELD OF THE INVENTION

The present disclosure provides improved adoptive T-cell compositions and their use for the treatment of multiple myeloma and other plasma cell dyscrasias.

BACKGROUND OF THE INVENTION

Multiple myeloma (MM) is a neoplasia of terminally differentiated B cells (plasma cells), characterized by clonal expansion of plasma cells in the bone marrow and often complicated by osteolytic bone disease, infections, renal insufficiency, and bone marrow failure (Dimopoulos et al.; Current treatment landscape for relapsed and/or refractory multiple myeloma. Nat Rev Clin Oncol 2015; 12:42-54). Current therapies for MM often cause remissions, but nearly all patients eventually relapse and die (Lonial et al.; Treatment options for relapsed and refractory multiple myeloma. Clinical Cancer Research. 2011; 17:1264-77; Rajkumar S V. Treatment of multiple myeloma. Nature Reviews Clinical Oncology. 2011; 8:479-91).

Standard treatment of MM consists of an initial induction using immunomodulatory agents (IMIDs) such as thalidomide, lenalidomide or pomalidomide and/or the proteasome inhibitor bortezomib combined with dexamethasone or chemotherapy, followed by autologous hematopoietic stem cell transplantation (auto-HSCT) for patients younger than 65 years and consolidation/maintenance therapy. Despite significant improvements in patient outcomes following the introduction of immunomodulatory drugs (IMIDs) and proteasome inhibitors (PIs) in the first-line setting (Kumar et al., Improved survival in multiple myeloma and the impact of novel therapies. Blood. 2008; 111 (5); 2516-2520), most patients eventually relapse, and the management of relapsed and/or refractory MM (RRMM) remains a challenge (Laubach et al., Management of relapsed multiple myeloma: recommendations of the International Myeloma Working Group. Leukemia. 2016; 30 (5); 1005-1017). The treatment landscape for patients with RRMM is rapidly changing following the recent approval of three drugs belonging to two novel classes of agent in this setting: a histone deacetylase (HDAC) inhibitor (HDI), panobinostat 5 (Farydak™, Novartis), and two monoclonal antibodies (mAbs)-daratumumab (Darzalex™, Janssen) and elotuzumab (Empliciti™, Bristol Myers Squibb). Furthermore, the addition of the second-generation IMIDs lenalidomide (Revlimid™, Celgene) and pomalidomide (Pomalyst™ Celgene) and the second-generation PIs carfilzomib (Kyprolis™, Amgen) and ixazomib (Ninlaro™, Takeda) provides additional within-class treatment options for patients with RRMM.

One of the clinically available types of immunotherapy for MM is allogeneic hematopoietic stem cell transplantation (allo-HSCT), a potentially curative option for patients with MM that offers several advantages, including a tumor-free graft and the potential for sustained immune-mediated disease control. However, historically high treatment-related mortality and conflicting reports from prospective studies in the United States and the European Union have limited the utilization of this method (Lonial et al.; Treatment options for relapsed and refractory multiple myeloma. Clinical Cancer Research. 2011; 17:1264-77, Salit et al.; Reduced-intensity allogeneic hematopoietic stem cell transplantation for multiple myeloma: A concise review. Clinical Lymphoma, Myeloma and Leukemia. 2011; 11:247-52).

Additional immunotherapeutic approaches to treat MM include agents that activate immune cells to target the tumor, such as chimeric antigen receptor (CAR) T cells and tumor antigen peptide and dendritic cell vaccines.

CAR T cells engineered to target antigens expressed on multiple myeloma cells represent a promising new area of exploration. Car T-cells are capable of direct multiple myeloma cell killing and T-cell immunity stimulation. Autologous transplantation followed by treatment with CAR T cells against CD19 (Kymriah™, Novartis) demonstrated activity in a patient with refractory multiple myeloma, leading to a complete remission lasting longer than previous remissions, but with subsequent relapse (Garfall et al.; Chimeric antigen receptor T cells against CD19 for multiple myeloma. N Engl J Med 2015; 373:1040-7). Promising results have also been shown using CAR T-cell therapy targeting the B-cell maturation antigen (BCMA) expressed by normal and malignant plasma cells. Preliminary results of a phase I trial of the CAR-BCMA in patients with advanced multiple myeloma showed strong anti-multiple myeloma activity at higher dose levels, with durable sCR achieved in two patients with a high disease burden and chemotherapy-resistant disease. Substantial but reversible toxicity was observed. This included cytopenias attributable to chemotherapy, fever, and signs of cytokine-release syndrome (Ali et al.; T cells expressing an anti-B-cell-maturation-antigen chimeric antigen receptor cause remissions of multiple myeloma. Blood 2016; 128:1688-700). Additional studies of other CAR T-cell therapies targeting CD38, CD138, and CS1 are currently under evaluation in clinical trials. Despite promising results, resistance and short duration of response is often noted with CAR-based immunotherapy. Loss of the CAR-specific antigen or limited proliferation of CAR T cells in vivo is often observed due to their inefficient activation or inhibition due to immunosuppressive microenvironment within the tumor stroma (Han et al.; Chimeric antigen receptor-engineered T cells for cancer immunotherapy: progress and challenges. J Hematol Oncol 2013; 6:47). This challenge seems to apply even more to multiple myeloma due to its phenotypic heterogeneity and the relative paucity of tumor-specific markers.

Another area of investigation in the treatment of MM is the use of cancer vaccines to elicit a tumor-specific immune response without the need for alloreactive lymphocytes. Various strategies have been examined and can be broadly divided into noncellular approaches using antigen-specific peptides and cellular techniques using tumor lysates and whole-cell DCs (Wen et al.; Tumor lysate-specific cytotoxic T lymphocytes in multiple myeloma: promising effector cells for immunotherapy. Blood 2002; 99:3280-5; Lee et al.; Induction of multiple myeloma-specific cytotoxic T lymphocyte stimulation by dendritic cell pulsing with purified and optimized myeloma cell lysates. Leuk Lymphoma 2007; 48:2022-31). Idiotype proteins, derived from the variable region of the clonal immunoglobulin, were some of the first antigenic targets investigated. Unfortunately, due to the poor immunogenic nature of the protein and the low expression of these proteins on the plasma cell surface, this approach did not meet expectations. On the other hand, subsequent identification of tumor-associated antigens such as MAGE, hTERT, WT1, XBP1, CS1, and CTA as targets was able to generate cellular responses when used in preclinical studies (Bae et al.; Myeloma-specific multiple peptides able to generate cytotoxic T lymphocytes: a potential therapeutic application in multiple myeloma and other plasma cell disorders. Clin Cancer Res 2012; 18:4850-60; Bae et al.; A multiepitope of XBP1, CD138 and CS1 peptides induces myeloma-specific cytotoxic T lymphocytes in T cells of smoldering myeloma patients. Leukemia 2015; 29:218-29), but the clinical result is still lacking.

A different vaccination approach involves patient-derived multiple myeloma cells fused with autologous DCs to take advantage of the ability of DCs to present several antigens from the cell to the host (Vasir et al.; Fusion of dendritic cells with multiple myeloma cells results in maturation and enhanced antigen presentation. Br J Haematol 2005; 129: 687-700). In a phase I and II trial, this approach resulted in the expansion of autologous multiple myeloma-specific T cells, was well tolerated, and demonstrated CRs in a quarter of the patients (Rosenblatt et al.; Vaccination with dendritic cell/tumor fusion cells results in cellular and humoral anti-tumor immune responses in patients with multiple myeloma. Blood 2011; 117:393-402).

Despite advances in treatment options over the last decade, patients with the malignant plasma cell disorder multiple myeloma (MM) typically have recurrent relapses (Kumar et al.; International Myeloma Working Group. Risk of progression and survival in multiple myeloma relapsing after therapy with IMIDs and bortezomib: a multicenter International Myeloma Working Group study. Leukemia. 2012; 26(1):149-157). Although there are several treatments available for relapsed patients, they have limited efficacy. In particular, patients who have had successive relapses or who are refractory to treatment have poor survival (Kumar et al.; International Myeloma Working Group. Risk of progression and survival in multiple myeloma relapsing after therapy with IMIDs and bortezomib: a multicenter International Myeloma Working Group study. Leukemia. 2012; 26(1): 149-157). A recent retrospective analysis of real-world survival outcomes reported a median overall survival (OS) of only 7.9 months in patients with ≥3 prior lines of therapy, including a proteasome inhibitor (PI) or an immunomodulatory drug (IMID), or who were double refractory to a PI and an IMID (Usmani et al.; Clinical efficacy of daratumumab monotherapy in patients with heavily pretreated relapsed or refractory multiple myeloma. Blood. 2016; 128 (1):37-44).

While progress has been made in immunotherapeutic approaches in MM and other plasma cell dyscrasias, there remains a strong need to improve the efficiency and outcomes of the therapy. As one example, there remains a need to improve adoptive immunotherapy for the treatment of plasma cell dyscrasias, including MM. Developing an effective antigen-specific adoptive T-cell therapy for plasma cell dyscrasias, including MM, would be a major advance.

SUMMARY OF THE INVENTION

Provided herein are activated adoptive T-cell compositions targeting plasma cell dyscrasias such as multiple myeloma and methods of treating plasma cell dyscrasias such as multiple myeloma using such compositions. The T-cell compositions of the present disclosure are activated against a select group of antigens associated with multiple myeloma (MMAAs) and, in certain embodiments, in combination with more widely expressed tumor associated antigens (TAAs). In particular, the T-cell compositions of the present disclosure are directed to the MMAAs selected from B-cell maturation antigen (BCMA), X box Protein 1 (XBP1), CS1, and CD138 (Syndecan-1), or a combination thereof. In certain embodiments, the T-cell composition includes T-cells activated to a TAA selected from preferentially expressed antigen of melanoma (PRAME), Survivin, and Wilms' Tumor 1 protein (WT1), or a combination thereof. In particular embodiments, the T-cell composition for administration comprises T-cell subpopulations activated against MMAAs selected from BCMA, XBP1, CS1, and CD138. In certain embodiments, the T-cell compositions further include T-cell subpopulations activated to the specific TAAs selected from PRAME, Survivin, and WT1. In certain embodiments, the T-cell compositions further include T-cell subpopulations activated to the specific TAAs selected from PRAME, Survivin, WT1, and MAGEA3. In certain embodiments, the T-cell composition for administration comprises T-cell subpopulations activated against MMAAs BCMA, XBP1, CS1, CD138, as well as TAAs PRAME, Survivin, and WT1. In certain embodiments, the subject is initially administered a T-cell composition comprising T-cell subpopulations activated against TAAs selected from PRAME, Survivin, and WT1, followed by administration of a T-cell composition comprising T-cell subpopulations activated against MMAAs selected from BCMA, XBP1, CS1, CD138 at a subsequent time period, for example 1, 2, 3, 4, 5, 6, 7, 8, 9, 10, 11, 12, or more than 12 weeks after the administration of the T-cell composition activated against the TAAs. In some embodiments, additional administrations of either the MMAA T-cell composition or TAA T-cell composition, for example 3, 4, 5, 6, 7, 8, 9 or 10 additional administrations. In certain embodiments, the subject is initially administered a T-cell composition comprising T-cell subpopulations activated against MMAAs selected from BCMA, XBP1, CS1, CD138, followed by administration of a T-cell composition comprising T-cell subpopulations activated against TAAs selected from PRAME, Survivin, and WT1 at a subsequent time period, for example 1, 2, 3, 4, 5, 6, 7, 8, 9, 10, 11, 12, or more than 12 weeks after the administration of the T-cell composition comprising T-cells activated against the MMAAs. In some embodiments, additional administrations of either the MMAA T-cell composition or TAA T-cell composition, for example 3, 4, 5, 6, 7, 8, 9 or 10 additional administrations.

The T-cell compositions for the treatment of plasma cell dyscrasias can be administered as a single composition comprising T-cell subpopulations activated to each of the particular MMAAs and/or TAAs targeted. In some embodiments, the subpopulations of T-cells are derived through the ex vivo expansion of a single population of T-cells, wherein the single population of T-cells are exposed to a pool of one or more antigenic peptides (epitopes) of each of the selected MMAAs and TAAs.

Alternatively, the T-cell compositions can be derived through the ex vivo expansion of separate T-cell populations exposed to one or more antigenic peptides of each of the selected MMAAs and TAAs separately, wherein following activation and expansion, the separate T-cell subpopulations are then combined into a single composition for administration. In another alternative, the T-cell compositions can be derived through the ex vivo expansion of separate T-cell populations exposed to one or more antigenic peptides of each of the selected MMAAs and TAAs separately, wherein following activation and expansion, the separate T-cell populations are each individually administered to the subject. In some embodiments, the separate T-cell populations are derived from the same donor source. In some embodiments, the separate T-cell populations are derived from one or more different donor sources.

The T-cell compositions described herein may be derived from a population of cells from an autologous source, an allogeneic source, for example a healthy donor not suffering from a plasma cell dyscrasia, or cord blood. Non-limiting exemplary methods of generating ex vivo primed and expanded T-cells capable of recognizing at least one antigenic peptide of a tumor antigen can be found in Shafer et al., Leuk Lymphoma (2010) 51(5):870-880; Cruz et al., Clin Cancer Res., (2011) 17(22): 7058-7066; Quintarelli et al., Blood (2011) 117(12): 3353-3362; Chapuis et al., Sci Transl Med (2013) 5(174):174ra27; and US 2017/0037369, all incorporated herein by reference.

In order to prime and activate the particular T-cell subpopulations of the described T-cell compositions, one or more antigenic peptides (epitopes) from the targeted MMAA or TAA is used. For example, a single antigenic peptide, multiple antigenic peptides, or a library of antigenic peptides can be used to prime and activate a T-cell subpopulation targeting each of the specific MMAAs and TAAs. In some embodiments, if more than one peptide from the MMAA or TAA is used, the peptide segments can be generated by making overlapping peptide fragments of the MMAA or TAA, as provided for example in commercially available peptide mixes, for example, PepMix™ peptide pools from JPT Peptide Technologies. Alternatively, generation of the T-cell composition can be accomplished through the ex vivo priming and activation of the T-cell subpopulations with selected antigenic epitopes of the targeted MMAA or TAA, for example, a single epitope or multiple specific epitopes of the MMAA or TAA. In some embodiments, the T-cell subpopulation is activated and primed with pooled peptides to a MMAA or TAA, wherein the pooled peptides include a library of overlapping peptides from the MMAA or TAA (peptide mix) which has been enriched by additionally including one or more specific known, identified, or heteroclitic epitopes of the MMAA or TAA. In some embodiments, the T-cell subpopulation is primed with overlapping peptides (or peptide mix), which has been further enriched with one or more specific neoantigens expressed by the patient's tumor. In some embodiments, the peptides used to prime the T-cells are the same length. In some embodiments, the peptides are of varying lengths. In other embodiments, the peptides included in the pool for priming the T-cells substantially only include known tumor antigenic epitopes. In some embodiments, the T-cell subpopulation is primed with one or more antigenic peptides expressed by the patient's tumor. In some embodiments, the T-cell subpopulation is primed with a neoantigen to a targeted MMAA or TAA. In some embodiments, the neoantigen is a mutated form of an endogenous protein derived through a single point mutation, a deletion, an insertion, a frameshift mutation, a fusion, mis-spliced peptide, or intron translation of the targeted MMAA or TAA.

In some embodiments, the T-cell composition is derived through the ex vivo expansion of separate T-cell populations, wherein the T-cell composition includes T-cell subpopulations primed separately to a pool of MMAA peptides comprising one or more antigenic peptides selected from BCMA, XBP1, CS1, and CD138, wherein each T-cell subpopulation is specific for a single MMAA. In some embodiments, the pooled MMAA peptides are comprised of overlapping peptides derived from MMAAs selected from SEQ ID NO: 1 (BCMA), SEQ ID NO: 71 or SEQ ID NO: 72 (XBP1), SEQ ID NO: 325 (CS1), and SEQ ID NO: 569 (CD138). In some embodiments, the pooled MMAA peptides are further enriched with one or more additional peptides selected from SEQ ID NO: 2-70 (BCMA), 73-324 (XBP1), 326-568 (CS1), and 570-813 (CD138). In some embodiments, the pooled MMAA peptides include one or more peptides selected from SEQ ID NO: 2-70 (BCMA), one or more peptides selected from SEQ ID NO: 73-324 (XBP1), one or more peptides selected from 326-568 (CS1), and one or more peptides from SEQ ID NO: 570-813 (CD138), or combinations thereof. In some aspects, the ratio of the T-cell subpopulations that comprise the T-cell composition is correlated with the tumor expression profile of the subject.

In some embodiments, the T-cell composition is derived through the ex vivo expansion of separate T-cell populations, wherein the T-cell composition includes separate T-cell subpopulations primed to a pool of TAA peptides comprising one or more antigenic peptides selected from PRAME, Survivin, and WT1. In some embodiments, the pooled TAA peptides are comprised of overlapping peptides derived from TAAs selected from SEQ ID NO: 814 (PRAME), SEQ ID NO: 883 (Survivin), and SEQ ID NO: 952 (WT1), or combinations thereof. In some embodiments, the pooled TAAs are further enriched with one or more additional peptides selected from SEQ ID NO: 815-882 (PRAME), 884-882 (Survivin), and 953-1212 (WT1), or combinations thereof. In some embodiments, the pooled TAA peptides include one or more peptides selected from SEQ ID NO: 815-882 (PRAME), one or more peptides selected from SEQ ID NO: 884-882 (Survivin), and one or more peptides selected from SEQ ID NO: 953-1212 (WT1), or combinations thereof. In some aspects, the ratio of the T-cell subpopulations that comprise the T-cell composition is correlated with the tumor expression profile of the subject.

In some embodiments, the T-cell composition is derived through the ex vivo expansion of separate T-cell populations, wherein the T-cell composition includes separate T-cell subpopulations primed to a pool of MMAA and TAA peptides comprising one or more antigenic peptides selected from BCMA, XBP1, CS1, CD138, PRAME, Survivin, and WT1. In some embodiments, the pooled MMAA and TAA peptides are comprised of overlapping peptides derived from MMAAs selected from SEQ ID NO: 1 (BCMA), SEQ ID NO: 71 or SEQ ID NO: 72 (XBP1), SEQ ID NO: 325 (CS1), SEQ ID NO: 569 (CD138) and TAAs selected from SEQ ID NO: 814 (PRAME), SEQ ID NO: 883 (Survivin), and SEQ ID NO: 952 (WT1), or combinations thereof. In some embodiments, the pooled MMMA peptides are further enriched with one or more additional peptides selected from SEQ ID NO: 2-70 (BCMA), 73-324 (XBP1), 326-568 (CS1), and 570-813 (CD138), or combinations thereof. In some embodiments, the pooled TAA peptides are further enriched with one or more additional peptides selected from SEQ ID NO: 815-882 (PRAME), 884-951 (Survivin), and 953-1212 (WT1), or combinations thereof. In some embodiments, the pooled MMAA peptides include one or more peptides selected from SEQ ID NO: 2-70 (BCMA), one or more peptides from SEQ ID NO: 73-324 (XBP1), one or more peptides selected from 326-568 (CS1), and one or more peptides from SEQ ID NO: 570-813 (CD138), or combinations thereof. In some embodiments, the pooled TAA peptides include one or more peptides selected from SEQ ID NO: 815-882 (PRAME), one or more peptides selected from SEQ ID NO: 884-951 (Survivin), and one or more peptides from SEQ ID NO: 953-1212 (WT1), or combinations thereof. In some aspects, the ratio of the T-cell subpopulations that comprise the T-cell composition is correlated with the tumor expression profile of the subject.

In some aspects, the T-cell composition is derived through the ex vivo expansion of separate T-cell populations, wherein the T-cell composition includes separate T-cell subpopulations primed to one or more antigenic peptides selected from SEQ ID NO: 2-70 (BCMA), one or more peptides selected from 73-324 (XBP1), one or more peptides selected from 326-568 (CS1), and one or more peptides from SEQ ID NO: 570-813 (CD138), or combinations thereof. In some aspects, the ratio of the T-cell subpopulations that comprise the T-cell composition is correlated with the tumor expression profile of the subject.

In some aspects, the T-cell composition is derived through the ex vivo expansion of separate T-cell populations, wherein the T-cell composition includes T-cell subpopulations primed to one or more antigenic peptides selected from SEQ ID NO: 815-882 (PRAME), one or more peptides selected from SEQ ID NO: 884-951 (Survivin), and one or more peptides selected from 953-1212 (WT1), or combinations thereof. In some aspects, the ratio of the T-cell subpopulations is correlated with the tumor expression profile of the subject.

In some aspects, the T-cell composition is derived through the ex vivo expansion of separate T-cell populations, wherein the T-cell composition includes T-cell subpopulations primed to one or more antigenic peptides selected from SEQ ID NO: 2-70 (BCMA), one or more peptides selected from 73-324 (XBP1), one or more peptides selected from 326-568 (CS1), one or more peptides from SEQ ID NO: 570-813 (CD138), one or more peptides selected from SEQ ID NO: 815-882 (PRAME), one or more peptides selected from SEQ ID NO: 884-951 (Survivin), and one or more peptides selected from 953-1212 (WT1), or combinations thereof. In some aspects, the ratio of the T-cell subpopulations is correlated with the tumor expression profile of the subject.

In some embodiments, the MMAA T-cell composition is derived from a single T-cell population, wherein the T-cell population has been exposed to a pool of MMAA peptides comprising one or more antigenic peptides selected from BCMA, XBP1, CS1, and CD138. In some embodiments, the pooled MMAA peptides are comprised of overlapping peptides derived from MMAAs selected from SEQ ID NO: 1 (BCMA), SEQ ID NO: 71 or SEQ ID NO: 72 (XBP1), SEQ ID NO: 325 (CS1), and SEQ ID NO: 569 (CD138), or combinations thereof. In some embodiments, the pooled MMAA peptides are further enriched with one or more additional peptides selected from SEQ ID NO: 2-70 (BCMA), 73-324 (XBP1), 326-568 (CS1), and 570-813 (CD138). In some embodiments, the pooled MMAA peptides include one or more peptides selected from SEQ ID NO: 2-70 (BCMA), one or more peptides selected from SEQ ID NO: 73-324 (XBP1), one or more peptides selected from 326-568 (CS1), and one or more peptides from SEQ ID NO: 570-813 (CD138), or combinations thereof.

In some embodiments, the TAA T-cell composition is derived from a single T-cell population, wherein the T-cell populations has been exposed to a pool of TAA peptides comprising one or more antigenic peptides selected from PRAME, Survivin, and WT1, or combinations thereof. In some embodiments, the pooled TAA peptides are comprised of overlapping peptides derived from TAAs selected from SEQ ID NO: 814 (PRAME), SEQ ID NO: 883 (Survivin), and SEQ ID NO: 952 (WT1), or combinations thereof. In some embodiments, the pooled TAAs are further enriched with one or more additional peptides selected from SEQ ID NO: 815-882 (PRAME), 884-882 (Survivin), and 953-1212 (WT1), or combinations thereof. In some embodiments, the pooled TAA peptides include one or more peptides selected from SEQ ID NO: 815-882 (PRAME), one or more peptides selected from SEQ ID NO: 884-882 (Survivin), and one or more peptides selected from SEQ ID NO: 953-1212 (WT1), or combinations thereof.

In some embodiments, the T-cell composition is derived from a single T-cell population, wherein the T-cell population has been exposed to a pool of MMAA and TAA peptides comprising one or more antigenic peptides selected from BCMA, XBP1, CS1, CD138, PRAME, Survivin, and WT1, or combinations thereof. In some embodiments, the pooled MMAA and TAA peptides are comprised of overlapping peptides derived from MMAAs selected from SEQ ID NO: 1 (BCMA), SEQ ID NO: 71 or SEQ ID NO: 72 (XBP1), SEQ ID NO: 325 (CS1), SEQ ID NO: 569 (CD138) and TAAs selected from SEQ ID NO: 814 (PRAME), SEQ ID NO: 883 (Survivin), and SEQ ID NO: 952 (WT1), or combinations thereof. In some embodiments, the pooled MMMA peptides are further enriched with one or more additional peptides selected from SEQ ID NO: 2-70 (BCMA), 73-324 (XBP1), 326-568 (CS1), and 570-813 (CD138), or combinations thereof. In some embodiments, the pooled TAA peptides are further enriched with one or more additional peptides selected from SEQ ID NO: 815-882 (PRAME), 884-951 (Survivin), and 953-1212 (WT1), or combinations thereof. In some embodiments, the pooled MMAA peptides include one or more peptides selected from SEQ ID NO: 2-70 (BCMA), one or more peptides from SEQ ID NO: 73-324 (XBP1), one or more peptides selected from 326-568 (CS1), and one or more peptides from SEQ ID NO: 570-813 (CD138), or combinations thereof. In some embodiments, the pooled TAA peptides include one or more peptides selected from SEQ ID NO: 815-882 (PRAME), one or more peptides selected from SEQ ID NO: 884-951 (Survivin), and one or more peptides from SEQ ID NO: 953-1212 (WT1), or combinations thereof.

In some aspects, the T-cell composition includes a single T-cell subpopulation that have been primed to one or more antigenic peptides selected from SEQ ID NO: 2-70 (BCMA), one or more peptides selected from 73-324 (XBP1), one or more peptides selected from 326-568 (CS1), or one or more peptides from SEQ ID NO: 570-813 (CD138), or combinations thereof.

In some aspects, the T-cell composition includes a single T-cell subpopulation that has been primed to one or more antigenic peptides selected from SEQ ID NO: 815-882 (PRAME), one or more peptides selected from SEQ ID NO: 884-951 (Survivin), and one or more peptides selected from 953-1212 (WT1), or combinations thereof.

In some aspects, the T-cell composition includes a single T-cell subpopulation that has been primed to one or antigenic peptides selected from SEQ ID NO: 2-70 (BCMA), one or more peptides selected from 73-324 (XBP1), one or more peptides selected from 326-568 (CS1), or one or more peptides from SEQ ID NO: 570-813 (CD138), one or more antigenic peptides selected from SEQ ID NO: 815-882 (PRAME), one or more peptides selected from SEQ ID NO: 884-951 (Survivin), and one or more peptides selected from 953-1212 (WT1), or combinations thereof.

The T-cell populations described herein include at least CD8+ T-cells and CD4+ T-cells that have been primed and are capable of targeting the selected MMAAs and TAAs described herein for tumor killing and/or cross presentation.

In certain embodiments, the T-cell composition further comprises activated γδ T-cells and/or activated CD3+ NKT cells capable of mediating anti-tumor responses. By including multiple activated immune effector cells with differing in vivo immune effector and biological functions in the T-cell compositions administered to a subject with a plasma cell dyscrasias, long lasting and durable responses to plasma cell dyscrasias are possible, increasing the ability of the administered T-cell composition to induce tumor specific epitope spreading, and reduce tumor immune surveillance avoidance. The inclusion of activated CD3+ NKT-cells and/or TS T-cells results in the additional release of cytokines that induce bystander T-cell activation and thus recruit other lymphocytes, including CD8+ T-cells, to aid in tumor cytolysis, including epitope spreading.

In some aspects, provided herein is a method of treating a subject with a plasma cell dyscrasia, for example MM, comprising administering to the subject a T-cell composition comprising two or more T-cell subpopulations, wherein each T-cell subpopulation is specific for a single MMAA; wherein each of the T-cell subpopulations are primed and expanded ex vivo separately from each other; and wherein each of the T-cell subpopulations are combined in the T-cell composition in a defined ratio. In some embodiments, the T-cell composition includes T-cell subpopulations specific to one or more MMAAs selected from the group consisting of BCMA, XBP1, CS1, and CD138.

In some aspects, provided herein is a method of treating a subject with a plasma cell dyscrasia, for example MM, comprising administering to the subject a T-cell composition comprising two or more T-cell subpopulations, wherein each T-cell subpopulation is specific for a single TAA; wherein each of the T-cell subpopulations are primed and expanded ex vivo separately from each other; and wherein each of the T-cell subpopulations are combined in the T-cell composition in a defined ratio. In some embodiments, the T-cell composition includes T-cell subpopulations specific to one or more TAAs selected from the group consisting of PRAME, Survivin, and WT1.

In some aspects, provided herein is a method of treating a subject with a plasma cell dyscrasia, for example MM, comprising administering to the subject a T-cell composition comprising two or more T-cell subpopulations, wherein each T-cell subpopulation is specific for a single MMAA or TAA; wherein each of the T-cell subpopulations are primed and expanded ex vivo separately from each other; and wherein each of the T-cell subpopulations are combined in the T-cell composition in a defined ratio. In some embodiments, the T-cell composition includes T-cell subpopulations specific to one or more MMAA and TAAs selected from the group consisting of BCMA, XBP1, CS1, CD138, PRAME, Survivin, and WT1, or combinations thereof.

In some aspects, provided herein is a method of treating a subject with a plasma cell dyscrasia, for example MM, comprising initially administering to the subject a T-cell composition comprising subpopulations of T-cells directed to PRAME, Survivin, and WT1, and subsequently administering to the subject a T-cell composition comprising subpopulations of T-cells directed to BCMA, XBP1, CS1, and CD138. In some embodiments, the T-cell composition comprising subpopulations of T-cells directed to BCMA, XBP1, CS1, and CD138 are administered about 1 week, 2 weeks, 3 weeks, 4 weeks, 5 weeks, 6 weeks, 8 weeks, 10 weeks, or 12 weeks, or more from the time the T-cell composition comprising subpopulations of T-cells directed to PRAME, Survivin, and WT1 are administered. In some aspects, multiple additional administrations of either T-cell composition are provided to the subject.

DETAILED DESCRIPTION OF THE INVENTION

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. The term "about" as used herein when referring to a measurable value such as an amount, a temporal duration, and the like, is meant to encompass variations of ±20%, ±10%, ±5%, ±1%, ±0.5%, or ±0.1% from the specified value, as such variations are appropriate to perform the disclosed methods.

The term "activates" as used herein means, in the context of a T-cell, that the T-cell is primed for recognizing antigen expressed on the surface of a target cell. In some embodiments, if the T-cell is primed it means that if exposed to a cell expressing the antigen, the T-cell is capable of binding to the cell through its T-cell receptor. In some embodiments, the activation is sufficient to cause a cytotoxic event, apoptosis, phagocytosis or death of the target cell.

The term "allogeneic" as used herein refers to medical therapy in which the donor and recipient are different individuals of the same species.

The term "antigen" as used herein refers to molecules, such as polypeptides, peptides, or glyco- or lipo-peptides that are recognized by the immune system, such as by the cellular or humoral arms of the human immune system. The term "antigen" includes antigenic determinants, such as peptides with lengths of about 6, 7, 8, 9, 10, 11, 12, 13, 14, 15, 16, 17, 18, 19, 20, 21, 22 or more amino acid residues that bind to MHC molecules, form parts of MHC Class I or II complexes, or that are recognized when complexed with such molecules.

The term "antigen presenting cell (APC)" as used herein refers to a class of cells capable of presenting one or more antigens in the form of peptide-MHC complex recognizable by specific effector cells of the immune system, and thereby inducing an effective cellular immune response against the antigen or antigens being presented. Examples of professional APCs are dendritic cells and macrophages, though any cell expressing MHC Class I or II molecules can potentially present peptide antigen.

The term "autologous" as used herein refers to medical therapy in which the donor and recipient are the same person.

The term "cord blood" as used herein has its normal meaning in the art and refers to blood that remains in the placenta and umbilical cord after birth and contains hematopoietic stem cells.

Cord blood may be fresh, cryopreserved, or obtained from a cord blood bank.

The term "cytokine" as used herein has its normal meaning in the art. Nonlimiting examples of cytokines used in the invention include IL-2, IL-6, IL-7, IL-12, IL-15, and IL-27.

The term "cytotoxic T-cell" or "cytotoxic T lymphocyte" as used herein is a type of immune cell that bears a CD8+ antigen and that can kill certain cells, including foreign cells, tumor cells, and cells infected with a virus. Cytotoxic T cells can be separated from other blood cells, grown ex vivo, and then given to a patient to kill tumor or viral cells. A cytotoxic T cell is a type of white blood cell and a type of lymphocyte.

The term "dendritic cell" or "DC" as used herein describes a diverse population of morphologically similar cell types found in a variety of lymphoid and non-lymphoid tissues, see Steinman, Ann. Rev. Immunol. 9:271-296 (1991).

The term "derivative" as used herein, when referring to peptides, means compounds having amino acid structural and functional analogs, for example, peptidomimetics having synthetic or non-natural amino acids (such as a norleucine) or amino acid analogues or non-natural side chains, so long as the derivative shares one or more functions or activities of polypeptides of the disclosure. The term "derivative" therefore include "mimetic" and "peptidomimetic" forms of the polypeptides disclosed herein. As used herein, a "non-natural side chain" is a modified or synthetic chain of atoms joined by covalent bond to the α-carbon atom, β-carbon atom, or 7-carbon atom which does not make up the backbone of the polypeptide chain of amino acids. The peptide analogs may comprise one or a combination of non-natural amino-acids chosen from: norvaline, tert-butylglycine, phenylglycine, He, 7-azatryptophan, 4-fluorophenylalanine, N-methyl-methionine, N-methyl-valine, N-methyl-alanine, sarcosine, N-methyl-tert-butylglycine, N-methyl-leucine, N-methyl-phenylglycine, N-methyl-isoleucine, N-methyl-tryptophan, N-methyl-7-azatryptophan, N-methyl-phenylalanine, N-methyl-4-fluorophenylalanine, N-methyl-threonine, N-methyl-tyrosine, N-methyl-valine, N-methyl-lysine, homocysteine, and Tyr; Xaa2 is absent, or an amino acid selected from the group consisting of Ala, D-Ala, N-methyl-alanine, Glu, N-methyl-glutamate, D-Glu, Gly, sarcosine, norleucine, Lys, D-Lys, Asn, D-Asn, D-Glu, Arg, D-Arg, Phe, D-Phe, N-methyl-phenylalanine, Gin, D-Gln, Asp, D-Asp, Ser, D-Ser, N-methyl-serine, Thr, D-Thr, N-methyl-threonine, D-Pro D-Leu, N-methyl-leucine, D-Ile, N-methyl-isoleucine, D-Val, N-methyl-valine, tert-butylglycine, D-tert-butylglycine, N-methyl-tert-butylglycine, Trp, D-Trp, N-methyl-tryptophan, D-Tyr, N-methyl-tyrosine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (5)-2-amino-3-(1H-tetrazol-5-yl)propanoic acid, Glu, Gly, N-methyl-glutamate, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, octylglycine, tranexamic acid, aminovaleric acid, and 2-(2-aminoethoxy)acetic acid. The natural side chain, or R group, of an alanine is a methyl group. In some embodiments, the non-natural side chain of the composition is a methyl group in which one or more of the hydrogen atoms is replaced by a deuterium atom. Non-natural side chains are disclosed in the art in the following publications: WO/2013/172954, WO2013123267, WO/2014/071241, WO/2014/138429, WO/2013/050615, WO/2013/050616, WO/2012/166559, US Application No. 20150094457, Ma, Z., and Hartman, M. C. (2012). In Vitro Selection of Unnatural Cyclic Peptide Libraries via mRNA Display. In J. A. Douthwaite & R. H. Jackson (Eds.), *Ribosome Display and Related Technologies: Methods and Protocols* (pp. 367-390). Springer New York., all of which are incorporated by reference in their entireties.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below. The term "analog" refers to any polypeptide comprising at least one α-amino acid and at least one non-native amino acid residue, wherein the polypeptide is structurally similar to a naturally occurring full-length protein and shares the biochemical or biological activity of the naturally occurring full-length protein upon which the analog is based.

The term "effector cell" as used herein describes a cell that can bind to or otherwise recognize an antigen and mediate an immune response. Tumor, virus, or other antigen-specific T-cells and NKT-cells are examples of effector cells.

The term "endogenous" as used herein refers to any material from or produced inside an organism, cell, tissue or system.

The term "epitope" or "antigenic determinant" as used herein refers to the part of an antigen that is recognized by the immune system, specifically by antibodies, B cells, or T cells.

The term "exogenous" as used herein refers to any material introduced from or produced outside an organism, cell, tissue or system.

The terms "functional fragment" means any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 85%, 80%, 75%, 70%, 65%, or 60% sequence identity to the wild-type sequence upon which the sequence is derived.

The term "fragment" is meant a portion of a polypeptide or nucleic acid molecule. This portion contains, preferably, at least about 5%, 10%, 20%, 30%, 40%, 50%, 60%, 70%, 80%, or about 90% of the entire length of the reference nucleic acid molecule or polypeptide. A fragment may contain about 5, 10, 20, 30, 40, 50, 60, 70, 80, 90, or 100, 200, 300, 400, 500, 600, 700, 800, 900, 1000 or more nucleotides or amino acids.

The term "HLA" as used herein refers to human leukocyte antigen. There are 7,196 HLA alleles. These are divided into 6 HLA class I and 6 HLA class II alleles for each individual (on two chromosomes). The HLA system or complex is a gene complex encoding the major histocompatibility complex (MHC) proteins in humans. HLAs corresponding to MHC Class I (A, B, or C) present peptides from within the cell and activate CD8-positive (i.e., cytotoxic) T-cells. HLAs corresponding to MHC Class II (DP, DM, DOA, DOB, DQ and DR) stimulate the multiplication of CD4-positive T-cells) which stimulate antibody-producing B-cells.

The term "isolated" as used herein means separated from components in which a material is ordinarily associated with. For example, an isolated cord blood mononuclear cell can be separated from red blood cells, plasma, and other components of cord blood.

The term "multiple myeloma-associated antigen" or "MMAA" as used herein is an antigen that is highly correlated with plasma cell dyscrasias such as multiple myeloma. They are not usually found, or are found to a lesser extent, on normal cells.

A "naive" T-cell or other immune effector cell as used herein is one that has not been exposed to or primed by an antigen or to an antigen-presenting cell presenting a peptide antigen capable of activating that cell.

A "peptide library" or "overlapping peptide library" as used herein within the meaning of the application is a complex mixture of peptides which in the aggregate covers the partial or complete sequence of a protein antigen. Successive peptides within the mixture overlap each other. For example, a peptide library may be constituted of peptides 15 amino acids in length which overlapping adjacent peptides in the library by 11 amino acid residues and which span the entire length of a protein antigen. In particular embodiments, the peptides in the library are about 7, 8, 9, 10, 11, 12, 13, 14, 15, 16, 17, 18, 19, 20, 21,22,23,24,25,26,27, 28,29,30, 31, 32, 33, 34, or about 35 or more amino acids in length, for example, and there is overlap of about 5, 6, 7, 8, 9, 10, 11, 12, 13, 14, 15, 16, 17, 18, 19, 20,21, 22, 23, 24, 25, 26, 27, 28, 29, 30, 31, 32, 33, or 34 amino acids in length. Peptide libraries are commercially available and may be custom-made for particular antigens. Methods for contacting, pulsing or loading antigen-presenting cells are well known and incorporated by reference to Ngo, et al (2014). Peptide libraries may be obtained from JPT and are incorporated by reference to the website at www.jpt.com/products/peptrack/peptide-libraries.

A "peripheral blood mononuclear cell" or "PBMC" as used herein is any peripheral blood cell having a round nucleus. These cells consist of lymphocytes (T cells, B cells, NK cells) and monocytes. In humans, lymphocytes make up the majority of the PBMC population, followed by monocytes, and only a small percentage of dendritic cells.

The term "precursor cell" as used herein refers to a cell which can differentiate or otherwise be transformed into a particular kind of cell. For example, a "T-cell precursor cell" can differentiate into a T-cell and a "dendritic precursor cell" can differentiate into a dendritic cell.

The "percent identity," "percent sequence identity," or "percent homology" or "percent sequence homology" of two polynucleotide or two polypeptide sequences is determined by comparing the sequences using the GAP computer program (a part of the GCG Wisconsin Package, version 10.3 (Accelrys, San Diego, Calif.)) using its default parameters. "Identical" or "identity" as used herein in the context of two or more nucleic acids or amino acid sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may he performed manually or by using a computer sequence algorithm such as BLAST or BLAST 2.0. Briefly, the BLAST algorithm, which stands for Basic Local Alignment Search Tool is suitable for determining sequence similarity. Softwar for performing BLAST analyses is publicly available through the National Center for Biotechnology Information (http://www.ncbi.nlm.nih.gov). This algorithm involves first identifying high scoring sequence pair (HSPs) by identifying short words of length Win the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, less than about 0.1, less than about 0.01, and less than about 0.001. Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "subject" or "host" or "patient" as used herein is a vertebrate, and, in some embodiments, a mammal, and, in some embodiments, a human. Mammals include, but are not limited to humans, simians, equines, bovines, porcines, canines, felines, murines, other farm animals, sport animals, or pets. Humans include those in need of virus- or other antigen-specific T-cells, such as those with lymphocytopenia, those who have undergone immune system ablation, those undergoing transplantation and/or immunosuppressive regimens, those having naïve or developing immune systems, such as neonates, or those undergoing cord blood or stem cell transplantation. In a typical embodiment, the term "patient" as used herein refers to a human.

A "T-cell population" or "T-cell subpopulation" is intended to include thymocytes, immature T lymphocytes, mature T lymphocytes, resting T lymphocytes and activated T-lymphocytes. The T-cell population or subpopulation can include ap T-cells, including CD4+ T-cells, CD8+ T cells, 78 T-cells, Natural Killer T-cells, or any other subset of T-cells.

The term "therapeutic effect" as used herein is meant to refer to some extent of relief of one or more of the symptoms of a disorder (e.g., multiple myeloma or those disorders disclosed herein) or its/their associated pathology. A "therapeutically effective amount" as used herein is meant to refer to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. A "therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved. The terms "treatment" or "treating" as used herein is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival.

The term "tumor-associated antigen expression profile" or "tumor antigen expression profile" as used herein, refers to a profile of expression levels of tumor-associated antigens within a malignancy or tumor. Tumor-associated antigen expression may be assessed by any suitable method known in the art including, without limitation, quantitative real time polymerase chain reaction (qPCR), cell staining, or other suitable techniques. Non-limiting exemplary methods for determining a tumor-associated antigen expression profile can be found in Ding et al., Cancer Bio Med (2012) 9: 73-76; Qin et al., Leukemia Research (2009) 33(3) 384-390; Weber et al., Leukemia (2009) 23: 1634-1642; Liu et al., J. Immunol (2006) 176: 3374-3382; Schuster et al., Int J Cancer (2004) 108: 219-227, which are incorporated by reference in their entireties.

The term "tumor-associated antigen" or "TAA" as used herein is an antigen that is highly correlated with certain tumor cells. They are not usually found, or are found to a lesser extent, on normal cells.

Multiple Myeloma Tumor Associated Antigens

The T-cell compositions of the present disclosure are directed to select MMAAs, and optionally, to select additional TAAs. The MMAAs are selected from B-cell maturation antigen (BCMA), X box Protein 1 (XBP1), CS1, and Syndecan-1 (CD138), or a combination thereof. In certain embodiments, the T-cell composition includes T-cells activated to a TAA selected from preferentially expressed antigen of melanoma (PRAME), Survivin, and Wilms' Tumor 1 protein (WT1), or a combination thereof. In certain embodiments, the T-cell composition includes T-cells activated to a TAA selected from preferentially expressed antigen of melanoma (PRAME), Survivin, Wilms' Tumor 1 protein (WT1), and melanoma associated antigen 3 (MAGE A3) or a combination thereof. In particular embodiments, the T-cell composition for administration comprises T-cells activated to the specific MMAAs selected from the group consisting of BCMA, XBP1, CS1, and CD138. In certain embodiments, the T-cell compositions further include T-cells activated to the specific TAAs selected from the group consisting of PRAME, Survivin, and WT1. In certain embodiments, the T-cell compositions further include T-cells activated to the specific TAAs selected from the group consisting of PRAME, Survivin, WT1, and MAGE A3. In certain embodiments, the T-cell composition for administration comprises T-cells activated against MMAAs selected from the group consisting of BCMA, XBP1, CS1, CD138, as well as TAAs from the group consisting of PRAME, Survivin, and WT1. In certain embodiments, the TAA MAGE A3 is included.

T-cell subpopulations activated to the targeted MMAAs and TAAs described herein can be prepared by pulsing antigen presenting cells with a single peptide or epitope, several peptides or epitopes, or with peptide libraries of the selected antigen, that for example, include peptides that are about 7, 8, 9, 10, 11, 12, 13, 14, 15, 16 or more amino acids long and overlapping one another by 5, 6, 7, 8, or 9 amino acids, in certain aspects. GMP-quality PepMix™ peptides directed to a number of tumor-associated antigens are commercially available, for example, through JPT Technologies and/or Miltenyi Biotec. In particular embodiments, the peptides are about 7, 8, 9, 10, 11, 12, 13, 14, 15, 16, 17, 18, 19, 20, 21, 22, 23, 24, 25, 26, 27, 28, 29, 30, 31, 32, 33, 34, or about 35 or more amino acids in length, for example, and there is overlap of about 5, 6, 7, 8, 9, 10, 11, 12, 13, 14, 15, 16, 17, 18, 19, 20, 21, 22, 23, 24, 25, 26, 27, 28, 29, 30, 31, 32, 33, or about 34 amino acids in length.

Much work has been done to determine specific epitopes of TAAs and the HLA alleles they are associated with. Non-limiting examples of specific epitopes of TAAs and the alleles they are associated with can be found in Kessler et al., J Exp Med. 2001 Jan. 1; 193(1):73-88; Oka et al. Immunogenetics. 2000 February; 51(2):99-107; Ohminami et al., Blood. 2000 Jan. 1; 95(1):286-93; Schmitz et al., Cancer Res. 2000 Sep. 1; 60(17):4845-9 and Bachinsky et al., Cancer Immun. 2005 Mar. 22; 5:6, which are each incorporated herein by reference.

B-Cell Maturation Antigen (BCMA)

B-cell maturation antigen, also known as BCMA/Tumor necrosis factor receptor superfamily member 17/CD269, is closely related to BAFF receptor (BAFF-R) and transmembrane activator and calcium modulator and cyclophilin ligand interactor (TACI), plays a central role in regulating B-cell maturation and differentiation into PC. These three functionally related receptors are type III transmembrane proteins lacking a signal-peptide and containing cysteine-rich extracellular domains. They promote B-cell survival at distinct stages of development by engaging APRIL and/or BAFF (Elgueta et al., The immortality of humoral immunity. Immunol. Rev. 2010; 236: 139-150). BCMA is expressed exclusively in B-cell lineage cells, particularly in the inter-follicular region of the germinal center (Chiu et al. Hodgkin lymphoma cells express TACI and BCMA receptors and generate survival and proliferation signals in response to BAFF and APRIL. Blood. 2007; 109(2):729-739) as well as on plasmablasts and differentiated PCs (Avery et al. BAFF selectively enhances the survival of plasmablasts generated from human memory B cells. J. Clin. Invest. 2003; 112(2): 286-297; O'Connor et al. BCMA is essential for the survival of long-lived bone marrow plasma cells. J. Exp. Med. 2004; 199(1):91-98). It is selectively induced during PC differentiation, associated with loss of BAFF-R (Darce et al., Divergent effects of BAFF on human memory B cell differentiation into Ig-secreting cells. *J. Immunol.* 2007; 178 (9):5612-5622). BCMA may enhance humoral immunity by stimulating the survival of normal PCs and plasmablasts (Avery et al. BAFF selectively enhances the survival of plasmablasts generated from human memory B cells. J. Clin. Invest. 2003; 112(2):286-297; Darce et al., Divergent effects of BAFF on human memory B cell differentiation into Ig-secreting cells. *J. Immunol.* 2007; 178(9):5612-5622); however, it is absent on naïve and most memory B cells. Thus, BCMA does not appear to be critical for overall B-cell homeostasis, but is required for optimal survival of long-lived PCs in the BM (O'Connor et al. BCMA is essential for the survival of long-lived bone marrow plasma cells. J. Exp. Med. 2004; 199(1):91-98; Xu et al., B-cell maturation protein, which binds the tumor necrosis factor family members BAFF and APRIL, is dispensable for humoral immune responses. Mol. Cell. Biol. 2001; 21(12):4067-4077). In MM, BCMA is widely expressed on malignant PCs at elevated levels (Claudio et al., A molecular compendium of genes expressed in multiple myeloma. Blood. 2002; 100(6): 2175-2186; Tai et al., Role of B-cell-activating factor in adhesion and growth of human multiple myeloma cells in the bone marrow microenvironment. Cancer Res. 2006; 66(13):6675-6682). Most recently, gene and protein expression profiling confirm that BCMA is the most selectively expressed cell surface receptor on MM cell lines and patient MM cells (Carpenter et al. B-cell maturation antigen is a promising target for adoptive T-cell therapy of multiple myeloma. Clin. Cancer Res. 2013; 19(8):2048-2060; Maus et al., Zoom zoom: racing CARs for Multiple Myeloma. Clin. Cancer Res. 2013; 19(8):1917-1919; Tai et al. Novel anti-B-cell maturation antigen antibody-drug conjugate (GSK2857916) selectively induces killing of multiple myeloma. Blood. 2014; 123(20):3128-3138; Frigyesi et al. Robust isolation of malignant plasma cells in multiple myeloma. Blood. 2014; 123(9):1336-1340). BCMA expression is increased with progression from normal to MGUS to SMM to active MM. Because BCMA protein is undetectable on normal human tissues except for PCs, it has a very restricted expression pattern (Carpenter et al. B-cell maturation antigen is a promising target for adoptive T-cell therapy of multiple myeloma. Clin. Cancer Res. 2013; 19(8):2048-2060). The other cell type with detectable BCMA mRNA and protein are pDCs (CD138-/BDCA-4+), which reside in the BM proximate to MM cells to promote their growth, survival and drug resistance (Chauhan et al. Functional interaction of plasmacytoid dendritic cells with multiple myeloma cells: a therapeutic target. Cancer Cell. 2009; 16(4):309-323). Its level is significantly lower (more than tenfold difference) on pDC versus CD138+ PC derived from the same patient (Tai et al. Novel anti-B-cell maturation antigen antibody-drug conjugate (GSK2857916) selectively induces killing of multiple myeloma. Blood. 2014; 123(20):3128-3138). Thus, BCMA might be functional in pDC, further promoting MM cell survival and development of drug resistance. Importantly, donor derived anti-BCMA mAbs are identified in MM patients in remission after allogeneic transplant with graft-versus-MM response following donor lymphocyte infusion (Bellucci et al. Graft-versus-tumor response in patients with multiple myeloma is associated with antibody response to BCMA, a plasma-cell membrane receptor. Blood. 2005; 105(10):3945-3950), further suggesting BCMA as a promising immunotherapeutic target in MM.

BCMA specific T-cells can be generated as described below using one or more antigenic peptides to BCMA, for example, derived from SEQ ID NO: 1. In some embodiments, the BCMA specific T-cells are generated using one or more antigenic peptides to BCMA, or modified or hetero-clitic peptide(s) derived from BCMA peptide(s). In some embodiments, BCMA specific T-cells are generated using a BCMA antigen library comprising peptides (for example 15mers) containing amino acid overlap (for example 11 amino acids of overlap) between each sequence formed by scanning the protein amino acid sequence SEQ ID NO: 1 (UNIPROT KB—Q02223 (TNR17_HUMAN)):

MLQMAGQCSQNEYFDSLLHACIPCQLRCSSNTP-PLTCQRYCNASVTNSVKGTNAILWTC LGLSLI-ISLAVFVLMFLLRKINSEPLKDEFKNTGSGLLG-MANIDLEKSRTGDEIILPRGLEY TVEECTCEDCIKSKPKVDSDHCFPLPAMEEGA-TILVTTKTNDYCKSLPAALSATEIEKSIS AR In some embodiments, the BCMA protein can comprise about 60%, 65%, 70%, 75%, 80%, 85%, 90%, 95%, or 99% sequence identity to SEQ ID NO:1.

In some embodiments, the BCMA specific T-cells are generated using one or more antigenic peptides derived from BCMA, or a modified or heteroclitic peptide derived from a BCMA peptide, selected from an amino acid sequence comprising NTPPLTCQRY (SEQ ID NO: 2); EIILPRGLEY (SEQ ID NO: 3); IILPRGLEY (SEQ ID NO: 4); DEIILPR-GLEY (SEQ ID NO: 5); SLAVFVLMFL (SEQ ID NO: 6); ILWTCLGLSL (SEQ ID NO: 7); CLGLSLIISL (SEQ ID NO: 8); VLMFLLRKI (SEQ ID NO: 9); HLPRGLEY (SEQ ID NO: 10); SLHSLAVF (SEQ ID NO: 11); FVLMFLLRK (SEQ ID NO: 12); ALSATEIEK (SEQ ID NO: 13);

AVFVLMFLLR (SEQ ID NO: 14); FVLMFLLRK (SEQ ID NO: 15); GMANIDLEK (SEQ ID NO: 16); ALSATEIEK (SEQ ID NO: 17); RTGDERLPR (SEQ ID NO: 18); DYCK-SLPAAL (SEQ ID NO: 19); YFDSLLHACI (SEQ ID NO: 20); EFKNTGSGLL (SEQ ID NO: 21); EFKNTGSGL (SEQ 15 ID NO: 22); EIJLPRGLEY (SEQ ID NO: 23); AVFVLMFLL (SEQ ID NO: 24); LVTTKTNDY (SEQ ID NO: 25); DEFKNTGSGL (SEQ ID NO: 26); EIEKSISAR (SEQ ID NO: 27); GATILVTTK (SEQ ID NO: 28); NTP-PLTCQR (SEQ ID NO: 29); FVLMFLLRK (SEQ ID NO: 30); LPRGLEYTV (SEQ ID NO: 31); EPLKDEFKNT (SEQ ID NO: 32); LPAALSATEI (SEQ ID NO: 33); LPA-MEEGATI (SEQ ID NO: 34); CIKSKPKVD (SEQ ID NO: 35); CIKSKPKV (SEQ ID NO: 36); SVKGTNAIL (SEQ ID NO: 37); EFKNTGSGL (SEQ ID NO: 38); ILVTTKTNDY (SEQ ID NO: 39); SLIISLAVF (SEQ ID NO: 40); SLAVFVLMF (SEQ ID NO: 41); GQCSQNEYF (SEQ ID NO: 42); TPPLTCQRY (SEQ ID NO: 43); KPKVDSDHCF (SEQ ID NO: 44); LPAALSATEI (SEQ ID NO: 45); LPA-MEEGATI (SEQ ID NO: 46); KSRTGDEII (SEQ ID NO: 47); KTNDYCKSL (SEQ ID NO: 48); ISLAVFVLM (SEQ ID NO: 49); NSEPLKDEF (SEQ ID NO: 50); MFLLRKIN-SEPLKDE (SEQ ID NO: 51); CLGLSLIISLAVFVL (SEQ ID NO: 52); AILWTCLGLSLIISL (SEQ ID NO: 53); GLS-LIISLAVFVLMF (SEQ ID NO: 54); KPKVDSDHCFPL-PAM (SEQ ID NO: 55); GSGLLGMANIDLEKS (SEQ ID NO: 56); GDEIILPRGLEYTVE (SEQ ID NO: 57); ATIL-VTTKTNDYCKS (SEQ ID NO: 58); KDEFKNTGSGLLGMA (SEQ ID NO: 59); CLGLSLI-ISLAVFVL (SEQ ID NO: 60); MFLLRKINSEPLKDE (SEQ ID NO: 61); ATILVTTKTNDYCKS (SEQ ID NO: 62); FVLMFLLRKINSEPL (SEQ ID NO: 63); NEYFD-SLLHACIPCQ (SEQ ID NO: 64); VFVLMFLLRKINSEP (SEQ ID NO: 65); HACIPCQLRCSSNTP (SEQ ID NO: 66); IISLAVFVLMFLLRK (SEQ ID NO: 67); CSQNEYFDSLLHAI (SEQ ID NO: 68); NAILWTCLGLS-LIIS (SEQ ID NO: 69); and CLGLSLIISLAVFVL (SEQ ID NO: 70).

In some embodiments, the BCMA peptide or derivative thereof can comprise about 60%, 65%, 70%, 75%, 80%, 85%, 90%, 95%, or 99% sequence identity to SEQ ID NOs:2-70 or a combination thereof.

In some embodiments, the BCMA specific T-cells are generated with peptides that recognize class I MHC molecules. In some embodiments, the BCMA specific T-cells are generated with peptides that recognize class II MHC molecules. In some embodiments, the BCMA specific T-cells are generated with peptides that recognize both class I and class II MHC molecules.

X Box Protein 1 (XBP1)

XBP1 is a transcription factor required for the terminal differentiation of B lymphocytes to plasma cells and is essential for immunoglobulin secretion (Reimold et al. Plasma cell differentiation requires the transcription factor XBP1. Nature. 2001; 412:300; Shaffer et al. Blimp-1 orchestrates plasma cell differentiation by extinguishing the mature B cell gene expression program. Immunity. 2002; 17:51-62). This antigen is a basic leucine zipper-containing transcription factor originally Identified as a protein binding to the cis-acting X box region in the promoter of human MHC class II genes (Liou et al. A new member of the leucine zipper class of proteins that binds to the HLA DR alpha promoter. Science. 1990; 247:1581-1584). XBP1 mRNA is processed by IRE1, an endoplasmic reticulum (ER) transmembrane protein that contains endoribonuclease and cytoplasmic protein kinase domains in response to ER stress (Yoshida et al., XBP1 mRNA is induced by ATF6 and spliced by IRE1 in response to ER stress to produce a highly active transcription factor. Cell. 2001; 107:881-891; Calfon et al. IRE1 couples endoplasmic reticulum load to secretary capacity by processing the XBP1 mRNA. Nature. 2002; 415:92-96; Lee et al. IRE1-mediated unconventional mRNA splicing and S2P-mediated ATF6 cleavage merge to regulate XBP1 in signaling the unfolded protein response. Genes Dev. 2002; 16:452-466). The mRNA spliced by IRE1 causes a reading frame shift which is translated into a spliced form of XBP1 protein that is an active transcription factor (Mori K. Frame switch splicing and regulated intramembrane proteolysis: key words to understand the unfolded protein response. Traffic. 2003; 4:519-528). To date, XBP1 is the only transcription factor found to be essential for plasma cell differentiation. XBP1 is uniformly expressed in all MM cells and cell lines and is selectively induced by exposure to IL-6 and has been implicated in the proliferation of malignant plasma cells (Bagratuni et al. XBPls levels are implicated in the biology and outcome of myeloma mediating different clinical outcomes to thalidomide-based treatments. Blood. 2010; 116:250-253; Patterson et al., IPI-504, a novel and soluble HSP-90 inhibitor, blocks the unfolded protein response in multiple myeloma cells. Cancer Chemother Pharmacol. 2008; 61:923-932; Acosta-Alvear et al. XBP1 controls diverse cell type- and condition-specific transcriptional regulatory networks. Mol Cell. 2007; 27:53-66; Wen et al. Identification of c-myc promoter-binding protein and X-box binding protein 1 as interleukin-6 target genes in human multiple myeloma cells. Int J Oncol. 1999; 15:173-178). Microarray analyses have identified XBP1 as a differentially expressed gene between the plasma cells and monoclonal gammopathy of undetermined significance (MGUS) and MM cells (Davies et al. Insights into the multistep transformation of MGUS to myeloma using microarray expression analysis. Blood. 2003; 102:4504-4511). Gene expression profiling studies have also confirmed the specific expression of XBP1 in MM (Zhan et al. Global gene expression profiling of multiple myeloma, monoclonal gammopathy of undetermined significance, and normal bone marrow plasma cells. Blood. 2002; 99:1745-1757). A recent study shows that a splice variant of XBP1 plays a crucial role in normal plasma cell differentiation (Iwakoshi et al., Plasma cell differentiation and the unfolded protein response intersect at the transcription factor XBP1. Nat Immunol. 2003; 4:321-329). XBP1 splicing is recognized to occur in terminal B cell differentiation and correlates with plasma cell differentiation. In addition, there is evidence that spliced XBP1 supports restoration of immunoglobulin production in XBP1–/– B cells and induces IL-6 secretion in normal plasma cells development (Pal et al. C/EBPbeta regulates transcription factors critical for proliferation and survival of multiple myeloma cells. Blood. 2009; 114:3890-3898; Zhang et al., The unfolded protein response sensor IRE1alpha is required at 2 distinct steps in B cell lymphopoiesis. J Clin Invest. 2005; 115:268-281; Brunsing et al. B- and T-cell development both involve activity of the unfolded protein response pathway. J Biol Chem. 2008; 283:17954-17961). It has also been shown that the relative mRNA expression levels of spliced XBP1 compared to XBP1 are differentially expressed in myeloma compared with normal plasma cells (Davies et al. Insights into the multistep transformation of MGUS to myeloma using microarray expression analysis. Blood. 2003; 102:4504-4511).

XBP1 specific T-cells can be generated as described below using one or more antigenic peptides to XBP1. In some embodiments, XBP1 specific T-cells are generated using a XBP1 antigen library comprising a pool of peptides (for example 15mers) containing amino acid. overlap (for example 11 amino acids of overlap) between each Sequence formed by scanning the protein amino acid SEQ ID NO: 71 (UNIPROT KB—P17861 (XBP1_HUMAN)):

```
MVVVAAAPNPADGTPKVLLLSGQPASAAGAPAGQALPLMVPAQRGASPE

AASGGLPQARKRQRLTHLSPEEKALRRKLKNRVAAQTARDRKKARMSEL

EQQVVDLEEENQKLLLENQLLREKTHGLVVENQELRQRLGMDALVAEEE

AEAKGNEVRPVAGSAESAALRLRAPLQQVQAQLSPLQNISPWILAVLTL

QIQSLISCWAFWTTWTQSCSSNALPQSLPAWRSSQRSTQKDPVPYQPPF

LCQWGRHQPSWKPLMN
```

In some embodiments, the XBP1 protein can comprise about 60%, 65%, 70%, 75%, 80%, 85%, 90%, 95%, or 99% sequence identity to SEQ ID NO: 71.

In some embodiments, XBP1 specific T-cells are generated using a XBP1 antigen library comprising peptides (for example 15mers) containing amino acid overlap (for example 11 amino acids of overlap) between each Sequence formed by scanning the protein amino acid sequence SEQ. ID. NO: 72 (Genbank Accession No. NP_001073007):

```
MVVVAAAPNPADGTPKVLLLSGQPASAAGAPAGQALPLMVPAQRGASPE

AASGGLPQARKRQRLTHLSPEEKALRRKLKNRVAAQTARDRKKARMSEL

EQQVVDLEEENQKLLLENQLLREKTHGLVVENQELRQRLGMDALVAEEE

AEAKGNEVRPVAGSAESAAGAGPVVTPPEHLPMDSGGID.SSDSESDIL

LGILDNLDPVMFFKCPSPEPASLEELPEVYPEGPSSLPASLSLSVGTSS

AKLEAINELIRFDHIYTKPLVLEIPSETESQANVVVKIEEAPLSPSEND

HPEFIVSVKEEPVEDDLVPELGISNLLSSSHCPKPSSCLLDAYSDCGYG

GSLSPFSDMSSLLGVNHSWEDTFANELFPQLISV
```

In some embodiments, the XBP-1 specific T-cells are generated using one or more antigenic peptides to XBP1, or a modified or heteroclitic peptide derived from an XBP1 peptide, selected from an amino acid sequence comprising YISPWILAV (SEQ ID NO: 73); YLFPQLISV (SEQ ID NO: 74); LLREKTHGLVVENQELRQR (SEQ ID NO: 75): ISP-WILAVL (SEQ ID NO: 76); LAVLTLQI (SEQ ID NO: 77); VLTLQIQS (SEQ ID NO: 78); or KLLLENQLL (SEQ ID NO: 79); ESDILLGILDNLDPV (SEQ ID NO: 80); ESDILLGILDNL (SEQ ID NO: 81); VYPEGPSSL (SEQ ID NO: 82); ELFPQLISV (SEQ ID NO: 83); LLREKTHGL (SEQ ID NO: 84); NISPWILAV (SEQ ID NO: 85); ILAVLTLQI (SEQ ID NO: 86); VLTLQIQSL (SEQ ID NO: 87); GILDNLDPV (SEQ ID NO: 88); ILLGILDNL (SEQ ID NO: 89); ELFPQLISV (SEQ ID NO: 90); YLFPQLISV (SEQ ID NO: 91); PWILAVLTL (SEQ ID NO: 92); ENQELRQRL (SEQ ID NO: 93); DGTPKVLLL (SEQ ID NO: 94); DLEEENQKL (SEQ ID NO: 95); SSNALPQSL (SEQ ID NO: 96); ISPWILAVL (SEQ ID NO: 97); VYPEGPSSL (SEQ ID NO: 98); GYGGSLSPF (SEQ ID NO: 99); PFSDMSSLL (SEQ ID NO: 100); LSPLQNISP-WILAVL (SEQ ID NO: 101); LSPLQNISPWILAVLT (SEQ ID NO: 102); LSPLQNISPWILAVLTL (SEQ ID NO: 103); LSPLQNISPWILAVLTLQ (SEQ ID NO: 104); LSPLQNIS-PWILAVLTLQI (SEQ ID NO: 105); LSPLQNISP-WILAVLTLQIQ (SEQ ID NO: 106); LSPLQNISP-WILAVLTLQIQS (SEQ ID NO: 107);

LSPLQNISPWILAVLTLQIQSL (SEQ ID NO: 108); LSPLQNISPWILAVLTLQIQSLI (SEQ ID NO: 109); LSPLQNISPWILAVLTLQIQSLIS (SEQ ID NO: 110); LSPLQNISPWILAVLTLQIQSLISC (SEQ ID NO: 111); LSPLQNISPWILAVLTLQIQSLISCW (SEQ ID NO: 112); LSPLQNISPWILAVLTLQIQSLISCWA (SEQ ID NO: 113); SPLQNISPWILAVL (SEQ ID NO: 114); SPLQNIS-PWILAVLT (SEQ ID NO: 115); SPLQNISPWILAVLTL (SEQ ID NO: 116); SPLQNISPWILAVLTLQ (SEQ ID NO: 117); SPLQNISPWILAVLTLQI (SEQ ID NO: 118); SPLQNISPWILAVLTLQIQ (SEQ ID NO: 119); SPLQNISPWILAVLTLQIQS (SEQ ID NO: 120); SPLQNISPWILAVLTLQIQSL (SEQ ID NO: 121); SPLQNISPWILAVLTLQIQSLI (SEQ ID NO: 122); SPLQNISPWILAVLTLQIQSLIS (SEQ ID NO: 123); SPLQNISPWILAVLTLQIQSLISC (SEQ ID NO: 124); SPLQNISPWILAVLTLQIQSLISCW (SEQ ID NO: 125); SPLQNISPWILAVLTLQIQSLISCWA (SEQ ID NO: 126); PLQNISPWILAVL (SEQ ID NO: 127); PLQNISP-WILAVLT (SEQ ID NO: 128); PLQNISPWILAVLTL (SEQ ID NO: 129); PLQNISPWILAVLTLQ (SEQ ID NO: 130); PLQNISPWILAVLTLQI (Seq ID. No. 131); PLQNISP-WILAVLTLQIQ (SEQ ID NO: 132); PLQNISP-WILAVLTLQIQS (SEQ ID NO: 133); PLQNISP-WILAVLTLQIQSL (SEQ ID NO: 134); PLQNISPWILAVLTLQIQSLI (SEQ ID NO: 135); PLQNISPWILAVLTLQIQSLIS (SEQ ID NO: 136); PLQNISPWILAVLTLQIQSLISC (SEQ ID NO: 137); PLQNISPWILAVLTLQIQSLISCW (SEQ ID NO: 138); PLQNISPWILAVLTLQIQSLISCWA (SEQ ID NO: 139); LQNISPWILAVL (SEQ ID NO: 140); LQNISPWILAVLT (SEQ ID NO: 141); LQNISPWILAVLTL (SEQ ID NO: 142); LQNISPWILAVLTLQ (SEQ ID NO: 143); LQNISP-WILAVLTLQI (SEQ ID NO: 144); LQNISP-WILAVLTLQIQ (SEQ ID NO: 145); LQNISP-WILAVLTLQIQS (SEQ ID NO: 146); LQNISPWILAVLTLQIQSL (SEQ ID NO: 147); LQNISP-WILAVLTLQIQSLI (SEQ ID NO: 148); LQNISP-WILAVLTLQIQSLIS (SEQ ID NO: 149); LQNISP-WILAVLTLQIQSLISC (SEQ ID NO: 150); LQNISPWILAVLTLQIQSLISCW (SEQ ID NO: 151); LQNISPWILAVLTLQIQSLISCWA (Seq ID. No. 152); QNISPWILAVL (SEQ ID NO: 153); QNISPWILAVLT (SEQ ID NO: 154); QNISPWILAVLTL (SEQ ID NO: 155); QNISPWILAVLTLQ (SEQ ID NO: 156); QNISP-WILAVLTLQI (SEQ ID NO: 157); QNISPWILAVLTLQIQ (SEQ ID NO: 158); QNISPWILAVLTLQIQS (SEQ ID NO: 159); QNISPWILAVLTLQIQSL (SEQ ID NO: 160); QNIS-PWILAVLTLQIQSLI (SEQ ID NO: 161); QNISP-WILAVLTLQIQSLIS (SEQ ID NO: 162); QNISP-WILAVLTLQIQSLISC (SEQ ID NO: 163); QNISPWILAVLTLQIQSLISCW (SEQ ID NO: 164); QNISPWILAVLTLQIQSLISCWA (SEQ ID NO: 165); NIS-PWILAVL (SEQ ID NO: 166); NISPWILAVLT (SEQ ID NO: 167); NISPWILAVLTL (SEQ ID NO: 168); NISP-WILAVLTLQ (SEQ ID NO: 169); NISPWILAVLTLQI (SEQ ID NO: 170); NISPWILAVLTLQIQ (SEQ ID NO: 171); NISPWILAVLTLQIQS (Seq ID. No. 172); NISP-WILAVLTLQIQSL (SEQ ID NO: 173); NISP-WILAVLTLQIQSLI (SEQ ID NO: 174); NISP-WILAVLTLQIQSLIS (SEQ ID NO: 175); NISPWILAVLTLQIQSLISC (SEQ ID NO: 176); NISP-WILAVLTLQIQSLISCW (SEQ ID NO: 177); NISP-WILAVLTLQIQSLISCWA (SEQ ID NO: 178); YISP-WILAVL (SEQ ID NO: 179); YISPWILAVLT (SEQ ID NO: 180); YISPWILAVLTL (SEQ ID NO: 181); YISP-WILAVLTLQ (SEQ ID NO: 182); YISPWILAVLTLQI (SEQ ID NO: 183); YISPWILAVLTLQIQ (SEQ ID NO: 184); YISPWILAVLTLQIQS (SEQ ID NO: 185); YISP-WILAVLTLQIQSL (SEQ ID NO: 186); YISP-WILAVLTLQIQSLI (SEQ ID NO: 187); YISP-WILAVLTLQIQSLIS (SEQ ID NO: 188); YISPWILAVLTLQIQSLISC (SEQ ID NO: 189); YISP-WILAVLTLQIQSLISCW (SEQ ID NO: 190); YISP-WILAVLTLQIQSLISCWA (SEQ ID NO: 191); ISP-WILAVL (SEQ ID NO: 192); ISPWILAVLT (SEQ ID NO: 193); ISPWILAVLTL (SEQ ID NO: 194); ISPWILAVLTLQ (SEQ ID NO: 195); ISPWILAVLTLQI (SEQ ID NO: 196); ISPWILAVLTLQIQ (SEQ ID NO: 197); ISP-WILAVLTLQIQS (SEQ ID NO: 198); ISP-WILAVLTLQIQSL (SEQ ID NO: 199); ISP-WILAVLTLQIQSLI (SEQ ID NO: 200); ISPWILAVLTLQIQSLIS (SEQ ID NO: 201); ISP-WILAVLTLQIQSLISC (SEQ ID NO: 202); ISP-WILAVLTLQIQSLISCW (SEQ ID NO: 203); ISP-WILAVLTLQIQSLISCWA (SEQ ID NO: 204); SPWILAVL (SEQ ID NO: 205); SPWILAVLT (SEQ ID NO: 206); SPWILAVLTL (SEQ ID NO: 207); SPWILAVLTLQ (SEQ ID NO: 208); SPWILAVLTLQI (SEQ ID NO: 209); SPWILAVLTLQIQ (SEQ ID NO: 210); SPWILAVLTLQIQS (SEQ ID NO: 211); SPWILAVLTLQIQSL (SEQ ID NO: 212); SPWILAVLTLQIQSLI (SEQ ID NO: 213); SPWILAVLTLQISSLIS (SEQ ID NO: 214); SPWILAVLTLQISSLISC (SEQ ID NO: 215); SPWILAVLTLQISSLISCW (SEQ ID NO: 216); SPWILAVLTLQISSLISCWA (SEQ ID NO: 217); PWILAVL (SEQ ID NO: 218); PWILAVLT (SEQ ID NO: 219); PWILAVLTL (SEQ ID NO: 220); PWILAVLTLQ (SEQ ID NO: 221); PWILAVLTLQI (SEQ ID NO: 222); PWILAVLTLQIQ (SEQ ID NO: 223); PWILAVLTLQIQS (SEQ ID NO: 224); PWILAVLTLQIQSL (SEQ ID NO: 225); PWILAVLTLQIQSLI (SEQ ID NO: 226); PWILAVLTLQIQSLIS (SEQ ID NO: 227); PWILAVLTLQIQSLISC (SEQ ID NO: 228); PWILAVLTLQIQSLISCW (SEQ ID NO: 229); PWILAVLTLQIQSLISCWA (SEQ ID NO: 230); WILAVL (SEQ ID NO: 231); WILAVLT (SEQ ID NO: 232); WILAVLTL (SEQ ID NO: 233); WILAVLTLQ (SEQ ID NO: 234); WILAVLTLQI (SEQ ID NO: 235); WILAVLTLQIQ (SEQ ID NO: 236); WILAVLTLQIQS (SEQ ID NO: 237); WILAVLTLQIQSL (SEQ ID NO: 238); WILAVLTLQIQSLI (SEQ ID NO: 239); WILAVLTLQIQS-LIS (SEQ ID NO: 240); WILAVLTLQIQSLISC (SEQ ID NO: 241); WILAVLTLQIQSLISCW (SEQ ID NO: 242); WILAVLTLQIQSLISCWA (SEQ ID NO: 243); ILAVL (SEQ ID NO: 244); ILAVLT (SEQ ID NO: 245); ILAVLTL (SEQ ID NO: 246); ILAVLTLQ (SEQ ID NO: 247); ILAVLTLQI (SEQ ID NO: 248); ILAVLTLQIQ (SEQ ID NO: 249); ILAVLTLQIQS (SEQ ID NO: 250); ILAVLTLQIQSL (SEQ ID NO: 251); ILAVLTLQIQSLI (SEQ ID NO: 252); ILAVLTLQIQSLIS (SEQ ID NO: 253); ILAVLTLQIQSLISC (SEQ ID NO: 254); ILAVLTLQIQSLISCW (SEQ ID NO: 255); ILAVLTLQIQSLISCWA (SEQ ID NO: 256); STQKDPVPY (SEQ ID NO: 257); RSTQKDPVPY (SEQ ID NO: 258); LLENQLLRE (SEQ ID NO: 259); QRSTQKDPVPY (SEQ ID NO: 260); LLREKTHGL (SEQ ID NO: 261); NISP-WILAV (SEQ ID NO: 262); ILAVLTLQI (SEQ ID NO: 263); VLTLQIQSL (SEQ ID NO: 264); LVAEEEAEAK (SEQ ID NO: 265); ALPLMVPAQR (SEQ ID NO: 266); RLTHLSPEEK (SEQ ID NO: 267); KLKNRVAAQT (SEQ ID NO: 268); GSAESAALR (SEQ ID NO: 269); ASG-GLPQARK (SEQ ID NO: 270); LSPEEKALRR (SEQ ID

NO: 271); ASGGLPQAR (SEQ ID NO: 272); VDLEEENQKL (SEQ ID NO: 273); DGTPKVLLL (SEQ ID NO: 274); KLLLENQLL (SEQ ID NO: 275); LTLQIQSLI (SEQ ID NO: 276); DGTPKVLLL (SEQ ID NO: 277); EVRPVAGSAE (SEQ ID NO: 278); AVLTLQIQSL (SEQ ID NO: 279); EVRPVAGSA (SEQ ID NO: 280); QALPLMVPAQR (SEQ ID NO: 281); EAASG-GLPQAR (SEQ ID NO: 282); VAGSAESAALR (SEQ ID NO: 283); NALPQSLPAWR (SEQ ID NO: 284); APAGQALPL (SEQ ID NO: 285); APLQQVQAQL (SEQ ID NO: 286); SPWILAVLTL (SEQ ID NO: 287); DPVPYQPPFL (SEQ ID NO: 288); LLREKTHGL (SEQ ID NO: 289); ALRLRAPL (SEQ ID NO: 290); RKKARMSEL (SEQ ID NO: 291); QARKRQRL (SEQ ID NO: 292); IQSLISCWAF (SEQ ID NO: 293); RLGMDALVAE (SEQ ID NO: 294); AQRGASPEAA (SEQ ID NO: 295); RLRAPLQQVQ (SEQ ID NO: 296); SPEAASGGL (SEQ ID NO: 297); NPADGTPKVL (SEQ ID NO: 298); LPQARKRQRL (SEQ ID NO: 299); APLQQVQAQL (SEQ ID NO: 300); RSTQKDPVPY (SEQ ID NO: 301); GSAE-SAALRL (SEQ ID NO: 302); ISCWAFWTTW (SEQ ID NO: 303); ASPEAASGGL (SEQ ID NO: 304); TPKVLLLSGQPASAA (SEQ ID NO: 305); VLLLSGQPASAAGAP (SEQ ID NO: 306); PLMVPAQR-GASPEAA (SEQ ID NO: 307); RAPLQQVQAQLSPLQ (SEQ ID NO: 308); VVDLEEENQKLLLEN (SEQ ID NO: 309); RQRLGMDALVAEEEA (SEQ ID NO: 310); PKVLLLSGQPASAAG (SEQ ID NO: 311); NQKLL-LENQLLREKT (SEQ ID NO: 312); 15 WTTWTQSCSSNALPQ (SEQ ID NO: 313); CWAFWTTWTQSCSSN (SEQ ID NO: 314); ENQLL-REKTHGLVVE (SEQ ID NO: 315); VRPVAGSAE-SAALRL (SEQ ID NO: 316); LPLMVPAQRGASPEA (SEQ ID NO: 317); ARKRQRLTHLSPEEK (SEQ ID NO: 318); PPFLCQWGRHQPSWK (SEQ ID NO: 319); RAPLQQVQAQLSPLQ (SEQ ID NO: 320); PQSL-PAWRSSQRSTQ (SEQ ID NO: 321); NQELRQRLGM-DALVA (SEQ ID NO: 322); 20 SAALRLRAPLQQVQA (SEQ ID NO: 323); QAQLSPLQNISPWIL (SEQ ID NO: 324); or a combination thereof.

In some embodiments, the XBP-1 peptide or derivative thereof comprises about 60%, 65%, 70%, 75%, 80%, 85%, 90%, 95%, or 99% sequence identity to SEQ ID NOs:72-324 or a combination thereof.

In some embodiments, the XBP1 specific T-cells are generated with peptides that recognize class I MHC molecules. In some embodiments, the XBP1 specific T-cells are generated with peptides that recognize class II MHC molecules. In some embodiments, the XBP1 specific T-cells are generated with peptides that recognize both class I and class II MHC molecules.

CS1

CS1 (also known as CD319, CRACC and SLAMF7) is a member of the Signaling Lymphocyte Activation Molecule (SLAM) Family and is expressed on NK cells, CD8+ T lymphocytes, B lymphocytes, and mature dendritic cells (Boles et al. Molecular cloning of CS1, a novel human natural killer cell receptor belonging to the CD2 subset of the immunoglobulin superfamily. Immunogenetics. 2001; 52:302-307; Bouchon et al. Activation of NK cell-mediated cytotoxicity by a SAP-independent receptor of the CD2 family. J Immunol. 2001; 167:5517-5521). CS1 is a homophilic receptor, and the CS1-CS1 interaction leads to activation of NK cell natural cytotoxicity (Kumaresan et al. CS1, a novel member of the CD2 family, is homophilic and regulates NK cell function. Mol Immunol. 2002; 39:1-8). The human CS1 gene is located on the long arm of chromosome 1 at 1q23-24 between CD48 and CD229 (Boles et al. 2B4 (CD244) and CS1: novel members of the CD2 subset of the immunoglobulin superfamily molecules expressed on natural killer cells and other leukocytes. Immunol Rev. 2001; 181:234-249). Human NK cells express two splice variants of CS1; CS1-S which lack the intracellular domain for activation, and the CS1-L which contain the intracellular domain and is thus capable of activating NK cytotoxicity (Lee et al. Molecular and functional characterization of a CS1 (CRACC) splice variant expressed in human NK cells that does not contain immunoreceptor tyrosine-based switch motifs. Eur J Immunol. 2004; 34:2791-2799). Both the isoforms of CS1 are membrane bound forms and are expressed in NK cells. However, only the CS1-L isoform is expressed in B cells and signaling through CS1 induce B cell proliferation and autocrine secretion (Lee et al. CS1 (CRACC, CD319) induces proliferation and autocrine cytokine expression on human B lymphocytes. J Immunol. 2007; 179:4672-4678).

CS1 is highly expressed in MM cell lines and patient MM cells, but not found on healthy tissue, primary tumor tissues, or hematologic and nonhematologic cancer cell lines (Tai et al. CS1 promotes multiple myeloma cell adhesion, clonogenic growth, and tumorigenicity via c-maf-mediated interactions with bone marrow stromal cells. Blood. 2009; 113: 4309-4318; Hsi et al. CS1, a potential new therapeutic antibody target for the treatment of multiple myeloma. Clin Cancer Res. 2008; 14:2775-2784). Moreover, there was a correlation between soluble CS1 in the patient sera and the disease stage (Tai et al. Anti-CS1 humanized monoclonal antibody HuLuc63 inhibits myeloma cell adhesion and induces antibody-dependent cellular cytotoxicity in the bone marrow milieu. Blood. 2008; 112:1329-1337). This indicates that soluble CS1 may be a useful biomarker for MM disease progression. The high expression of CS1 on MM cells make it an attractive target for treatment of this disease. It has also been reported that CS1 may contribute to tumor promoting activity of MM cells (Tai et al. CS1 promotes multiple myeloma cell adhesion, clonogenic growth, and tumorigenicity via c-maf-mediated interactions with bone marrow stromal cells. Blood. 2009; 113:4309-4318).

CS1 specific T-cells can be generated as described below using one or more antigenic peptides to CS1. In some embodiments, CS1 specific T-cells are generated using a CS1 antigen library comprising a pool of peptides (for example 15mers) containing amino acid overlap (for example 11 amino acids of overlap) between each sequence formed by scanning the protein amino acid SEQ ID NO: 325 (UNIPROT KB—Q9NQ25 (SLAF7_HUMAN)):

```
MAGSPTCLTLIYILWQLTGSAASGPVKELVGSVGGAVTFPLKSKVKQVD

SIVWTFNTTPLVTIQPEGGTIIVTQNRNRERVDFPDGGYSLKLSKLKKN

DSGIYYVGIYSSSLQQPSTQEYVLHVYEHLSKPKVTMGLQSNKNGTCVT

NLTCCMEHGEEDVIYTWKALGQAANESHNGSILPISWRWGESDMTFICV

ARNPVSRNFSSPILARKLCEGAADDPDSSMVLLCLLLVPLLLSLFVLGL

FLWFLKRERQEEYIEEKKRVDICRETPNICPHSGENTEYDTIPHTNRTI

LKEDPANTVYSTVEIPKKMENPHSLLTMPDTPRLFAYENVI
```

In some embodiments, the CS1 protein comprises about 60%, 65%, 70%, 75%, 80%, 85%, 90%, 95%, or 99% sequence identity to SEQ ID NO: 325.

In some embodiments, the CS1 specific T-cells are generated using one or more antigenic peptides to CS1, or a modified or heteroclitic peptide derived from an CS1 peptide, selected from an amino acid sequence comprising: LLLSLFVLGL (SEQ ID NO: 326); SLFVLGLFL (SEQ ID NO: 327); LLVPLLLSL (SEQ ID NO: 328); TLIYILWQL (SEQ ID NO: 329); GYSLKLSKL (SEQ ID NO: 330); DFPDGGYSL (SEQ ID NO: 331); TMPDTPRLF (SEQ ID NO: 332); RWGESDMTF (SEQ ID NO: 333); LFVLGLFLW (SEQ ID NO: 334); KMENPHSLL (SEQ ID NO: 335); VLLCLLLVPLLLSLFV (SEQ ID NO: 336); VLLCLLLVPLLLSLFVL (SEQ ID NO: 337); VLLCLLL-VPLLLSLFVLG (SEQ ID NO: 338); VLLCLLL-VPLLLSLFVLGL (SEQ ID NO: 339); VLLCLLL-VPLLLSLFVLGLF (SEQ ID NO: 340); VLLCLLLVPLLLSLFVLGLFL (SEQ ID NO: 341); VLLCLLLVPLLLSLFVLGLFLW (SEQ ID NO: 342); VLLCLLLVPLLLSLFVLGLFLWF (SEQ ID NO: 343); VLLCLLLVPLLLSLFVLGLFLWFL (SEQ ID NO: 344); VLLCLLLVPLLLSLFVLGLFLWFLK (SEQ ID NO: 345); VLLCLLLVPLLLSLFVLGLFLWFLKR (SEQ ID NO: 346); VLLCLLLVPLLLSLFVLGLFLWFLKRE (SEQ ID NO: 347); LLCLLLVPLLLSLFV (SEQ ID NO: 348); LLCLLLVPLLLSLFVL (SEQ ID NO: 349); LLCLLL-VPLLLSLFVLG (SEQ ID NO: 350); LLCLLL-VPLLLSLFVLGL (SEQ ID NO: 351); LLCLLL-VPLLLSLFVLGLF (SEQ ID NO: 352); LLCLLLVPLLLSLFVLGLFL (SEQ ID NO: 353); LLCLLLVPLLLSLFVLGLFLW (SEQ ID NO: 354); LLCLLLVPLLLSLFVLGLFLWF (SEQ ID NO: 355); LLCLLLVPLLLSLFVLGLFLWFL (SEQ ID NO: 356); LLCLLLVPLLLSLFVLGLFLWFLK (SEQ ID NO: 357); LLCLLLVPLLLSLFVLGLFLWFLKR (SEQ ID NO: 358); LLCLLLVPLLLSLFVLGLFLWFLKRE (SEQ ID NO: 359); LCLLLVPLLLSLFV (SEQ ID NO: 360); LCLLL-VPLLLSLFVL (SEQ ID NO: 361); LCLLL-VPLLLSLFVLG (SEQ ID NO: 362); LCLLL-VPLLLSLFVLGL (SEQ ID NO: 363); LCLLLVPLLLSLFVLGLF (SEQ ID NO: 364); LCLLL-VPLLLSLFVLGLFL (SEQ ID NO: 365); LCLLL-VPLLLSLFVLGLFLW (SEQ ID NO: 366); LCLLL-VPLLLSLFVLGLFLWF (SEQ ID NO: 367); LCLLLVPLLLSLFVLGLFLWFL (SEQ ID NO: 368); LCLLLVPLLLSLFVLGLFLWFLK (SEQ ID NO: 369); LCLLLVPLLLSLFVLGLFLWFLKR (SEQ ID NO: 370); LCLLLVPLLLSLFVLGLFLWFLKRE (SEQ ID NO: 371); CLLLVPLLLSLFV (SEQ ID NO: 372); CLLL-VPLLLSLFVL (SEQ ID NO: 373); CLLLVPLLLSLFVLG (SEQ ID NO: 374); CLLLVPLLLSLFVLGL (SEQ ID NO: 375); CLLLVPLLLSLFVLGLF (SEQ ID NO: 376); CLLL-VPLLLSLFVLGLFL (SEQ ID NO: 377); CLLL-VPLLLSLFVLGLFLW (SEQ ID NO: 378); CLLL-VPLLLSLFVLGLFLWF (SEQ ID NO: 379); CLLLVPLLLSLFVLGLFLWFL (SEQ ID NO: 3 80); CLLLVPLLLS LFVLGLFLWFLK (SEQ ID NO: 3 81); CLLLVPLLLSLFVLGLFLWFLKR (SEQ ID NO: 382); CLLLVPLLLSLFVLGLFLWFLKRE (SEQ ID NO: 383); LLLVPLLLSLFV (SEQ ID NO: 384); LLLVPLLLSLFVL (SEQ ID NO: 385); LLLVPLLLSLFVLG (SEQ ID NO: 386); LLLVPLLLSLFVLGL (SEQ ID NO: 387); LLL-VPLLLSLFVLGLF (SEQ ID NO: 388); LLL-VPLLLSLFVLGLFL (SEQ ID NO: 389); LLL-VPLLLSLFVLGLFLW (SEQ ID NO: 390); LLLVPLLLSLFVLGLFLWF (SEQ ID NO: 391); LLL-VPLLLSLFVLGLFLWFL (SEQ ID NO: 392); LLL-VPLLLSLFVLGLFLWFLK (SEQ ID NO: 393); VPLLLSLFVLGLFLWFLKR (SEQ ID NO: 394); LLLVPLLLSLFVLGLFLWFLKRE (SEQ ID NO: 395); LLVPLLLSLFV (SEQ ID NO: 396); LLVPLLLSLFVL (SEQ ID NO: 397); LLVPLLLSLFVLG (SEQ ID NO: 398); LLVPLLLSLFVLGL (SEQ ID NO: 399); LLVPLLLSLFVLGLF (SEQ ID NO: 400); LLVPLLLSLFVLGLFL (SEQ ID NO: 401); LLVPLLLSLFVLGLFLW (SEQ ID NO: 402); LLVPLLLSLFVLGLFLWF (SEQ ID NO: 403); LLVPLLLSLFVLGLFLWFL (SEQ ID NO: 404); LLVPLLLSLFVLGLFLWFLK (SEQ ID NO: 405); LLVPLLLSLFVLGLFLWFLKR (SEQ ID NO: 406); LLVPLLLSLFVLGLFLWFLKRE (SEQ ID NO: 407); LVPLLLSLFV (SEQ ID NO: 408); LVPLLLSLFVL (SEQ ID NO: 409); LVPLLLSLFVLG (SEQ ID NO: 410); LVPLLLSLFVLGL (SEQ ID NO: 411); LVPLLLSLFVLGLF (SEQ ID NO: 412); LVPLLLSLFVLGLFL (SEQ ID NO: 413); LVPLLLSLFVLGLFLW (SEQ ID NO: 414); LVPLLLSLFVLGLFLWF (SEQ ID NO: 415); LVPLLLSLFVLGLFLWFL (SEQ ID NO: 416); LVPLLLSLFVLGLFLWFLK (SEQ ID NO: 417); LVPLLLSLFVLGLFLWFLKR (SEQ ID NO: 418); LVPLLLSLFVLGLFLWFLKRE (SEQ ID NO: 419); VPLLLSLFV (SEQ ID NO: 420); VPLLLSLFVL (SEQ ID NO: 421); VPLLLSLFVLG (SEQ ID NO: 422); VPLLLSLFVLGL (SEQ ID NO: 423); VPLLLSLFVLGLF (SEQ ID NO: 424); VPLLLSLFVLGLFL (SEQ ID NO: 425); VPLLLSLFVLGLFLW (SEQ ID NO: 426); VPLLLSLFVLGLFLWF (SEQ ID NO: 427); VPLLLSLFVLGLFLWFL (SEQ ID NO: 428); VPLLLSLFVLGLFLWFLK (SEQ ID NO: 429); VPLLLSLFVLGLFLWFLKR (SEQ ID NO: 430); VPLLLSLFVLGLFLWFLKRE (SEQ ID NO: 431); PLLLSLFV (SEQ ID NO: 432); PLLLSLFVL (SEQ ID NO: 433); PLLLSLFVLG (SEQ ID NO: 434); PLLLSLFVLGL (SEQ ID NO: 435); PLLLSLFVLGLF (SEQ ID NO: 436); PLLLSLFVLGLFL (SEQ ID NO: 437); PLLLSLFVLGLFLW (SEQ ID NO: 438); PLLLSLFVLGLFLWF (SEQ ID NO: 439); PLLLSLFVLGLFLWFL (SEQ ID NO: 440); PLLLSLFVLGLFLWFLK (SEQ ID NO: 441); PLLLSLFVLGLFLWFLKR (SEQ ID NO: 442); PLLLSLFVLGLFLWFLKRE (SEQ ID NO: 443); LLLSLFV (SEQ ID NO: 444); LLLSLFVL (SEQ ID NO: 445); LLLSLFVLG (SEQ ID NO: 446); LLLSLFVLGL (SEQ ID NO: 447); LLLSLFVLGLF (SEQ ID NO: 448); LLLSLFVLGLFL (SEQ ID NO: 449); LLLSLFVLGLFLW (SEQ ID NO: 450); LLLSLFVLGLFLWF (SEQ ID NO: 451); LLLSLFVLGLFLWFL (SEQ ID NO: 452); LLLSLFVLGLFLWFLK (SEQ ID NO: 453); LLLSLFVLGLFLWFLKR (SEQ ID NO: 454); LLLSLFVLGLFLWFLKRE (SEQ ID NO: 455); LLSLFV (SEQ ID NO: 456); LLSLFVL (SEQ ID NO: 457); LLSLFVLG (SEQ ID NO: 458); LLSLFVLGL (SEQ ID NO: 459); LLSLFVLGLF (SEQ ID NO: 460); LLSLFVLGLFL (SEQ ID NO: 461); LLSLFVLGLFLW (Seq.. ID. No. 462); LLSLFVLGLFLWF (SEQ ID NO: 463); LLSLFVLGLFLWFL (SEQ ID NO: 464); LLSLFVLGLFLWFLK (SEQ ID NO: 465); LLSLFVLGLFLWFLKR (SEQ ID NO: 466); LLSLFVLGLFLWFLKRE (SEQ ID NO: 467); LSLFV (SEQ ID NO: 468); LSLFVL (SEQ ID NO: 469); LSLFVLG (SEQ ID NO: 470); LSLFVLGL (SEQ ID NO: 471); LSLFVLGLF (SEQ ID NO: 472); LSLFVLGLFL (SEQ ID NO: 473); LSLFVLGLFLW (SEQ ID NO: 474); LSLFVLGLFLWF (SEQ ID NO: 475); LSLFVLGLFLWFL (SEQ ID NO: 476); LSLFVLGLFLWFLK (SEQ ID NO: 477); LSLFVLGLFLWFLKR (SEQ ID NO: 478); LSLFVLGLFLWFLKRE (SEQ ID NO: 479); SLFVL (SEQ ID NO: 480); SLFVLG (SEQ ID NO: 481); SLFVLGL (SEQ ID NO: 482); SLFVLGLF (SEQ ID NO: 483); SLFVLGLFL (SEQ ID NO: 484); SLFVLGLFLW (SEQ ID NO: 485); SLFVLGLFLWF (SEQ ID NO: 486); SLFVLGLFLWFL (SEQ ID NO: 487); SLFVLGLFLWFLK (SEQ ID NO: 488); SLFVLGLFLWFLKR (SEQ ID NO: 489); SLFVLGLFLWFLKRE (SEQ ID NO: 490); LFVLG (SEQ ID NO: 491); LFVLGL (SEQ ID NO: 492); LFVLGLF (SEQ ID NO: 493); LFVLGLFL (SEQ ID NO: 494); LFVLGLFLW (SEQ ID NO: 495); LFVLGLFLWF (SEQ ID NO: 496); LFVLGLFLWFL (SEQ ID NO: 497); LFVLGLFLWFLK (SEQ ID NO: 498); LFVLGLFLW-FLKR (SEQ ID NO: 499); LFVLGLFLWFLKRE (SEQ ID NO: 500); KEDPANTVY (SEQ ID NO: 501); MPDTPRL-FAY (SEQ ID NO: 502); STQEYVLHVY (SEQ ID NO: 503); RVDFPDGGY (SEQ ID NO: 504); LLVPLLLSL (SEQ ID NO: 505); LLLVPLLLSL (SEQ ID NO: 506); LLLSLFVLGL (SEQ ID NO: 507); VLLCLLLVPL (SEQ ID NO: 508); SLKLSKLKK (SEQ ID NO: 509); KVTMGLQSNK (SEQ ID NO: 510); VLHVYEHLSK (SEQ ID NO: 511); HVYEHLSKPK (SEQ ID NO: 512); GSAASGPVK (SEQ ID NO: 513); YSLKLSKLKK (SEQ ID NO: 514); TVYSTVEIPK (SEQ ID NO: 515); CVAR-NPVSR (SEQ ID NO: 516); GYSLKLSKL (SEQ ID NO: 517); EYVLHVYEHL (SEQ ID NO: 518); YYVGIYSSSL (SEQ ID NO: 519); DFPDGGYSL (SEQ ID NO: 520); DVIYTWKAL (SEQ ID NO: 521); QVDSIVWTF (SEQ ID NO: 522); ERVDFPDGGY (SEQ ID NO: 523); STQEYVLHVY (SEQ ID NO: 524); CVARNPVSR (SEQ ID NO: 525); FSSPILARK (SEQ ID NO: 526); TVYSTVEIPK (SEQ ID NO: 527); ESDMTFICVAR (SEQ ID NO: 528); FPDGGYSLKL (SEQ ID NO: 529); MPDT-PRLFA (SEQ ID NO: 530); QPSTQEYVL (SEQ ID NO: 531); DPDSSMVLL (SEQ ID NO: 532); PLKSKVKQV (SEQ ID NO: 533); KPKVTMGL (SEQ ID NO: 534); PLKSKVKQ (SEQ ID NO: 535); EEKKRVDI (SEQ ID NO: 536); KQVDSIVWTF (SEQ ID NO: 537); LLVPLLLSLF (SEQ ID NO: 538); LQQPSTQEY (SEQ ID NO: 539); TQEYVLHVY (SEQ ID NO: 540); MPDTPRL-FAY (SEQ ID NO: 541); VPLLLSLFVL (SEQ ID NO: 542); DPDSSMVLL (SEQ ID NO: 543); FPDGGYSLKL (SEQ ID NO: 544); KSKVKQVDSI (SEQ ID NO: 545); FSSPI-LARKL (SEQ ID NO: 546); DTIPHTNRTI (SEQ ID NO: 547); SSPILARKL (SEQ ID NO: 548); IYILWQLTGSAASGP (SEQ ID NO: 549); GIYYVGIYSSSLQQP (SEQ ID NO: 550); LLL-VPLLLSLFVLGL (SEQ ID NO: 551); LIYILWQLTGSAASG (SEQ ID NO: 552); LWFLKRER-QEEYIEE (SEQ ID NO: 553); YDTIPHTNRTILKED (SEQ ID NO: 554); RTILKEDPANTVYST (SEQ ID NO: 555); SMVLLCLLLVPLLLS (SEQ ID NO: 556); GIYYVGIYSSSLQQP (SEQ ID NO: 557); VGSVG-GAVTFPLKSK (SEQ ID NO: 558); YILWQLTGSAASGPV (SEQ ID NO: 559); SIVWTFNTTPLVTIQ (SEQ ID NO: 560); SLKLSKLK-KNDSGIY (SEQ ID NO: 561); LHVYEHLSKPKVTMG (SEQ ID NO: 562); DMTFICVARNPVSRN (SEQ ID NO: 563); NTEYDTIPHTNRTIL (SEQ ID NO: 564); EDVIYTWKALGQAAN (SEQ ID NO: 565); EYVLHVYEHLSKPKV (SEQ ID NO: 566); LFVLGLFLWFLKRER (SEQ ID NO: 567); DSIVWTFNTTPLVTI (SEQ ID NO: 568); or a combination thereof.

In some embodiments, the CS1 peptide or derivative thereof comprises about 60%, 65%, 70%, 75%, 80%, 85%, 90%, 95%, or 99% sequence identity to SEQ ID NO: 326-568 or a combination thereof.

In some embodiments, the CS1 specific T-cells are generated with peptides that recognize class I MHC molecules. In some embodiments, the CS1 specific T-cells are generated with peptides that recognize class II MHC molecules. In some embodiments, the CS1 specific T-cells are generated with peptides that recognize both class I and class II MHC molecules.

Syndecan-1 (CD138)

Syndecan-1 (CD138) is a cell surface heparan sulfate-bearing proteoglycan that plays an important role in regulating myeloma. CD138 is expressed by all myeloma tumors within the bone marrow and is present in relatively high levels on the surface of most myeloma tumor cells. The extracellular domain of this proteoglycan can be cleaved from the cell surface by sheddases, and high levels of shed CD138 correlate with poor prognosis in myeloma patients. Shed CD138 remains biologically active and can participate in regulating many cellular behaviors, including myeloma growth. Much of CD138 function is mediated by its heparan sulfate chains that bind to, and regulate the activity of, many of the factors known to influence myeloma growth (e.g. IL-6,3 IL-7, IL-8, VEGF, HGF, fibroblast growth factor 2, and fibroblast growth factor family ligands). Signaling events propagated by these growth factors, particularly those events occurring between tumor cell and bone marrow components, are critical to the growth and development of myeloma. In addition, CD138 becomes lodged within fibrotic regions of bone marrow following treatment of patients. This residual CD138 may retain growth factors that aid in forming niches that facilitate tumor relapse. Thus, both on the cell surface and within the extracellular matrix, CD138 is strategically placed to act as an important moderator of cross-talk between tumor and host cells, thereby promoting the growth and maintenance of the tumor as an "organ" and contributing to development of refractory disease.

CD138 specific T-cells can be generated as described below using one or more antigenic peptides to CD138. In some embodiments, CD138 specific T-cells are generated using a CD138 antigen library comprising a pool of peptides (for example 15mers) containing amino acid overlap (for example 11 amino acids of overlap) between each sequence formed by scanning the protein amino acid sequence SEQ ID NO: 569 (UNIPROT KB—P18827 (SDC1_HUMAN)):

```
MRRAALWLWLCALALSLQPALPQIVATNLPPEDQDGSGDDSDNESGSGA

GALQDITLSQQTPSTWKDTQLLTAIPTSPEPTGLEATAASTSTLPAGEG

PKEGEAVVLPEVEPGLTAREQEATPRPRETTQLPTTHQASTTTATTAQE

PATSHPHRDMQPGHHETSTPAGPSQADLHTPHTEDGGPSATERAAEDGA

SSQLPAAEGSGEQDFTFETSGENTAVVAVEPDRRNQSPVDQGATGASQG

LLDRKEVLGGVIAGGLVGLIFAVCLVGFMLYRMKKKDEGSYSLEEPKQA

NGGAYQKPTKQEEFYA
```

In some embodiments, the CD138 protein comprises e about 60%, 65%, 70%, 75%, 80%, 85%, 90%, 95%, or 99% sequence identity to SEQ ID NO: 569.

In some embodiments, the CD138 specific T-cells are generated using one or more antigenic peptides to CD138, or a modified or heteroclitic peptide derived from an CD138 peptide, selected from an amino acid sequence comprising: VIAGGLVGL (SEQ ID NO: 570); GLVGLIFAV (SEQ ID NO: 571); ALWLWLCAL (SEQ ID NO: 572); WLWL-CALAL (SEQ ID NO: 573); IFAVCLVGF (SEQ ID NO:

574); VLPEVEPGL (SEQ ID NO: 575); LPQIVATNL (SEQ ID NO: 576); LALSLQPAL (SEQ ID NO: 577); GLL-DRKEVL (SEQ ID NO: 578); VGLIFAVCL (SEQ ID NO: 579); SLQPALPQI (SEQ ID NO: 580); EVLGGVIAG-GLVGLIFAV (SEQ ID NO: 581); EVLGGVIAGGLVGLI-FAVC (SEQ ID NO: 582); EVLGGVIAGGLVGLIFAVCL (SEQ ID NO: 583); EVLGGVIAGGLVGLIFAVCLV (SEQ ID NO: 584); EVLGGVIAGGLVGLIFAVCLVG (SEQ ID NO: 585); EVLGGVIAGGLVGLIFAVCLVGF (SEQ ID NO: 586); EVLGGVIAGGLVGLIFAVCLVGFM (SEQ ID NO: 587); EVLGGVIAGGLVGLIFAVCLVGFML (SEQ ID NO: 588); EVLGGVIAGGLVGLIFAVCLVGFMLY (SEQ ID NO: 589); EVLGGVIAGGLVGLIFAVCLVGFMLYR (SEQ ID NO: 590); EVLGGVIAGGLVGLIFAVCLVGFM-LYRM (SEQ ID NO: 591); VLGGVIAGGLVGLIFAV (SEQ ID NO: 592); VLGGVIAGGLVGLIFAVC (SEQ ID NO: 593); VLGGVIAGGLVGLIFAVCL (SEQ ID NO: 594); VLGGVIAGGLVGLIFAVCLV (SEQ ID NO: 595); VLGGVIAGGLVGLIFAVCLVG (SEQ ID NO: 596); VLGGVIAGGLVGLIFAVCLVGF (SEQ ID NO: 597); VLGGVIAGGLVGLIFAVCLVGFM (SEQ ID NO: 598); VLGGVIAGGLVGLIFAVCLVGFML (SEQ ID NO: 599); VLGGVIAGGLVGLIFAVCLVGFMLY (SEQ ID NO: 600); VLGGVIAGGLVGLIFAVCLVGFMLYR (SEQ ID NO: 601); VLGGVIAGGLVGLIFAVCLVGFMLYRM (SEQ ID NO: 602); LGGVIAGGLVGLIFAV (SEQ ID NO: 603); LGGVIAGGLVGLIFAVC (SEQ ID NO: 604); LGGVIAG-GLVGLIFAVCL (SEQ ID NO: 605); LGGVIAGGLVGLI-FAVCLV (SEQ ID NO: 606); LGGVIAGGLVGLI-FAVCLVG (SEQ ID NO: 607); LGGVIAGGLVGLIFAVCLVGF (SEQ ID NO: 608); LGGVIAGGLVGLIFAVCLVGFM (SEQ ID NO: 609); LGGVIAGGLVGLIFAVCLVGFML (SEQ ID NO: 610); LGGVIAGGLVGLIFAVCLVGFMLY (SEQ ID NO: 611); LGGVIAGGLVGLIFAVCLVGFMLYR (SEQ ID NO: 612); LGGVIAGGLVGLIFAVCLVGFMLYRM (SEQ ID NO: 613); GGVIAGGLVGLIFAV (SEQ ID NO: 614); GGVI-AGGLVGLIFAVC (SEQ ID NO: 615); GGVIAGGLVGLI-FAVCL (SEQ ID NO: 616); GGVIAGGLVGLIFAVCLV (SEQ ID NO: 617); GGVIAGGLVGLIFAVCLVG (SEQ ID NO: 618); GGVIAGGLVGLIFAVCLVGF (SEQ ID NO: 619); GGVIAGGLVGLIFAVCLVGFM (SEQ ID NO: 620); GGVIAGGLVGLIFAVCLVGFML (SEQ ID NO: 621); GGVIAGGLVGLIFAVCLVGFMLY (SEQ ID NO: 622); GGVIAGGLVGLIFAVCLVGFMLYR (SEQ ID NO: 623); GGVIAGGLVGLIFAVCLVGFMLYRM (SEQ ID NO: 624); GVIAGGLVGLIFAV (SEQ ID NO: 625); GVIAG-GLVGLIFAVC (SEQ ID NO: 626); GVIAGGLVGLI-FAVCL (SEQ ID NO: 627); GVIAGGLVGLIFAVCLV (SEQ ID NO: 628); GVIAGGLVGLIFAVCLVG (SEQ ID NO: 629); GVIAGGLVGLIFAVCLVGF (SEQ ID NO: 630); GVIAGGLVGLIFAVCLVGFM (SEQ ID NO: 631); GVI-AGGLVGLIFAVCLVGFML (SEQ ID NO: 632); GVIAG-GLVGLIFAVCLVGFMLY (SEQ ID NO: 633); GVIAG-GLVGLIFAVCLVGFMLYR (SEQ ID NO: 634); GVIAGGLVGLIFAVCLVGFMLYRM (SEQ ID NO: 635); VIAGGLVGLIFAV (SEQ ID NO: 636); VIAGGLVGLI-FAVC (SEQ ID NO: 637); VIAGGLVGLIFAVCL (SEQ ID NO: 638); VIAGGLVGLIFAVCLV (SEQ ID NO: 639); VIAGGLVGLIFAVCLVG (SEQ ID NO: 640); VIAG-GLVGLIFAVCLVGF (SEQ ID NO: 641); VIAGGLVGLI-FAVCLVGFM (SEQ ID NO: 642); VIAGGLVGLI-FAVCLVGFML (SEQ ID NO: 643); VIAGGLVGLIFAVCLVGFMLY (SEQ ID NO: 644); VIAGGLVGLIFAVCLVGFMLYR (SEQ ID NO: 645); VIAGGLVGLIFAVCLVGFMLYRM (SEQ ID NO: 646); IAGGLVGLIFAV (SEQ ID NO: 647); IAGGLVGLIFAVC (SEQ ID NO: 648); IAGGLVGLIFAVCL (SEQ ID NO: 649); IAGGLVGLIFAVCLV (SEQ ID NO: 650); IAG-GLVGLIFAVCLVG (SEQ ID NO: 651); IAGGLVGLI-FAVCLVGF (SEQ ID NO: 652); IAGGLVGLI-FAVCLVGFM (SEQ ID NO: 653); IAGGLVGLIFAVCLVGFML (SEQ ID NO: 654); IAG-GLVGLIFAVCLVGFMLY (SEQ ID NO: 655); IAG-GLVGLIFAVCLVGFMLYR (SEQ ID NO: 656); IAG-GLVGLIFAVCLVGFMLYRM (SEQ ID NO: 657); AGGLVGLIFAV (SEQ ID NO: 658); AGGLVGLIFAVC (SEQ ID NO: 659); AGGLVGLIFAVCL (SEQ ID NO: 660); AGGLVGLIFAVCLV (SEQ ID NO: 661); AGGLVGLI-FAVCLVG (SEQ ID NO: 662); AGGLVGLIFAVCLVGF (SEQ ID NO: 663); AGGLVGLIFAVCLVGFM (SEQ ID NO: 664); AGGLVGLIFAVCLVGFML (SEQ ID NO: 665); AGGLVGLIFAVCLVGFMLY (SEQ ID NO: 666); AGGLVGLIFAVCLVGFMLYR (SEQ ID NO: 667); AGGLVGLIFAVCLVGFMLYRM (SEQ ID NO: 668); GGLVGLIFAV (SEQ ID NO: 669); GGLVGLIFAVC (SEQ ID NO: 670); GGLVGLIFAVCL (SEQ ID NO: 671); GGLVGLIFAVCLV (SEQ ID NO: 672); GGLVGLI-FAVCLVG (SEQ ID NO: 673); GGLVGLIFAVCLVGF (SEQ ID NO: 674); GGLVGLIFAVCLVGFM (SEQ ID NO: 675); GGLVGLIFAVCLVGFML (SEQ ID NO: 676); GGLVGLIFAVCLVGFMLY (SEQ ID NO: 677); GGLVGLIFAVCLVGFMLYR (SEQ ID NO: 678); GGLVGLIFAVCLVGFMLYRM (SEQ ID NO: 679); GLVGLIFAV (SEQ ID NO: 680); GLVGLIFAVC (SEQ ID NO: 681); GLVGLIFAVCL (SEQ ID NO: 682); GLVGLI-FAVCLV (SEQ ID NO: 683); GLVGLIFAVCLVG (SEQ ID NO: 684); GLVGLIFAVCLVGF (SEQ ID NO: 685); GLVGLIFAVCLVGFM (SEQ ID NO: 686); GLVGLI-FAVCLVGFML (SEQ ID NO: 687); GLVGLI-FAVCLVGFMLY (SEQ ID NO: 688); GLVGLI-FAVCLVGFMLYR (SEQ ID NO: 689); GLVGLIFAVCLVGFMLYRM (SEQ ID NO: 690); LVGLI-FAV (SEQ ID NO: 691); LVGLIFAVC (SEQ ID NO: 692); LVGLIFAVCL (SEQ ID NO: 693); LVGLIFAVCLV (SEQ ID NO: 694); LVGLIFAVCLVG (SEQ ID NO: 695); LVGLIFAVCLVGF (SEQ ID NO: 696); LVGLI-FAVCLVGFM (SEQ ID NO: 697); LVGLIFAVCLVGFML (SEQ ID NO: 698); LVGLIFAVCLVGFMLY (SEQ ID NO: 699); LVGLIFAVCLVGFMLYR (SEQ ID NO: 700); LVGLIFAVCLVGFMLYRM (SEQ ID NO: 701); VGLIFAV (SEQ ID NO: 702); VGLIFAVC (SEQ ID NO: 703); VGLI-FAVCL (SEQ ID NO: 704); VGLIFAVCLV (SEQ ID NO: 705); VGLIFAVCLVG (SEQ ID NO: 706); VGLI-FAVCLVGF (SEQ ID NO: 707); VGLIFAVCLVGFM (SEQ ID NO: 708); VGLIFAVCLVGFML (SEQ ID NO: 709); VGLIFAVCLVGFMLY (SEQ ID NO: 710); VGLI-FAVCLVGFMLYR (SEQ ID NO: 711); VGLI-FAVCLVGFMLYRM (SEQ ID NO: 712); GLIFAV (SEQ ID NO: 713); GLIFAVC (SEQ ID NO: 714); GLIFAVCL (SEQ ID NO: 715); GLIFAVCLV (SEQ ID NO: 716); GLI-FAVCLVG (SEQ ID NO: 717); GLIFAVCLVGF (SEQ ID NO: 718); GLIFAVCLVGFM (SEQ ID NO: 719); GLI-FAVCLVGFML (SEQ ID NO: 720); GLIFAVCLVGFMLY (SEQ ID NO: 721); GLIFAVCLVGFMLYR (SEQ ID NO: 722); GLIFAVCLVGFMLYRM (SEQ ID NO: 723); LIFAV (SEQ ID NO: 724); LIFAVC (SEQ ID NO: 725); LIFAVCL (SEQ ID NO: 726); LIFAVCLV (SEQ ID NO: 727); LIFAVCLVG (SEQ ID NO: 728); LIFAVCLVGF (SEQ ID NO: 729); LIFAVCLVGFM (SEQ ID NO: 730); LIFAVCLVGFML (SEQ ID NO: 731); LIFAVCLVGFMLY (SEQ ID NO: 732); LIFAVCLVGFMLYR (SEQ ID NO: 733); LIFAVCLVGFMLYRM (SEQ ID NO: 734); IFAV (SEQ ID NO: 735); IFAVC (SEQ ID NO: 736); IFAVCL (SEQ ID NO: 737); IFAVCLV (SEQ ID NO: 738); IFAVCLVG (SEQ ID NO: 739); IFAVCLVGF (SEQ ID NO: 740); IFAVCLVGFM (SEQ ID NO: 741); IFAVCLVGFML (SEQ ID NO: 742); IFAVCLVGFMLY (SEQ ID NO: 743); IFAVCLVGFMLYR (SEQ ID NO: 744); IFAVCLVGFM-LYRM (SEQ ID NO: 745); VCLVGFMLY (SEQ ID NO: 746); AVCLVGFMLY (SEQ ID NO: 747); YRMKKKDE-GSY (SEQ ID NO: 748); YQKPTKQEEFY (SEQ ID NO: 749); VIAGGLVGL (SEQ ID NO: 750); GLVGLIFAV (SEQ ID NO: 751); ALWLWLCAL (SEQ ID NO: 752); SLQPALPQI (SEQ ID NO: 753); GVIAGGLVG (SEQ ID NO: 754); TLPAGEGPK (SEQ ID NO: 755); QANG-GAYQK (SEQ ID NO: 756); GLEATAASTS (SEQ ID NO: 757); STLPAGEGPK (SEQ ID NO: 758); ASQGLLDRK (SEQ ID NO: 759); GSYSLEEPK (SEQ ID NO: 760); AVVAVEPDRR (SEQ ID NO: 761); VLPEVEPGL (SEQ ID NO: 762); IFAVCLVGF (SEQ ID NO: 763); NFSGSGA-GAL (SEQ ID NO: 764); VVLPEVEPGL (SEQ ID NO: 765); EVEPGLTAR (SEQ ID NO: 766); EVLGGVIAG (SEQ ID NO: 767); GVIAGGLVGL (SEQ ID NO: 768); EVLGGVIAGG (SEQ ID NO: 769); EVEPGLTAR (SEQ ID NO: 770); LTAREQEATPR (SEQ ID NO: 771); GASQGLLDR (SEQ ID NO: 772); EVLGGVIAG (SEQ ID NO: 773); TPRPRETTQL (SEQ ID NO: 774); TPAGP-SQADL (SEQ ID NO: 775); TPSTWKDTQL (SEQ ID NO: 776); GPKEGEAVVL (SEQ ID NO: 777); LLDRKEVL (SEQ ID NO: 778); GLLDRKEVL (SEQ ID NO: 779); RPRETTQL (SEQ ID NO: 780); TWKDTQLL (SEQ ID NO: 781); AVCLVGFMLY (SEQ ID NO: 782); YQKPTKQEEF (SEQ ID NO: 783); ALQDITLSQ (SEQ ID NO: 784); GVIAGGLVGL (SEQ ID NO: 785); GPKEG-EAVVL (SEQ ID NO: 786); LPQIVATNL (SEQ ID NO: 787); KPTKQEEFY (SEQ ID NO: 788); TPSTWKDTQL (SEQ ID NO: 789); GSGEQDFTF (SEQ ID NO: 790); LSQQTPSTW (SEQ ID NO: 791); ATSHPHRDM (SEQ ID NO: 792); PATSHPHRDM (SEQ ID NO: 793); AALWLWLCALALSLQ (SEQ ID NO: 794); KEVLGGVI-AGGLVGL (SEQ ID NO: 795); QPALPQIVATNLPPE (SEQ ID NO: 796); GGLVGLIFAVCLVGF (SEQ ID NO: 797); VVAVEPDRRNQSPVD (SEQ ID NO: 798); LCAL-ALSLQPALPQI (SEQ ID NO: 799); EAVVLPEVEPGL-TAR (SEQ ID NO: 800); ASQGLLDRKEVLGGV (SEQ ID NO: 801); DFTFETSGENTAVVA (SEQ ID NO: 802); LWLWLCALALSLQPA (SEQ ID NO: 803); SDNFSGSGAGALQDI (SEQ ID NO: 804); LCAL-ALSLQPALPQI (SEQ ID NO: 805); FMLYRMKKKDEG-SYS (SEQ ID NO: 806); HRDMQPGHHETSTPA (SEQ ID NO: 807); VVAVEPDRRNQSPVD (SEQ ID NO: 808); GFMLYRMKKKDEGSY (SEQ ID NO: 809); RAALWLWLCALALSL (SEQ ID NO: 810); ALALSLQPALPQIVA (SEQ ID NO: 811); GGLVGLI-FAVCLVGF (SEQ ID NO: 812); or AVCLVGFM-LYRMKKK (SEQ ID NO: 813); or a combination thereof.

In some embodiments, the CD138 peptide or derivative thereof comprises about 60%, 65%, 70%, 75%, 80%, 85%, 90%, 95%, or 99% sequence identity to SEQ ID NO: 570-813 or a combination thereof.

In some embodiments, the CD138 specific T-cells are generated with peptides that recognize class I MHC molecules. In some embodiments, the CD138 specific T-cells are generated with peptides that recognize class II MHC molecules. In some embodiments, the CD138 specific T-cells are generated with peptides that recognize both class I and class II MHC molecules.

Tumor-Associated Antigens

In addition to the MMAAs described above, the T-cell composition can further include T-cells activated to a TAA selected from preferentially expressed antigen of melanoma (PRAME), Survivin, and Wilms' Tumor 1 protein (WT1), or a combination thereof.

PRAME

Although Preferentially Expressed Antigen of Melanoma (PRAME) was first identified as an antigen associated with melanoma, it has been associated with many other cancers including sarcoma, lung and head and neck cancer, and renal cancer including Wilms tumor. PRAME expression is minimal in healthy tissues such as the gonads, adrenal glands, bone marrow, and brain with highest expression in the testes (Epping et al., Cancer Research (2006) 66 (22) 10639-10642). To date, the function of this protein in healthy tissues is unknown, although studies have suggested PRAME is involved in proliferation and survival in leukemia cells (Yin Leukemia Research (2011) 35 (9) 1159-1160).

In neuroblastoma PRAME expression was detected in 93% of all patients and in 100% of patients with advanced disease. There was a highly significant association of PRAME expression with both higher tumor stage and the age of patients at diagnosis, both high-risk features (Oberthuer et al., Clinical Cancer Research (2004) 10 (13) 4307-4313). Approximately 70% of osteosarcoma patient specimens expressed PRAME and high expression was associated with poor prognosis and pulmonary metastatic disease (Tan et al., Biochemical and biophysical research communications (2012) 419 (4) 801-808; Toledo et al., Journal of ortho sci (2011) 16 (4) 458-466; Segal et al., Cancer Immunity (2005) 5:4). Soft tissue sarcomas such as synovial cell sarcoma, myxoid/round cell liposarcoma, and malignant fibrous histiocytoma also have been found to express PRAME Segal et al., Cancer Immunity (2005) 5:4).

PRAME specific T-cells can be generated as described below using one or more antigenic peptides to PRAME. In some embodiments, the PRAME specific T-cells are generated using one or more antigenic peptides to PRAME, or a modified or heteroclitic peptide derived from a PRAME peptide. In some embodiments, PRAME specific T-cells are generated using a PRAME antigen library comprising a pool of peptides (for example 15mers) containing amino acid overlap (for example 11 amino acids of overlap) between each Sequence formed by scanning the protein amino acid sequence SEQ ID NO: 814 (UNIPROT KB—P78395) for human melanoma antigen preferentially expressed in tumors (PRAME):

```
MERRRLWGSIQSRYISMSVWTSPRRLVELAGQSLLKDEALAIAALELLP

RELFPPLFMAAFDGRHSQTLKAMVQAWPFTCLPLGVLMKGQHLHLETFK

AVLDGLDVLLAQEVRPRRWKLQVLDLRKNSHQDFWTVWSGNRASLYSFP

EPEAAQPMTKKRKVDGLSTEAEQPFIPVEVLVDLFLKEGACDELFSYLI

EKVKRKKNVLRLCCKKLKIFAMPMQDIKMILKMVQLDSIEDLEVTCTWK

LPTLAKFSPYLGQMINLRRLLLSHIHASSYISPEKEEQYIAQFTSQFLS

LQCLQALYVDSLFFLRGRLDQLLRHVMNPLETLSITNCRLSEGDVMHLS

QSPSVSQLSVLSLSGVMLTDVSPEPLQALLERASATLQDLVFDECGITD

DQLLALLPSLSHCSQLTTLSFYGNSISISALQSLLQHLIGLSNLTHVLY

PVPLESYEDIHGTLHLERLAYLHARLRELLCELGRPSMVWLSANPCPHC

GDRTFYDPEPILCPCFMPN
```

In some embodiments, the PRAME protein comprises about 60%, 65%, 70%, 75%, 80%, 85%, 90%, 95%, or 99% sequence identity to SEQ ID NO: 814.

Overlapping antigenic libraries are commercially available, for example, from JPT (Product code: PM-OIP4 PepMix™ Human (Prame/OIP4)). In some embodiments, the PRAME specific T-cells are generated using a commercially available overlapping antigenic library made up of PRAME peptides.

In some embodiments, the PRAME specific T-cells are generated using one or more antigenic peptides to PRAME, or a modified or heteroclitic peptide derived from a PRAME peptide, selected from an amino acid sequence comprising: GTLHLERLAY (SEQ ID NO: 815); PTLAKFSPY (SEQ ID NO: 816); CSQLTTLSFY (SEQ ID NO: 817); LSNLTHVLY (SEQ ID NO: 818); ALLERASATL (SEQ ID NO: 819); QLLALLPSL (SEQ ID NO: 820); SLLQHLIGL (SEQ ID NO: 821); RLRELLCEL (SEQ ID NO: 822); CLPLGVLMK (SEQ ID NO: 823); ELAGQSLLK (SEQ ID NO: 824); KLQVLDLRK (SEQ ID NO: 825); RLSEGDVMH (SEQ ID NO: 826); KVKRKKNVLR (SEQ ID NO: 827); PMQDIKMILK (SEQ ID NO: 828); CTWKLPTLAK (SEQ ID NO: 829); AIAALELLPR (SEQ ID NO: 830); SYEDIHGTL (SEQ ID NO: 831); PYLGQMINL (SEQ ID NO: 832); LYVDSLFFL (SEQ ID NO: 833); QYIAQFTSQF (SEQ ID NO: 834); ETFKAVLDGL (SEQ ID NO: 835); DVSPEPLQAL (SEQ ID NO: 836); EVRPRRWKL (SEQ ID NO: 837); ETFKAVLDG (SEQ ID NO: 838); EAAQPMTKK (SEQ ID NO: 839); EVLVDLFLK (SEQ ID NO: 840); ELFSYLIEK (SEQ ID NO: 841); ETLSITNCR (SEQ ID NO: 842); LPRELFPPL (SEQ ID NO: 843); QPFIPVEVL (SEQ ID NO: 844); RPRRWKLQVL (SEQ ID NO: 845); SPSVSQLSVL (SEQ ID NO: 846); TKKRKVDGL (SEQ ID NO: 847); FLRGRLDQL (SEQ ID NO: 848); KVKRKKNVL (SEQ ID NO: 849); HARLRELL (SEQ ID NO: 850); VLYPVPLESY (SEQ ID NO: 851); RLWGSIQSRY (SEQ ID NO: 852); GLSNLTHVLY (SEQ ID NO: 853); RLCCKKLKIF (SEQ ID NO: 854); IPVEVLVDL (SEQ ID NO: 855); LPRELFPPL (SEQ ID NO: 856); SPEPLQALL (SEQ ID NO: 857); RPRRWKLQVL (SEQ ID NO: 858); KAMVQAWPF (SEQ ID NO: 859); MSVWTSPRRL (SEQ ID NO: 860); AALELLPREL (SEQ ID NO: 861); KAVLDGLDVL (SEQ ID NO: 862); PRRLVELAGQSLLKD (SEQ ID NO: 863); LDGLDVLLAQEVRPR (SEQ ID NO: 864); FLSLQCLQALYVDSL (SEQ ID NO: 865); RHVMNPLETLSITNC (SEQ ID NO: 866); ECGITDDQLLALLPS (SEQ ID NO: 867); LKMVQLDSIEDLEVT (SEQ ID NO: 868); LQALYVDSLFFLRGR (SEQ ID NO: 869); RRLVELAGQSLLKDE (SEQ ID NO: 870); RRLWGSIQSRYISMS (SEQ ID NO: 871); IEDLEVTCTWKLPTL (SEQ ID NO: 872); GDVMHLSQSPSVSQL (SEQ ID NO: 873); MVQLDSIEDLEVTCT (SEQ ID NO: 874); TWKLPTLAKFSPYLG (SEQ ID NO: 875); QSRYISMSVWTSPRR (SEQ ID NO: 876); AQPMTKKRKVDGLST (SEQ ID NO: 877); TSQFLSLQCLQALYV (SEQ ID NO: 878); HLHLETFKAVLDGLD (SEQ ID NO: 879); PVPLESYEDIHGTLH (SEQ ID NO: 880); YISMSVWTSPRRLVE (SEQ ID NO: 881); or PLFMAAFDGRHSQTL (SEQ ID NO: 882); or a combination thereof.

In some embodiments, the PRAME peptide or derivative thereof comprises about 60%, 65%, 70%, 75%, 80%, 85%, 90%, 95%, or 99% sequence identity to SEQ ID NO: 815-882 or a combination thereof.

In some embodiments, the PRAME specific T-cells are generated with peptides that recognize class I MHC molecules. In some embodiments, the PRAME specific T-cells are generated with peptides that recognize class II MHC molecules. In some embodiments, the PRAME specific T-cells are generated with peptides that recognize both class I and class II MHC molecules.

Survivin

Survivin is a protein that regulates apoptosis and proliferation of hematopoietic stem cells. While expressed highly during normal fetal development, in most mature tissues, expression is absent, with the exception of possible low-level expression in healthy hematopoietic stem cells (Shinozawa et al., Leukemia Research (2000) 24 (11) 965-970).

Survivin is highly expressed in most cancers including esophageal, non-small-cell lung cancer, central nervous system tumors, breast cancer, colorectal cancer, melanoma, gastric cancer, sarcomas, osteosarcoma, pancreatic cancer, oral cancer, cervical cancer, hepatocellular carcinoma and hematologic malignancies (Fukuda et al., Molecular Cancer Therapeutics (2006) 5 (5) 1087-1098; Tamm et al., Cancer research (1998) 58 (23) 5315-5320; Coughlin et al. Journal of Clin One (2006) 24 (36) 5725-5734). Survivin expression has been detected uniformly in neuroblastoma tumor cells (Coughlin et al. Journal of Clin One (2006) 24 (36) 5725-5734).

Survivin has been associated with chemotherapy resistant disease, increased tumor recurrence, and poor patient survival. Targeted therapy against the surviving antigen is an attractive cancer treatment strategy (Fukuda et al., Molecular Cancer Therapeutics (2006) 5 (5) 1087-1098).

Survivin specific T-cells can be generated as described below using one or more antigenic peptides to Survivin. In some embodiments, the Survivin specific T-cells are generated using one or more antigenic peptides to Survivin, or a modified or heteroclitic peptide derived from a Survivin peptide. In some embodiments, Survivin specific T-cells are generated using a Survivin antigen library comprising a pool of peptides (for example 15mers) containing amino acid overlap (for example 11 amino acids of overlap) between each Sequence formed by scanning the protein amino acid sequence SEQ ID NO: 883 (UNIPROT KB—015392) for human baculoviral inhibitor of apoptosis repeat-containing 5 (Survivin):

```
MGAPTLPPAWQPFLKDHRISTFKNWPFLEGCACTPERMAEAGFIHCPTE

NEPDLQCFFCFKELEGWEPDDDPIEEHKKHSSGCAFLSVKKQFEELTLG

EFLKLDRERAKNKIAKETNNKKKEFEETAKKVRRAIEQLAAMD
```

In some embodiments, the Survivin protein comprises about 60%, 65%, 70%, 75%, 80%, 85%, 90%, 95%, or 99% sequence identity to SEQ ID NO: 883.

Overlapping antigenic libraries are commercially available, for example, from JPT, for example, from JPT (Product Code: PM-Survivin (PepMix™ Human (Survivin)). In some embodiments, the Survivin specific T-cells are generated using a commercially available overlapping antigenic library made up of Survivin peptides.

In some embodiments, the Survivin specific T-cells are generated using one or more antigenic peptides to Survivin, or a modified or heteroclitic peptide derived from a Survivin peptide, selected from an amino acid sequence comprising: PTENEPDLQC (SEQ ID NO: 884); PTENEPDLQCF (SEQ ID NO: 885); PTENEPDLQ (SEQ ID NO: 886); LTLGE-FLKL (SEQ ID NO: 887); TLPPAWQPFL (SEQ ID NO: 888); LTLGEFLKL (SEQ ID NO: 889); KVRRAIEQL (SEQ ID NO: 890); RAIEQLAAM (SEQ ID NO: 891);

KLDRERAKNK (SEQ ID NO: 892); FLKDHRISTF (SEQ ID NO: 893); FLKLDRERAK (SEQ ID NO: 894); ELTLGEFLK (SEQ ID NO: 895); SSGCAFLSVK (SEQ ID NO: 896); SGCAFLSVKK (SEQ ID NO: 897); TLGE-FLKLDR (SEQ ID NO: 898); DLQCFFCFK (SEQ ID NO: 899); AFLSVKKQF (SEQ ID NO: 900); QFEELTLGEF (SEQ ID NO: 901); LTLGEFLKL (SEQ ID NO: 902); TLPPAWQPF (SEQ ID NO: 903); ETNNKKKEF (SEQ ID NO: 904); ENEPDLQCF (SEQ ID NO: 905); ETAKKVRRA (SEQ ID NO: 906); KVRRAIEQL (SEQ ID NO: 907); LTLGEFLKLDR (SEQ ID NO: 908); PAWQP-FLKDHR (SEQ ID NO: 909); SSGCAFLSVKK (SEQ ID NO: 910); EFEETAKKVRR (SEQ ID NO: 911); LPPAWQPFL (SEQ ID NO: 912); CPTENEPDL (SEQ ID NO: 913); EPDLQCFFCF (SEQ ID NO: 914); WPFLEGCACT (SEQ ID NO: 915); RAKNKIAKE (SEQ ID NO: 916); AKKVRRAI (SEQ ID NO: 917); FLSVKKQF (SEQ ID NO: 918); RAKNKIAK (SEQ ID NO: 919); TLPPAWQPF (SEQ ID NO: 920); FLKDHRISTF (SEQ ID NO: 921); KQFEELTLGE (SEQ ID NO: 922); KQFEELTLG (SEQ ID NO: 923); LPPAWQPFL (SEQ ID NO: 924); CPTENEPDL (SEQ ID NO: 925); TPER-MAEAGF (SEQ ID NO: 926); EPDLQCFFCF (SEQ ID NO: 927); TAKKVRRAI (SEQ ID NO: 928); RAIEQ-LAAM (SEQ ID NO: 929); KVRRAIEQL (SEQ ID NO: 930); ETAKKVRRAI (SEQ ID NO: 931); FFCFKELEGWEPDDD (SEQ ID NO: 932); FKNWP-FLEGCACTPE (SEQ ID NO: 933); LGEFLKL-DRERAKNK (SEQ ID NO: 934); NWPFLEGCACTPERM (SEQ ID NO: 935); GEFLKLDRERAKNKI (SEQ ID NO: 936); WQPFLKDHRISTFKN (SEQ ID NO: 937); PTE-NEPDLQCFFCFK (SEQ ID NO: 938); APTLPPAWQP-FLKDH (SEQ ID NO: 939); AKKVRRAIEQLAAMD (SEQ ID NO: 940); APTLPPAWQPFLKDH (SEQ ID NO: 941); DHRISTFKNWPFLEG (SEQ ID NO: 942); LEGCACTPERMAEAG (SEQ ID NO: 943); LGEFLKL-DRERAKNK (SEQ ID NO: 944); GCAFLSVKKQFEELT (SEQ ID NO: 945); FFCFKELEGWEPDDD (SEQ ID NO: 946); DDPIEEHKKHSSGCA (SEQ ID NO: 947); ELTLGEFLKLDRERA (SEQ ID NO: 948); ISTFKNWP-FLEGCAC (SEQ ID NO: 949); LQCFFCFKELEGWEP (SEQ ID NO: 950); or EPDLQCFFCFKELEG (SEQ ID NO: 951); or a combination thereof.

In some embodiments, the Survivin peptide or derivative thereof comprises about 60%, 65%, 70%, 75%, 80%, 85%, 90%, 95%, or 99% sequence identity to SEQ ID NO: 884-951 or a combination thereof.

In some embodiments, the Survivin specific T-cells are generated with peptides that recognize class I MHC molecules. In some embodiments, the Survivin specific T-cells are generated with peptides that recognize class II MHC molecules. In some embodiments, the Survivin specific T-cells are generated with peptides that recognize both class I and class II MHC molecules.

WT1

Wilms tumor gene (WT1) is a gene found in post-natal kidney (podocytes), pancreas, fat, gonads, and hematopoietic stem cells, in addition to tumors of the kidney and hematopoietic system (Chau et al., Trends in Genetics (2012) 28 (10) 515-524). In healthy hematopoietic stem cells, WT1 encodes a transcription factor through which it regulates cell cycle activities such as proliferation, cell death, differentiation (Scharnhorst et al., Gene (2001) 273 (2) 141-161). In recovering marrow, WT1 is expressed to a greater degree than in homeostasis (Boublikova et al., Leukemia (2006) 20 (2) 254-263). Despite the expression of WT1 in healthy stem cells and recovering marrow states, studies to date using antisense or directed cytotoxic therapy against this antigen have not revealed adverse effects on the healthy stem cell population (Rosenfeld et al., Leukemia (2003) 17 (7) 1301-1312).

WT1 is overexpressed in Wilms tumor, soft tissue sarcomas including rhabdomyosarcoma (91.7%) and malignant peripheral nerve sheath tumor (71.4%), ovarian and prostate and cancers (Lee et al., Experimental Cell Research (2001) 264 (1) 74-99; Barbolina et al., Cancer (2008) 112 (7) 1632-1641; Kim et al., World journal of surg one (2014) 12:214; Brett et al., Molecular Cancer (2013) 12:3). In ovarian cancer WT1 expression was frequently identified in primary tumors and was retained in paired peritoneal metastases. WT1 expression in prostate cancer was associated with high-grade disease and may play a role in migration and metastasis.

WT1 specific T-cells can be generated as described below using one or more antigenic peptides to WT1. In some embodiments, the WT1 specific T-cells are generated using one or more antigenic peptides to WT1, or a modified or heteroclitic peptide derived from a WT1 peptide. In some embodiments, WT1 specific T-cells are generated using a WT1 antigen library comprising a pool of peptides (for example 15mers) containing amino acid overlap (for example 11 amino acids of overlap) between each sequence formed by scanning the protein amino acid sequence SEQ ID NO: 952 UNIPROT KB—P19544 (WT1_HUMAN):

```
MGSDVRDLNALLPAVPSLGGGGGCALPVSGAAQWAPVLDFAPPGASAYG

SLGGPAPPPAPPPPPPPPPPHSFIKQEPSWGGAEPHEEQCLSAFTVHFSG

QFTGTAGACRYGPFGPPPPSQASSGQARMFPNAPYLPSCLESQPAIRNQ

GYSTVTFDGTPSYGHTPSHHAAQFPNHSFKHEDPMGQQGSLGEQQYSVP

PPVYGCHTPTDSCTGSQALLLRTPYSSDNLYQMTSQLECMTWNQMNLGA

TLKGVAAGSSSSVKWTEGQSNHSTGYESDNHTTPILCGAQYRIHTHGVF

RGIQDVRRVPGVAPTLVRSASETSEKRPFMCAYPGCNKRYFKLSHLQMH

SRKHTGEKPYQCDFKDCERRFSRSDQLKRHQRRHTGVKPFQCKTCQRKF

SRSDHLKTHTRTHTGKTSEKPFSCRWPSCQKKFARSDELVRHHNMHQRN

MTKLQLAL
```

In some embodiments, the WT1 protein comprises about 60%, 65%, 70%, 75%, 80%, 85%, 90%, 95%, or 99% sequence identity to SEQ ID NO: 952.

The antigenic library is commercially available, for example, from JPT (Product Code: PM-WT1: Pep Mix Human (WT1/WT33)). In some embodiments, the WT1 specific T-cells are generated using a commercially available overlapping antigenic library made up of WT1 peptides.

In some embodiments, the WT1 specific T-cells are generated using one or more antigenic peptides to WT1, or a modified or heteroclitic peptide derived from a WT1 peptide, selected from an amino acid sequence comprising: SRQRPHPGALRNPTA (SEQ ID NO: 953); PHPGALRNP-TACPLP (SEQ ID NO: 954); ALRNPTACPLPHFPP (SEQ ID NO: 955); PTACPLPHFPPSLPP (SEQ ID NO: 956); PLPHFPPSLPPTHSP (SEQ ID NO: 957); FPPSLPPTHSPTHPP (SEQ ID NO: 958); LPPTHSPTHP-PRAGT (SEQ ID NO: 959); HSPTHPPRAGTAAQA (SEQ ID NO: 960); HPPRAGTAAQAPGPR (SEQ ID NO: 961); AGTAAQAPGPRRLLA (SEQ ID NO: 962); AQAPGPRRLLAAILD (SEQ ID NO: 963); GPRRL-LAAILDFLLL (SEQ ID NO: 964); LLAAILDFLLLQDPA (SEQ ID NO: 965); ILDFLLLQDPASTCV (SEQ ID NO: 966); LLLQDPASTCVPEPA (SEQ ID NO: 967); DPASTCVPEPASQHT (SEQ ID NO: 968); TCV-PEPASQHTLRSG (SEQ ID NO: 969); EPASQHTLRSGPGCL (SEQ ID NO: 970); QHTLRSGPGCLQQPE (SEQ ID NO: 971); RSGPGCLQQPEQQGV (SEQ ID NO: 972); GCLQQPEQQGVRDPG (SEQ ID NO: 973); QPEQQGVRDPGGIWA (SEQ ID NO: 974); QGVRDPG-GIWAKLGA (SEQ ID NO: 975); DPGGIWAKLGAAEAS (SEQ ID NO: 976); IWAKLGAAEASAERL (SEQ ID NO: 977); LGAAEASAERLQGRR (SEQ ID NO: 978); EASAERLQGRRSRGA (SEQ ID NO: 979); ERLQGRRSRGASGSE (SEQ ID NO: 980); GRRSR-GASGSEPQQM (SEQ ID NO: 981); RGASGSEPQQMGSDV (SEQ ID NO: 982); GSEPQQMGSDVRDLN (SEQ ID NO: 983); QQMGSDVRDLNALLP (SEQ ID NO: 984); SDVRDLNALLPAVPS (SEQ ID NO: 985); DLNALL-PAVPSLGGG (SEQ ID NO: 986); LLPAVPSLGGGGGCA (SEQ ID NO: 987); VPSLGGGGGCALPVS (SEQ ID NO: 988); GGGGGCALPVSGAAQ (SEQ ID NO: 989); GCALPVSGAAQWAPV (SEQ ID NO: 990); PVSGAAQWAPVLDFA (SEQ ID NO: 991); AAQWAPVLDFAPPGA (SEQ ID NO: 992); APVLD-FAPPGASAYG (SEQ ID NO: 993); DFAPP-GASAYGSLGG (SEQ ID NO: 994); PGASAYGSLGGPAPP (SEQ ID NO: 995); AYGSLGGPAPPPAPP (SEQ ID NO: 996); LGGPAPP-PAPPPPPP (SEQ ID NO: 997); APPPAPPPPPPPPPH (SEQ ID NO: 998); APPPPPPPPPHSFIK (SEQ ID NO: 999); PPPPPPHSFIKQEPS (SEQ ID NO: 1000); PPHS-FIKQEPSWGGA (SEQ ID NO: 1001); FIKQEPSWGGAE-PHE (SEQ ID NO: 1002); EPSWGGAEPHEEQCL (SEQ ID NO: 1003); GGAEPHEEQCLSAFT (SEQ ID NO: 1004); PHEEQCLSAFTVHFS (SEQ ID NO: 1005); QCL-SAFTVHFSGQFT (SEQ ID NO: 1006); AFTVHFSGQFTGTAG (SEQ ID NO: 1007); HFSGQFTGTAGACRY (SEQ ID NO: 1008); QFTGTA-GACRYGPFG (SEQ ID NO: 1009); TAGACRYGPFGPPPP (SEQ ID NO: 1010); CRYGPFGPPPPSQAS (SEQ ID NO: 1011); PFGPPPP-SQASSGQA (SEQ ID NO: 1012); PPPSQASSGQARMFP (SEQ ID NO: 1013); QASSGQARMFPNAPY (SEQ ID NO: 1014); GQARMFPNAPYLPSC (SEQ ID NO: 1015); MFPNAPYLPSCLESQ (SEQ ID NO: 1016); APYLP-SCLESQPAIR (SEQ ID NO: 1017); PSCLESQPAIRNQGY (SEQ ID NO: 1018); ESQPAIRNQGYSTVT (SEQ ID NO: 1019); AIRNQGYSTVTFDGT (SEQ ID NO: 1020); QGYSTVTFDGTPSYG (SEQ ID NO: 1021); TVTFDGTPSYGHTPS (SEQ ID NO: 1022); DGTPSYGHTPSHHAA (SEQ ID NO: 1023); SYGHTP-SHHAAQFPN (SEQ ID NO: 1024); TPSHHAAQFPNHSFK (SEQ ID NO: 1025); HAAQFPNHSFKHEDP (SEQ ID NO: 1026); FPNHSFKHEDPMGQQ (SEQ ID NO: 1027); SFKHEDPMGQQGSLG (SEQ ID NO: 1028); EDPMGQQGSLGEQQY (SEQ ID NO: 1029); GQQGSLGEQQYSVPP (SEQ ID NO: 1030); SLGEQQYSVPPPVYG (SEQ ID NO: 1031); QQYSVPPPVYGCHTP (SEQ ID NO: 1032); VPPPVYGCHTPTDSC (SEQ ID NO: 1033); VYGCHTPTDSCTGSQ (SEQ ID NO: 1034); HTPTD-SCTGSQALLL (SEQ ID NO: 1035); DSCTGSQALLLRTPY (SEQ ID NO: 1036); GSQALLLRTPYSSDN (SEQ ID NO: 1037); LLLRTPYSSDNLYQM (SEQ ID NO: 1038); TPYSSDN- LYQMTSQL (SEQ ID NO: 1039); SDNLYQNHSQLECMT (SEQ ID NO: 1040); YQMTSQLECMTWNQM (SEQ ID NO: 1041); SQLECMTWNQMNLGA (SEQ ID NO: 1042); CMTWNQMNLGATLKG (SEQ ID NO: 1043); NQMNLGATLKGVAAG (SEQ ID NO: 1044); LGATLKGVAAGSSSS (SEQ ID NO: 1045); LKGVAAGSSSSVKWT (SEQ ID NO: 1046); AAGSSSSVKWTEGQS (SEQ ID NO: 1047); SSSVKWTEGQSNHST (SEQ ID NO: 1048); KWTEGQSNHSTGYES (SEQ ID NO: 1049); GQSNHSTGYESDNHT (SEQ ID NO: 1050); HSTGYEsDNHTTPIL (SEQ ID NO: 1051); YESDNHTTPILCGAQ (SEQ ID NO: 1052); NHTTPILCGAQYRIH (SEQ ID NO: 1053); PILCGAQYRIHTHGV (SEQ ID NO: 1054); GAQYRIHTHGVFRGI (SEQ ID NO: 1055); RIHTHGVERGIQDVR (SEQ ID NO: 1056); HGVFRGIQDVRRVPG (SEQ ID NO: 1057); RGIQDVRRVPGVAPT (SEQ ID NO: 1058); DVRRVPGVAPTLVRS (SEQ ID NO: 1059); VPGVAPTLVRSASET (SEQ ID NO: 1060); APTLVRSA-SETSEKR (SEQ ID NO: 1061); VRSASETSEKRPFMC (SEQ ID NO: 1062); SETSEKRPFMCAYPG (SEQ ID NO: 1063); EKRPFMCAYPGCNKR (SEQ ID NO: 1064); FMCAYPGCNKRYFKL (SEQ ID NO: 1065); YPGCNK-RYFKLSHLQ (SEQ ID NO: 1066); NKRYFKLSHLQMHSR (SEQ ID NO: 1067); FKLSHLQMHSRKHTG (SEQ ID NO: 1068); HLQMHSRKHTGEKPY (SEQ ID NO: 1069); HSRKHT-GEKPYQCDF (SEQ ID NO: 1070); HTGEKPYQCDFKDCE (SEQ ID NO: 1071); KPYQCDFKDCERRFS (SEQ ID NO: 1072); CDFKDCERRFSRSDQ (SEQ ID NO: 1073); DCERRFSRSDQLKRH (SEQ ID NO: 1074); RFSRSDQLKRHQRRH (SEQ ID NO: 1075); SDQLKRHQRRHTGVK (SEQ ID NO: 1076); KRHQR-RHTGVKPFQC (SEQ ID NO: 1077); RRHTGVKPFQCK-TCQ (SEQ ID NO: 1078); GVKPFQCKTCQRKFS (SEQ ID NO: 1079); FQCKTCQRKFSRSDH (SEQ ID NO: 1080); TCQRKFSRSDHLKTH (SEQ ID NO: 1081); KFSRSDHLKTHTRTH (SEQ ID NO: 1082); SDHLKTH-TRTHTGKT (SEQ ID NO: 1083); KTHTRTHTGKTSEKP (SEQ ID NO: 1084); RTHTGKTSEKPFSCR (SEQ ID NO: 1085); GKTSEKPFSCRWPSC (SEQ ID NO: 1086); EKPFSCRWPSCQKKF (SEQ ID NO: 1087); SCRWP-SCQKKFARSD (SEQ ID NO: 1088); PSCQKKFARS-DELVR (SEQ ID NO: 1089); KKFARSDELVRHHNM (SEQ ID NO: 1090); RSDELVRHHNMHQRN (SEQ ID NO: 1091); LVRHHNMHQRNMTKL (SEQ ID NO: 1092); HNMHQRNMTKLQLAL (SEQ ID NO: 1093); RQRPHP-GAL (SEQ ID NO: 1094); GALRNPTAC (SEQ ID NO: 1095); PLPHFPPSL (SEQ ID NO: 1096); HFPPSLPPT (SEQ ID NO: 1097); THSPTHPPR (SEQ ID NO: 1098); AILDFLLLQ (SEQ ID NO: 1099); PGCLQQPEQ (SEQ ID NO: 1100); PGCLQQPEQQG (SEQ ID NO: 1101); KLGAAEASA (SEQ ID NO: 1102); ASGSEPQQM (SEQ ID NO: 1103); RDLNALLPAV (SEQ ID NO: 1104); GGCALPVSGA (SEQ ID NO: 1105); GAAQWAPVL (SEQ ID NO: 1106); LDFAPPGAS (SEQ ID NO: 1107); LDFAPPGASAY (SEQ ID NO: 1108); SAYGSLGGP (SEQ ID NO: 1109); PAPPPPPP (SEQ ID NO: 1110); ACRYGPFGP (SEQ ID NO: 1111); SGQARMFPN (SEQ ID NO: 1112); RMFPNAPYL (SEQ ID NO: 1113); PSCLESQPA (SEQ ID NO: 1114); NQGYSTVTF (SEQ ID NO: 1115); HHAAQFPNH (SEQ ID NO: 1116); HSFKHEDPM (SEQ ID NO: 1117); CHTPTDSCT (SEQ ID NO: 1118); CTGSQALLL (SEQ ID NO: 1119); TDSCTGSQA (SEQ ID NO: 1120); RTPYSSDNL (SEQ ID NO: 1121); NLYQMTSQLE (SEQ ID NO: 1122); WNQMNLGAT (SEQ ID NO: 1123); NQMNLGATL (SEQ ID NO: 1124); WNQMNLGATLK (SEQ ID NO: 1125); CMTWNQMNLGATLKG (SEQ ID NO: 1126); NLGATLKGV (SEQ ID NO: 1127); LGATLKGVAA (SEQ ID NO: 1128); TLGVAAGS (SEQ ID NO: 1129); GYESDNHTT (SEQ ID NO: 1130); FMCAYPGCNK (SEQ ID NO: 1131); KRPFMCAYPGC (SEQ ID NO: 1132); RKFSRSDHL (SEQ ID NO: 1133); LKTHTRTHT (SEQ ID NO: 1134); NMHQRNHTKL (SEQ ID NO: 1135); LLAAILDFL (SEQ ID NO: 1136); CLQQPEQQGV (SEQ ID NO: 1137); DLNALLPAV (SEQ ID NO: 1138); ALL-PAVPSL (SEQ ID NO: 1139); VLDFAPPGA (SEQ ID NO: 1140); CMTWNQMNL (SEQ ID NO: 1141); QARMFPNAPY (SEQ ID NO: 1142); ALRNPTACPL (SEQ ID NO: 1143); YPGCNKRYF (SEQ ID NO: 1144); TSEKRPFMCAY (SEQ ID NO: 1145); STVTFDGTPSY (SEQ ID NO: 1146); VTFDGTPSY (SEQ ID NO: 1147); HTTPILCGAQY (SEQ ID NO: 1148); ALLPAVPSL (SEQ ID NO: 1149); DLNALLPAV (SEQ ID NO: 1150); SLGEQQYSV (SEQ ID NO: 1151); SLGGGGGCAL (SEQ ID NO: 1152); DVRRVPGVAP (SEQ ID NO: 1153); RVPGVAPTL (SEQ ID NO: 1154); RIHTHGVFR (SEQ ID NO: 1155); DVRRVPGVA (SEQ ID NO: 1156); CTGSQALLLR (SEQ ID NO: 1157); GVFRGIQDVR (SEQ ID NO: 1158); RSASETSEK (SEQ ID NO: 1159); (FSRSDQLKR (SEQ ID NO: 1160); AYPGCNKRYF (SEQ ID NO: 1161); QYRIHTHGVF (SEQ ID NO: 1162); AFTVHFSGQF (SEQ ID NO: 1163); DFKDCERRF (SEQ ID NO: 1164); DVRDLNALL (SEQ ID NO: 1165); VTFDGTPSY (SEQ ID NO: 1166); TVTFDGTPSY (SEQ ID NO: 1167); FTVHFSGQF (SEQ ID NO: 1168); GVFRGIQDVRR (SEQ ID NO: 1169); FTGTAGACR (SEQ ID NO: 1170); TTPILCGAQYR (SEQ ID NO: 1171); ELVRHHNMHQR (SEQ ID NO: 1172); DPMGQQGSL (SEQ ID NO: 1173); PPGASAYGSL (SEQ ID NO: 1174); PPPPPHSFI (SEQ ID NO: 1175); PPPPPPHSF (SEQ ID NO: 1176); MTKLQLAL (SEQ ID NO: 1177); EPHEEQCL (SEQ ID NO: 1178); ETSEKRPF (SEQ ID NO: 1179); CNKRYFKL (SEQ ID NO: 1180); QQYSVPPPVY (SEQ ID NO: 1181); TVTFDGTPSY (SEQ ID NO: 1182); QQGSLGEQQY (SEQ ID NO: 1183); SQALLLRTPY (SEQ ID NO: 1184); TPYSSDNLY (SEQ ID NO: 1185); PPGASAYGSL (SEQ ID NO: 1186); QPAIRNQGY (SEQ ID NO: 1187); DPMGQQGSL (SEQ ID NO: 1188); ASSGQARMF (SEQ ID NO: 1189); RVPGVAPTL (SEQ ID NO: 1190); ASETSEKRPF (SEQ ID NO: 1191); QASSGQARMF (SEQ ID NO: 1192); ASAYGSLGGPAPPPA (SEQ ID NO: 1193); GSDVRDLNALLPAVP (SEQ ID NO: 1194); IQDVRRVPGVAPTLV (SEQ ID NO: 1195); VRDLNALL-PAVPSLG (SEQ ID NO: 1196); YSTVTFDGTPSYGHT (SEQ ID NO: 1197); MGSDVRDLNALLPAV (SEQ ID NO: 1198); YQCDFKDCERRFSRS (SEQ ID NO: 1199); VPSLGGGGGCALPVS (SEQ ID NO: 1200); TPSYGHTP-SHHAAQF (SEQ ID NO: 1201); TVTFDGTPSYGHTPS (SEQ ID NO: 1202); LSAFTVHFSGQFTGT (SEQ ID NO: 1203); TPTDSCTGSQALLLR (SEQ ID NO: 1204); FRGIQDVRRVPGVAP (SEQ ID NO: 1205); NKRYFKLSHLQMHSR (SEQ ID NO: 1206); QCDFKDCERRFSRSD (SEQ ID NO: 1207); STGYESDNHTTPILC (SEQ ID NO: 1208); WAPVLD-FAPPGASAY (SEQ ID NO: 1209); RPFMCAYPGCNK-RYF (SEQ ID NO: 1210); GSDVRDLNALLPAVP (SEQ ID NO: 1211); or NALLPAVPSLGGGGG (SEQ ID NO: 1212); or a combination thereof.

In some embodiments, the WT1 peptide or derivative thereof comprises about 60%, 65%, 70%, 75%, 80%, 85%, 90%, 95%, or 99% sequence identity to SEQ ID NO: 953-1212 or a combination thereof.

In some embodiments, the WT1 specific T-cells are generated with peptides that recognize class I MHC molecules. In some embodiments, the WT1 specific T-cells are generated with peptides that recognize class II MHC molecules. In some embodiments, the WT1 specific T-cells are generated with peptides that recognize both class I and class II MHC molecules.

Additional Tumor Associated Antigens

Additional T-cells activated be reactive to the TAAs described below may also be included in the T-cell compositions described herein Tumor-associated antigens (TAA) can be loosely categorized as oncofetal (typically only expressed in fetal tissues and in cancerous somatic cells), oncoviral (encoded by tumorigenic transforming viruses), overexpressed/accumulated (expressed by both normal and neoplastic tissue, with the level of expression highly elevated in neoplasia), cancer-testis (expressed only by cancer cells and adult reproductive tissues such as testis and placenta), lineage-restricted (expressed largely by a single cancer histotype), mutated (only expressed by cancer as a result of genetic mutation or alteration in transcription), post-translationally altered (tumor-associated alterations in glycosylation, etc.), or Idiotypic (highly polymorphic genes where a tumor cell expresses a specific "clonotype", i.e., as in B cell, T cell lymphoma/leukemia resulting from clonal aberrancies). Although they are preferentially expressed by tumor cells, TAAs are oftentimes found in normal tissues. However, their expression differs from that of normal tissues by their degree of expression in the tumor, alterations in their protein structure in comparison with their normal counterparts or by their aberrant subcellular localization within malignant or tumor cells.

Examples of oncofetal tumor associated antigens include Carcinoembryonic antigen (CEA), immature laminin receptor, and tumor-associated glycoprotein (TAG) 72. Examples of overexpressed/accumulated include BING-4, calcium-activated chloride channel (CLCA) 2, Cyclin B1, 9D7, epithelial cell adhesion molecule (Ep-Cam), EphA3, Her2/neu, telomerase, mesothelin, orphan tyrosine kinase receptor (ROR1), stomach cancer-associated protein tyrosine phosphatase 1 (SAP-1), and Survivin.

Examples of cancer-testis antigens include the b melanoma antigen (BAGE) family, cancer-associated gene (CAGE) family, G antigen (GAGE) family, melanoma antigen (MAGE) family, sarcoma antigen (SAGE) family and X antigen (XAGE) family, CT9, CT10, NY-ESO-1, L antigen (LAGE) 1, Melanoma antigen preferentially expressed in tumors (PRAME), and synovial sarcoma X (SSX) 2. Examples of lineage restricted tumor antigens include melanoma antigen recognized by T cells-1/2 (Melan-A/MART-1/2), Gp100/pmell7, tyrosine-related protein (TRP) 1 and 2, P. polypeptide, melanocortin 1 receptor (MC1R), and prostate-specific antigen. Examples of mutated tumor antigens include β-catenin, breast cancer antigen (BRCA) 1/2, cyclin-dependent kinase (CDK) 4, chronic myelogenous leukemia antigen (CML) 66, fibronectin, p53, Ras, and TGF-βRII. An example of a post-translationally altered tumor antigen is mucin (MUC) 1. Examples of Idiotypic tumor antigens include immunoglobulin (Ig) and T cell receptor (TCR).

In some embodiments, the antigen associated with the disease or disorder is selected from the group consisting of CD19, CD20, CD22, hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine receptor, HMW-MAA, IL-22R-alpha, IL-13R-alpha, kdr, kappa light chain, Lewis Y, MUC16 (CA-125), PSCA, NKG2D Ligands, oncofetal antigen, VEGF-R2, PSMA, estrogen receptor, progesterone receptor, ephrinB2, CD123, c-Met and/or biotinylated molecules, and/or molecules expressed by HIV, HCV, HBV or other pathogens.

Exemplary tumor antigens include at least the following: carcinoembryonic antigen (CEA) for bowel cancers; CA-125 for ovarian cancer; MUC1 or epithelial tumor antigen (ETA) or CA15-3 for breast cancer; tyrosinase or melanoma-associated antigen (MAGE) for malignant melanoma; and abnormal products of ras, p53 for a variety of types of tumors; alphafetoprotein for hepatoma, ovarian, or testicular cancer; beta subunit of hCG for men with testicular cancer; prostate specific antigen for prostate cancer; beta 2 microglobulin for multiple myeloma and in some lymphomas; CA19-9 for colorectal, bile duct, and pancreatic cancer; chromogranin A for lung and prostate cancer; TA90 for melanoma, soft tissue sarcomas, and breast, colon, and lung cancer. Examples of TAAs are known in the art, for example in N. Vigneron, "Human Tumor Antigens and Cancer Immunotherapy," BioMed Research International, vol. 2015, Article ID. 948501, 17 pages, 2015. 20 doi: 10.1155/2015/948501; Ilyas et al., J Immunol. (2015) Dec. 1; 195(11): 5117-5122; Coulie et al., Nature Reviews Cancer (2014) volume 14, pages 135-146; Cheever et al., Clin Cancer Res. (2009) Sep. 1;15(17):5323-37, which are incorporated by reference herein in its entirety.

Examples of oncoviral TAAs include human papilloma virus (HPV) L1, E6 and E7, Epstein-Barr Virus (EBV) Epstein-Barr nuclear antigen (EBNA), EBV viral capsid antigen (VCA) Igm or IgG, EBV early antigen (EA), latent membrane protein (LMP) 1 and 2, hepatitis B surface antigen (HBsAg), hepatitis B e antigen (HBeAg), hepatitis B core antigen (HBcAg), hepatitis B x antigen (HBxAg), hepatitis C core antigen (HCV core Ag), Human T-Lymphotropic Virus Type 1 core antigen (HTLV-1 core antigen), HTLV-1 Tax antigen, HTLV-1 Group specific (Gag) antigens, HTLV-1 envelope (Env), HTLV-1 protease antigens (Pro), HTLV-1 Tof, HTLV-1 Rof, HTLV-1 polymerase (Pro) antigen, Human T-Lymphotropic Virus Type 2 core antigen (HTLV-2 core antigen), HTLV-2 Tax antigen, HTLV-2 Group specific (Gag) antigens, HTLV-2 envelope (Env), HTLV-2 protease antigens (Pro), HTLV-2 Tof, HTLV-2 Rof, HTLV-2 polymerase (Pro) antigen, latency-associated nuclear antigen (LANA), human herpesvirus-8 (HHV-8) K8.1, Merkel cell polyomavirus large T antigen (LTAg), and Merkel cell polyomavirus small T antigen (sTAg).

Elevated expression of certain types of glycolipids, for example gangliosides, is associated with the promotion of tumor survival in certain types of cancers. Examples of gangliosides include, for example, GM1b, GD1c, GM3, GM2, GM1a, GD1a, GT1a, GD3, GD2, GD1b, GT1b, GQ1b, GT3, GT2, GT1c, GQ1c, and GP1c. Examples of ganglioside derivatives include, for example, 9-O-Ac-GD3, 9-O-Ac-GD2, 5-N-de-GM3, N-glycolyl GM3, NeuGcGM3, and fucosyl-GM1. Exemplary gangliosides that are often present in higher levels in tumors, for example melanoma, small-cell lung cancer, sarcoma, and neuroblastoma, include GD3, GM2, and GD2.

In addition to the TAAs described above, another class of TAAs is tumor-specific neoantigens, which arise via mutations that alter amino acid coding sequences (non-synonymous somatic mutations). Some of these mutated peptides can be expressed, processed and presented on the cell surface, and subsequently recognized by T cells. Because normal tissues do not possess these somatic mutations, neoantigen-specific T cells are not subject to central and peripheral tolerance, and also lack the ability to induce normal tissue destruction. See, e.g., Lu & Robins, Cancer Immunotherapy Targeting Neoantigens, Seminars in Immunology, Volume 28, Issue 1, February 2016, Pages 22-27, incorporated herein by reference.

In some embodiments, the T-cell composition includes a T-cell subpopulation activated to an oncoviral TAA selected from a group consisting of human papilloma virus (HPV) E6 and E7, Epstein-Barr Virus (EBV) Epstein-Barr nuclear antigen (EBNA), latent membrane protein (LMP) 1, and LMP2. In some embodiments, at least one T-cell subpopulation is specific to HPV E6.

In some embodiments, a T-cell includes a T-cell subpopulation activated to an overexpressed/accumulated TAA selected from a group consisting of BING-4, calcium-activated chloride channel (CLCA) 2, Cyclin $B_1$, 9D7, epithelial cell adhesion molecule (Ep-Cam), EphA3, Her2/neu, L1 cell adhesion molecule (L1-Cam), telomerase, mesothelin, and stomach cancer-associated protein tyrosine phosphatase 1 (SAP-1).

In some embodiments, the T-cell composition includes a T-cell subpopulation activated to a cancer-testis antigen selected from the group consisting of the b melanoma antigen (BAGE) family, cancer-associated gene (CAGE) family, G antigen (GAGE) family, melanoma antigen (MAGE) family, sarcoma antigen (SAGE) family and X antigen (XAGE) family, cutaneous T cell lymphoma associated antigen family (cTAGE), Interleukin-13 receptor subunit alpha-1 (IL13RA), CT9, Putative tumor antigen NA88-A, leucine zipper protein 4 (LUZP4), NY-ESO-1, L antigen (LAGE) 1, helicase antigen (HAGE), lipase I (LIPI), synovial sarcoma X (SSX) family, sperm protein associated with the nucleus on the chromosome X (SPANX) family, cancer/testis antigen 2 (CTAG2), calcium-binding tyrosine phosphorylation-regulated fibrous sheath protein (CABYR), acrosin binding protein (ACRBP), centrosomal protein 55 (CEP55) and Synaptonemal Complex Protein 1 (SYCP1). In a preferred embodiment, the T-cell composition includes a T-cell subpopulation activated to MAGE A3.

In some embodiments, the T-cell compositions includes a T-cell subpopulation activated to a lineage restricted tumor antigen selected from the group consisting of melanoma antigen recognized by T cells-1/2 (Melan-A/MART-1/2), Gp100/pmel17, tyrosinase, tyrosine-related protein (TRP) 1 and 2, P. polypeptide, melanocortin 1 receptor (MC1R), and prostate-specific antigen. In some embodiments, at least one T-cell subpopulation is specific to Melan-A/MART-1/2.

In some embodiments, the T-cell composition includes a T-cell subpopulation activated to a mutated TAA selected from a group consisting of β-catenin, breast cancer antigen (BRCA) 1/2, cyclin-dependent kinase (CDK) 4, chronic myelogenous leukemia antigen (CML) 66, fibronectin, MART-2, p53, Ras, TGF-βRII, and truncated epithelial growth factor (tEGFR).

In some embodiments, the T-cell composition includes a T-cell subpopulation activated to post-translationally altered TAA mucin (MUC) 1.

In some embodiments, the T-cell composition includes a T-cell subpopulation activated to an Idiotypic TAA selected from a group consisting of immunoglobulin (Ig) and T-cell receptor (TCR).

T-Cell Populations

The present disclosure provides isolated, activated T-cell compositions for the treatment of multiple myeloma. The T-cell compositions include CD4$^+$ and CD8$^+$ T-cells, and may also include additional lymphocytic cell subsets, wherein the different lymphocytic cell subsets include CD3$^+$/CD56$^+$ Natural Killer T-cells (CD3$^+$ NKT) and TCR γδ T-cells. In some embodiments, the activated T-cell compositions are comprised of a fixed ratio of CD4$^+$ T-cells, CD8$^+$ T-cells, CD3$^+$/CD56$^+$ Natural Killer T-cells (CD3$^+$ NKT), and TCR γδ T-cells.

In some embodiments, the T-cells in the composition comprise a TCR that binds to the disclosed MM antigens or tumor antigens. Thus, the TCRs can bind to one or more of the peptides having the amino acid sequence of SEQ ID NO: 1-1212, one or more of the peptides having about 60, 65, 70, 75, 80, 85, 90, 95, or 99% sequence identity to the peptides having the amino acid sequence of SEQ ID NO: 1-1212, or one or more derivatives thereof. In some embodiments, all T-cells in the T-cell composition comprise a TCR that binds to the same MM antigen or tumor antigen. In some embodiments, the T-cell composition comprises at least two different T-cells wherein the at least two different T-cells each comprise a TCR that binds to a different MM antigen or tumor antigen than the other T-cell.

In some embodiments, the T-cell composition can comprise T-cells genetically engineered to comprise a TCR that binds to a specific antigen. For example, the genetically engineered T-cells can comprise TCRs that can bind to one or more of the peptides having the amino acid sequence of SEQ ID NO: 1-1212, one or more of the peptides having about 60, 65, 70, 75, 80, 85, 90, 95, or 99% sequence identity to the peptides having the amino acid sequence of SEQ ID NO: 1-1212, or one or more derivatives thereof. Thus, the genetically engineered T-cells are non-naturally occurring.

As will be understood by one skilled in the art, the TCR comprised in the T-cells of the present disclosure is a disulfide-linked membrane-anchored heterodimeric protein normally consisting of the highly variable alpha (a) and beta (0) chains expressed as part of a complex with the invariant CD3 chain molecules. T-cells expressing this type of receptor are referred to as α:β (or αβ) T-cells, though a minority of T-cells express an alternate receptor, formed by variable gamma (γ) and delta (δ) chains, referred as γδ T-cells. Each chain is composed of two extracellular domains: a variable (V) region and a constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex. The variable domain of both the TCR α-chain and β-chain each have three hypervariable or complementarity determining regions (CDRs). There is also an additional area of hypervariability on the β-chain (HV4) that does not normally contact antigen and, therefore, is not considered a CDR. The constant domain of the TCR consists of short connecting sequences in which a cysteine residue forms disulfide bonds, which form a link between the two chains.

The constant region of the TCR α-chain may comprise the following sequence:

```
                                    (SEQ ID NO: 1213)
IQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKL

VEKSFETDTNLNFQNLSVIGFRILLLKVAGFNLLMTLRLWSS.
```

Thus, in some embodiments, the T-cells of the present disclosure may comprise a constant region in the α-chain comprising at least about 60%, 65%, 70%, 75%, 80%, 85%, 90%, 95%, or 99% sequence identity to SEQ ID NO: 1213. In some embodiments, the T-cells of the present disclosure may comprise a constant region in the α-chain comprising the amino acid sequence of SEQ ID NO: 1213.

The constant region of the TCR β-chain may comprise the following sequence:

```
                                        (SEQ ID NO: 1214)
DLNKVFPPPEVAVFEPSEAEISHTQKATLVCLATGFFPDHVELSWWVNGK

EVHSGVSTDPQPLKEQPALNDSRYCLSSRLRVSATFWQNPRNHFRCQVQ

FYGLSENDEWTQDRAKPVTQIVSAEAWGRADCGFTSVSYQQGVLSATIL

YEILLGKATLYAVLVSALVLMAMVKRKDF.
```

Thus, in some embodiments, the T-cells of the present disclosure may comprise a constant region in the β-chain comprising at least about 60%, 65%, 70%, 75%, 80%, 85%, 90%, 95%, or 99% sequence identity to SEQ ID NO: 1214. In some embodiments, the T-cells of the present disclosure may comprise a constant region in the α-chain comprising the amino acid sequence of SEQ ID NO: 1214.

In some embodiments, the T-cells of the present disclosure may comprise a constant region in the α-chain comprising at least about 60%, 65%, 70%, 75%, 80%, 85%, 90%, 95%, or 99% sequence identity to SEQ ID NO: 1213 and a constant region in the β-chain comprising at least about 60%, 65%, 70%, 75%, 80%, 85%, 90%, 95%, or 99% sequence identity to SEQ ID NO: 1214. In some embodiments, the T-cells of the present disclosure may comprise a constant region in the α-chain comprising the amino acid sequence of SEQ ID NO: 1213 and a constant region in the β-chain comprising the amino acid sequence of SEQ ID NO: 1214.

In some embodiments, the TCR comprised in the T-cells of the present disclosure binds specifically to the antigen used for priming the T-cells with a $K_D$ of about 1 μM or less. In some embodiments, the TCR comprised in the T-cells of the present disclosure binds specifically to the antigen used for priming the T-cells with a $K_D$ of about ≤1 μM, ≤100 nM, ≤10 nM, ≤1 nM or ≤100 μM. In some embodiments, the TCR comprised in the T-cells of the present disclosure binds specifically to the antigen used for priming the T-cells with a $K_D$ of from about 1 nM to about 1 μM. In some embodiments, the TCR comprised in the T-cells of the present disclosure binds specifically to the antigen used for priming the T-cells with a $K_D$ of from about 1 nM to about 100 nM, from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, or from about 900 nM to about 1 μM. The $K_D$ measurement can be made by any of the known methods. In some embodiments therefore, the T-cells of the present disclosure may be prepared by a method with a step of priming the primary cells for a time period and at a concentration of antigen sufficient to result in any of the aforementioned binding affinities. The resultant T-cells may be further clonally expanded.

CD4⁺ T-cells

The cell compositions of the present disclosure include CD4⁺ T-cells activated against an MMAA or TAA described herein. CD4⁺ T-cells are the primary orchestrators of the adaptive immune response, mediating a variety of cellular and humoral responses against pathogens and cancer. Although CD4⁺ T-cells are thought to lack the capacity to directly kill or engulf pathogens, they are powerful activators of effector cells such as macrophages, cytotoxic T cells, and B cells. CD4⁺ T-cells generally do not express or are negative for CD8, CD25, CD44, CD117, CD127, or TCR γ/δ.

CD4⁺ T-cells are crucial in achieving a regulated effective immune response to pathogens and tumors. Naive CD4⁺ T-cells are activated after interaction with antigen-MHC complex and differentiate into specific subtypes depending mainly on the cytokine milieu of the microenvironment. Besides the classical T-helper 1 ($T_{h1}$) and T-helper 2 ($T_{h2}$), other CD4⁺ T-cell subsets have been identified, including T-helper 17 ($T_{h17}$), regulatory T cell ($T_{reg}$), follicular helper T-cell ($T_{fh}$), and T-helper 9 ($T_{h9}$), each with a characteristic cytokine profile. For a particular phenotype to be differentiated, a set of cytokine signaling pathways coupled with activation of lineage-specific transcription factors and epigenetic modifications at appropriate genes are required. The effector functions of these cells are mediated by the cytokines secreted by the differentiated cells.

The CD4⁺ T-cells included in the T-cell compositions described herein are preferably of the T-helper 1 ($T_{h1}$)-type. $T_{h1}$ cells are involved with the elimination of intracellular pathogens and are associated with organ-specific autoimmunity (G. del Prete, "Human Th1 and Th2 lymphocytes: their role in the pathophysiology of atopy," Allergy, vol. 47, no. 5, pp. 450-455, 1992). They mainly secrete IFN-γ, lymphotoxin α (Lfα), and IL-2. IFN-γ is essential for the activation of mononuclear phagocytes, including macrophages, microglial cells, thereby resulting in enhanced phagocytic activity (H. W. Murray, B. Y. Rubin, and S. M. Carriero, "Human mononuclear phagocyte antiprotozoal mechanisms: Oxygen-dependent vs oxygen-independent activity against intracellular *Toxoplasma gondii*," Journal of Immunology, vol. 134, no. 3, pp. 1982-1988, 198). IFNγ is believed to exert its effect through the activation of IFNγ-responsive genes, which account for more than 200 (U. Boehm, T. Klamp, M. Groot, and J. C. Howard, "Cellular responses to interferon-γ," Annual Review of Immunology, vol. 15, pp. 749-795, 1997). IL-2 promotes proliferation of CD8+ T cells with acquisition of cytolytic phenotype (H. P. Kim, J. Imbert, and W. J. Leonard, "Both integrated and differential regulation of components of the IL-2/IL-2 receptor system," Cytokine and Growth Factor Reviews, vol. 17, no. 5, pp. 349-366, 2006; L. Gattinoni, C. A. Klebanoff, D. C. Palmer et al., "Acquisition of full effector function in vitro paradoxically impairs the in vivo antitumor efficacy of adoptively transferred CD8+ T cells," Journal of Clinical Investigation, vol. 115, no. 6, pp. 1616-1626, 2005). Besides its role as T cell growth factor, IL-2 also promotes the development of CD8⁺ memory cells after antigen priming, and thus participating in ensuring a robust secondary immune response (M. A. Williams, A. J. Tyznik, and M. J. Bevan, "Interleukin-2 signals during priming are required for secondary expansion of CD8⁺ memory T cells," Nature, vol. 441, no. 7095, pp. 890-893, 2006). Cell markers typically associated with CD4+ $T_{h1}$-cells include CD3, CD4, CD119 (IFN-γ Rα), CD183 (CXCR3), CD195 (CCR5), CD218a (IL-18Rα), LT-βR, and CD366 (Tim-3).

Regulatory T cells ($T_{reg}$) are a subpopulation of CD4⁺ T-cells that maintain homeostasis and tolerance within the immune system. FOXP3⁺CD25⁺CD4⁺ regulatory T (Treg) cells, which suppress aberrant immune response against self-antigens, also suppress anti-tumor immune responses. Infiltration of a large number of $T_{reg}$ cells into tumor tissues is often associated with poor prognosis. In some embodiments, the CD4⁺ T-cells of the present disclosure are depleted or substantially depleted of $T_{reg}$ cells. Various cell surface molecules, including chemokine receptors such as CCR4, that are specifically expressed by effector $T_{reg}$ cells can be targeted for the negative selection of $T_{regs}$ as provided herein. Cell markers typically associated with CD4$^+$ $T_{reg}$-cells include CD3, CD4, CD25 (IL-2Rα), CD39, CD73, CD103, CD152 (CTLA-4), GARP, GITR, and LAP (TGF-β).

CD8$^+$ T-cells

The cell compositions of the present disclosure include CD8$^+$ T-cells activated against an MMAA or TAA described herein. CD8$^+$ T-cells are a subset of T-cells that express an αβ T-cell receptor (TCR) and are responsible for the direct killing of infected, damaged, and dysfunctional cells, including tumor cells. CD8$^+$ T cells, like CD4$^+$ Helper T cells, are generated in the thymus. However, rather than the CD4 molecule, cytotoxic T cells express a dimeric co-receptor—CD8—usually composed of one CD8α and one CD8β chain. CD8$^+$ T-cells recognize peptides presented by MHC Class I molecules, found on all nucleated cells. The CD8 heterodimer binds to a conserved portion (the α3 region) of MHC Class I during T cell/antigen presenting cell interactions.

CD8$^+$ T cells (often called cytotoxic T lymphocytes, or CTLs) are very important for immune defense against intracellular pathogens, including viruses and bacteria, and for tumor surveillance. When a CD8$^+$ T cell recognizes its antigen and becomes activated, it has three major mechanisms to kill infected or malignant cells. The first is secretion of cytokines, primarily TNF-α and IFN-γ, which have anti-tumor and anti-viral microbial effects.

The second major function is the production and release of cytotoxic granules. These granules, also found in NK cells, contain two families of proteins—perforin, and granzymes. Perforin forms a pore in the membrane of the target cell, similar to the membrane attack complex of complement. This pore allows the granzymes also contained in the cytotoxic granules to enter the infected or malignant cell. Granzymes are serine proteases which cleave the proteins inside the cell, shutting down the production of viral proteins and ultimately resulting in apoptosis of the target cell.

The cytotoxic granules are released only in the direction of the target cell, aligned along the immune synapse, to avoid non-specific bystander damage to healthy surrounding tissue. CD8$^+$ T-cells are able to release their granules, kill an infected cell, then move to a new target and kill again, often referred to as serial killing.

The third major function of CD8+ T-cell destruction of infected cells is via Fas/FasL interactions. Activated CD8+ T-cells express FasL on the cell surface, which binds to its receptor, Fas, on the surface of the target cell. This binding causes the Fas molecules on the surface of the target cell to trimerize, which pulls together signaling molecules. These signaling molecules result in the activation of the caspase cascade, which also results in apoptosis of the target cell. Because CD8$^+$ T-cells can express both molecules, Fas/FasL interactions are a mechanism by which CD8+ T-cells can kill each other, called fratricide, to eliminate immune effector cells during the contraction phase at the end of an immune response.

Cell markers typically expressed by CD8$^+$ T-cells (or which CD8$^+$ T-cells are positive for) include CD3$^+$, CD8$^+$, and TCR α/β$^+$, and which CD8$^+$ T-cells are negative for are CD25, CD44, CD117, CD127, and TCR γ/δ.

CD3$^+$/CD56$^+$ Natural Killer T-Cells (NKT)

In certain aspects of the present disclosure, the cell compositions described herein include CD3$^+$ NKT-cells. The CD3$^+$ NKT-cells are activated. In certain embodiments, the CD3$^+$ NKT-cells can be primed against one or more specific glycolipid antigens, for example one or more gangliosides. In certain embodiments, the CD3$^+$ NKT-cells are exposed to one or more specific antigens. In certain embodiments, the CD3$^+$ NKT-cells are exposed to one or more specific antigens and cultured in the same culture as the CD4$^+$ T-cells and CD8$^+$ T-cells, or combination thereof, wherein they are activated during culturing. In some embodiments, the CD3$^+$ NKT-cells are activated separately from other cells of the composition. In some embodiments, the CD3$^+$ NKT-cells are separately activated.

Natural killer T (NKT) cells are a specialized population of T cells that express a semi-invariant T cell receptor (TCR αβ) and surface antigens typically associated with natural killer cells. In humans, the TCRs of NKT cells almost always contain Vα24/Jα18 paired with a TCRβ chain containing Vβ11. The TCR on NKT cells is unique in that it recognizes glycolipid antigens presented by the MHC I-like molecule CD1d. Most NKT cells, known as type I NKT cells, express an invariant TCR α-chain and one of a small number of TCR β-chains. The TCRs present on type I NKT cells is capable of recognizing the antigen α-glucosylceramide (α-GalCer). Within this group, distinguishable subpopulations have been identified, including CD4$^+$CD8$^-$ NKT-cells, CD4$^-$CD8$^-$ NKT-cells, and CD4$^-$CD8$^+$ T-cells.

NKT-cells also include a smaller population of NKT cells, known as type II NKT-cells (or noninvariant NKT-cells), which express a wider range of TCR α-chains, but do not recognize the α-GalCer antigen.

NKT-cells contribute to antibacterial and antiviral immune responses and promote tumor-related immunosurveillance or immunosuppression. Like natural killer cells, NKT-cells can also induce perforin-, Fas-, and TNF-related cytotoxicity. Activated NKT-cells are capable of producing IFN-γ and IL-4.

Cell markers typically expressed by NKT-cells (or which NKT-cells are positive for) include CD16, CD94, NKG2D, CD3, and CD56. NKT-cells generally do not express or are negative for CD14 and CD33.

γδ T-Cells

In certain aspects of the present disclosure, the T-cell compositions described herein include γδ T-cells. The γδ T-cells are activated. In certain embodiments, the γδ T-cells are exposed to one or more specific antigens. In certain embodiments, the γδ T-cells are exposed to one or more specific antigens and cultured in the same culture as the CD3$^+$ NKT-cells, CD4$^+$ T-cells, and/or CD8$^+$ T-cells, or combination thereof, wherein they are activated during culturing. In some embodiments, the γδ T-cells are activated separately from other cells of the composition. In some embodiments, the γδ T-cells cells are separately activated.

γδ T-cells are a subset of T-cells defined by the genetic composition of their T Cell Receptor (TCR). γδ T-cells account for up to 10% of circulating lymphocytes and operate at the interface between innate and adaptive immunity. γδ T-cells recognize genomic, metabolic, and signaling perturbations associated with the transformed state. γδT-cells release perforin and granzymes, express both FAS and TRAIL, engage in Fc receptor-dependent effector functions and produce a range of immunomodulatory cytokines, including tumor necrosis factor (TNF) and interferon (IFN)-γ. γδ T-cells act as efficient antigen-presenting cells, enabling the perpetuation of immune attack through adaptive mechanisms. Finally, since these cells are not HLA-restricted, they do not elicit graft versus host disease.

Vγ9Vδ2 cells have endogenous cytotoxicity against various tumors; following activation, they can acquire phenotypic characteristics of professional antigen-presenting cells (γδ-APCs), including capacity for cross presentation of tumor-associated antigens. γδ T cells of the Vδ1 subtype have naturally more naive memory ($T_{naive}$) phenotype, a reduced susceptibility to activation-induced cell death, and their natural residency in tissues.

Unlike αβ T-cells, most γδ T cells lack CD4 and CD8 and share a number of markers associated with natural killer cells or antigen-presenting cells such as Fc gamma RIII/CD16 and Toll-like receptors. Cell markers typically associated with γδ T-cells or which γδ T-cells are positive for include TCR γ/δ, CD2, CD3, CD7, CD16, CXCR4, and NKG2D. γδ T-cells do not express or are negative for TCR α/β.

Exhaustion Markers

In some aspects of the invention, the T-cell compositions of the present disclosure may be further selected (or conditioned) for the presence or lack of one or more markers associated with, for example, maturation or exhaustion.

T cell exhaustion ($T_{ex}$) is a state of dysfunction that results from persistent antigen and inflammation, both of which commonly occur in cancer tissue. The reversal or prevention of exhaustion is a major area of research for cancer immunotherapy. $T_{ex}$ cell populations can be analyzed using multiple phenotypic parameters, either alone or in combination.

In some aspects, the cell composition in the fixed ratios described herein has less than about 15% of cells expressing a marker associated with $T_{ex}$. In some embodiments, the cell compositions have less than about 10% of cells expressing a marker associated with $T_{ex}$. In some embodiments, the cell composition has less than 5% of cells expressing a marker associated with $T_{ex}$. In some embodiments, the cell composition has less than about 5%, 4%, 3%, 2%, 1% or less of cells expressing a marker associated with $T_{ex}$.

Hallmarks commonly used to monitor T cell exhaustion are known in the art and include, but are not limited to, programmed cell death-1 (PD-1), CTLA-4/CD152 (Cytotoxic T-Lymphocyte Antigen 4), LAG-3 (Lymphocyte activation gene-3; CD223), TIM-3 (T cell immunoglobulin and mucin domain-3), 2B4/CD244/SLAMF4, CD160, and TIGIT (T cell Immunoreceptor with Ig and ITIM domains).

PD-1 (Programmed Death-1 receptor) is a key regulator of the threshold of immune response and peripheral immune tolerance. It is expressed on activated T cells, B cells, monocytes, and dendritic cells and binds to PD-L1 or PD-L2. PD-1 ligation induces co-inhibitory signals in T cells promoting their apoptosis, anergy, and functional exhaustion.

In some aspects of the invention, provided herein is a cell composition in the fixed ratios described herein, wherein the population has less than about 15% of cells expressing PD-1. In some embodiments, the composition has less than about 10% of cells expressing PD-1. In some embodiments, the composition of has less than about 5% of cells expressing PD-1. In some embodiments, the composition has less than about 5%, 4%, 3%, 2%, 1% or less of cells expressing PD-1.

CTLA-4/CD152 (Cytotoxic T-Lymphocyte Antigen 4) is a transmembrane T cell inhibitory molecule that is expressed as a covalent homodimer. CTLA-4 is recruited from intracellular vesicles to the immunological synapse beginning 1-2 days after T cell activation. It forms a linear lattice with B7-1 on APC, inducing negative regulatory signals and ending CD28-dependent T cell activation. Mice deleted for CTLA-4 develop lethal autoimmune reactions due to continued T cell activation and poor control by regulatory T cells which constitutively express CTLA-4.

In some aspects of the invention, provided herein is a cell composition described herein wherein the population has less than about 15% of cells expressing CTLA-4. In some embodiments, the composition has less than about 10% of cells expressing CTLA-4. In some embodiments, the composition has less than 5% of cells expressing CTLA-4. In some embodiments, the composition has less than about 5%, 4%, 3%, 2%, 1% or less of cells expressing CTLA-4.

LAG-3 (Lymphocyte activation gene-3; CD223) is a transmembrane protein that binds to MHC class II molecules and negatively regulates T cell receptor signaling. It is expressed on activated T cells, NK cells, and plasmacytoid dendritic cells (pDC). LAG-3 limits the expansion of activated T cells and pDC in response to select stimuli. Proteolytic shedding of LAG-3 enables normal T cell activation by removing the negative regulation. Binding of a homodimerized soluble LAG-3/Ig fusion protein to MHC class II molecules induces maturation of immature DC as well as secretion of pro-inflammatory cytokines by cytotoxic CD8$^+$ T cells and NK cells.

In some aspects of the invention, provided herein is a cell composition in the fixed ratios described herein wherein the population of cells has less than about 15% of cells expressing LAG-3. In some embodiments, the composition has less than about 10% of cells expressing LAG-3. In some embodiments, the composition has less than about 5% of cells expressing LAG-3. In some embodiments, the composition has less than about 5%, 4%, 3%, 2%, 1% or less of cells expressing LAG-3.

TIM-3 (T cell immunoglobulin and mucin domain-3), also known as HAVCR2 is an immunosuppressive protein that enhances tolerance and inhibits anti-tumor immunity. It is upregulated on several populations of activated myeloid cells (macrophage, monocyte, dendritic cell, microglia, mast cell) and T cells (Th1, CD8$^+$, NK, $T_{reg}$). TIM-3 ligation by Galectin-9 attenuates CD8$^+$ and Th1 cell responses and promotes the activity of $T_{reg}$ and myeloid derived suppressor cells. Dendritic cell-expressed TIM-3 dampens inflammation by enabling the phagocytosis of apoptotic cells and the cross-presentation of apoptotic cell antigens. TIM-3 also binds the alarmin HMGB1, thereby preventing the activation of TLRs in response to released tumor cell DNA.

In some aspects of the invention, provided herein is a cell composition in the fixed ratios described herein wherein the composition has less than about 15% of cells expressing TIM-3. In some embodiments, the composition has less than about 10% of cells expressing TIM-3. In some embodiments, the composition has less than about 5% of cells expressing TIM-3. In some embodiments, the composition has less than about 5%, 4%, 3%, 2%, 1% or less of cells expressing TIM-3.

2B4, also known as CD244, is a cell surface glycoprotein belonging to the CD2 subgroup of the immunoglobulin superfamily. It acts as a high-affinity receptor for CD48. It is expressed by natural killer (NK) cells and CD8$^+$ T cell subsets. It can regulate killing by CD8$^+$ T cells and NK cells, and IFN-gamma secretion by NK cells. It may also regulate NK cell and T cell proliferation.

In some aspects of the invention, provided herein is a cell composition in the fixed ratios described herein, wherein the composition has less than about 15% of cells expressing 2B4. In some embodiments, the composition has less than about 10% of cells expressing 2B4. In some embodiments, the composition has less than about 5% of cells expressing 2B4. In some embodiments, the composition has less than about 5%, 4%, 3%, 2%, 1% or less of cells expressing 2B4.

CD160 is a GPI-anchored glycoprotein with one Ig-like V-type domain. On a subpopulation of cytolytic T cells and NK cells, CD160 functions as a broad specificity receptor for MHC class I and related molecules. When expressed on vascular endothelial cells, CD160 propagates anti-angiogenic signals and promotes apoptosis.

In some aspects of the invention, provided herein is a T-cell composition described herein, wherein the cell compositon has less than about 15% of cells expressing CD160. In some embodiments, the composition has less than about 10% of cells expressing CD160. In some embodiments, the composition has less than about 5% of cells expressing CD160. In some embodiments, the composition has less than about 5%, 4%, 3%, 2%, 1% or less of cells expressing CD160.

TIGIT (T cell Immunoreceptor with Ig and ITIM domains), also called Vstm3, Vsig9, and WUCAM, is a transmembrane protein in the CD28 family of the Ig superfamily proteins. TIGIT is expressed on NK cells and subsets of activated, memory and regulatory T cells, and particularly on follicular helper T cells within secondary lymphoid organs. It binds to CD155/PVR/Necl-5 and Nectin-2/CD112/PVRL2 on dendritic cells (DC) and endothelium. Binding of TIGIT by DC induces IL-10 release and inhibits IL-12 production. Ligation of TIGIT on T cells downregulates TCR-mediated activation and subsequent proliferation, while NK cell TIGIT ligation blocks NK cell cytotoxicity. CD155 and Nectin-2 also interact with DNAM-1/CD226 and CD96/Tactile, and TIGIT binding to CD155 can antagonize the effects of DNAM-1. Soluble TIGIT is able to compete with DNAM-1 for CD155 binding and attenuates T cell responses, while mice lacking TIGIT show increased T cell responses and susceptibility to autoimmune challenges.

In some aspects of the invention, provided herein is a T-cell composition described herein, wherein the cell composition has less than about 15% of cells expressing TIGIT. In some embodiments, the composition has less than about 10% of cells expressing TIGIT. In some embodiments, the composition has less than about 5% of cells expressing TIGIT. In some embodiments, the composition has less than about 5%, 4%, 3%, 2%, 1% or less of cells expressing TIGIT.

In some aspects of the invention, provided herein is a T-cell composition described herein, wherein the cell population has less than about 15% of cells expressing a marker associated with $T_{ex}$. In some embodiments, the composition has less than about 10% of cells expressing a marker associated with $T_{ex}$. In some embodiments, the composition has less than about 5% of cells expressing a marker associated with $T_{ex}$. In some embodiments, the composition has less than about 5%, 4%, 3%, 2%, 1% or less of cells expressing a marker associated with $T_{ex}$. In some embodiments, the $T_{ex}$ marker is PD-1. In some embodiments, the $T_{ex}$ marking is CTLA-4. In some embodiments, the $T_{ex}$ marker is TIM3. In some embodiments, the $T_{ex}$ is Lag3. In some embodiments, the $T_{ex}$ is 2B4. In some embodiments, the $T_{ex}$ is CD160. In some embodiments, the $T_{ex}$ is TIGIT. In some embodiments, the composition comprises less than 10% of TAA-Ls expressing one of PD-1, CTLA-4, TIM3, LAG3, 2B4, CD160, TIGIT, or a combination thereof. In some embodiments, the composition comprises less than 5% of TAA-Ls expressing one of PD-1, CTLA-4, TIM3, LAG3, 2B4, CD160, TIGIT, or a combination thereof. In some embodiments, the composition comprises less than about 5%, 4%, 3%, 2%, 1% or less of the cell population expressing one of PD-1, CTLA-4, TIM3, LAG3, 2B4, CD160, TIGIT, or a combination thereof.

Methods for identifying cells having these particular markers are well known in the art.

T-Cell Subpopulations in T-Cell Compositions

The T-cell composition of the present disclosure are comprised of multiple T-cell subpopulations each targeting an MMAA or TAA. The T-cell subpopulations used to create the T-cell compositions can be generated from a single population of cells, wherein the population is exposed to a pool of one or antigenic peptides for each of the targeted MMAAs and TAAs. Alternatively, each subpopulation is exposed to a one or more antigenic peptides from a single MMAA or TAA and combined in a single dosage form for administration, or each administered separately.

In some embodiments, the T-cell composition comprises T-cell subpopulations in a ratio or percentage reflective or correlative of the relative identified MMAA and TAA expression profile of the patient's multiple myeloma. In some embodiments, the T-cell subpopulations targeting each MMAA or TAA are in about an equal ratio, that is, that the composition comprises about equal numbers of T-cells activated to each of the targeted MMAAs or TAAs.

The ratios of the T-cell subpopulations in the composition may be selected based on the knowledge of the patient's tumor characteristics or the healthcare provider's best judgement. For example, if the composition comprises four T-cell subpopulations targeting BCMA, CS1, XBP1, and CD138, the T-cell composition may comprise about 25% of each T-cell subpopulation, or, a varied percentage of each T-cell subpopulation. In some embodiments, the percentage of each of the T-cell subpopulations is based on the MMAA and TAA expression profile of the subject with multiple myeloma.

In a particular embodiment, the T-cell composition comprises at least three T-cell subpopulations, wherein the T-cell subpopulations are specific to MMAAs selected from BCMA, CS1, XBP1, and CD138. In a particular embodiment, the T-cell composition comprises T-cell subpopulations specific to CS1, XBP1, and CD138. In a particular embodiment, the T-cell composition comprises T-cell subpopulations specific to BCMA, XBP1, and CD138. In a particular embodiment, the T-cell composition consists of T-cell subpopulations specific to BCMA, XBP1, and CS1. In a particular embodiment, the T-cell composition comprises T-cell subpopulations specific to BCMA, CS1, and CD138. In some embodiments, the composition further comprises at least one T-cell subpopulation specific to a TAA selected from WT1, PRAME, Survivin, and MAGE-A3.

In a particular embodiment, the T-cell composition comprises at least four T-cell subpopulations, wherein the T-cell subpopulations are specific to MMAAs BCMA, CS1, XBP1, and CD138. In a particular embodiment, the T-cell composition consists of T-cell subpopulations specific to BCMA, CS1, XBP1, and CD138. In some embodiments, the composition further comprises at least one T-cell subpopulation specific to a TAA selected from WT1, PRAME, Survivin, and MAGE-A3.

In a particular embodiment, the T-cell composition comprises at least five T-cell subpopulations, wherein the T-cell subpopulations are specific to MMAAs BCMA, CS1, XBP1, and CD138 and at least one TAA selected from PRAME, WT1, and Survivin. In a particular embodiment, the T-cell composition comprises T-cell subpopulations specific to BCMA, CS1, XBP1, CD138, and WT1. In a particular embodiment, the T-cell composition comprises T-cell subpopulations specific to BCMA, CS1, XBP1, CD138, and PRAME. In a particular embodiment, the T-cell composition comprises T-cell subpopulations specific to BCMA, CS1, XBP1, CD138, and Survivin. In some embodiments, the composition further comprises at least one additional T-cell subpopulation specific to MAGE-A3.

In a particular embodiment, the T-cell composition comprises at least six T-cell subpopulations, wherein the T-cell subpopulations are specific to MMAAs BCMA, CS1, XBP1, and CD138 and at least two TAAs selected from PRAME, WT1, and Survivin. In a particular embodiment, the T-cell composition comprises T-cell subpopulations specific to BCMA, CS1, 30 XBP1, CD138, WT1, and PRAME. In a particular embodiment, the T-cell composition comprises T-cell subpopulations specific to BCMA, CS1, XBP-1, CD138, WT1, and Survivin. In a particular embodiment, the T-cell composition comprises T-cell subpopulations specific to BCMA, CS1, XBP1, CD138, PRAME, and Survivin. In some embodiments, the composition further comprises at least one additional T-cell subpopulation specific to MAGE-A3.

In a particular embodiment, the T-cell composition comprises at least seven T-cell subpopulations, wherein the T-cell subpopulations are specific to MMAAs BCMA, CS1, XBP1, and CD138 and TAAs PRAME, WT1, and Survivin. In a particular embodiment, the T-cell composition consists of T-cell subpopulations specific to BCMA, CS1, XBP1, CD138, WT1, PRAME, and Survivin. In some embodiments, the composition further comprises at least one additional T-cell subpopulation specific to MAGE-A3.

In a particular embodiment, the T-cell composition comprises at least eight T-cell subpopulations, wherein the T-cell subpopulations are specific to MMAAs BCMA, CS1, XBP1, and CD138 and TAAs PRAME, WT1, Survivin, and MAGE-A3. In a particular embodiment, the T-cell composition consists of T-cell subpopulations specific to BCMA, CS1, XBP1, CD138, WT1, PRAME, Survivin, and MAGE-A3.

In some embodiments, the mononuclear cell sample from which the activated T-cell subpopulations are derived is from the human to which the composition is also administered (autologous).

In some embodiments, the activated T-cell composition is derived from a cell donor (allogeneic). In certain embodiments, the allogeneic T-cell composition has at least one HLA allele or HLA allele combination in common with the patient. In certain embodiments, the allogeneic T-cell composition has more than one HLA allele or HLA allele combination in common with the patient. In certain embodiments, the tumor-associated antigen activity of the T-cell composition is through at least one HLA allele or HLA allele combination in common with the patient. In certain embodiments, the allogeneic T-cell composition is recognized through the same shared HLA restriction. In certain embodiments, the allogeneic T-cell composition is recognized through different shared HLA restrictions.

Method of Treating a Patient with a Plasma Cell Dyscrasia by Administering a T-Cell Composition Described Herein The invention includes a method to treat a patient with a plasma cell dyscrasia, for example multiple myeloma, typically a human, by administering an effective amount of a T-cell composition described herein. As provided herein, the described activated T-cell compositions may be administered to a human suffering from a plasma cell dyscrasia, including but not limited to multiple myeloma. Plasma cell dyscrasias are cancers of the plasma cells. They result from the abnormal proliferation of a monoclonal population of plasma cells that may or may not secrete detectable levels of a monoclonal immunoglobulin or paraprotein commonly referred to as M (myeloma) protein. Non-limiting examples of plasma cell dyscrasias include monoclonal gammopathy of undermined significance (MGUS), Non-IgM MGUS, light chain MGUS, monoclonal gammopathy of renal significance, smoldering multiple myeloma (MM), Non-IgM smoldering multiple myeloma, smoldering Waldenström's macroglobulinemia, light chain smoldering multiple myeloma, amyloidosis, AL amyloidosis, AH amyloidosis, POEMS (Polyneuropathy, Organomegaly, Endocrinopathy, Plasma cell) disorder, cryoglobulinemia, solitary plasmacytoma, non-secretory multiple myeloma, plasma cell myeloma with concomitant chronic lymphocytic leukemia/monoclonal β-cell lymphocytosis, Waldenström macroglobulinemia (WM), multiple myeloma (MM), light chain multiple myeloma, plasma cell leukemia, α Heavy chain disease, γ Heavy chain disease, and μ Heavy chain disease.

Methods for administration of cells for adoptive cell therapy are known and may be used in connection with the provided methods and activated T-cell compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338, each of which are incorporated by reference in their entireties.

The dose administered may vary. In some embodiments, the T-cell composition is administered to a patient, such as a human in a dose ranging from about $1\times10^6$ cells/m$^2$ to about $1\times10^8$ cells/m$^2$. The dose can be a single dose, for example, comprising the combination of all of the T-cell subpopulations, or multiple separate doses, wherein each dose comprises a separate T-cell subpopulation and the collective separate doses of T-cell subpopulations comprise the total T-cell composition. In some embodiments, the T-cell composition dosage is about $1\times10^6$ cells/m$^2$, $2\times10^6$ cells/m$^2$, $3\times10^6$ cells/m$^2$, $4\times10^6$ cells/m$^2$, $5\times10^6$ cells/m$^2$, $6\times10^6$ cells/m$^2$, $7\times10^6$ cells/m$^2$, $8\times10^6$ cells/m$^2$, $9\times10^6$ cells/m$^2$, $1\times10^7$ cells/m$^2$, $2\times10^7$ cells/m$^2$, $3\times10^7$ cells/m$^2$, $4\times10^7$ cells/m$^2$, $5\times10^7$ cells/m$^2$, $6\times10^7$ cells/m$^2$, $7\times10^7$ cells/m$^2$, $8\times10^7$ cells/m$^2$, $9\times10^7$ cells/m$^2$, or about $1\times10^8$ cells/m$^2$.

The T-cell composition may be administered by any suitable method. In some embodiments, the T-cell composition is administered to a patient, such as a human as an infusion and in a particular embodiment, an infusion with a total volume of 1 to 10 cc. In some embodiments, the T-cell composition is administered to a patient as a 1, 2, 3, 4, 5, 6, 7, 8, 9, or 10 cc infusion. In some embodiments, the T-cell composition when present as an infusion is administered to a patient over 10, 20, 30, 40, 50, 60 or more minutes to the patient in need thereof.

In some embodiments, a patient receiving an infusion has vital signs monitored before, during, and 1-hour post infusion of the T-cell composition. In certain embodiments, patients with stable disease (SD), partial response (PR), or complete response (CR) up to 6 weeks after initial infusion may be eligible to receive additional infusions, for example, 1, 2, 3, 4, 5, 6, 7, 8, 9 or 10 additional infusions several weeks apart, for example, up to about 2, 3, 4, 5, 6, 7, 8, 9 or 10 weeks apart.

In some aspects provided herein, the subject is first administered an activated T-cell composition comprising T-cells activated to the TAAs WT1, PRAME, and Survivin or some combination thereof, and then, at a time point later, administered an activated T-cell composition comprising T-cell cells activated to MMAAs BCMA, XBP1, CS1, and CD138 or some combination thereof. In some embodiments, the composition further comprises at least one additional T-cell subpopulation specific to MAGE-A3.

In some aspects provided herein, the subject is first administered an activated T-cell composition comprising T-cells activated to the MMAAs BCMA, XBP1, CS1, and CD138 or some combination thereof, and then, at a time point later, administered an activated T-cell composition comprising T-cell cells activated to TAAs WT1, PRAME, and Survivin or some combination thereof. In some embodiments, the composition further comprises at least one additional T-cell subpopulation specific to MAGE-A3.

Method of Inducing an Antigen-Specific Immune Response in a Patient with a Plasma Cell Dyscrasia by Administering a T-Cell Composition Described Herein Disclosed are methods of inducing an antigen-specific immune response in a patient with a plasma cell dyscrasia by administering a T-cell composition described herein. For example, the antigen-specific immune response can be a BCMA-, XBP1-, CS1-, or CD138-specific immune response or a combination thereof. In some aspects, the antigen-specific immune response can be WT1, PRAME, Survivin, or a combination thereof. As provided herein, the described activated T-cell compositions may be administered to a human suffering from a plasma cell dyscrasia, including but not limited to multiple myeloma. Plasma cell dyscrasias are cancers of the plasma cells. They result from the abnormal proliferation of a monoclonal population of plasma cells that may or may not secrete detectable levels of a monoclonal immunoglobulin or paraprotein commonly referred to as M (myeloma) protein. Non-limiting examples of plasma cell dyscrasias are those described herein.

In some embodiments, methods of inducing an antigen-specific immune response can comprise activating a T cell population to one or more MMAAs, TAAs or a combination thereof, forming an activated T cell population, and administering a T-cell composition to the patient, wherein the T-cell composition comprises the activated T cell population. In some embodiments, prior to activating a T cell population, the T cell population can be isolated from a donor in the methods described herein. In some embodiments, the T-cell composition can be a combination of MMAA activated T cells and TAA activated T cells. In some embodiments, separate T-cell composition can be administered—one for MMAA T-cells and one for TAA T-cells. The MMAA T-cell compositions can be specific to a single MM antigen or to a combination of MM antigens. The TAA T-cell compositions can be specific to a single tumor antigen or to a combination of tumor antigens.

Methods for administration of cells for adoptive cell therapy are known and may be used in connection with the provided methods and activated T-cell compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

The dose administered may vary. In some embodiments, the T-cell composition is administered to a patient, such as a human in a dose ranging from $1 \times 10^6$ cells/m2 to $1 \times 10^8$ cells/m2. The dose can be a single dose, for example, comprising the combination of all of the T-cell subpopulations, or multiple separate doses, wherein each dose comprises a separate T-cell subpopulation and the collective separate doses of T-cell subpopulations comprise the total T-cell composition. In some embodiments, the T-cell composition dosage is $1 \times 10^6$ cells/m², $2 \times 10^6$ cells/m², $3 \times 10^6$ cells/m², $4 \times 10^6$ cells/m², $5 \times 10^6$ cells/m², $6 \times 10^6$ cells/m², $7 \times 10^6$ cells/m², $8 \times 10^6$ cells/m², $9 \times 10^6$ cells/m², $1 \times 10^7$ cells/m², $2 \times 10^7$ cells/m², $3 \times 10^7$ cells/m², $4 \times 10^7$ cells/m², $5 \times 10^7$ cells/m², $6 \times 10^7$ cells/m², $7 \times 10^7$ cells/m², $8 \times 10^7$ cells/m², $9 \times 10^7$ cells/m², or $1 \times 10^8$ cells/m².

The T-cell composition may be administered by any suitable method. In some embodiments, the T-cell composition is administered to a patient, such as a human as an infusion and in a particular embodiment, an infusion with a total volume of 1 to 10 cc. In some embodiments, the T-cell composition is administered to a patient as a 1, 2, 3, 4, 5, 6, 7, 8, 9, or 10 cc infusion. In some embodiments, the T-cell composition when present as an infusion is administered to a patient over about 10, 20, 30, 40, 50, 60 or more minutes to the patient in need thereof.

In some embodiments, a patient receiving an infusion has vital signs monitored before, during, and 1-hour post infusion of the T-cell composition. In certain embodiments, patients with stable disease (SD), partial response (PR), or complete response (CR) up to 6 weeks after initial infusion may be eligible to receive additional infusions, for example, about 1, 2, 3, 4, 5, 6, 7, 8, 9 or 10 additional infusions several weeks apart, for example, up to about 2, 3, 4, 5, 6, 7, 8, 9 or 10 weeks apart.

In some aspects provided herein, the subject is first administered an activated T-cell composition comprising T-cells activated to the TAAs WT1, PRAME, and Survivin or some combination thereof, and then, at a time point later, administered an activated T-cell composition comprising T-cell cells activated to MMAAs BCMA, XBP1, CS1, and CD138 or some combination thereof. In some embodiments, the composition further comprises at least one additional T-cell subpopulation specific to MAGE-A3.

In some aspects provided herein, the subject is first administered an activated T-cell composition comprising T-cells activated to the MMAAs BCMA, XBP1, CS1, and CD138 or some combination thereof, and then, at a time point later, administered an activated T-cell composition comprising T-cell cells activated to TAAs WT1, PRAME, and Survivin or some combination thereof. In some embodiments, the composition further comprises at least one additional T-cell subpopulation specific to MAGE-A3.

Determining the Tumors' Antigen Expression Profile

Determining an MMAA and TAA expression profile can be performed by any method known in the art. Non-limiting exemplary methods for determining a tumor-associated antigen expression profile can be found in Ding et al., Cancer Bio Med (2012) 9: 73-76; Qin et al., Leukemia Research (2009) 33(3) 384-390; and Weber et al., Leukemia (2009) 23: 1634-1642.

In some embodiments, MMAA/TAA expression profiles are generated from a sample collected from a patient with multiple myeloma. In some embodiments, the sample is selected from a group consisting of blood, bone marrow, and tumor biopsy.

In some embodiments, the MMAA/TAA expression profile is determined from a blood sample of a patient with multiple myeloma. In some embodiments, the MMAA/TAA expression profile is determined from a bone marrow sample of a patient with multiple myeloma. In some embodiments, the MMAA/TAA expression profile is determined from a tumor biopsy sample of a patient with multiple myeloma.

In some embodiments, genetic material is extracted from the sample collected from a patient with multiple myeloma.

In some embodiments, the genetic material is selected from a group consisting of total RNA, messenger RNA and genomic DNA.

After extraction of genetic material, quantitative reverse transcriptase polymerase chain reaction (qPCR) is performed on the genetic material utilizing primers developed from MMAAs/TAAs of interest.

The patient's tumor cells can be checked for reactivity against activated T-cell subpopulations and/or the T-cell composition of the present disclosure using any known methods, including cytotoxicity assays described herein.

Determining the Levels of Circulating MMAA/TAA-Specific T-Cells

Determining the levels of circulating MMAA/TAA-specific T-cells after infusion of the T-cell composition can be performed by any method known in the art. Non-limiting exemplary methods for determining levels of circulating MMAA/TAA-specific T-cells include Elispot assay, intracellular cytokine staining, multimer analysis, and TCR Sequencing and can be found in Chapuis et al., Sci Transl Med (2013) 5(174): 174ra27 and Hanley et al., Sci Transl Med (2015) 7(285): 285ra63, which are incorporated herein by reference. In some embodiments, levels of circulating MMAA/TAA-specific T-cells is determined from a sample collected from a patient with multiple myeloma treated with a T-cell composition. In some embodiments, the sample is selected from a group consisting of blood, peripheral blood mononuclear cells, and bone marrow.

In some embodiments, the levels of circulating MMAA/TAA-specific T-cells is determined from a blood sample of a patient with a multiple myeloma treated with a T-cell composition. In some embodiments, the levels of circulating MMAA/TAA-specific T-cells is determined from a peripheral blood mononuclear cell sample of a patient with multiple myeloma treated with a T-cell composition. In some embodiments, the levels of circulating MMAA/TAA-specific T-cells is determined from a bone marrow sample of a patient multiple myeloma treated with a T-cell composition.

In some embodiments, the levels of circulating MMAA/TAA-specific T-cells is determined using an Elispot assay. In some embodiments, the levels of circulating MMAA/TAA-specific T-cells is determined using an intracellular cytokine staining assay. In some embodiments, the levels of circulating MMAA/TAA-specific T-cells is determined using multimer analysis. In some embodiments, the levels of circulating MMAA/TAA-specific T-cells is determined by TCR Sequencing.

Product Release Testing and Characterization of T-Cell Compositions

Prior to infusion, the activated T-cell composition may be characterized for safety and release testing. Product release testing, also known as lot or batch release testing, is an important step in the quality control process of drug substances and drug products. This testing verifies that a T-cell composition meets a pre-determined set of specifications. Pre-determined release specifications for the T-cell composition includes confirmation that the cell product is >70% viable, has <5.0 EU/ml of endotoxin, is negative for aerobic, anaerobic, fungal pathogens and mycoplasma, and lacks reactivity to allogeneic PHA blasts, for example, with less than 10% lysis to PHA blasts. The phenotype of the T-cell composition may be determined with requirements for clearance to contain, in one non-limiting embodiment, <2% dendritic cells and <2% B cells. The HLA Identity between the composition and the donor is also confirmed.

Antigen specificity of the T-cell composition can be tested via an Interferon-γ Enzyme-Linked Immunospot (IFNγ ELISpot) assay. Other cytokines can also be utilized to measure antigen specificity including TNFα and IL-4. Pre-stimulated effector cells and target cells pulsed with the MMAA or TAA of interest are incubated in a 96-well plate (pre-incubated with anti-INF-γ antibody) at an E/T ratio of 1:2. They are compared with no-MMAA/TAA control, an irrelevant peptide not used for T-cell generation, and SEB as a positive control. After washing, the plates are incubated with a biotinylated anti-IFN-x antibody. Spots are detected by incubating with streptavidin-coupled alkaline phosphatase and substrate. Spot forming cells (SFCs) are counted and evaluated using an automated plate reader.

The phenotype of the T-cell composition can be determined by extracellular antibody staining with anti-CD3, CD4, CD8, CD45, CD19, CD16, CD56, CD14, CD45, CD83, HLA-DR, TCRαβ, TCRγδ and analyzed on a flow cytometer. Annexin-V and PI antibodies can be used as viability controls, and data analyzed with FlowJo Flow Cytometry software (Treestar, Ashland, OR, USA).

The lytic capacity of T-cell compositions can be evaluated via $^{51}$Chromium ($^{51}$Cr) and Europium (Eu)-release cytotoxicity assays to test recognition and lysis of target cells by the T-cell subpopulations.

Typically, activated primed T-cells (effector cells) can be tested against $^{51}$Cr-labeled target cells at effector-to-target ratios of, for example, 40:1, 20:1, 10:1, and 5:1. Cytolytic activity can be determined by measuring $^{51}$Cr release into the supernatant on a gamma-counter. Spontaneous release is assessed by incubating target cells alone, and maximum lysis by adding 1% Triton X-100. Specific lysis was calculated as: specific lysis (%)=(experimental release—spontaneous release)/(maximum release—spontaneous release)× 100.

Europium-release assays can also be utilized to measure the lytic capacity of T-cell compositions. This is a non-radioactive alternative to the conventional Chromium-51 ($^{51}$Cr) release assay and works on the same principle as the radioactive assay. Target cells are first loaded with an acetoxymethyl ester of BATDA. The ligand penetrates the cell membrane quickly. Within the cell, the ester bonds are hydrolyzed to form a hydrophilic ligand (TDA), which no longer passes through the cell membrane. If cells are lysed by an effector cell, TDA is released outside the cell into the supernatant. Upon addition of Europium solution to the supernatant, Europium can form a highly fluorescent and stable chelate with the released TDA (EuTDA). The measured fluorescence signal correlates directly with the number of lysed cells in the cytotoxicity assay.

Specific lysis was calculated as: specific lysis (%)= (experimental release–spontaneous release)/ (maximum release–spontaneous release)×100.

Monitoring

Following administration of the cells, the biological activity of the administered T-cell populations in some embodiments is measured, e.g., by any of a number of known methods. Parameters to assess include specific binding of a T-cell or other immune cell to antigen, in vivo, e.g., by imaging, or ex vivo, e.g., by ELISA or flow cytometry. In certain embodiments, the ability of the administered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004), all incorporated herein by reference. In certain embodiments, the biological activity of the cells is measured by assaying expression and/or secretion of one or more cytokines, such as IFNγ, IL-2, and TNF. In some aspects the biological activity is measured by assessing clinical outcome, such as reduction in tumor burden or load.

Combination Therapies

In some aspects of the invention, the T-cell compositions disclosed herein can be beneficially administered in combination with another therapeutic regimen for beneficial, additive, or synergistic effects.

In some embodiments, the T-cell composition is administered in combination with another therapy to treat a hematological malignancy. The second therapy can be a pharmaceutical or a biologic agent (for example an antibody) to increase the efficacy of treatment with a combined or synergistic approach.

In some embodiments, the additional therapy is a monoclonal antibody (MAb). Some MAbs stimulate an immune response that destroys tumor cells. Similar to the antibodies produced naturally by B cells, these MAbs "coat" the tumor cell surface, triggering its destruction by the immune system. FDA-approved MAbs of this type include rituximab, which targets the CD20 antigen found on non-Hodgkin lymphoma cells, and alemtuzumab, which targets the CD52 antigen found on β-cell chronic lymphocytic leukemia (CLL) cells. Rituximab may also trigger cell death (apoptosis) directly. Another group of MAbs stimulates an anti-tumor immune response by binding to receptors on the surface of immune cells and inhibiting signals that prevent immune cells from attacking the body's own tissues, including tumor cells. Other MAbs interfere with the action of proteins that are necessary for tumor growth. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR). MAbs that bind to cell surface growth factor receptors prevent the targeted receptors from sending their normal growth-promoting signals. They may also trigger apoptosis and activate the immune system to destroy tumor cells. Another group of tumor therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a tumor cell, and the cell-killing substance is taken up by the cell. FDA-approved conjugated MAbs that work this way include 90Y-ibritumomab tiuxetan, which targets the CD20 antigen to deliver radioactive yttrium-90 to B-cell non-Hodgkin lymphoma cells; $^{131}$I-tositumomab, which targets the CD20 antigen to deliver radioactive $^{131}$I to non-Hodgkin lymphoma cells.

In some embodiments, the additional agent is an immune checkpoint inhibitor (ICI), for example, but not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combinations thereof.

In some embodiments, the immune checkpoint inhibitor is a PD-1 inhibitor that blocks the interaction of PD-1 and PD-L1 by binding to the PD-1 receptor, and in turn inhibits immune suppression. In some embodiments, the immune checkpoint inhibitor is a PD-1 immune checkpoint inhibitor selected from nivolumab (Opdivo®), pembrolizumab (Keytruda®), pidilizumab, AMP-224 (AstraZeneca and MedImmune), PF-06801591 (Pfizer), MEDI0680 (Astra-Zeneca), PDR001 (Novartis), REGN2810 (Regeneron), MGA012 (MacroGenics), BGB-A317 (BeiGene) SHR-12-1 (Jiangsu Hengrui Medicine Company and Incyte Corporation), TSR-042 (Tesaro), and the PD-L1/VISTA inhibitor CA-170 (Curis Inc.).

In some embodiments, the immune checkpoint inhibitor is the PD-1 immune checkpoint inhibitor nivolumab (Opdivo®). In another aspect of this embodiment, the immune checkpoint inhibitor is the PD-1 immune checkpoint inhibitor pembrolizumab (Keytruda®). In an additional aspect of this embodiment, the immune checkpoint inhibitor is the PD-1 immune checkpoint inhibitor pidilizumab (Medivation).

In some embodiments, the immune checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, atezolizumab, durvalumab, KN035CA-170 (Curis Inc.), and LY3300054 (Eli Lilly).

In some embodiments, the immune checkpoint inhibitor is the PD-L1 immune checkpoint inhibitor atezolizumab (Tecentriq®). In another aspect of this embodiment, the immune checkpoint inhibitor is durvalumab (AstraZeneca and MedImmune). In yet another aspect of the embodiment, the immune checkpoint inhibitor is KN035 (Alphamab). An additional example of a PD-L1 immune checkpoint inhibitor is BMS-936559 (Bristol-Myers Squibb).

In some aspects of this embodiment, the immune checkpoint inhibitor is a CTLA-4 immune checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In some embodiments, the CTLA-4 immune checkpoint inhibitor is ipilimumab (Yervoy®) administered in an effective amount In another embodiment, the immune checkpoint inhibitor is a LAG-3 immune checkpoint inhibitor. Examples of LAG-3 immune checkpoint inhibitors include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). In yet another aspect of this embodiment, the immune checkpoint inhibitor is a TIM-3 immune checkpoint inhibitor. A specific TIM-3 inhibitor includes, but is not limited to, TSR-022 (Tesaro).

Other immune checkpoint inhibitors for use in combination with the invention described herein include, but are not limited to, B7-H3/CD276 immune checkpoint inhibitors such as MGA217, indoleamine 2,3-dioxygenase (ID.O) immune checkpoint inhibitors such as Indoximod and INCB024360, killer immunoglobulin-like receptors (KIRs) immune checkpoint inhibitors such as Lirilumab (BMS-986015), carcinoembryonic antigen cell adhesion molecule (CEACAM) inhibitors (e.g., CEACAM-1, -3 and/or -5). Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10: 1371/journal-.pone.0021146), or cross-reacts with CEACAM-1 and CEACAM-5 as described in, e.g., WO 2013/054331 and US 2014/0271618. Still other checkpoint inhibitors can be molecules directed to B and T lymphocyte attenuator molecule (BTLA), for example as described in Zhang et al., Clin Exp Immunol. 2011 January; 163(1): 77-87.

Current chemotherapeutic drugs that may be used in combination with the T-cell composition described herein include cytarabine (cytosine arabinoside or ara-C) and the anthracycline drugs (such as daunorubicin/daunomycin, idarubicin, and mitoxantrone). Some of the other chemo drugs that may be used include: Cladribine (Leustatin®, 2-CdA), Fludarabine (Fludara®), Topotecan, Etoposide (VP-16), 6-thioguanine (6-TG), Hydroxyurea (Hydrea®), corticosteroid drugs, such as prednisone or dexamethasone (Decadron®), Methotrexate (MTX), 6-mercaptopurine (6-MP), Azacitidine (Vidaza®), Decitabine (Dacogen®). Additional drugs include dasatinib and checkpoint inhibitors such as nivolumab, pembrolizumab, and atezolizumab.

Current chemotherapeutic drugs that may be used in combination with the T-cell composition described herein include: purine analogs such as fludarabine (Fludara®), pentostatin (Nipent®), and cladribine (2-CdA, Leustatin®), and alkylating agents, which include chlorambucil (Leukeran®) and cyclophosphamide (Cytoxan®) and bendamustine (Treanda®). Other drugs include doxorubicin (Adriamycin®), methotrexate, oxaliplatin, vincristine (Oncovin®), etoposide (VP-16), and cytarabine (ara-C). Other drugs include Rituximab (Rituxan), Obinutuzumab (Gazyva™), Ofatumumab (Arzerra®), Alemtuzumab (Campath®) and Ibrutinib (Imbruvica™) Current chemotherapeutic drugs that may be used in combination with the T-cell composition described herein include: Interferon, imatinib (Gleevec), the chemo drug hydroxyurea (Hydrea®), cytarabine (Ara-C), busulfan, cyclophosphamide (Cytoxan®), and vincristine (Oncovin®) and omacetaxine (Synribo®).

Current chemotherapeutic drugs that may be used in combination with the T-cell composition described herein include Deferasirox (Exjade®), cytarabine with Idarubicin, cytarabine with topotecan, and cytarabine with fludarabine, Hydroxyurea (hydroxycarbamate, Hydrea®), azacytidine (Vidaza®) and decitabine (Dacogen®).

Current chemotherapeutic drugs that may be used in combination with the T-cell composition described herein include those used for multiple myeloma include pomalidomide (Pomalyst®), Carfilzomib (Kyprolis™), Everolimus (Afinitor®), dexamethasone (Decadron), prednisone and methylprednisolone (Solu-medrol®) and hydrocortisone.

Current chemotherapeutic drugs that may be used in combination with the T-cell composition described herein include Brentuximab vedotin (Adcetris™): anti-CD-30, Rituximab, Adriamycin® (doxorubicin), Bleomycin, Vinblastine, and Dacarbazine (DTIC).

Current chemotherapeutic drugs that may be used in combination with the T-cell composition described herein include Rituximab (Rituxan®), Ibritumomab (Zevalin®), tositumomab (Bexxar®), Alemtuzumab (Campath®) (CD52 antigen), Ofatumumab (Arzerra®), Brentuximab vedotin (Adcetris®) and Lenalidomide (Revlimid®).

A more general list of suitable chemotherapeutic agents includes, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cytarabine, Cytarabine, cytochalasin B, Cytoxan, Dacarbazine, Dactinomycin, dactinomycin (formerly actinomycin), daunorubicin HCl, daunorubicin citrate, denileukin diftitox, Dexrazoxane, Dibromomannitol, dihydroxy anthracin dione, Docetaxel, dolasetron mesylate, doxorubicin HCl, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCl, glucocorticoids, goserelin acetate, gramicidin D, granisetron HCl, hydroxyurea, Idarubicin HCl, ifosfamide, interferon α-2b, irinotecan HCl, letrozole, leucovorin calcium, leuprolide acetate, levamisole HCl, lidocaine, lomustine, maytansinoid, mechlorethamine HCl, medroxyprogesterone acetate, megestrol acetate, melphalan HCl, mercaptopurine, mesna, methotrexate, methyltestosterone, mithramycin, mitomycin C, mitotane, mitoxantrone, nilutamide, octreotide acetate, ondansetron HCl, paclitaxel, pamidronate disodium, pentostatin, pilocarpine HCl, plimycin, polifeprosan 20 with carmustine implant, porfimer sodium, procaine, procarbazine HCl, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with the T-cell compositions disclosed herein can include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

In some aspects of the present disclosure, the T-cell compositions disclosed herein are administered in combination with at least one immunosuppressive agent. The immunosuppressive agent may be selected from the group consisting of a calcineurin inhibitor, e.g. a cyclosporin or an ascomycin, e.g. Cyclosporin A (NEORAL®), tacrolimus, a mTOR inhibitor, e.g. rapamycin or a derivative thereof, e.g. Sirolimus (RAPAMUNE®), Everolimus (Certican®), temsirolimus, biolimus-7, biolimus-9, a rapalog, e.g. azathioprine, campath 1H, a S1P receptor modulator, e.g. fingolimod or an analogue thereof, an anti-IL-8 antibody, mycophenolic acid. or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, 15-deoxyspergualin, tresperimus, Leflunomide ARAVA®, anti-CD25, anti-IL2R, Basiliximab (SIMULECT®), Daclizumab (ZENAPAX®), mizorbine, methotrexate, dexamethasone, pimecrolimus (Elidel®), abatacept, belatacept, etanercept (Enbrel®), adalimumab (Humira®), infliximab (Remicade®), an anti-LFA-1 antibody, natalizumab (Antegren®), Enlimomab, ABX-CBL, antithymocyte immunoglobulin, siplizumab, and efalizumab.

In some aspects of the present disclosure, the T-cell composition described herein can be administered in combination with at least one anti-inflammatory agent. The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid., mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidaβ sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

In some aspects of the present disclosure, the T-cell composition described herein can be administered in combination with at least one immunomodulatory agent.

Methods of Manufacturing T-Cell Compositions Described Herein

T-cell compositions specific for a targeted MMAA or TAA described herein can be generated using any known method in the art or as described herein. Activated T-cell subpopulations that recognize at least one epitope of an antigen of a tumor can be generated by any method known in the art or as described herein. Non-limiting exemplary methods of generating activated T-cell subpopulations that recognize at least one epitope of an antigen of a tumor can be found in, for example Shafer et al., Leuk Lymphoma (2010) 51(5):870-880; Cruz et al., Clin Cancer Res., (2011) 17(22): 7058-7066; Quintarelli et al., Blood (2011) 117(12): 3353-3362; and Chapuis et al., Sci Transl Med (2013) 5(174):174ra27, all incorporated herein by reference.

Generally, generating the T-cell compositions of the present disclosure may involve (i) collecting a peripheral blood mononuclear cell product from a donor; (ii) determining the HLA subtype of the mononuclear cell product; (iii) separating the monocytes and the lymphocytes of the mononuclear cell product; (iv) generating and maturing dendritic cells (DCs) from the monocytes; (v) pulsing the DCs with a MMAA or TAA described herein; (vi) optionally carrying out a CD45RA$^+$ selection to isolate naïve lymphocytes; (vii) stimulating the naïve lymphocytes with the peptide-pulsed DCs in the presence of a cytokine cocktail; (viii) repeating the T cell stimulation with fresh peptide-pulsed DCs or other peptide-pulsed antigen presenting cells in the presence of a cytokine cocktail; (ix) harvesting the MMAA or TAA activated T-cells and cryopreserving for future use.

The T-cell composition can be administered as a single composition comprising a multiplicity of T-cell subpopulations activated to each of the particular MMAAs and/or TAAs targeted. In some embodiments, the subpopulations of T-cells are derived through the ex vivo expansion of a single population of T-cells, wherein the single population of T-cells are exposed to a pool of one or more antigenic peptides (epitopes) of each of the selected MMAAs and TAAs.

Alternatively, the T-cell compositions can be derived through the ex vivo expansion of separate T-cell populations exposed to one or more antigenic peptides of each of the selected MMAAs and TAAs separately, wherein following activation and expansion, the separate T-cell subpopulations are then combined into a single composition for administration. In another alternative, the T-cell compositions can be derived through the ex vivo expansion of separate T-cell populations exposed to one or more antigenic peptides of each of the selected MMAAs and TAAs separately, wherein following activation and expansion, the separate T-cell populations are each individually administered to the subject. In some embodiments, the separate T-cell populations are derived from the same donor source. In some embodiments, the separate T-cell populations are derived from one or more different donor sources.

Collecting a Peripheral Blood Mononuclear Cell Product from a Donor

The generation of T-cell populations specific to the MMAAs and TAAs described herein generally requires a peripheral blood mononuclear cell (PBMC) product from a donor, either an allogeneic or autologous donor, as a starting material. Isolation of PBMCs is well known in the art. Non-limiting exemplary methods of isolating PBMCs are provided in Grievink, H. W., et al. (2016) "Comparison of three isolation techniques for human peripheral blood mononuclear cells: Cell recovery and viability, population composition, and cell functionality," Biopreservation and BioBanking, which is incorporated herein by reference. The PBMC product can be isolated from whole blood, an apheresis sample, a leukapheresis sample, or a bone marrow sample provided by a donor. In some embodiments, the starting material is an apheresis sample, which provides a large number of initially starting mononuclear cells, potentially allowing a large number of different T-cell subpopulations to be generated. In some embodiments, the PBMC product is isolated from a sample containing peripheral blood mononuclear cells (PBMCs) provided by a donor. In some embodiments, the donor is a healthy donor. In some embodiments, the PBMC product is derived from cord blood. In some embodiments, the donor is the same donor providing stem cells for a hematopoietic stem cell transplant (HSCT).

Determining HLA Subtype

When the T-cell composition is generated from an allogeneic, healthy donor, the HLA subtype profile of the donor source is determined and characterized. Determining HLA subtype (i.e., typing the HLA loci) can be performed by any method known in the art. Non-limiting exemplary methods for determining HLA subtype can be found in Lange, V., et al., BMC Genomics (2014)15: 63; Erlich, H., Tissue Antigens (2012) 80:1-11; Bontadini, A., Methods (2012) 56:471-476; Dunn, P. P., Int J Immunogenet (2011) 38:463-473; and Hurley, C. K., "DNA-based typing of HLA for transplantation." in Leffell, M. S., et al., eds., Handbook of Human Immunology, 1997. Boca Raton: CRC Press, each independently incorporated herein by reference. Preferably, the HLA-subtyping of each donor source is as complete as possible.

In some embodiments, the determined HLA subtypes include at least 4 HLA loci, preferably HLA-A, HLA-B, HLA-C, and HLA-DRB1. In some embodiments, the determined HLA subtypes include at least 6 HLA loci. In some embodiments, the determined HLA subtypes include at least 6 HLA loci. In some embodiments, the determined HLA subtypes include all of the known HLA loci. In general, typing more HLA loci is preferable for practicing the invention, since the more HLA loci that are typed, the more likely the allogeneic T-cell subpopulations selected will have highest activity relative to other allogeneic T-cell subpopulations that have HLA alleles or HLA allele combinations in common with the patient or the diseased cells in the patient.

Separating the Monocytes and the Lymphocytes of the Peripheral Blood Mononuclear Cell Product In general, the PBMC product may be separated into various cell-types, for example, into platelets, red blood cells, lymphocytes, and monocytes, and the lymphocytes and monocytes retained for initial generation of the T-cell composition. Methods for separating PBMCs are known in the art. Non-limiting exemplary methods of separating monocytes and lymphocytes include Vissers et al., J Immunol Methods. 1988 Jun. 13; 110(2):203-7 and Wahl et al., Current Protocols in Immunology (2005) 7.6A.1-7.6A.10, which are incorporated herein by reference. For example, the separation of the monocytes can occur by plate adherence, by CD14⁺ selection, or other known methods. The monocyte fraction is generally retained in order to generate dendritic cells used as an antigen presenting cell in the T-cell composition manufacture. The lymphocyte fraction of the PBMC product can be cryopreserved until needed, for example, aliquots of the lymphocyte fraction ($\sim$5$\times$10$^7$ cells) can be cryopreserved separately for both Phytohemagglutinin (PHA) Blast expansion and T-cell composition generation.

Generating Dendritic Cells

The generation of mature dendritic cells used for antigen presentation to prime T-cells is well known in the art. Non-limiting exemplary methods are included in Nair et al., "Isolation and generation of human dendritic cells." Current protocols in immunology (2012) 0 7: Unit7.32. doi:10.1002/0471142735.im0732s99 and Castiello et al., Cancer Immunol Immunother, 2011 Apr.;60(4):457-66, which are incorporated herein by reference. For example, the monocyte fraction can be plated into a closed system bioreactor such as the Quantum Cell Expansion System, and the cells allowed to adhere for 2-4 hours at which point 1,000 U/mL of IL-4 and 800 U/mL GM-CSF can be added. The concentration of GM-CSF and IL-4 can be maintained. The dendritic cells can be matured using a cytokine cocktail. In some embodiments the cytokine cocktail consists of LPS (30 ng/mL), IL-4 (1,000 U/mL), GM-CSF (800 U/mL), TNF-Alpha (10 ng/mL), IL-6 (100 ng/mL), and IL-1beta (10 ng/mL). The dendritic cell maturation generally occurs in 2 to 5 days. In some embodiments, the adherent DCs are harvested and counted using a hemocytometer. In some embodiments, a portion of the DCs are cryopreserved for additional further stimulations.

Pulsing the Dendritic Cells

The non-mature and mature dendritic cells are pulsed with one or more peptides from a targeted MMAA and/or TAA. For example, the dendritic cells can be pulsed using one or more antigenic peptides, for example one or more specific epitopes. Alternatively, the dendritic cells can be pulsed using a peptide mix comprising overlapping peptides from the targeted MMAA and/or TAA. Methods of pulsing a dendritic cell with a tumor antigen are known. For example, about 100 ng of one or more peptides of the MMAA and/or TAA, for example a peptide library (peptide mix), can be added per 10 million dendritic cells and incubated for about 30 to 120 minutes.

Naïve T-Cell Selection of Lymphocytes

In order to increase the potential number of specific TAA activated T-cells and reduce T-cells that target other antigens, in some embodiments it is preferable to utilize naïve T-cells as a starting material. To isolate naïve T-cells, the lymphocytes can undergo a selection, for example CD45RA⁺ cells selection. CD45RA⁺ cell selection methods are generally known in the art. Non-limiting exemplary methods are found in Richards et al., Immune memory in CD4⁺CD45RA⁺ T cells. Immunology. 1997; 91(3):331-339 and McBreen et al., J Virol. 2001 May; 75(9): 4091-4102, which are incorporated herein by reference. For example, to select for CD45RA⁺ cells, the cells can be labeled using 1 vial of CD45RA microbeads from Miltenyi Biotec per 1$\times$10$^{11}$ cells after 5-30 minutes of incubation with 100 mL of CliniMACS buffer and approximately 3 mL of 10% human IVIG, 10 ug/mL DNAase I, and 200 mg/mL of magnesium chloride. After 30 minutes, cells will be washed sufficiently and resuspended in 20 mL of CliniMACS buffer. The bag will then be set up on the CLINIMACS Plus device and the selection program can be run according to manufacturer's recommendations. After the program is completed, cells can be counted, washed and resuspended in "CTL Media" consisting of 44.5% EHAA Click's, 44.5% Advanced RPMI, 10% Human Serum, and 1% GlutaMAX.

Stimulating Naïve T Cells with Peptide-Pulsed Dendritic Cells

Prior to stimulating naïve T-cells with the dendritic cells, it may be preferable to irradiate the DCs, for example, at 25 Gy. The MMAA and/or TAA antigenic peptide pulsed DCs and naïve T-cells are then co-cultured. The naïve T-cells can be co-cultured in a ratio range of DCs to T cells of about 1:5-1:50, for example, 1:5; 1:10, 1:15, 1:20, 1:25, 1:30, 1:35, 1:40, 1:45, or about 1:50. The DCs and T-cells are generally co-cultured with cytokines. In some embodiments, the cytokines are selected from a group consisting of IL-6 (100 ng/mL), IL-7 (10 ng/mL), IL-15 (5 ng/mL), IL-12 (10 ng/mL), and IL-21 (10 ng/mL).

Second T Cell Stimulation

In general, some embodiments include a step to further stimulate the T-cell subpopulations with one or additional stimulation procedures. The additional stimulation can be performed with, for example, fresh DCs pulsed with the same antigenic peptides as used in the first stimulation, similarly to as described above. In some embodiments, the cytokines used during the second stimulation are selected from a group consisting of IL-7 (10 ng/mL) and IL-2 (100 U/mL).

Alternatively, peptide-pulsed PHA blasts can be used as the antigen presenting cell. The use of peptide-pulsed PHA blasts to stimulate and expand T-cells are well known in the art. Non-limiting exemplary methods can be found in Weber et al., Clin Cancer Res. 2013 Sep. 15; 19(18): 5079-5091 and Ngo et al., J Immunother. 2014 May; 37(4): 193-203, which are incorporated herein by reference. The peptide-pulsed PHA blasts can be used to expand the T-cell subpopulation in a ratio range of PHA blasts to expanded T cells of 10:1-1:10. For example, the ratio of PHA blasts to T cells can be 10:1, between 10:1 and 9:1, between 9:1 and 8:1, between 8:1 and 7:1, between 7:1 and 6:1, between 6:1 and 5:1, between 5:1 and 4:1, between 4:1 and 3:1, between 3:1 and 2:1, between 2:1 and 1:1, between 1:1 and 1:2, between 1:2 and 1:3, between 1:3 and 1:4, between 1:4 and 1:5, between 1:5 and 1:6, between 1:6 and 1:7, between 1:7 and 1:8, between 1:8 and 1:9, between 1:9 and 1:10. In general, cytokines are included in the co-culture, and are selected from the group consisting of IL-7 (10 ng/mL) and IL-2 (100 U/mL).

Additional T-Cell Expansion and T-Cell Subpopulation Harvest

Additional T cell stimulations may be necessary to generate the necessary number of activated T-cells for use in the T-cell composition. Following any stimulation and expansion, the activated T-cells are harvested, washed, and concentrated. In some embodiments, a solution containing a final concentration of 10% dimethyl sulfoxide (DMSO), 50% human serum albumin (HSA), and 40% Hank's Balanced Salt Solution (HBSS) will then be added to the cryopreservation bag. In some embodiments, the T-cell composition will be cryopreserved in liquid nitrogen.

Further Characterization of the T-Cell Composition

The T-cell composition of the present disclosure are HLA-typed and can be further characterized prior to administration. For example, the T-cell composition may be further characterized by, for example, one or more of i) determining the MMAA or TAA specificity of the T-cell composition; ii) Identifying the tumor associated antigen epitope(s) the T-cell composition is specific to; iii) determining whether the T-cell composition includes MHC Class I or Class II restricted subsets or a combination of both; iv) correlating antigenic activity through the T-cell's corresponding HLA-allele; and v) characterizing the T-cell compositions immune effector subtype concentration, for example, the population of effector memory cells, central memory cells, γδ T-cells, CD8+, CD4+, NKT-cell. Wherein the T-cell composition is derived from separate T-cell populations and subsequently combined or intended for administration separately, each of the separate T-cell subpopulations can be characterized as above.

Determining the Tumor Associated Antigen Specificity of the T-Cell Composition

The T-cell composition can be further characterized by determining the specificity for the chosen targeted tumor antigen. Specificity can be determined using any known procedure, for example, an ELISA based immunospot assay (ELISpot). In some embodiments, antigen specificity of the T-cell composition is determined by ELISpot assay. ELISpot assays are widely used to monitor adaptive immune responses in both humans and animals. The method was originally developed from the standard ELISA assay to measure antibody secretion from B cells (Czerkinsky C. et al. (1983). A solid-phase enzyme-linked immunospot (ELIS-POT) assay for enumeration of specific antibody-secreting cells. J. Immunol Methods 65: 109-21), which is incorporated herein by reference. The assay has since been adapted to detect secreted cytokines from T cells, for example IFN-γ, and is an essential tool for understanding the helper T cell response.

A T-cell ELISpot assay generally comprises the following steps:

i) a capture antibody specific for the chosen analyte, for example IFN-γ, is coated onto a PVDF plate;

ii) the plate is blocked, usually with a serum;

iii) the T-cell composition is added along with the specific, targeted antigen; iv) plates are incubated and secreted cytokines, for example IFN-γ, are captured by the immobilized antibody on the PVDF surface;

v) after washing, a biotinylated detection antibody is added to allow detection of the captured cytokine; and vi) the secreted cytokine is visualized using an avidin-HRP or avidin-ALP conjugate and a colored precipitating substrate.

Each colored spot represents a cytokine secreting cell. The spots can be counted by eye or by using an automated plate-reader. Many different cytokines can be detected using this method including IL-2, IL-4, IL-17, IFN γ, TNFα, and granzyme B. The size of the spot is an indication of the per cell productivity and the avidity of the binding. Generally, the higher the avidity of the T cell recognition the higher the productivity resulting in large, well-defined spots.

Identifying the Antigenic Epitope(s) the T-Cell Subpopulation is Specific to

When more than one peptide or epitope, for example a peptide mix, is used in activating the T-cells, the T-cell composition can be further characterized by identifying the specific antigenic epitope or epitopes to which the underlying T-cell subpopulations of the composition are specific to. Determining epitope specificity is generally known in the art. Non-limiting exemplary methods include Ohminami et al., Blood. 2000 Jan. 1; 95(1):286-93; Oka et al., Immunogenetics. 2000 Feb;51(2):99-107; and Bachinsky et al., Cancer Immun. 2005 Mar. 22; 5:6, which are each incorporated herein by reference. For example, to identify the epitopes with specific activity antigen peptides can be grouped into pools in which each peptide is represented in two or more pools as a quick screening tool in an Elispot assay, and the pools showing activity determined. Common peptides represented in both pools can then be further screened to identify the specific peptide epitopes to which the T-cells show activity.

Determining the T-Cell Composition's MHC-Class I or Class II Restricted Subsets

The T-cell composition can be further characterized by determining the MHC Class I or Class II subset restriction response. This is done to determine whether epitope recognition is mediated by CD8+ (class I) or CD4+ (class II) T-cells. General methods for determining the MHC Class I or Class II response are generally known in the art. A non-limiting exemplary method is found in Weber et al., Clin Cancer Res. 2013 Sep. 15; 19(18): 5079-5091, which is incorporated herein by reference. For example, to determine HLA restriction response, T cells can be pre-incubated with class I or II blocking antibodies for 1 hour before the addition of antigen peptides in an ELISPOT assay using autologous peptide-pulsed PHA blasts as targets with unpulsed PHA blasts as a control. IFNγ-secretion is measured in the presence of each blocking antibody. When pre-incubated with a class I blocking antibody, if IFNγ-secretion is reduced to background levels, then class I restriction and the epitope recognition is mediated by CD8+ T cells. When pre-incubated with a class II blocking antibody, if IFNγ-secretion is reduced to background levels, then class II restriction and the epitope recognition is mediated by CD4+ T cells.

The direct detection of antigen-specific T cells using tetramers of soluble peptide-major histocompatibilty complex (pMHC) molecules is widely used in both basic and clinical immunology. Tetrameric complexes of HLA molecules can be used to stain antigen-specific T cells in FACS analysis. In vitro synthesized soluble HLA-peptide complexes are used as tetrameric complexes to stain antigen specific T cells in FACS analysis (Altman et al., Science 274: 94-96, 1996). T-cell compositions specific for targeted MMAAs and/or TAAs are stained with CD8 fluorescein isothiocyanate (FITC) and with phycoerythrin (PE)-labeled MHC pentamers at various timepoints during in vitro stimulation. Antigen specificity is measured by flow cytometry. Correlating Antigenic Activity Through the T-Cell's Corresponding HLA-Allele The T-cell composition can be further characterized by correlating antigenic activity through the T-cell population's corresponding HLA-allele. Correlating antigenic activity through the corresponding HLA-allele can be done using any known method. For example, In some embodiments, an HLA restriction assay is used to determine antigen activity through a corresponding allele. Methods to determine T cell restriction are known in the art and involve inhibition with locus specific antibodies, followed by antigen presentation assays (ELISPOT) with panels of cell lines matched or mismatched at the various loci of interest (see, e.g., (Oseroff et al., J Immunol (2010) 185(2): 943-955; Oseroff et al., J Immunol (2012) 189(2): 679-688; Wang Curr Protocols in immunol (2009) Chap. 20, page 10; Wilson et al., J. Virol. (2001) 75(9): 4195-4207), each independently incorporated herein by reference. Because epitope binding to HLA class II molecules is absolutely necessary (but not sufficient) for T cell activation, data from in vitro HLA binding assays has also been useful to narrow down the possible restrictions (Arlehamn et al., J Immunol (2012b) 188(10):5020-5031). This is usually accomplished by testing a given epitope for binding to the specific HLA molecules expressed in a specific donor and eliminating from further consideration HLA molecules to which the epitope does not bind. To determine the HLA restriction of the identified epitope, T cells can be plated in an IFN-γ ELISPOT assay with antigenic peptide pulsed PHA blasts that match at a single allele, measuring the strongest antigen activity, and identifying the corresponding allele.
Characterizing the T-cell Composition's Immune Effector Subtype Concentration The T-cell composition is likely to comprise different lymphocytic cell subsets, for example, a combination of CD4+ T-cells, CD8+ T-cells, CD3+/CD56+ Natural Killer T-cells (CD3+ NKT), and TCR γδ T-cells (γδ T-cells). In particular, the T-cell composition may include at least CD4+ T-cells and CD8+ T-cells that have been primed and are capable of targeting MMAA and/or TAA expressing cell for tumor killing and/or cross presentation. The T-cell composition may further comprise activated γδ T-cells and/or activated CD3+/CD56+ NKT cells capable of mediating anti-tumor responses. Accordingly, the T-cell composition may be further characterized by determining the population of various lymphocytic subtypes, and the further classification of such subtypes, for example, by determining the presence or absence of certain clusters of differentiation (CD) markers, or other cell surface markers, expressed by the cells and determinative of cell subtype.

In some embodiments, the T-cell composition may be analyzed to determine CD8+ T-cell population, CD4+ T-cell population, γδ T-cell population, NKT-cell population, and other populations of lymphocytic subtypes. For example, the population of CD4+ T-cells within the T-cell composition may be determined, and the CD4+ T-cell subtypes further determined. For example, the CD4+ T-cell population may be determined, and then further defined, for example, by identifying the population of T-helper 1 (Th1), T-helper 2 (Th2), T-helper 17 (Th17), regulatory T cell ($T_{reg}$), follicular helper T-cell (Tfh), and T-helper 9 (Th9). Likewise, the other lymphocytic subtypes comprising the T-cell compositions can be determined and further characterized.

In addition, the T-cell composition can be further characterized, for example, for the presence, or lack thereof, of one or more markers associated with, for example, maturation or exhaustion. T cell exhaustion ($T_{ex}$) is a state of dysfunction that results from persistent antigen and inflammation, both of which commonly occur in tumor tissue. The reversal or prevention of exhaustion is a major area of research for tumor immunotherapy. $T_{ex}$ cell populations can be analyzed using multiple phenotypic parameters, either alone or in combination. Hallmarks commonly used to monitor T cell exhaustion are known in the art and include, but are not limited to, programmed cell death-1 (PD-1), CTLA-4/CD152 (Cytotoxic T-Lymphocyte Antigen 4), LAG-3 (Lymphocyte activation gene-3; CD223), TIM-3 (T cell immunoglobulin and mucin domain-3), 2B4/CD244/ SLAMF4, CD160, and TIGIT (T cell Immunoreceptor with Ig and ITIM domains).

The T-cell composition of the described compositions described herein can be subjected to further selection, if desired. For example, a particular T-cell composition described herein can undergo further selection through depletion or enriching for a sub-population. For example, following priming, expansion, and selection, the cells can be further selected for other cluster of differentiation (CD) markers, either positively or negatively. For example, following selection of for example CD4+ T-cells, the CD4+ T-cells can be further subjected to selection for, for example, a central memory T-cells ($T_{cm}$). For example, the enrichment for CD4+ $T_{cm}$ cells comprises negative selection for cells expression a surface marker present on naïve T cells, such as CD45RA, or positive selection for cells expressing a surface marker present on $T_{cm}$ cells and not present on naïve T-cells, for example CD45RO, CD62L, CCR7, CD27, CD127, and/ or CD44. In addition, the T-cell compositions described herein can be further selected to eliminate cells expressing certain exhaustion markers, for example, programmed cell death-1 (PD-1), CTLA-4/CD152 (Cytotoxic T-Lymphocyte Antigen 4), LAG-3 (Lymphocyte activation gene-3; CD223), TIM-3 (T cell immunoglobulin and mucin domain-3), 2B4/CD244/SLAMF4, CD160, and TIGIT (T cell Immunoreceptor with Ig and ITIM domains)

Methods for characterizing lymphocytic cell subtypes are well known in the art, for example flow cytometry, which is described in Pockley et al., Curr Protoc Toxicol. 2015 Nov. 2; 66:18.8.1-34, which is incorporated herein by reference.

Identifying the T-Cell Composition Most Suitable for Administration

When the T-cell composition is derived from a donor source, the characterization of the T-cell composition allows for the selection of the most appropriate T-cell composition for any given patient. In addition, wherein the T-cell composition is derived by the combination of separately primed and expanded T-cell subpopulations to each MMAA or TAA, the characterization of each T-cell subpopulation allows for the selection of the most appropriate T-cell subpopulation to include in the T-cell composition. The goal is to match the product with the patient that has the both the highest HLA match and greatest TAA activity through the greatest number of shared alleles. In some embodiments, the T-cell composition has at least one shared allele or allele combination with MMAA and/or TAA activity through that allele or allele combination. In some embodiments, the T-cell composition has greater than 1 shared allele or allele combination with MMAA/TAA activity through that allele or allele combination. In some embodiments, the T-cell composition with the most shared alleles or allele combinations and highest specificity through those shared alleles and allele combinations is provided to a human in need thereof. For example, if T-cell composition 1 has a 5/8 HLA match with the patient with MMAA/TAA activity through 3 shared alleles or allele combinations, while T-cell composition 2 is a 6/8 HLA match with the patient with MMAA/TAA activity through 1 shared allele the skilled practitioner would select T-cell composition 1 as it has MMAA/TAA activity through a greater number of shared alleles.

Testing T-Cell Composition Reactivity Against Patient's Tumor

The cytolytic activity of an activated T-cell composition against a patient's tumor can be evaluated. A method of testing reactivity of T-cell subpopulations against tumor cells are well known. Non-limiting exemplary methods include Jedema et al., Blood (2004) 103:2677-2682; Noto et al., J Vis Exp. 2013; (82): 51105 and Baumgaertner et al., Bio-protocol "Chromium-51 ($^{51}$Cr) Release Assay to Assess Human T Cells for Functional Avidity and Tumor Cell Recognition." (2016) 6(16): e1906. For example, the T-cell composition can be incubated with the patient's tumor and the percent lysis of the tumor cells determined. For example, a biopsy or blood sample will be collected from the patient. Target cells from the patient are fluorescence labeled with carboxyfluorescein succinimidyl ester (CFSE, Invitrogen), peptide-pulsed and incubated with activated T-cell compositions at a 40:1 effector-to-target ratios for 6-8 hrs. Ethidium homodimer (Invitrogen) is added after incubation to stain dead cells. Samples are acquired on a BD Fortessa Flow Cytometer. The number of live target cells is determined by gating on carboxyfluorescein succinimidyl ester-positive, ethidium homodimer-negative cells, and used to calculate cytolytic activity as follows: Lysis (%)=100−((live target cells/sample/live target cells control)×100).

T-cell compositions with the highest levels of reactivity against a patient's tumor can be selected for administration to the patient, providing a higher likelihood of successful therapeutic efficacy.

Banked T-Cell Subpopulations Directed to Single Tumor Antigens

In some aspects, the T-cell composition is derived by combining T-cell subpopulations primed and expanded to each targeted MMAA and TAA separately. The establishment of a T-cell subpopulation bank comprising discrete, characterized T-cell subpopulations for selection and inclusion in a T-cell composition bypasses the need for an immediately available donor and eliminates the wait required for autologous T cell production, while providing the ability to select only T-cell subpopulation targeting relevant MMAAs and/or TAAs expressed by the subject's tumor. Preparing T-cell subpopulations directed to specific tumor antigens by using donors, for example healthy volunteers or cord blood, allows the production and banking of T-cell subpopulations readily available for administration. Because the T-cell subpopulations are characterized, the selection of suitable T-cell subpopulations can be quickly determined based on minimal information from the patient, for example HLA-subtype and, optionally MMAA/TAA expression profile.

From a single donor a T cell composition can be generated for use in multiple patients who share HLA alleles that have activity towards a specific MMAA/TAA. The T-cell subpopulation bank of the present disclosure includes a population of T-cell subpopulations which have been characterized as described herein. For example, the T-cell subpopulations of the bank are characterized as to HLA-subtype and one or more of i) MMAA/TAA specificity of the T-cell subpopulation; ii) MMAA/TAA epitope(s) the T-cell subpopulation is specific to; iii) T-cell subpopulation MHC Class I and Class II restricted subsets; iv) antigenic activity through the T-cell's corresponding HLA-allele; and v) immune effector subtype concentration, for example, the population of effector memory cells, central memory cells, γδ T-cells, CD8$^+$, CD4$^+$, NKT-cell.

In some embodiments, the present disclosure includes generating a T-cell subpopulation bank comprising: (i) obtaining eligible donor samples; (ii) generating T-cell subpopulations specific to a single MMAA or TAA; (iii) characterizing the T-cell subpopulation; (iv) cryopreserving the T-cell subpopulation; and (v) generating a database of T-cell subpopulation composition characterization data. In some embodiments, the T-cell subpopulations are stored according to their donor source. In some embodiments, the T-cell subpopulations are stored by MMAA/TAA specificity. In some embodiments, the T-cell subpopulations are stored by human leukocyte antigen (HLA) subtype and restrictions.

The banked T-cell subpopulations described herein are used to comprise a T-cell composition for administration to subject having a plasma cell dyscrasias, for example multiple myeloma, following the determination of the patient's HLA subtype and, optionally, MMAA/TAA expression profile of the subject's tumor.

What is claimed:

1. A method of treating a plasma cell dyscrasia in a subject in need thereof, comprising administering to the subject a therapeutically effective amount of a composition, wherein the composition is created by combining two or more T-cell subpopulations that have been separately primed and expanded ex vivo against one or more multiple myeloma associated antigens (MMAAs), wherein the one or more MMAAs are selected from the group consisting of B-cell maturation antigen (BCMA), X-box Protein 1 (XBP1), CS1, and Syndecan-1 (CD138), and wherein each separate T-cell subpopulation is specific for a single MMAA.

2. The method of claim 1, wherein the composition further comprises one or more T-cell subpopulations that have been separately primed and expanded ex vivo against one or more tumor associated antigens (TAAs) selected from the group consisting of preferentially expressed antigen in melanoma (PRAME), Survivin, and Wilm's Tumor 1 (WT1).

3. The method of claim 2, wherein the composition further comprises a T-cell subpopulation that has been primed and expanded ex vivo activated to MAGE-A3.

4. The method of claim 1, wherein the composition is derived from an allogeneic source or an autologous source.

5. The method of claim 1, wherein the plasma cell dyscrasia is multiple myeloma.

6. A method of treating a plasma cell dyscrasia in a subject in need thereof, comprising administering to the subject (i) a first composition that is created by combining one or more T-cell subpopulations that have been separately primed and expanded ex vivo against one or more multiple myeloma associated antigens (MMAAs) selected from the group consisting of B-cell maturation antigen (BCMA), X-box Protein 1 (XBP1), CS1, and Syndecan-1 (CD138); and (ii) a second composition that is created by combining one or more T-cell subpopulations that have been separately primed and expanded ex vivo against one or more tumor associated antigens (TAAs) selected from the group consisting of preferentially expressed antigen in melanoma (PRAME), Survivin, and Wilm's Tumor 1 (WT1).

7. The method of claim 6, wherein the first and second compositions are combined prior to administration.

8. The method of claim 6, wherein each separate T-cell subpopulation is specific for a single antigen.

9. The method of claim 6, wherein the first and second compositions are derived from an allogeneic source or an autologous source.

10. The method of claim 6, wherein the plasma cell dyscrasia is multiple myeloma.

* * * * *

SEQUENCE LISTING

<160> NUMBER OF SEQ ID NOS: 1214

<210> SEQ ID NO 1
<211> LENGTH: 184
<212> TYPE: PRT
<213> ORGANISM: Homo sapiens -continued

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 10
<212> TYPE: PRT
<213> ORGANISM: Artificial Sequence
<220> FEATURE:
<223> OTHER INFORMATION: BCMA peptide

<400> SEQUENCE: 2

Asn Thr Pro Pro Leu Thr Cys Gln Arg Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: BCMA peptide

<400> SEQUENCE: 3

Glu Ile Ile Leu Pro Arg Gly Leu Glu Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: BCMA peptide

<400> SEQUENCE: 4

Ile Ile Leu Pro Arg Gly Leu Glu Tyr
1               5

```
<210> SEQ ID NO 5
<211> LENGTH: 11
<212> TYPE: PRT
<213> ORGANISM: Artificial Sequence
<220> FEATURE:
<223> OTHER INFORMATION: BCMA peptide

<400> SEQUENCE: 5

Asp Glu Ile Ile Leu Pro Arg Gly Leu Glu Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: BCMA peptide

<400> SEQUENCE: 6

Ser Leu Ala Val Phe Val Leu Met Phe Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: BCMA peptide

<400> SEQUENCE: 7

Ile Leu Trp Thr Cys Leu Gly Leu Ser Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: BCMA peptide

<400> SEQUENCE: 8

Cys Leu Gly Leu Ser Leu Ile Ile Ser Leu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: BCMA peptide

<400> SEQUENCE: 9

Val Leu Met Phe Leu Leu Arg Lys Ile
1               5

<210> SEQ ID NO 10
<211> LENGTH: 9
<212> TYPE: PRT
<213> ORGANISM: Artificial Sequence
<220> FEATURE:
<223> OTHER INFORMATION: BCMA peptide

<400> SEQUENCE: 10

Ile Ile Leu Pro Arg Gly Leu Glu Tyr
1               5

<210> SEQ ID NO 11
```

```
<211> LENGTH: 9
<212> TYPE: PRT
<213> ORGANISM: Artificial Sequence
<220> FEATURE:
<223> OTHER INFORMATION: BCMA peptide

<400> SEQUENCE: 11

Ser Leu Ile Ile Ser Leu Ala Val Phe
1               5

<210> SEQ ID NO 12
<211> LENGTH: 9
<212> TYPE: PRT
<213> ORGANISM: Artificial Sequence
<220> FEATURE:
<223> OTHER INFORMATION: BCMA peptide

<400> SEQUENCE: 12

Phe Val Leu Met Phe Leu Leu Arg Lys
1               5

<210> SEQ ID NO 13
<211> LENGTH: 9
<212> TYPE: PRT
<213> ORGANISM: Artificial Sequence
<220> FEATURE:
<223> OTHER INFORMATION: BCMA peptide

<400> SEQUENCE: 13

Ala Leu Ser Ala Thr Glu Ile Glu Lys
1               5

<210> SEQ ID NO 14
<211> LENGTH: 10
<212> TYPE: PRT
<213> ORGANISM: Artificial Sequence
<220> FEATURE:
<223> OTHER INFORMATION: BCMA peptide

<400> SEQUENCE: 14

Ala Val Phe Val Leu Met Phe Leu Leu Arg
1               5                   10

<210> SEQ ID NO 15
<211> LENGTH: 9
<212> TYPE: PRT
<213> ORGANISM: Artificial Sequence
<220> FEATURE:
<223> OTHER INFORMATION: BCMA peptide

<400> SEQUENCE: 15

Phe Val Leu Met Phe Leu Leu Arg Lys
1               5

<210> SEQ ID NO 16
<211> LENGTH: 9
<212> TYPE: PRT
<213> ORGANISM: Artificial Sequence
<220> FEATURE:
<223> OTHER INFORMATION: BCMA peptide

<400> SEQUENCE: 16

Gly Met Ala Asn Ile Asp Leu Glu Lys
1               5

<210> SEQ ID NO 17
<211> LENGTH: 9
```

<212> TYPE: PRT
<213> ORGANISM: Artificial Sequence
<220> FEATURE:
<223> OTHER INFORMATION: BCMA peptide

<400> SEQUENCE: 17

Ala Leu Ser Ala Thr Glu Ile Glu Lys
1               5

<210> SEQ ID NO 18
<211> LENGTH: 10
<212> TYPE: PRT
<213> ORGANISM: Artificial Sequence
<220> FEATURE:
<223> OTHER INFORMATION: BCMA peptide

<400> SEQUENCE: 18

Arg Thr Gly Asp Glu Ile Ile Leu Pro Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: BCMA peptide

<400> SEQUENCE: 19

Asp Tyr Cys Lys Ser Leu Pro Ala Ala Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: BCMA peptide

<400> SEQUENCE: 20

Tyr Phe Asp Ser Leu Leu His Ala Cys Ile
1               5                   10

<210> SEQ ID NO 21
<211> LENGTH: 10
<212> TYPE: PRT
<213> ORGANISM: Artificial Sequence
<220> FEATURE:
<223> OTHER INFORMATION: BCMA peptide

<400> SEQUENCE: 21

Glu Phe Lys Asn Thr Gly Ser Gly Leu Leu
1               5                   10

<210> SEQ ID NO 22
<211> LENGTH: 9
<212> TYPE: PRT
<213> ORGANISM: Artificial Sequence
<220> FEATURE:
<223> OTHER INFORMATION: BCMA peptide

<400> SEQUENCE: 22

Glu Phe Lys Asn Thr Gly Ser Gly Leu
1               5

<210> SEQ ID NO 23
<211> LENGTH: 10
<212> TYPE: PRT

<213> ORGANISM: Artificial Sequence
<220> FEATURE:
<223> OTHER INFORMATION: BCMA peptide

<400> SEQUENCE: 23

Glu Ile Ile Leu Pro Arg Gly Leu Glu Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: BCMA peptide

<400> SEQUENCE: 24

Ala Val Phe Val Leu Met Phe Leu Leu
1               5

<210> SEQ ID NO 25
<211> LENGTH: 9
<212> TYPE: PRT
<213> ORGANISM: Artificial Sequence
<220> FEATURE:
<223> OTHER INFORMATION: BCMA peptide

<400> SEQUENCE: 25

Leu Val Thr Thr Lys Thr Asn Asp Tyr
1               5

<210> SEQ ID NO 26
<211> LENGTH: 10
<212> TYPE: PRT
<213> ORGANISM: Artificial Sequence
<220> FEATURE:
<223> OTHER INFORMATION: BCMA peptide

<400> SEQUENCE: 26

Asp Glu Phe Lys Asn Thr Gly Ser Gly Leu
1               5                   10

<210> SEQ ID NO 27
<211> LENGTH: 9
<212> TYPE: PRT
<213> ORGANISM: Artificial Sequence
<220> FEATURE:
<223> OTHER INFORMATION: BCMA peptide

<400> SEQUENCE: 27

Glu Ile Glu Lys Ser Ile Ser Ala Arg
1               5

<210> SEQ ID NO 28
<211> LENGTH: 9
<212> TYPE: PRT
<213> ORGANISM: Artificial Sequence
<220> FEATURE:
<223> OTHER INFORMATION: BCMA peptide

<400> SEQUENCE: 28

Gly Ala Thr Ile Leu Val Thr Thr Lys
1               5

<210> SEQ ID NO 29
<211> LENGTH: 9
<212> TYPE: PRT
<213> ORGANISM: Artificial Sequence

```
<220> FEATURE:
<223> OTHER INFORMATION: BCMA peptide

<400> SEQUENCE: 29

Asn Thr Pro Pro Leu Thr Cys Gln Arg
1               5

<210> SEQ ID NO 30
<211> LENGTH: 9
<212> TYPE: PRT
<213> ORGANISM: Artificial Sequence
<220> FEATURE:
<223> OTHER INFORMATION: BCMA peptide

<400> SEQUENCE: 30

Phe Val Leu Met Phe Leu Leu Arg Lys
1               5

<210> SEQ ID NO 31
<211> LENGTH: 9
<212> TYPE: PRT
<213> ORGANISM: Artificial Sequence
<220> FEATURE:
<223> OTHER INFORMATION: BCMA peptide

<400> SEQUENCE: 31

Leu Pro Arg Gly Leu Glu Tyr Thr Val
1               5

<210> SEQ ID NO 32
<211> LENGTH: 10
<212> TYPE: PRT
<213> ORGANISM: Artificial Sequence
<220> FEATURE:
<223> OTHER INFORMATION: BCMA peptide

<400> SEQUENCE: 32

Glu Pro Leu Lys Asp Glu Phe Lys Asn Thr
1               5                   10

<210> SEQ ID NO 33
<211> LENGTH: 10
<212> TYPE: PRT
<213> ORGANISM: Artificial Sequence
<220> FEATURE:
<223> OTHER INFORMATION: BCMA peptide

<400> SEQUENCE: 33

Leu Pro Ala Ala Leu Ser Ala Thr Glu Ile
1               5                   10

<210> SEQ ID NO 34
<211> LENGTH: 10
<212> TYPE: PRT
<213> ORGANISM: Artificial Sequence
<220> FEATURE:
<223> OTHER INFORMATION: BCMA peptide

<400> SEQUENCE: 34

Leu Pro Ala Ala Leu Ser Ala Thr Glu Ile
1               5                   10

<210> SEQ ID NO 35
<211> LENGTH: 9
<212> TYPE: PRT
<213> ORGANISM: Artificial Sequence
<220> FEATURE:
```

-continued

```
<223> OTHER INFORMATION: BCMA peptide

<400> SEQUENCE: 35

Cys Ile Lys Ser Lys Pro Lys Val Asp
1               5

<210> SEQ ID NO 36
<211> LENGTH: 8
<212> TYPE: PRT
<213> ORGANISM: Artificial Sequence
<220> FEATURE:
<223> OTHER INFORMATION: BCMA peptide

<400> SEQUENCE: 36

Cys Ile Lys Ser Lys Pro Lys Val
1               5

<210> SEQ ID NO 37
<211> LENGTH: 9
<212> TYPE: PRT
<213> ORGANISM: Artificial Sequence
<220> FEATURE:
<223> OTHER INFORMATION: BCMA peptide

<400> SEQUENCE: 37

Ser Val Lys Gly Thr Asn Ala Ile Leu
1               5

<210> SEQ ID NO 38
<211> LENGTH: 9
<212> TYPE: PRT
<213> ORGANISM: Artificial Sequence
<220> FEATURE:
<223> OTHER INFORMATION: BCMA peptide

<400> SEQUENCE: 38

Glu Phe Lys Asn Thr Gly Ser Gly Leu
1               5

<210> SEQ ID NO 39
<211> LENGTH: 10
<212> TYPE: PRT
<213> ORGANISM: Artificial Sequence
<220> FEATURE:
<223> OTHER INFORMATION: BCMA peptide

<400> SEQUENCE: 39

Ile Leu Val Thr Thr Lys Thr Asn Asp Tyr
1               5                   10

<210> SEQ ID NO 40
<211> LENGTH: 9
<212> TYPE: PRT
<213> ORGANISM: Artificial Sequence
<220> FEATURE:
<223> OTHER INFORMATION: BCMA peptide

<400> SEQUENCE: 40

Ser Leu Ile Ile Ser Leu Ala Val Phe
1               5

<210> SEQ ID NO 41
<211> LENGTH: 9
<212> TYPE: PRT
<213> ORGANISM: Artificial Sequence
<220> FEATURE:
<223> OTHER INFORMATION: BCMA peptide
```

-continued

```
<400> SEQUENCE: 41

Ser Leu Ala Val Phe Val Leu Met Phe
1               5

<210> SEQ ID NO 42
<211> LENGTH: 9
<212> TYPE: PRT
<213> ORGANISM: Artificial Sequence
<220> FEATURE:
<223> OTHER INFORMATION: BCMA peptide

<400> SEQUENCE: 42

Gly Gln Cys Ser Gln Asn Glu Tyr Phe
1               5

<210> SEQ ID NO 43
<211> LENGTH: 9
<212> TYPE: PRT
<213> ORGANISM: Artificial Sequence
<220> FEATURE:
<223> OTHER INFORMATION: BCMA peptide

<400> SEQUENCE: 43

Thr Pro Pro Leu Thr Cys Gln Arg Tyr
1               5

<210> SEQ ID NO 44
<211> LENGTH: 10
<212> TYPE: PRT
<213> ORGANISM: Artificial Sequence
<220> FEATURE:
<223> OTHER INFORMATION: BCMA peptide

<400> SEQUENCE: 44

Lys Pro Lys Val Asp Ser Asp His Cys Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: BCMA peptide

<400> SEQUENCE: 45

Leu Pro Ala Ala Leu Ser Ala Thr Glu Ile
1               5                   10

<210> SEQ ID NO 46
<211> LENGTH: 10
<212> TYPE: PRT
<213> ORGANISM: Artificial Sequence
<220> FEATURE:
<223> OTHER INFORMATION: BCMA peptide

<400> SEQUENCE: 46

Leu Pro Ala Met Glu Glu Gly Ala Thr Ile
1               5                   10

<210> SEQ ID NO 47
<211> LENGTH: 9
<212> TYPE: PRT
<213> ORGANISM: Artificial Sequence
<220> FEATURE:
<223> OTHER INFORMATION: BCMA peptide
```

```
<400> SEQUENCE: 47

Lys Ser Arg Thr Gly Asp Glu Ile Ile
1               5

<210> SEQ ID NO 48
<211> LENGTH: 9
<212> TYPE: PRT
<213> ORGANISM: Artificial Sequence
<220> FEATURE:
<223> OTHER INFORMATION: BCMA peptide

<400> SEQUENCE: 48

Lys Thr Asn Asp Tyr Cys Lys Ser Leu
1               5

<210> SEQ ID NO 49
<211> LENGTH: 9
<212> TYPE: PRT
<213> ORGANISM: Artificial Sequence
<220> FEATURE:
<223> OTHER INFORMATION: BCMA peptide

<400> SEQUENCE: 49

Ile Ser Leu Ala Val Phe Val Leu Met
1               5

<210> SEQ ID NO 50
<211> LENGTH: 9
<212> TYPE: PRT
<213> ORGANISM: Artificial Sequence
<220> FEATURE:
<223> OTHER INFORMATION: BCMA peptide

<400> SEQUENCE: 50

Asn Ser Glu Pro Leu Lys Asp Glu Phe
1               5

<210> SEQ ID NO 51
<211> LENGTH: 15
<212> TYPE: PRT
<213> ORGANISM: Artificial Sequence
<220> FEATURE:
<223> OTHER INFORMATION: BCMA peptide

<400> SEQUENCE: 51

Met Phe Leu Leu Arg Lys Ile Asn Ser Glu Pro Leu Lys Asp Glu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: BCMA peptide

<400> SEQUENCE: 52

Cys Leu Gly Leu Ser Leu Ile Ile Ser Leu Ala Val Phe Val Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: BCMA peptide

<400> SEQUENCE: 53
```

-continued

```
Ala Ile Leu Trp Thr Cys Leu Gly Leu Ser Leu Ile Ile Ser Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: BCMA peptide

<400> SEQUENCE: 54

Gly Leu Ser Leu Ile Ile Ser Leu Ala Val Phe Val Leu Met Phe
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: BCMA peptide

<400> SEQUENCE: 55

Lys Pro Lys Val Asp Ser Asp His Cys Phe Pro Leu Pro Ala Met
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: BCMA peptide

<400> SEQUENCE: 56

Gly Ser Gly Leu Leu Gly Met Ala Asn Ile Asp Leu Glu Lys Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: BCMA peptide

<400> SEQUENCE: 57

Gly Asp Glu Ile Ile Leu Pro Arg Gly Leu Glu Tyr Thr Val Glu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: BCMA peptide

<400> SEQUENCE: 58

Ala Thr Ile Leu Val Thr Thr Lys Thr Asn Asp Tyr Cys Lys Ser
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: BCMA peptide

<400> SEQUENCE: 59
```

-continued

```
Lys Asp Glu Phe Lys Asn Thr Gly Ser Gly Leu Leu Gly Met Ala
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: BCMA peptide

<400> SEQUENCE: 60

Cys Leu Gly Leu Ser Leu Ile Ile Ser Leu Ala Val Phe Val Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: BCMA peptide

<400> SEQUENCE: 61

Met Phe Leu Leu Arg Lys Ile Asn Ser Glu Pro Leu Lys Asp Glu
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: BCMA peptide

<400> SEQUENCE: 62

Ala Thr Ile Leu Val Thr Thr Lys Thr Asn Asp Tyr Cys Lys Ser
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: BCMA peptide

<400> SEQUENCE: 63

Phe Val Leu Met Phe Leu Leu Arg Lys Ile Asn Ser Glu Pro Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: BCMA peptide

<400> SEQUENCE: 64

Asn Glu Tyr Phe Asp Ser Leu Leu His Ala Cys Ile Pro Cys Gln
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: BCMA peptide

<400> SEQUENCE: 65

Val Phe Val Leu Met Phe Leu Leu Arg Lys Ile Asn Ser Glu Pro
```

-continued

```
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: BCMA peptide

<400> SEQUENCE: 66

```
His Ala Cys Ile Pro Cys Gln Leu Arg Cys Ser Ser Asn Thr Pro
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: BCMA peptide

<400> SEQUENCE: 67

```
Ile Ile Ser Leu Ala Val Phe Val Leu Met Phe Leu Leu Arg Lys
1               5                   10                  15
```

<210> SEQ ID NO 68
<211> LENGTH: 13
<212> TYPE: PRT
<213> ORGANISM: Artificial Sequence
<220> FEATURE:
<223> OTHER INFORMATION: BCMA peptide

<400> SEQUENCE: 68

```
Cys Ser Gln Asn Glu Tyr Phe Asp Ser Leu Leu His Ala
1               5                   10
```

<210> SEQ ID NO 69
<211> LENGTH: 15
<212> TYPE: PRT
<213> ORGANISM: Artificial Sequence
<220> FEATURE:
<223> OTHER INFORMATION: BCMA peptide

<400> SEQUENCE: 69

```
Asn Ala Ile Leu Trp Thr Cys Leu Gly Leu Ser Leu Ile Ile Ser
1               5                   10                  15
```

<210> SEQ ID NO 70
<211> LENGTH: 15
<212> TYPE: PRT
<213> ORGANISM: Artificial Sequence
<220> FEATURE:
<223> OTHER INFORMATION: BCMA peptide

<400> SEQUENCE: 70

```
Cys Leu Gly Leu Ser Leu Ile Ile Ser Leu Ala Val Phe Val Leu
1               5                   10                  15
```

<210> SEQ ID NO 71
<211> LENGTH: 261
<212> TYPE: PRT
<213> ORGANISM: Homo sapiens

<400> SEQUENCE: 71

```
Met Val Val Val Ala Ala Ala Pro Asn Pro Ala Asp Gly Thr Pro Lys
1               5                   10                  15
```

```
Val Leu Leu Leu Ser Gly Gln Pro Ala Ser Ala Ala Gly Ala Pro Ala
```

-continued

```
                 20                  25                  30

Gly Gln Ala Leu Pro Leu Met Val Pro Ala Gln Arg Gly Ala Ser Pro
          35                  40                  45

Glu Ala Ala Ser Gly Gly Leu Pro Gln Ala Arg Lys Arg Gln Arg Leu
     50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
               85                  90                  95

Glu Leu Glu Gln Gln Val Val Asp Leu Glu Glu Glu Asn Gln Lys Leu
               100                 105                 110

Leu Leu Glu Asn Gln Leu Leu Arg Glu Lys Thr His Gly Leu Val Val
          115                 120                 125

Glu Asn Gln Glu Leu Arg Gln Arg Leu Gly Met Asp Ala Leu Val Ala
          130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
               165                 170                 175

Gln Ala Gln Leu Ser Pro Leu Gln Asn Ile Ser Pro Trp Ile Leu Ala
          180                 185                 190

Val Leu Thr Leu Gln Ile Gln Ser Leu Ile Ser Cys Trp Ala Phe Trp
          195                 200                 205

Thr Thr Trp Thr Gln Ser Cys Ser Ser Asn Ala Leu Pro Gln Ser Leu
     210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
               245                 250                 255

Lys Pro Leu Met Asn
          260

<210> SEQ ID NO 72
<211> LENGTH: 376
<212> TYPE: PRT
<213> ORGANISM: Homo sapiens

<400> SEQUENCE: 72

Met Val Val Val Ala Ala Ala Pro Asn Pro Ala Asp Gly Thr Pro Lys
1                   5                   10                  15

Val Leu Leu Leu Ser Gly Gln Pro Ala Ser Ala Ala Gly Ala Pro Ala
          20                  25                  30

Gly Gln Ala Leu Pro Leu Met Val Pro Ala Gln Arg Gly Ala Ser Pro
          35                  40                  45

Glu Ala Ala Ser Gly Gly Leu Pro Gln Ala Arg Lys Arg Gln Arg Leu
     50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
               85                  90                  95

Glu Leu Glu Gln Gln Val Val Asp Leu Glu Glu Glu Asn Gln Lys Leu
               100                 105                 110

Leu Leu Glu Asn Gln Leu Leu Arg Glu Lys Thr His Gly Leu Val Val
          115                 120                 125
```

```
Glu Asn Gln Glu Leu Arg Gln Arg Leu Gly Met Asp Ala Leu Val Ala
    130             135             140

Glu Glu Glu Ala Glu Ala Lys Gly Asn Glu Val Arg Pro Val Ala Gly
145             150             155             160

Ser Ala Glu Ser Ala Ala Gly Ala Gly Pro Val Val Thr Pro Pro Glu
            165             170             175

His Leu Pro Met Asp Ser Gly Gly Ile Asp Ser Ser Asp Ser Glu Ser
            180             185             190

Asp Ile Leu Leu Gly Ile Leu Asp Asn Leu Asp Pro Val Met Phe Phe
            195             200             205

Lys Cys Pro Ser Pro Glu Pro Ala Ser Leu Glu Glu Leu Pro Glu Val
    210             215             220

Tyr Pro Glu Gly Pro Ser Ser Leu Pro Ala Ser Leu Ser Leu Ser Val
225             230             235             240

Gly Thr Ser Ser Ala Lys Leu Glu Ala Ile Asn Glu Leu Ile Arg Phe
            245             250             255

Asp His Ile Tyr Thr Lys Pro Leu Val Leu Glu Ile Pro Ser Glu Thr
            260             265             270

Glu Ser Gln Ala Asn Val Val Val Lys Ile Glu Glu Ala Pro Leu Ser
            275             280             285

Pro Ser Glu Asn Asp His Pro Glu Phe Ile Val Ser Val Lys Glu Glu
    290             295             300

Pro Val Glu Asp Asp Leu Val Pro Glu Leu Gly Ile Ser Asn Leu Leu
305             310             315             320

Ser Ser Ser His Cys Pro Lys Pro Ser Ser Cys Leu Leu Asp Ala Tyr
            325             330             335

Ser Asp Cys Gly Tyr Gly Gly Ser Leu Ser Pro Phe Ser Asp Met Ser
            340             345             350

Ser Leu Leu Gly Val Asn His Ser Trp Glu Asp Thr Phe Ala Asn Glu
            355             360             365

Leu Phe Pro Gln Leu Ile Ser Val
    370             375
```

<210> SEQ ID NO 73
<211> LENGTH: 9
<212> TYPE: PRT
<213> ORGANISM: Artificial Sequence
<220> FEATURE:
<223> OTHER INFORMATION: XBP1 peptide

<400> SEQUENCE: 73

```
Tyr Ile Ser Pro Trp Ile Leu Ala Val
1               5
```

<210> SEQ ID NO 74
<211> LENGTH: 9
<212> TYPE: PRT
<213> ORGANISM: Artificial Sequence
<220> FEATURE:
<223> OTHER INFORMATION: XBP1 peptide

<400> SEQUENCE: 74

```
Tyr Leu Phe Pro Gln Leu Ile Ser Val
1               5
```

<210> SEQ ID NO 75
<211> LENGTH: 19
<212> TYPE: PRT
<213> ORGANISM: Artificial Sequence
<220> FEATURE:
<223> OTHER INFORMATION: XBP1 peptide

<400> SEQUENCE: 75

Leu Leu Arg Glu Lys Thr His Gly Leu Val Val Glu Asn Gln Glu Leu
1               5                   10                  15

Arg Gln Arg

<210> SEQ ID NO 76
<211> LENGTH: 9
<212> TYPE: PRT
<213> ORGANISM: Artificial Sequence
<220> FEATURE:
<223> OTHER INFORMATION: XBP1 peptide

<400> SEQUENCE: 76

Ile Ser Pro Trp Ile Leu Ala Val Leu
1               5

<210> SEQ ID NO 77
<211> LENGTH: 8
<212> TYPE: PRT
<213> ORGANISM: Artificial Sequence
<220> FEATURE:
<223> OTHER INFORMATION: XBP1 peptide

<400> SEQUENCE: 77

Leu Ala Val Leu Thr Leu Gln Ile
1               5

<210> SEQ ID NO 78
<211> LENGTH: 8
<212> TYPE: PRT
<213> ORGANISM: Artificial Sequence
<220> FEATURE:
<223> OTHER INFORMATION: XBP1 peptide

<400> SEQUENCE: 78

Val Leu Thr Leu Gln Ile Gln Ser
1               5

<210> SEQ ID NO 79
<211> LENGTH: 9
<212> TYPE: PRT
<213> ORGANISM: Artificial Sequence
<220> FEATURE:
<223> OTHER INFORMATION: XBP1 peptide

<400> SEQUENCE: 79

Lys Leu Leu Leu Glu Asn Gln Leu Leu
1               5

<210> SEQ ID NO 80
<211> LENGTH: 15
<212> TYPE: PRT
<213> ORGANISM: Artificial Sequence
<220> FEATURE:
<223> OTHER INFORMATION: XBP1 peptide

<400> SEQUENCE: 80

Glu Ser Asp Ile Leu Leu Gly Ile Leu Asp Asn Leu Asp Pro Val
1               5                   10                  15

<210> SEQ ID NO 81
<211> LENGTH: 12
<212> TYPE: PRT

-continued

<213> ORGANISM: Artificial Sequence
<220> FEATURE:
<223> OTHER INFORMATION: XBP1 peptide

<400> SEQUENCE: 81

Glu Ser Asp Ile Leu Leu Gly Ile Leu Asp Asn Leu
1               5                   10

<210> SEQ ID NO 82
<211> LENGTH: 9
<212> TYPE: PRT
<213> ORGANISM: Artificial Sequence
<220> FEATURE:
<223> OTHER INFORMATION: XBP1 peptide

<400> SEQUENCE: 82

Val Tyr Pro Glu Gly Pro Ser Ser Leu
1               5

<210> SEQ ID NO 83
<211> LENGTH: 9
<212> TYPE: PRT
<213> ORGANISM: Artificial Sequence
<220> FEATURE:
<223> OTHER INFORMATION: XBP1 peptide

<400> SEQUENCE: 83

Glu Leu Phe Pro Gln Leu Ile Ser Val
1               5

<210> SEQ ID NO 84
<211> LENGTH: 9
<212> TYPE: PRT
<213> ORGANISM: Artificial Sequence
<220> FEATURE:
<223> OTHER INFORMATION: XBP1 peptide

<400> SEQUENCE: 84

Leu Leu Arg Glu Lys Thr His Gly Leu
1               5

<210> SEQ ID NO 85
<211> LENGTH: 9
<212> TYPE: PRT
<213> ORGANISM: Artificial Sequence
<220> FEATURE:
<223> OTHER INFORMATION: XBP1 peptide

<400> SEQUENCE: 85

Asn Ile Ser Pro Trp Ile Leu Ala Val
1               5

<210> SEQ ID NO 86
<211> LENGTH: 9
<212> TYPE: PRT
<213> ORGANISM: Artificial Sequence
<220> FEATURE:
<223> OTHER INFORMATION: XBP1 peptide

<400> SEQUENCE: 86

Ile Leu Ala Val Leu Thr Leu Gln Ile
1               5

<210> SEQ ID NO 87
<211> LENGTH: 9
<212> TYPE: PRT
<213> ORGANISM: Artificial Sequence -continued

```
<220> FEATURE:
<223> OTHER INFORMATION: XBP1 peptide

<400> SEQUENCE: 87

Val Leu Thr Leu Gln Ile Gln Ser Leu
1               5

<210> SEQ ID NO 88
<211> LENGTH: 9
<212> TYPE: PRT
<213> ORGANISM: Artificial Sequence
<220> FEATURE:
<223> OTHER INFORMATION: XBP1 peptide

<400> SEQUENCE: 88

Gly Ile Leu Asp Asn Leu Asp Pro Val
1               5

<210> SEQ ID NO 89
<211> LENGTH: 9
<212> TYPE: PRT
<213> ORGANISM: Artificial Sequence
<220> FEATURE:
<223> OTHER INFORMATION: XBP1 peptide

<400> SEQUENCE: 89

Ile Leu Leu Gly Ile Leu Asp Asn Leu
1               5

<210> SEQ ID NO 90
<211> LENGTH: 9
<212> TYPE: PRT
<213> ORGANISM: Artificial Sequence
<220> FEATURE:
<223> OTHER INFORMATION: XBP1 peptide

<400> SEQUENCE: 90

Glu Leu Phe Pro Gln Leu Ile Ser Val
1               5

<210> SEQ ID NO 91
<211> LENGTH: 9
<212> TYPE: PRT
<213> ORGANISM: Artificial Sequence
<220> FEATURE:
<223> OTHER INFORMATION: XBP1 peptide

<400> SEQUENCE: 91

Tyr Leu Phe Pro Gln Leu Ile Ser Val
1               5

<210> SEQ ID NO 92
<211> LENGTH: 9
<212> TYPE: PRT
<213> ORGANISM: Artificial Sequence
<220> FEATURE:
<223> OTHER INFORMATION: XBP1 peptide

<400> SEQUENCE: 92

Pro Trp Ile Leu Ala Val Leu Thr Leu
1               5

<210> SEQ ID NO 93
<211> LENGTH: 9
<212> TYPE: PRT
<213> ORGANISM: Artificial Sequence
<220> FEATURE:
```

<223> OTHER INFORMATION: XBP1 peptide

<400> SEQUENCE: 93

Glu Asn Gln Glu Leu Arg Gln Arg Leu
1               5

<210> SEQ ID NO 94
<211> LENGTH: 9
<212> TYPE: PRT
<213> ORGANISM: Artificial Sequence
<220> FEATURE:
<223> OTHER INFORMATION: XBP1 peptide

<400> SEQUENCE: 94

Asp Gly Thr Pro Lys Val Leu Leu Leu
1               5

<210> SEQ ID NO 95
<211> LENGTH: 9
<212> TYPE: PRT
<213> ORGANISM: Artificial Sequence
<220> FEATURE:
<223> OTHER INFORMATION: XBP1 peptide

<400> SEQUENCE: 95

Asp Leu Glu Glu Glu Asn Gln Lys Leu
1               5

<210> SEQ ID NO 96
<211> LENGTH: 9
<212> TYPE: PRT
<213> ORGANISM: Artificial Sequence
<220> FEATURE:
<223> OTHER INFORMATION: XBP1 peptide

<400> SEQUENCE: 96

Ser Ser Asn Ala Leu Pro Gln Ser Leu
1               5

<210> SEQ ID NO 97
<211> LENGTH: 9
<212> TYPE: PRT
<213> ORGANISM: Artificial Sequence
<220> FEATURE:
<223> OTHER INFORMATION: XBP1 peptide

<400> SEQUENCE: 97

Ile Ser Pro Trp Ile Leu Ala Val Leu
1               5

<210> SEQ ID NO 98
<211> LENGTH: 9
<212> TYPE: PRT
<213> ORGANISM: Artificial Sequence
<220> FEATURE:
<223> OTHER INFORMATION: XBP1 peptide

<400> SEQUENCE: 98

Val Tyr Pro Glu Gly Pro Ser Ser Leu
1               5

<210> SEQ ID NO 99
<211> LENGTH: 9
<212> TYPE: PRT
<213> ORGANISM: Artificial Sequence
<220> FEATURE:
<223> OTHER INFORMATION: XBP1 peptide -continued

```
<400> SEQUENCE: 99

Gly Tyr Gly Gly Ser Leu Ser Pro Phe
1               5

<210> SEQ ID NO 100
<211> LENGTH: 9
<212> TYPE: PRT
<213> ORGANISM: Artificial Sequence
<220> FEATURE:
<223> OTHER INFORMATION: XBP1 peptide

<400> SEQUENCE: 100

Pro Phe Ser Asp Met Ser Ser Leu Leu
1               5

<210> SEQ ID NO 101
<211> LENGTH: 15
<212> TYPE: PRT
<213> ORGANISM: Artificial Sequence
<220> FEATURE:
<223> OTHER INFORMATION: XBP1 peptide

<400> SEQUENCE: 101

Leu Ser Pro Leu Gln Asn Ile Ser Pro Trp Ile Leu Ala Val Leu
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: XBP1 peptide

<400> SEQUENCE: 102

Leu Ser Pro Leu Gln Asn Ile Ser Pro Trp Ile Leu Ala Val Leu Thr
1               5                   10                  15

<210> SEQ ID NO 103
<211> LENGTH: 17
<212> TYPE: PRT
<213> ORGANISM: Artificial Sequence
<220> FEATURE:
<223> OTHER INFORMATION: XBP1 peptide

<400> SEQUENCE: 103

Leu Ser Pro Leu Gln Asn Ile Ser Pro Trp Ile Leu Ala Val Leu Thr
1               5                   10                  15

Leu

<210> SEQ ID NO 104
<211> LENGTH: 18
<212> TYPE: PRT
<213> ORGANISM: Artificial Sequence
<220> FEATURE:
<223> OTHER INFORMATION: XBP1 peptide

<400> SEQUENCE: 104

Leu Ser Pro Leu Gln Asn Ile Ser Pro Trp Ile Leu Ala Val Leu Thr
1               5                   10                  15

Leu Gln

<210> SEQ ID NO 105
<211> LENGTH: 19
<212> TYPE: PRT
```

<213> ORGANISM: Artificial Sequence
<220> FEATURE:
<223> OTHER INFORMATION: XBP1 peptide

<400> SEQUENCE: 105

Leu Ser Pro Leu Gln Asn Ile Ser Pro Trp Ile Leu Ala Val Leu Thr
1               5                   10                  15

Leu Gln Ile

<210> SEQ ID NO 106
<211> LENGTH: 20
<212> TYPE: PRT
<213> ORGANISM: Artificial Sequence
<220> FEATURE:
<223> OTHER INFORMATION: XBP1 peptide

<400> SEQUENCE: 106

Leu Ser Pro Leu Gln Asn Ile Ser Pro Trp Ile Leu Ala Val Leu Thr
1               5                   10                  15

Leu Gln Ile Gln
            20

<210> SEQ ID NO 107
<211> LENGTH: 21
<212> TYPE: PRT
<213> ORGANISM: Artificial Sequence
<220> FEATURE:
<223> OTHER INFORMATION: XBP1 peptide

<400> SEQUENCE: 107

Leu Ser Pro Leu Gln Asn Ile Ser Pro Trp Ile Leu Ala Val Leu Thr
1               5                   10                  15

Leu Gln Ile Gln Ser
            20

<210> SEQ ID NO 108
<211> LENGTH: 22
<212> TYPE: PRT
<213> ORGANISM: Artificial Sequence
<220> FEATURE:
<223> OTHER INFORMATION: XBP1 peptide

<400> SEQUENCE: 108

Leu Ser Pro Leu Gln Asn Ile Ser Pro Trp Ile Leu Ala Val Leu Thr
1               5                   10                  15

Leu Gln Ile Gln Ser Leu
            20

<210> SEQ ID NO 109
<211> LENGTH: 23
<212> TYPE: PRT
<213> ORGANISM: Artificial Sequence
<220> FEATURE:
<223> OTHER INFORMATION: XBP1 peptide

<400> SEQUENCE: 109

Leu Ser Pro Leu Gln Asn Ile Ser Pro Trp Ile Leu Ala Val Leu Thr
1               5                   10                  15

Leu Gln Ile Gln Ser Leu Ile
            20

<210> SEQ ID NO 110
<211> LENGTH: 24
<212> TYPE: PRT

-continued

<213> ORGANISM: Artificial Sequence
<220> FEATURE:
<223> OTHER INFORMATION: XBP1 peptide

<400> SEQUENCE: 110

Leu Ser Pro Leu Gln Asn Ile Ser Pro Trp Ile Leu Ala Val Leu Thr
1               5                   10                  15

Leu Gln Ile Gln Ser Leu Ile Ser
            20

<210> SEQ ID NO 111
<211> LENGTH: 24
<212> TYPE: PRT
<213> ORGANISM: Artificial Sequence
<220> FEATURE:
<223> OTHER INFORMATION: XBP1 peptide

<400> SEQUENCE: 111

Leu Ser Pro Leu Gln Asn Ile Ser Pro Trp Ile Leu Ala Val Leu Thr
1               5                   10                  15

Leu Gln Ile Gln Ser Leu Ile Ser
            20

<210> SEQ ID NO 112
<211> LENGTH: 26
<212> TYPE: PRT
<213> ORGANISM: Artificial Sequence
<220> FEATURE:
<223> OTHER INFORMATION: XBP1 peptide

<400> SEQUENCE: 112

Leu Ser Pro Leu Gln Asn Ile Ser Pro Trp Ile Leu Ala Val Leu Thr
1               5                   10                  15

Leu Gln Ile Gln Ser Leu Ile Ser Cys Trp
            20                  25

<210> SEQ ID NO 113
<211> LENGTH: 27
<212> TYPE: PRT
<213> ORGANISM: Artificial Sequence
<220> FEATURE:
<223> OTHER INFORMATION: XBP1 peptide

<400> SEQUENCE: 113

Leu Ser Pro Leu Gln Asn Ile Ser Pro Trp Ile Leu Ala Val Leu Thr
1               5                   10                  15

Leu Gln Ile Gln Ser Leu Ile Ser Cys Trp Ala
            20                  25

<210> SEQ ID NO 114
<211> LENGTH: 14
<212> TYPE: PRT
<213> ORGANISM: Artificial Sequence
<220> FEATURE:
<223> OTHER INFORMATION: XBP1 peptide

<400> SEQUENCE: 114

Ser Pro Leu Gln Asn Ile Ser Pro Trp Ile Leu Ala Val Leu
1               5                   10

<210> SEQ ID NO 115
<211> LENGTH: 15
<212> TYPE: PRT
<213> ORGANISM: Artificial Sequence
<220> FEATURE:

<223> OTHER INFORMATION: XBP1 peptide

<400> SEQUENCE: 115

Ser Pro Leu Gln Asn Ile Ser Pro Trp Ile Leu Ala Val Leu Thr
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: XBP1 peptide

<400> SEQUENCE: 116

Ser Pro Leu Gln Asn Ile Ser Pro Trp Ile Leu Ala Val Leu Thr Leu
1               5                   10                  15

<210> SEQ ID NO 117
<211> LENGTH: 17
<212> TYPE: PRT
<213> ORGANISM: Artificial Sequence
<220> FEATURE:
<223> OTHER INFORMATION: XBP1 peptide

<400> SEQUENCE: 117

Ser Pro Leu Gln Asn Ile Ser Pro Trp Ile Leu Ala Val Leu Thr Leu
1               5                   10                  15

Gln

<210> SEQ ID NO 118
<211> LENGTH: 18
<212> TYPE: PRT
<213> ORGANISM: Artificial Sequence
<220> FEATURE:
<223> OTHER INFORMATION: XBP1 peptide

<400> SEQUENCE: 118

Ser Pro Leu Gln Asn Ile Ser Pro Trp Ile Leu Ala Val Leu Thr Leu
1               5                   10                  15

Gln Ile

<210> SEQ ID NO 119
<211> LENGTH: 19
<212> TYPE: PRT
<213> ORGANISM: Artificial Sequence
<220> FEATURE:
<223> OTHER INFORMATION: XBP1 peptide

<400> SEQUENCE: 119

Ser Pro Leu Gln Asn Ile Ser Pro Trp Ile Leu Ala Val Leu Thr Leu
1               5                   10                  15

Gln Ile Gln

<210> SEQ ID NO 120
<211> LENGTH: 20
<212> TYPE: PRT
<213> ORGANISM: Artificial Sequence
<220> FEATURE:
<223> OTHER INFORMATION: XBP1 protein

<400> SEQUENCE: 120

Ser Pro Leu Gln Asn Ile Ser Pro Trp Ile Leu Ala Val Leu Thr Leu
1               5                   10                  15

Gln Ile Gln Ser

```
            20

<210> SEQ ID NO 121
<211> LENGTH: 21
<212> TYPE: PRT
<213> ORGANISM: Artificial Sequence
<220> FEATURE:
<223> OTHER INFORMATION: XBP1 protein

<400> SEQUENCE: 121

Ser Pro Leu Gln Asn Ile Ser Pro Trp Ile Leu Ala Val Leu Thr Leu
1               5                   10                  15

Gln Ile Gln Ser Leu
            20

<210> SEQ ID NO 122
<211> LENGTH: 22
<212> TYPE: PRT
<213> ORGANISM: Artificial Sequence
<220> FEATURE:
<223> OTHER INFORMATION: XBP1 peptide

<400> SEQUENCE: 122

Ser Pro Leu Gln Asn Ile Ser Pro Trp Ile Leu Ala Val Leu Thr Leu
1               5                   10                  15

Gln Ile Gln Ser Leu Ile
            20

<210> SEQ ID NO 123
<211> LENGTH: 23
<212> TYPE: PRT
<213> ORGANISM: Artificial Sequence
<220> FEATURE:
<223> OTHER INFORMATION: XBP1 peptide

<400> SEQUENCE: 123

Ser Pro Leu Gln Asn Ile Ser Pro Trp Ile Leu Ala Val Leu Thr Leu
1               5                   10                  15

Gln Ile Gln Ser Leu Ile Ser
            20

<210> SEQ ID NO 124
<211> LENGTH: 24
<212> TYPE: PRT
<213> ORGANISM: Artificial Sequence
<220> FEATURE:
<223> OTHER INFORMATION: XBP1 protein

<400> SEQUENCE: 124

Ser Pro Leu Gln Asn Ile Ser Pro Trp Ile Leu Ala Val Leu Thr Leu
1               5                   10                  15

Gln Ile Gln Ser Leu Ile Ser Cys
            20

<210> SEQ ID NO 125
<211> LENGTH: 25
<212> TYPE: PRT
<213> ORGANISM: Artificial Sequence
<220> FEATURE:
<223> OTHER INFORMATION: XBP1 peptide

<400> SEQUENCE: 125

Ser Pro Leu Gln Asn Ile Ser Pro Trp Ile Leu Ala Val Leu Thr Leu
1               5                   10                  15
```

```
Gln Ile Gln Ser Leu Ile Ser Cys Trp
        20                  25

<210> SEQ ID NO 126
<211> LENGTH: 26
<212> TYPE: PRT
<213> ORGANISM: Artificial Sequence
<220> FEATURE:
<223> OTHER INFORMATION: XBP1 peptide

<400> SEQUENCE: 126

Ser Pro Leu Gln Asn Ile Ser Pro Trp Ile Leu Ala Val Leu Thr Leu
1               5                   10                  15

Gln Ile Gln Ser Leu Ile Ser Cys Trp Ala
        20                  25

<210> SEQ ID NO 127
<211> LENGTH: 13
<212> TYPE: PRT
<213> ORGANISM: Artificial Sequence
<220> FEATURE:
<223> OTHER INFORMATION: XBP1 peptide

<400> SEQUENCE: 127

Pro Leu Gln Asn Ile Ser Pro Trp Ile Leu Ala Val Leu
1               5                   10

<210> SEQ ID NO 128
<211> LENGTH: 14
<212> TYPE: PRT
<213> ORGANISM: Artificial Sequence
<220> FEATURE:
<223> OTHER INFORMATION: XBP1 peptide

<400> SEQUENCE: 128

Pro Leu Gln Asn Ile Ser Pro Trp Ile Leu Ala Val Leu Thr
1               5                   10

<210> SEQ ID NO 129
<211> LENGTH: 15
<212> TYPE: PRT
<213> ORGANISM: Artificial Sequence
<220> FEATURE:
<223> OTHER INFORMATION: XBP1 peptide

<400> SEQUENCE: 129

Pro Leu Gln Asn Ile Ser Pro Trp Ile Leu Ala Val Leu Thr Leu
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: XBP1 peptide

<400> SEQUENCE: 130

Pro Leu Gln Asn Ile Ser Pro Trp Ile Leu Ala Val Leu Thr Leu Gln
1               5                   10                  15

<210> SEQ ID NO 131
<211> LENGTH: 17
<212> TYPE: PRT
<213> ORGANISM: Artificial Sequence
<220> FEATURE:
<223> OTHER INFORMATION: XBP1 peptide
```

```
<400> SEQUENCE: 131

Pro Leu Gln Asn Ile Ser Pro Trp Ile Leu Ala Val Leu Thr Leu Gln
1               5                   10                  15

Ile

<210> SEQ ID NO 132
<211> LENGTH: 18
<212> TYPE: PRT
<213> ORGANISM: Artificial Sequence
<220> FEATURE:
<223> OTHER INFORMATION: XBP1 peptide

<400> SEQUENCE: 132

Pro Leu Gln Asn Ile Ser Pro Trp Ile Leu Ala Val Leu Thr Leu Gln
1               5                   10                  15

Ile Gln

<210> SEQ ID NO 133
<211> LENGTH: 19
<212> TYPE: PRT
<213> ORGANISM: Artificial Sequence
<220> FEATURE:
<223> OTHER INFORMATION: XBP1 peptide

<400> SEQUENCE: 133

Pro Leu Gln Asn Ile Ser Pro Trp Ile Leu Ala Val Leu Thr Leu Gln
1               5                   10                  15

Ile Gln Ser

<210> SEQ ID NO 134
<211> LENGTH: 20
<212> TYPE: PRT
<213> ORGANISM: Artificial Sequence
<220> FEATURE:
<223> OTHER INFORMATION: XBP1 peptide

<400> SEQUENCE: 134

Pro Leu Gln Asn Ile Ser Pro Trp Ile Leu Ala Val Leu Thr Leu Gln
1               5                   10                  15

Ile Gln Ser Leu
            20

<210> SEQ ID NO 135
<211> LENGTH: 21
<212> TYPE: PRT
<213> ORGANISM: Artificial Sequence
<220> FEATURE:
<223> OTHER INFORMATION: XBP1 peptide

<400> SEQUENCE: 135

Pro Leu Gln Asn Ile Ser Pro Trp Ile Leu Ala Val Leu Thr Leu Gln
1               5                   10                  15

Ile Gln Ser Leu Ile
            20

<210> SEQ ID NO 136
<211> LENGTH: 22
<212> TYPE: PRT
<213> ORGANISM: Artificial Sequence
<220> FEATURE:
<223> OTHER INFORMATION: XBP1 peptide

<400> SEQUENCE: 136
```

-continued

```
Pro Leu Gln Asn Ile Ser Pro Trp Ile Leu Ala Val Leu Thr Leu Gln
1               5                   10                  15

Ile Gln Ser Leu Ile Ser
            20

<210> SEQ ID NO 137
<211> LENGTH: 23
<212> TYPE: PRT
<213> ORGANISM: Artificial Sequence
<220> FEATURE:
<223> OTHER INFORMATION: XBP1 peptide

<400> SEQUENCE: 137

Pro Leu Gln Asn Ile Ser Pro Trp Ile Leu Ala Val Leu Thr Leu Gln
1               5                   10                  15

Ile Gln Ser Leu Ile Ser Cys
            20

<210> SEQ ID NO 138
<211> LENGTH: 24
<212> TYPE: PRT
<213> ORGANISM: Artificial Sequence
<220> FEATURE:
<223> OTHER INFORMATION: XBP1 peptide

<400> SEQUENCE: 138

Pro Leu Gln Asn Ile Ser Pro Trp Ile Leu Ala Val Leu Thr Leu Gln
1               5                   10                  15

Ile Gln Ser Leu Ile Ser Cys Trp
            20

<210> SEQ ID NO 139
<211> LENGTH: 25
<212> TYPE: PRT
<213> ORGANISM: Artificial Sequence
<220> FEATURE:
<223> OTHER INFORMATION: XBP1 peptide

<400> SEQUENCE: 139

Pro Leu Gln Asn Ile Ser Pro Trp Ile Leu Ala Val Leu Thr Leu Gln
1               5                   10                  15

Ile Gln Ser Leu Ile Ser Cys Trp Ala
            20              25

<210> SEQ ID NO 140
<211> LENGTH: 12
<212> TYPE: PRT
<213> ORGANISM: Artificial Sequence
<220> FEATURE:
<223> OTHER INFORMATION: XBP1 peptide

<400> SEQUENCE: 140

Leu Gln Asn Ile Ser Pro Trp Ile Leu Ala Val Leu
1               5                   10

<210> SEQ ID NO 141
<211> LENGTH: 13
<212> TYPE: PRT
<213> ORGANISM: Artificial Sequence
<220> FEATURE:
<223> OTHER INFORMATION: XBP1 peptide

<400> SEQUENCE: 141

Leu Gln Asn Ile Ser Pro Trp Ile Leu Ala Val Leu Thr
1               5                   10
```

-continued

```
<210> SEQ ID NO 142
<211> LENGTH: 14
<212> TYPE: PRT
<213> ORGANISM: Artificial Sequence
<220> FEATURE:
<223> OTHER INFORMATION: XBP1 peptide

<400> SEQUENCE: 142

Leu Gln Asn Ile Ser Pro Trp Ile Leu Ala Val Leu Thr Leu
1               5                   10

<210> SEQ ID NO 143
<211> LENGTH: 15
<212> TYPE: PRT
<213> ORGANISM: Artificial Sequence
<220> FEATURE:
<223> OTHER INFORMATION: XBP1 peptide

<400> SEQUENCE: 143

Leu Gln Asn Ile Ser Pro Trp Ile Leu Ala Val Leu Thr Leu Gln
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: XBP1 peptide

<400> SEQUENCE: 144

Leu Gln Asn Ile Ser Pro Trp Ile Leu Ala Val Leu Thr Leu Gln Ile
1               5                   10                  15

<210> SEQ ID NO 145
<211> LENGTH: 17
<212> TYPE: PRT
<213> ORGANISM: Artificial Sequence
<220> FEATURE:
<223> OTHER INFORMATION: XBP1 peptide

<400> SEQUENCE: 145

Leu Gln Asn Ile Ser Pro Trp Ile Leu Ala Val Leu Thr Leu Gln Ile
1               5                   10                  15

Gln

<210> SEQ ID NO 146
<211> LENGTH: 18
<212> TYPE: PRT
<213> ORGANISM: Artificial Sequence
<220> FEATURE:
<223> OTHER INFORMATION: XBP1 peptide

<400> SEQUENCE: 146

Leu Gln Asn Ile Ser Pro Trp Ile Leu Ala Val Leu Thr Leu Gln Ile
1               5                   10                  15

Gln Ser

<210> SEQ ID NO 147
<211> LENGTH: 19
<212> TYPE: PRT
<213> ORGANISM: Artificial Sequence
<220> FEATURE:
<223> OTHER INFORMATION: XBP1 peptide

<400> SEQUENCE: 147
```

Leu Gln Asn Ile Ser Pro Trp Ile Leu Ala Val Leu Thr Leu Gln Ile
1               5                   10                  15

Gln Ser Leu

<210> SEQ ID NO 148
<211> LENGTH: 20
<212> TYPE: PRT
<213> ORGANISM: Artificial Sequence
<220> FEATURE:
<223> OTHER INFORMATION: XBP1 peptide

<400> SEQUENCE: 148

Leu Gln Asn Ile Ser Pro Trp Ile Leu Ala Val Leu Thr Leu Gln Ile
1               5                   10                  15

Gln Ser Leu Ile
          20

<210> SEQ ID NO 149
<211> LENGTH: 21
<212> TYPE: PRT
<213> ORGANISM: Artificial Sequence
<220> FEATURE:
<223> OTHER INFORMATION: XBP1 peptide

<400> SEQUENCE: 149

Leu Gln Asn Ile Ser Pro Trp Ile Leu Ala Val Leu Thr Leu Gln Ile
1               5                   10                  15

Gln Ser Leu Ile Ser
          20

<210> SEQ ID NO 150
<211> LENGTH: 22
<212> TYPE: PRT
<213> ORGANISM: Artificial Sequence
<220> FEATURE:
<223> OTHER INFORMATION: XBP1 peptide

<400> SEQUENCE: 150

Leu Gln Asn Ile Ser Pro Trp Ile Leu Ala Val Leu Thr Leu Gln Ile
1               5                   10                  15

Gln Ser Leu Ile Ser Cys
          20

<210> SEQ ID NO 151
<211> LENGTH: 23
<212> TYPE: PRT
<213> ORGANISM: Artificial Sequence
<220> FEATURE:
<223> OTHER INFORMATION: XBP1 peptide

<400> SEQUENCE: 151

Leu Gln Asn Ile Ser Pro Trp Ile Leu Ala Val Leu Thr Leu Gln Ile
1               5                   10                  15

Gln Ser Leu Ile Ser Cys Trp
          20

<210> SEQ ID NO 152
<211> LENGTH: 24
<212> TYPE: PRT
<213> ORGANISM: Artificial Sequence
<220> FEATURE:
<223> OTHER INFORMATION: XBP1 peptide

<400> SEQUENCE: 152

-continued

```
Leu Gln Asn Ile Ser Pro Trp Ile Leu Ala Val Leu Thr Leu Gln Ile
1               5                   10                  15

Gln Ser Leu Ile Ser Cys Trp Ala
            20

<210> SEQ ID NO 153
<211> LENGTH: 11
<212> TYPE: PRT
<213> ORGANISM: Artificial Sequence
<220> FEATURE:
<223> OTHER INFORMATION: XBP1 peptide

<400> SEQUENCE: 153

Gln Asn Ile Ser Pro Trp Ile Leu Ala Val Leu
1               5                   10

<210> SEQ ID NO 154
<211> LENGTH: 12
<212> TYPE: PRT
<213> ORGANISM: Artificial Sequence
<220> FEATURE:
<223> OTHER INFORMATION: XBP1 peptide

<400> SEQUENCE: 154

Gln Asn Ile Ser Pro Trp Ile Leu Ala Val Leu Thr
1               5                   10

<210> SEQ ID NO 155
<211> LENGTH: 13
<212> TYPE: PRT
<213> ORGANISM: Artificial Sequence
<220> FEATURE:
<223> OTHER INFORMATION: XBP1 peptide

<400> SEQUENCE: 155

Gln Asn Ile Ser Pro Trp Ile Leu Ala Val Leu Thr Leu
1               5                   10

<210> SEQ ID NO 156
<211> LENGTH: 14
<212> TYPE: PRT
<213> ORGANISM: Artificial Sequence
<220> FEATURE:
<223> OTHER INFORMATION: XBP1 peptide

<400> SEQUENCE: 156

Gln Asn Ile Ser Pro Trp Ile Leu Ala Val Leu Thr Leu Gln
1               5                   10

<210> SEQ ID NO 157
<211> LENGTH: 15
<212> TYPE: PRT
<213> ORGANISM: Artificial Sequence
<220> FEATURE:
<223> OTHER INFORMATION: XBP1 peptide

<400> SEQUENCE: 157

Gln Asn Ile Ser Pro Trp Ile Leu Ala Val Leu Thr Leu Gln Ile
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: XBP1 peptide
```

<400> SEQUENCE: 158

Gln Asn Ile Ser Pro Trp Ile Leu Ala Val Leu Thr Leu Gln Ile Gln
1               5                   10                  15

<210> SEQ ID NO 159
<211> LENGTH: 17
<212> TYPE: PRT
<213> ORGANISM: Artificial Sequence
<220> FEATURE:
<223> OTHER INFORMATION: XBP1 peptide

<400> SEQUENCE: 159

Gln Asn Ile Ser Pro Trp Ile Leu Ala Val Leu Thr Leu Gln Ile Gln
1               5                   10                  15

Ser

<210> SEQ ID NO 160
<211> LENGTH: 18
<212> TYPE: PRT
<213> ORGANISM: Artificial Sequence
<220> FEATURE:
<223> OTHER INFORMATION: XBP1 peptide

<400> SEQUENCE: 160

Gln Asn Ile Ser Pro Trp Ile Leu Ala Val Leu Thr Leu Gln Ile Gln
1               5                   10                  15

Ser Leu

<210> SEQ ID NO 161
<211> LENGTH: 19
<212> TYPE: PRT
<213> ORGANISM: Artificial Sequence
<220> FEATURE:
<223> OTHER INFORMATION: XBP1 peptide

<400> SEQUENCE: 161

Gln Asn Ile Ser Pro Trp Ile Leu Ala Val Leu Thr Leu Gln Ile Gln
1               5                   10                  15

Ser Leu Ile

<210> SEQ ID NO 162
<211> LENGTH: 20
<212> TYPE: PRT
<213> ORGANISM: Artificial Sequence
<220> FEATURE:
<223> OTHER INFORMATION: XBP1 peptide

<400> SEQUENCE: 162

Gln Asn Ile Ser Pro Trp Ile Leu Ala Val Leu Thr Leu Gln Ile Gln
1               5                   10                  15

Ser Leu Ile Ser
            20

<210> SEQ ID NO 163
<211> LENGTH: 21
<212> TYPE: PRT
<213> ORGANISM: Artificial Sequence
<220> FEATURE:
<223> OTHER INFORMATION: XBP1 peptide

<400> SEQUENCE: 163

Gln Asn Ile Ser Pro Trp Ile Leu Ala Val Leu Thr Leu Gln Ile Gln
1               5                   10                  15

```
Ser Leu Ile Ser Cys
            20

<210> SEQ ID NO 164
<211> LENGTH: 22
<212> TYPE: PRT
<213> ORGANISM: Artificial Sequence
<220> FEATURE:
<223> OTHER INFORMATION: XBP1 peptide

<400> SEQUENCE: 164

Gln Asn Ile Ser Pro Trp Ile Leu Ala Val Leu Thr Leu Gln Ile Gln
1               5                   10                  15

Ser Leu Ile Ser Cys Trp
            20

<210> SEQ ID NO 165
<211> LENGTH: 23
<212> TYPE: PRT
<213> ORGANISM: Artificial Sequence
<220> FEATURE:
<223> OTHER INFORMATION: XBP1 peptide

<400> SEQUENCE: 165

Gln Asn Ile Ser Pro Trp Ile Leu Ala Val Leu Thr Leu Gln Ile Gln
1               5                   10                  15

Ser Leu Ile Ser Cys Trp Ala
            20

<210> SEQ ID NO 166
<211> LENGTH: 10
<212> TYPE: PRT
<213> ORGANISM: Artificial Sequence
<220> FEATURE:
<223> OTHER INFORMATION: XBP1 peptide

<400> SEQUENCE: 166

Asn Ile Ser Pro Trp Ile Leu Ala Val Leu
1               5                   10

<210> SEQ ID NO 167
<211> LENGTH: 11
<212> TYPE: PRT
<213> ORGANISM: Artificial Sequence
<220> FEATURE:
<223> OTHER INFORMATION: XBP1 peptide

<400> SEQUENCE: 167

Asn Ile Ser Pro Trp Ile Leu Ala Val Leu Thr
1               5                   10

<210> SEQ ID NO 168
<211> LENGTH: 12
<212> TYPE: PRT
<213> ORGANISM: Artificial Sequence
<220> FEATURE:
<223> OTHER INFORMATION: XBP1 peptide

<400> SEQUENCE: 168

Asn Ile Ser Pro Trp Ile Leu Ala Val Leu Thr Leu
1               5                   10

<210> SEQ ID NO 169
<211> LENGTH: 13
<212> TYPE: PRT
```

```
<213> ORGANISM: Artificial Sequence
<220> FEATURE:
<223> OTHER INFORMATION: XBP1 peptide

<400> SEQUENCE: 169

Asn Ile Ser Pro Trp Ile Leu Ala Val Leu Thr Leu Gln
1               5                   10

<210> SEQ ID NO 170
<211> LENGTH: 14
<212> TYPE: PRT
<213> ORGANISM: Artificial Sequence
<220> FEATURE:
<223> OTHER INFORMATION: XBP1 peptide

<400> SEQUENCE: 170

Asn Ile Ser Pro Trp Ile Leu Ala Val Leu Thr Leu Gln Ile
1               5                   10

<210> SEQ ID NO 171
<211> LENGTH: 15
<212> TYPE: PRT
<213> ORGANISM: Artificial Sequence
<220> FEATURE:
<223> OTHER INFORMATION: XBP1 peptide

<400> SEQUENCE: 171

Asn Ile Ser Pro Trp Ile Leu Ala Val Leu Thr Leu Gln Ile Gln
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: XBP1 peptide

<400> SEQUENCE: 172

Asn Ile Ser Pro Trp Ile Leu Ala Val Leu Thr Leu Gln Ile Gln Ser
1               5                   10                  15

<210> SEQ ID NO 173
<211> LENGTH: 17
<212> TYPE: PRT
<213> ORGANISM: Artificial Sequence
<220> FEATURE:
<223> OTHER INFORMATION: XBP1 peptide

<400> SEQUENCE: 173

Asn Ile Ser Pro Trp Ile Leu Ala Val Leu Thr Leu Gln Ile Gln Ser
1               5                   10                  15

Leu

<210> SEQ ID NO 174
<211> LENGTH: 18
<212> TYPE: PRT
<213> ORGANISM: Artificial Sequence
<220> FEATURE:
<223> OTHER INFORMATION: XBP1 peptide

<400> SEQUENCE: 174

Asn Ile Ser Pro Trp Ile Leu Ala Val Leu Thr Leu Gln Ile Gln Ser
1               5                   10                  15

Leu Ile
```

```
<210> SEQ ID NO 175
<211> LENGTH: 19
<212> TYPE: PRT
<213> ORGANISM: Artificial Sequence
<220> FEATURE:
<223> OTHER INFORMATION: XBP1 peptide

<400> SEQUENCE: 175

Asn Ile Ser Pro Trp Ile Leu Ala Val Leu Thr Leu Gln Ile Gln Ser
1               5                   10                  15

Leu Ile Ser

<210> SEQ ID NO 176
<211> LENGTH: 20
<212> TYPE: PRT
<213> ORGANISM: Artificial Sequence
<220> FEATURE:
<223> OTHER INFORMATION: XBP1 peptide

<400> SEQUENCE: 176

Asn Ile Ser Pro Trp Ile Leu Ala Val Leu Thr Leu Gln Ile Gln Ser
1               5                   10                  15

Leu Ile Ser Cys
            20

<210> SEQ ID NO 177
<211> LENGTH: 21
<212> TYPE: PRT
<213> ORGANISM: Artificial Sequence
<220> FEATURE:
<223> OTHER INFORMATION: XBP1 peptide

<400> SEQUENCE: 177

Asn Ile Ser Pro Trp Ile Leu Ala Val Leu Thr Leu Gln Ile Gln Ser
1               5                   10                  15

Leu Ile Ser Cys Trp
            20

<210> SEQ ID NO 178
<211> LENGTH: 22
<212> TYPE: PRT
<213> ORGANISM: Artificial Sequence
<220> FEATURE:
<223> OTHER INFORMATION: XBP1 peptide

<400> SEQUENCE: 178

Asn Ile Ser Pro Trp Ile Leu Ala Val Leu Thr Leu Gln Ile Gln Ser
1               5                   10                  15

Leu Ile Ser Cys Trp Ala
            20

<210> SEQ ID NO 179
<211> LENGTH: 10
<212> TYPE: PRT
<213> ORGANISM: Artificial Sequence
<220> FEATURE:
<223> OTHER INFORMATION: XBP1 peptide

<400> SEQUENCE: 179

Tyr Ile Ser Pro Trp Ile Leu Ala Val Leu
1               5                   10

<210> SEQ ID NO 180
<211> LENGTH: 11
<212> TYPE: PRT
```

<213> ORGANISM: Artificial Sequence
<220> FEATURE:
<223> OTHER INFORMATION: XBP1 peptide

<400> SEQUENCE: 180

Tyr Ile Ser Pro Trp Ile Leu Ala Val Leu Thr
1               5                   10

<210> SEQ ID NO 181
<211> LENGTH: 12
<212> TYPE: PRT
<213> ORGANISM: Artificial Sequence
<220> FEATURE:
<223> OTHER INFORMATION: XBP1 peptide

<400> SEQUENCE: 181

Tyr Ile Ser Pro Trp Ile Leu Ala Val Leu Thr Leu
1               5                   10

<210> SEQ ID NO 182
<211> LENGTH: 13
<212> TYPE: PRT
<213> ORGANISM: Artificial Sequence
<220> FEATURE:
<223> OTHER INFORMATION: XBP1 peptide

<400> SEQUENCE: 182

Tyr Ile Ser Pro Trp Ile Leu Ala Val Leu Thr Leu Gln
1               5                   10

<210> SEQ ID NO 183
<211> LENGTH: 14
<212> TYPE: PRT
<213> ORGANISM: Artificial Sequence
<220> FEATURE:
<223> OTHER INFORMATION: XBP1 peptide

<400> SEQUENCE: 183

Tyr Ile Ser Pro Trp Ile Leu Ala Val Leu Thr Leu Gln Ile
1               5                   10

<210> SEQ ID NO 184
<211> LENGTH: 15
<212> TYPE: PRT
<213> ORGANISM: Artificial Sequence
<220> FEATURE:
<223> OTHER INFORMATION: XBP1 peptide

<400> SEQUENCE: 184

Tyr Ile Ser Pro Trp Ile Leu Ala Val Leu Thr Leu Gln Ile Gln
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: XBP1 peptide

<400> SEQUENCE: 185

Tyr Ile Ser Pro Trp Ile Leu Ala Val Leu Thr Leu Gln Ile Gln Ser
1               5                   10                  15

<210> SEQ ID NO 186
<211> LENGTH: 17
<212> TYPE: PRT
<213> ORGANISM: Artificial Sequence

```
<220> FEATURE:
<223> OTHER INFORMATION: XBP1 peptide

<400> SEQUENCE: 186

Tyr Ile Ser Pro Trp Ile Leu Ala Val Leu Thr Leu Gln Ile Gln Ser
1               5                   10                  15

Leu

<210> SEQ ID NO 187
<211> LENGTH: 18
<212> TYPE: PRT
<213> ORGANISM: Artificial Sequence
<220> FEATURE:
<223> OTHER INFORMATION: XBP1 peptide

<400> SEQUENCE: 187

Tyr Ile Ser Pro Trp Ile Leu Ala Val Leu Thr Leu Gln Ile Gln Ser
1               5                   10                  15

Leu Ile

<210> SEQ ID NO 188
<211> LENGTH: 19
<212> TYPE: PRT
<213> ORGANISM: Artificial Sequence
<220> FEATURE:
<223> OTHER INFORMATION: XBP1 peptide

<400> SEQUENCE: 188

Tyr Ile Ser Pro Trp Ile Leu Ala Val Leu Thr Leu Gln Ile Gln Ser
1               5                   10                  15

Leu Ile Ser

<210> SEQ ID NO 189
<211> LENGTH: 20
<212> TYPE: PRT
<213> ORGANISM: Artificial Sequence
<220> FEATURE:
<223> OTHER INFORMATION: XBP1 peptide

<400> SEQUENCE: 189

Tyr Ile Ser Pro Trp Ile Leu Ala Val Leu Thr Leu Gln Ile Gln Ser
1               5                   10                  15

Leu Ile Ser Cys
            20

<210> SEQ ID NO 190
<211> LENGTH: 21
<212> TYPE: PRT
<213> ORGANISM: Artificial Sequence
<220> FEATURE:
<223> OTHER INFORMATION: XBP1 peptide

<400> SEQUENCE: 190

Tyr Ile Ser Pro Trp Ile Leu Ala Val Leu Thr Leu Gln Ile Gln Ser
1               5                   10                  15

Leu Ile Ser Cys Trp
            20

<210> SEQ ID NO 191
<211> LENGTH: 22
<212> TYPE: PRT
<213> ORGANISM: Artificial Sequence
<220> FEATURE:
<223> OTHER INFORMATION: XBP1 peptide
```

<400> SEQUENCE: 191

Tyr Ile Ser Pro Trp Ile Leu Ala Val Leu Thr Leu Gln Ile Gln Ser
1               5                   10                  15

Leu Ile Ser Cys Trp Ala
            20

<210> SEQ ID NO 192
<211> LENGTH: 9
<212> TYPE: PRT
<213> ORGANISM: Artificial Sequence
<220> FEATURE:
<223> OTHER INFORMATION: XBP1 peptide

<400> SEQUENCE: 192

Ile Ser Pro Trp Ile Leu Ala Val Leu
1               5

<210> SEQ ID NO 193
<211> LENGTH: 10
<212> TYPE: PRT
<213> ORGANISM: Artificial Sequence
<220> FEATURE:
<223> OTHER INFORMATION: XBP1 peptide

<400> SEQUENCE: 193

Ile Ser Pro Trp Ile Leu Ala Val Leu Thr
1               5                   10

<210> SEQ ID NO 194
<211> LENGTH: 11
<212> TYPE: PRT
<213> ORGANISM: Artificial Sequence
<220> FEATURE:
<223> OTHER INFORMATION: XBP1 peptide

<400> SEQUENCE: 194

Ile Ser Pro Trp Ile Leu Ala Val Leu Thr Leu
1               5                   10

<210> SEQ ID NO 195
<211> LENGTH: 12
<212> TYPE: PRT
<213> ORGANISM: Artificial Sequence
<220> FEATURE:
<223> OTHER INFORMATION: XBP1 peptide

<400> SEQUENCE: 195

Ile Ser Pro Trp Ile Leu Ala Val Leu Thr Leu Gln
1               5                   10

<210> SEQ ID NO 196
<211> LENGTH: 13
<212> TYPE: PRT
<213> ORGANISM: Artificial Sequence
<220> FEATURE:
<223> OTHER INFORMATION: XBP1 peptide

<400> SEQUENCE: 196

Ile Ser Pro Trp Ile Leu Ala Val Leu Thr Leu Gln Ile
1               5                   10

<210> SEQ ID NO 197
<211> LENGTH: 14
<212> TYPE: PRT
<213> ORGANISM: Artificial Sequence -continued

```
<220> FEATURE:
<223> OTHER INFORMATION: XBP1 peptide

<400> SEQUENCE: 197

Ile Ser Pro Trp Ile Leu Ala Val Leu Thr Leu Gln Ile Gln
1               5                   10

<210> SEQ ID NO 198
<211> LENGTH: 15
<212> TYPE: PRT
<213> ORGANISM: Artificial Sequence
<220> FEATURE:
<223> OTHER INFORMATION: XBP1 peptide

<400> SEQUENCE: 198

Ile Ser Pro Trp Ile Leu Ala Val Leu Thr Leu Gln Ile Gln Ser
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: XBP1 peptide

<400> SEQUENCE: 199

Ile Ser Pro Trp Ile Leu Ala Val Leu Thr Leu Gln Ile Gln Ser Leu
1               5                   10                  15

<210> SEQ ID NO 200
<211> LENGTH: 17
<212> TYPE: PRT
<213> ORGANISM: Artificial Sequence
<220> FEATURE:
<223> OTHER INFORMATION: XBP1 peptide

<400> SEQUENCE: 200

Ile Ser Pro Trp Ile Leu Ala Val Leu Thr Leu Gln Ile Gln Ser Leu
1               5                   10                  15

Ile

<210> SEQ ID NO 201
<211> LENGTH: 18
<212> TYPE: PRT
<213> ORGANISM: Artificial Sequence
<220> FEATURE:
<223> OTHER INFORMATION: XBP1 peptide

<400> SEQUENCE: 201

Ile Ser Pro Trp Ile Leu Ala Val Leu Thr Leu Gln Ile Gln Ser Leu
1               5                   10                  15

Ile Ser

<210> SEQ ID NO 202
<211> LENGTH: 19
<212> TYPE: PRT
<213> ORGANISM: Artificial Sequence
<220> FEATURE:
<223> OTHER INFORMATION: XBP1 peptide

<400> SEQUENCE: 202

Ile Ser Pro Trp Ile Leu Ala Val Leu Thr Leu Gln Ile Gln Ser Leu
1               5                   10                  15

Ile Ser Cys
```

```
<210> SEQ ID NO 203
<211> LENGTH: 20
<212> TYPE: PRT
<213> ORGANISM: Artificial Sequence
<220> FEATURE:
<223> OTHER INFORMATION: XBP1 peptide

<400> SEQUENCE: 203

Ile Ser Pro Trp Ile Leu Ala Val Leu Thr Leu Gln Ile Gln Ser Leu
1               5                   10                  15

Ile Ser Cys Trp
            20

<210> SEQ ID NO 204
<211> LENGTH: 21
<212> TYPE: PRT
<213> ORGANISM: Artificial Sequence
<220> FEATURE:
<223> OTHER INFORMATION: XBP1 peptide

<400> SEQUENCE: 204

Ile Ser Pro Trp Ile Leu Ala Val Leu Thr Leu Gln Ile Gln Ser Leu
1               5                   10                  15

Ile Ser Cys Trp Ala
            20

<210> SEQ ID NO 205
<211> LENGTH: 8
<212> TYPE: PRT
<213> ORGANISM: Artificial Sequence
<220> FEATURE:
<223> OTHER INFORMATION: XBP1 peptide

<400> SEQUENCE: 205

Ser Pro Trp Ile Leu Ala Val Leu
1               5

<210> SEQ ID NO 206
<211> LENGTH: 9
<212> TYPE: PRT
<213> ORGANISM: Artificial Sequence
<220> FEATURE:
<223> OTHER INFORMATION: XBP1 peptide

<400> SEQUENCE: 206

Ser Pro Trp Ile Leu Ala Val Leu Thr
1               5

<210> SEQ ID NO 207
<211> LENGTH: 10
<212> TYPE: PRT
<213> ORGANISM: Artificial Sequence
<220> FEATURE:
<223> OTHER INFORMATION: XBP1 peptide

<400> SEQUENCE: 207

Ser Pro Trp Ile Leu Ala Val Leu Thr Leu
1               5                   10

<210> SEQ ID NO 208
<211> LENGTH: 11
<212> TYPE: PRT
<213> ORGANISM: Artificial Sequence
<220> FEATURE:
<223> OTHER INFORMATION: XBP1 peptide
```

```
<400> SEQUENCE: 208

Ser Pro Trp Ile Leu Ala Val Leu Thr Leu Gln
1               5                   10

<210> SEQ ID NO 209
<211> LENGTH: 12
<212> TYPE: PRT
<213> ORGANISM: Artificial Sequence
<220> FEATURE:
<223> OTHER INFORMATION: XBP1 peptide

<400> SEQUENCE: 209

Ser Pro Trp Ile Leu Ala Val Leu Thr Leu Gln Ile
1               5                   10

<210> SEQ ID NO 210
<211> LENGTH: 13
<212> TYPE: PRT
<213> ORGANISM: Artificial Sequence
<220> FEATURE:
<223> OTHER INFORMATION: XBP1 peptide

<400> SEQUENCE: 210

Ser Pro Trp Ile Leu Ala Val Leu Thr Leu Gln Ile Gln
1               5                   10

<210> SEQ ID NO 211
<211> LENGTH: 14
<212> TYPE: PRT
<213> ORGANISM: Artificial Sequence
<220> FEATURE:
<223> OTHER INFORMATION: XBP1 peptide

<400> SEQUENCE: 211

Ser Pro Trp Ile Leu Ala Val Leu Thr Leu Gln Ile Gln Ser
1               5                   10

<210> SEQ ID NO 212
<211> LENGTH: 15
<212> TYPE: PRT
<213> ORGANISM: Artificial Sequence
<220> FEATURE:
<223> OTHER INFORMATION: XBP1 peptide

<400> SEQUENCE: 212

Ser Pro Trp Ile Leu Ala Val Leu Thr Leu Gln Ile Gln Ser Leu
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: XBP1 peptide

<400> SEQUENCE: 213

Ser Pro Trp Ile Leu Ala Val Leu Thr Leu Gln Ile Gln Ser Leu Ile
1               5                   10                  15

<210> SEQ ID NO 214
<211> LENGTH: 17
<212> TYPE: PRT
<213> ORGANISM: Artificial Sequence
<220> FEATURE:
<223> OTHER INFORMATION: XBP1 peptide

<400> SEQUENCE: 214
```

-continued

```
Ser Pro Trp Ile Leu Ala Val Leu Thr Leu Gln Ile Ser Ser Leu Ile
1               5                   10                  15

Ser
```

```
<210> SEQ ID NO 215
<211> LENGTH: 18
<212> TYPE: PRT
<213> ORGANISM: Artificial Sequence
<220> FEATURE:
<223> OTHER INFORMATION: XBP1 peptide

<400> SEQUENCE: 215

Ser Pro Trp Ile Leu Ala Val Leu Thr Leu Gln Ile Ser Ser Leu Ile
1               5                   10                  15

Ser Cys
```

```
<210> SEQ ID NO 216
<211> LENGTH: 19
<212> TYPE: PRT
<213> ORGANISM: Artificial Sequence
<220> FEATURE:
<223> OTHER INFORMATION: XBP1 peptide

<400> SEQUENCE: 216

Ser Pro Trp Ile Leu Ala Val Leu Thr Leu Gln Ile Ser Ser Leu Ile
1               5                   10                  15

Ser Cys Trp
```

```
<210> SEQ ID NO 217
<211> LENGTH: 20
<212> TYPE: PRT
<213> ORGANISM: Artificial Sequence
<220> FEATURE:
<223> OTHER INFORMATION: XBP1 peptide

<400> SEQUENCE: 217

Ser Pro Trp Ile Leu Ala Val Leu Thr Leu Gln Ile Ser Ser Leu Ile
1               5                   10                  15

Ser Cys Trp Ala
            20
```

```
<210> SEQ ID NO 218
<211> LENGTH: 7
<212> TYPE: PRT
<213> ORGANISM: Artificial Sequence
<220> FEATURE:
<223> OTHER INFORMATION: XBP1 peptide

<400> SEQUENCE: 218

Pro Trp Ile Leu Ala Val Leu
1               5
```

```
<210> SEQ ID NO 219
<211> LENGTH: 8
<212> TYPE: PRT
<213> ORGANISM: Artificial Sequence
<220> FEATURE:
<223> OTHER INFORMATION: XBP1 peptide

<400> SEQUENCE: 219

Pro Trp Ile Leu Ala Val Leu Thr
1               5
```

-continued

```
<210> SEQ ID NO 220
<211> LENGTH: 9
<212> TYPE: PRT
<213> ORGANISM: Artificial Sequence
<220> FEATURE:
<223> OTHER INFORMATION: XBP1 peptide

<400> SEQUENCE: 220

Pro Trp Ile Leu Ala Val Leu Thr Leu
1               5

<210> SEQ ID NO 221
<211> LENGTH: 10
<212> TYPE: PRT
<213> ORGANISM: Artificial Sequence
<220> FEATURE:
<223> OTHER INFORMATION: XBP1 peptide

<400> SEQUENCE: 221

Pro Trp Ile Leu Ala Val Leu Thr Leu Gln
1               5                   10

<210> SEQ ID NO 222
<211> LENGTH: 11
<212> TYPE: PRT
<213> ORGANISM: Artificial Sequence
<220> FEATURE:
<223> OTHER INFORMATION: XBP1 peptide

<400> SEQUENCE: 222

Pro Trp Ile Leu Ala Val Leu Thr Leu Gln Ile
1               5                   10

<210> SEQ ID NO 223
<211> LENGTH: 12
<212> TYPE: PRT
<213> ORGANISM: Artificial Sequence
<220> FEATURE:
<223> OTHER INFORMATION: XBP1 peptide

<400> SEQUENCE: 223

Pro Trp Ile Leu Ala Val Leu Thr Leu Gln Ile Gln
1               5                   10

<210> SEQ ID NO 224
<211> LENGTH: 13
<212> TYPE: PRT
<213> ORGANISM: Artificial Sequence
<220> FEATURE:
<223> OTHER INFORMATION: XBP1 peptide

<400> SEQUENCE: 224

Pro Trp Ile Leu Ala Val Leu Thr Leu Gln Ile Gln Ser
1               5                   10

<210> SEQ ID NO 225
<211> LENGTH: 14
<212> TYPE: PRT
<213> ORGANISM: Artificial Sequence
<220> FEATURE:
<223> OTHER INFORMATION: XBP1 peptide

<400> SEQUENCE: 225

Pro Trp Ile Leu Ala Val Leu Thr Leu Gln Ile Gln Ser Leu
1               5                   10

<210> SEQ ID NO 226
```

-continued

```
<211> LENGTH: 15
<212> TYPE: PRT
<213> ORGANISM: Artificial Sequence
<220> FEATURE:
<223> OTHER INFORMATION: XBP1 peptide

<400> SEQUENCE: 226

Pro Trp Ile Leu Ala Val Leu Thr Leu Gln Ile Gln Ser Leu Ile
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: XBP1 peptide

<400> SEQUENCE: 227

Pro Trp Ile Leu Ala Val Leu Thr Leu Gln Ile Gln Ser Leu Ile Ser
1               5                   10                  15

<210> SEQ ID NO 228
<211> LENGTH: 17
<212> TYPE: PRT
<213> ORGANISM: Artificial Sequence
<220> FEATURE:
<223> OTHER INFORMATION: XBP1 peptide

<400> SEQUENCE: 228

Pro Trp Ile Leu Ala Val Leu Thr Leu Gln Ile Gln Ser Leu Ile Ser
1               5                   10                  15

Cys

<210> SEQ ID NO 229
<211> LENGTH: 18
<212> TYPE: PRT
<213> ORGANISM: Artificial Sequence
<220> FEATURE:
<223> OTHER INFORMATION: XBP1 peptide

<400> SEQUENCE: 229

Pro Trp Ile Leu Ala Val Leu Thr Leu Gln Ile Gln Ser Leu Ile Ser
1               5                   10                  15

Cys Trp

<210> SEQ ID NO 230
<211> LENGTH: 19
<212> TYPE: PRT
<213> ORGANISM: Artificial Sequence
<220> FEATURE:
<223> OTHER INFORMATION: XBP1 peptide

<400> SEQUENCE: 230

Pro Trp Ile Leu Ala Val Leu Thr Leu Gln Ile Gln Ser Leu Ile Ser
1               5                   10                  15

Cys Trp Ala

<210> SEQ ID NO 231
<211> LENGTH: 6
<212> TYPE: PRT
<213> ORGANISM: Artificial Sequence
<220> FEATURE:
<223> OTHER INFORMATION: XBP1 peptide

<400> SEQUENCE: 231
```

-continued

```
Trp Ile Leu Ala Val Leu
1               5

<210> SEQ ID NO 232
<211> LENGTH: 7
<212> TYPE: PRT
<213> ORGANISM: Artificial Sequence
<220> FEATURE:
<223> OTHER INFORMATION: XBP1 peptide

<400> SEQUENCE: 232

Trp Ile Leu Ala Val Leu Thr
1               5

<210> SEQ ID NO 233
<211> LENGTH: 8
<212> TYPE: PRT
<213> ORGANISM: Artificial Sequence
<220> FEATURE:
<223> OTHER INFORMATION: XBP1 peptide

<400> SEQUENCE: 233

Trp Ile Leu Ala Val Leu Thr Leu
1               5

<210> SEQ ID NO 234
<211> LENGTH: 9
<212> TYPE: PRT
<213> ORGANISM: Artificial Sequence
<220> FEATURE:
<223> OTHER INFORMATION: XBP1 peptide

<400> SEQUENCE: 234

Trp Ile Leu Ala Val Leu Thr Leu Gln
1               5

<210> SEQ ID NO 235
<211> LENGTH: 10
<212> TYPE: PRT
<213> ORGANISM: Artificial Sequence
<220> FEATURE:
<223> OTHER INFORMATION: XBP1 peptide

<400> SEQUENCE: 235

Trp Ile Leu Ala Val Leu Thr Leu Gln Ile
1               5                   10

<210> SEQ ID NO 236
<211> LENGTH: 11
<212> TYPE: PRT
<213> ORGANISM: Artificial Sequence
<220> FEATURE:
<223> OTHER INFORMATION: XBP1 peptide

<400> SEQUENCE: 236

Trp Ile Leu Ala Val Leu Thr Leu Gln Ile Gln
1               5                   10

<210> SEQ ID NO 237
<211> LENGTH: 12
<212> TYPE: PRT
<213> ORGANISM: Artificial Sequence
<220> FEATURE:
<223> OTHER INFORMATION: XBP1 peptide

<400> SEQUENCE: 237

Trp Ile Leu Ala Val Leu Thr Leu Gln Ile Gln Ser
```

-continued

```
1               5                   10

<210> SEQ ID NO 238
<211> LENGTH: 13
<212> TYPE: PRT
<213> ORGANISM: Artificial Sequence
<220> FEATURE:
<223> OTHER INFORMATION: XBP1 peptide

<400> SEQUENCE: 238

Trp Ile Leu Ala Val Leu Thr Leu Gln Ile Gln Ser Leu
1               5                   10

<210> SEQ ID NO 239
<211> LENGTH: 14
<212> TYPE: PRT
<213> ORGANISM: Artificial Sequence
<220> FEATURE:
<223> OTHER INFORMATION: XBP1 peptide

<400> SEQUENCE: 239

Trp Ile Leu Ala Val Leu Thr Leu Gln Ile Gln Ser Leu Ile
1               5                   10

<210> SEQ ID NO 240
<211> LENGTH: 15
<212> TYPE: PRT
<213> ORGANISM: Artificial Sequence
<220> FEATURE:
<223> OTHER INFORMATION: XBP1 peptide

<400> SEQUENCE: 240

Trp Ile Leu Ala Val Leu Thr Leu Gln Ile Gln Ser Leu Ile Ser
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: XBP1 peptide

<400> SEQUENCE: 241

Trp Ile Leu Ala Val Leu Thr Leu Gln Ile Gln Ser Leu Ile Ser Cys
1               5                   10                  15

<210> SEQ ID NO 242
<211> LENGTH: 17
<212> TYPE: PRT
<213> ORGANISM: Artificial Sequence
<220> FEATURE:
<223> OTHER INFORMATION: XBP1 peptide

<400> SEQUENCE: 242

Trp Ile Leu Ala Val Leu Thr Leu Gln Ile Gln Ser Leu Ile Ser Cys
1               5                   10                  15

Trp

<210> SEQ ID NO 243
<211> LENGTH: 18
<212> TYPE: PRT
<213> ORGANISM: Artificial Sequence
<220> FEATURE:
<223> OTHER INFORMATION: XBP1 peptide

<400> SEQUENCE: 243
```

```
Trp Ile Leu Ala Val Leu Thr Leu Gln Ile Gln Ser Leu Ile Ser Cys
1               5                   10                  15

Trp Ala

<210> SEQ ID NO 244
<211> LENGTH: 5
<212> TYPE: PRT
<213> ORGANISM: Artificial Sequence
<220> FEATURE:
<223> OTHER INFORMATION: XBP1 peptide

<400> SEQUENCE: 244

Ile Leu Ala Val Leu
1               5

<210> SEQ ID NO 245
<211> LENGTH: 6
<212> TYPE: PRT
<213> ORGANISM: Artificial Sequence
<220> FEATURE:
<223> OTHER INFORMATION: XBP1 peptide

<400> SEQUENCE: 245

Ile Leu Ala Val Leu Thr
1               5

<210> SEQ ID NO 246
<211> LENGTH: 7
<212> TYPE: PRT
<213> ORGANISM: Artificial Sequence
<220> FEATURE:
<223> OTHER INFORMATION: XBP1 peptide

<400> SEQUENCE: 246

Ile Leu Ala Val Leu Thr Leu
1               5

<210> SEQ ID NO 247
<211> LENGTH: 8
<212> TYPE: PRT
<213> ORGANISM: Artificial Sequence
<220> FEATURE:
<223> OTHER INFORMATION: XBP1 peptide

<400> SEQUENCE: 247

Ile Leu Ala Val Leu Thr Leu Gln
1               5

<210> SEQ ID NO 248
<211> LENGTH: 9
<212> TYPE: PRT
<213> ORGANISM: Artificial Sequence
<220> FEATURE:
<223> OTHER INFORMATION: XBP1 peptide

<400> SEQUENCE: 248

Ile Leu Ala Val Leu Thr Leu Gln Ile
1               5

<210> SEQ ID NO 249
<211> LENGTH: 10
<212> TYPE: PRT
<213> ORGANISM: Artificial Sequence
<220> FEATURE:
<223> OTHER INFORMATION: XBP1 peptide

<400> SEQUENCE: 249
```

-continued

```
Ile Leu Ala Val Leu Thr Leu Gln Ile Gln
1               5                   10

<210> SEQ ID NO 250
<211> LENGTH: 11
<212> TYPE: PRT
<213> ORGANISM: Artificial Sequence
<220> FEATURE:
<223> OTHER INFORMATION: XBP1 peptide

<400> SEQUENCE: 250

Ile Leu Ala Val Leu Thr Leu Gln Ile Gln Ser
1               5                   10

<210> SEQ ID NO 251
<211> LENGTH: 12
<212> TYPE: PRT
<213> ORGANISM: Artificial Sequence
<220> FEATURE:
<223> OTHER INFORMATION: XBP1 peptide

<400> SEQUENCE: 251

Ile Leu Ala Val Leu Thr Leu Gln Ile Gln Ser Leu
1               5                   10

<210> SEQ ID NO 252
<211> LENGTH: 13
<212> TYPE: PRT
<213> ORGANISM: Artificial Sequence
<220> FEATURE:
<223> OTHER INFORMATION: XBP1 peptide

<400> SEQUENCE: 252

Ile Leu Ala Val Leu Thr Leu Gln Ile Gln Ser Leu Ile
1               5                   10

<210> SEQ ID NO 253
<211> LENGTH: 14
<212> TYPE: PRT
<213> ORGANISM: Artificial Sequence
<220> FEATURE:
<223> OTHER INFORMATION: XBP1 peptide

<400> SEQUENCE: 253

Ile Leu Ala Val Leu Thr Leu Gln Ile Gln Ser Leu Ile Ser
1               5                   10

<210> SEQ ID NO 254
<211> LENGTH: 15
<212> TYPE: PRT
<213> ORGANISM: Artificial Sequence
<220> FEATURE:
<223> OTHER INFORMATION: XBP1 peptide

<400> SEQUENCE: 254

Ile Leu Ala Val Leu Thr Leu Gln Ile Gln Ser Leu Ile Ser Cys
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: XBP1 peptide

<400> SEQUENCE: 255
```

-continued

```
Ile Leu Ala Val Leu Thr Leu Gln Ile Gln Ser Leu Ile Ser Cys Trp
1               5                   10                  15

<210> SEQ ID NO 256
<211> LENGTH: 17
<212> TYPE: PRT
<213> ORGANISM: Artificial Sequence
<220> FEATURE:
<223> OTHER INFORMATION: XBP1 peptide

<400> SEQUENCE: 256

Ile Leu Ala Val Leu Thr Leu Gln Ile Gln Ser Leu Ile Ser Cys Trp
1               5                   10                  15

Ala

<210> SEQ ID NO 257
<211> LENGTH: 9
<212> TYPE: PRT
<213> ORGANISM: Artificial Sequence
<220> FEATURE:
<223> OTHER INFORMATION: XBP1 peptide

<400> SEQUENCE: 257

Ser Thr Gln Lys Asp Pro Val Pro Tyr
1               5

<210> SEQ ID NO 258
<211> LENGTH: 10
<212> TYPE: PRT
<213> ORGANISM: Artificial Sequence
<220> FEATURE:
<223> OTHER INFORMATION: XBP1 peptide

<400> SEQUENCE: 258

Arg Ser Thr Gln Lys Asp Pro Val Pro Tyr
1               5                   10

<210> SEQ ID NO 259
<211> LENGTH: 9
<212> TYPE: PRT
<213> ORGANISM: Artificial Sequence
<220> FEATURE:
<223> OTHER INFORMATION: XBP1 peptide

<400> SEQUENCE: 259

Leu Leu Glu Asn Gln Leu Leu Arg Glu
1               5

<210> SEQ ID NO 260
<211> LENGTH: 11
<212> TYPE: PRT
<213> ORGANISM: Artificial Sequence
<220> FEATURE:
<223> OTHER INFORMATION: XBP1 peptide

<400> SEQUENCE: 260

Gln Arg Ser Thr Gln Lys Asp Pro Val Pro Tyr
1               5                   10

<210> SEQ ID NO 261
<211> LENGTH: 9
<212> TYPE: PRT
<213> ORGANISM: Artificial Sequence
<220> FEATURE:
<223> OTHER INFORMATION: XBP1 peptide

<400> SEQUENCE: 261
```

-continued

```
Leu Leu Arg Glu Lys Thr His Gly Leu
1               5

<210> SEQ ID NO 262
<211> LENGTH: 9
<212> TYPE: PRT
<213> ORGANISM: Artificial Sequence
<220> FEATURE:
<223> OTHER INFORMATION: XBP1 peptide

<400> SEQUENCE: 262

Asn Ile Ser Pro Trp Ile Leu Ala Val
1               5

<210> SEQ ID NO 263
<211> LENGTH: 9
<212> TYPE: PRT
<213> ORGANISM: Artificial Sequence
<220> FEATURE:
<223> OTHER INFORMATION: XBP1 peptide

<400> SEQUENCE: 263

Ile Leu Ala Val Leu Thr Leu Gln Ile
1               5

<210> SEQ ID NO 264
<211> LENGTH: 9
<212> TYPE: PRT
<213> ORGANISM: Artificial Sequence
<220> FEATURE:
<223> OTHER INFORMATION: XBP1 peptide

<400> SEQUENCE: 264

Val Leu Thr Leu Gln Ile Gln Ser Leu
1               5

<210> SEQ ID NO 265
<211> LENGTH: 10
<212> TYPE: PRT
<213> ORGANISM: Artificial Sequence
<220> FEATURE:
<223> OTHER INFORMATION: XBP1 peptide

<400> SEQUENCE: 265

Leu Val Ala Glu Glu Glu Ala Glu Ala Lys
1               5                   10

<210> SEQ ID NO 266
<211> LENGTH: 10
<212> TYPE: PRT
<213> ORGANISM: Artificial Sequence
<220> FEATURE:
<223> OTHER INFORMATION: XBP1 peptide

<400> SEQUENCE: 266

Ala Leu Pro Leu Met Val Pro Ala Gln Arg
1               5                   10

<210> SEQ ID NO 267
<211> LENGTH: 10
<212> TYPE: PRT
<213> ORGANISM: Artificial Sequence
<220> FEATURE:
<223> OTHER INFORMATION: XBP1 peptide

<400> SEQUENCE: 267
```

```
Arg Leu Thr His Leu Ser Pro Glu Glu Lys
1               5                   10
```

<210> SEQ ID NO 268
<211> LENGTH: 10
<212> TYPE: PRT
<213> ORGANISM: Artificial Sequence
<220> FEATURE:
<223> OTHER INFORMATION: XBP1 peptide

<400> SEQUENCE: 268

```
Lys Leu Lys Asn Arg Val Ala Ala Gln Thr
1               5                   10
```

<210> SEQ ID NO 269
<211> LENGTH: 9
<212> TYPE: PRT
<213> ORGANISM: Artificial Sequence
<220> FEATURE:
<223> OTHER INFORMATION: XBP1 peptide

<400> SEQUENCE: 269

```
Gly Ser Ala Glu Ser Ala Ala Leu Arg
1               5
```

<210> SEQ ID NO 270
<211> LENGTH: 10
<212> TYPE: PRT
<213> ORGANISM: Artificial Sequence
<220> FEATURE:
<223> OTHER INFORMATION: XBP1 peptide

<400> SEQUENCE: 270

```
Ala Ser Gly Gly Leu Pro Gln Ala Arg Lys
1               5                   10
```

<210> SEQ ID NO 271
<211> LENGTH: 10
<212> TYPE: PRT
<213> ORGANISM: Artificial Sequence
<220> FEATURE:
<223> OTHER INFORMATION: XBP1 peptide

<400> SEQUENCE: 271

```
Leu Ser Pro Glu Glu Lys Ala Leu Arg Arg
1               5                   10
```

<210> SEQ ID NO 272
<211> LENGTH: 9
<212> TYPE: PRT
<213> ORGANISM: Artificial Sequence
<220> FEATURE:
<223> OTHER INFORMATION: XBP1 peptide

<400> SEQUENCE: 272

```
Ala Ser Gly Gly Leu Pro Gln Ala Arg
1               5
```

<210> SEQ ID NO 273
<211> LENGTH: 10
<212> TYPE: PRT
<213> ORGANISM: Artificial Sequence
<220> FEATURE:
<223> OTHER INFORMATION: XBP1 peptide

<400> SEQUENCE: 273

```
Val Asp Leu Glu Glu Glu Asn Gln Lys Leu
```

-continued

```
1               5               10

<210> SEQ ID NO 274
<211> LENGTH: 9
<212> TYPE: PRT
<213> ORGANISM: Artificial Sequence
<220> FEATURE:
<223> OTHER INFORMATION: XBP1 peptide

<400> SEQUENCE: 274

Asp Gly Thr Pro Lys Val Leu Leu Leu
1               5

<210> SEQ ID NO 275
<211> LENGTH: 9
<212> TYPE: PRT
<213> ORGANISM: Artificial Sequence
<220> FEATURE:
<223> OTHER INFORMATION: XBP1 peptide

<400> SEQUENCE: 275

Lys Leu Leu Leu Glu Asn Gln Leu Leu
1               5

<210> SEQ ID NO 276
<211> LENGTH: 9
<212> TYPE: PRT
<213> ORGANISM: Artificial Sequence
<220> FEATURE:
<223> OTHER INFORMATION: XBP1 peptide

<400> SEQUENCE: 276

Leu Thr Leu Gln Ile Gln Ser Leu Ile
1               5

<210> SEQ ID NO 277
<211> LENGTH: 9
<212> TYPE: PRT
<213> ORGANISM: Artificial Sequence
<220> FEATURE:
<223> OTHER INFORMATION: XBP1 peptide

<400> SEQUENCE: 277

Asp Gly Thr Pro Lys Val Leu Leu Leu
1               5

<210> SEQ ID NO 278
<211> LENGTH: 10
<212> TYPE: PRT
<213> ORGANISM: Artificial Sequence
<220> FEATURE:
<223> OTHER INFORMATION: XBP1 peptide

<400> SEQUENCE: 278

Glu Val Arg Pro Val Ala Gly Ser Ala Glu
1               5               10

<210> SEQ ID NO 279
<211> LENGTH: 10
<212> TYPE: PRT
<213> ORGANISM: Artificial Sequence
<220> FEATURE:
<223> OTHER INFORMATION: XBP1 peptide

<400> SEQUENCE: 279

Ala Val Leu Thr Leu Gln Ile Gln Ser Leu
1               5               10
```

<210> SEQ ID NO 280
<211> LENGTH: 9
<212> TYPE: PRT
<213> ORGANISM: Artificial Sequence
<220> FEATURE:
<223> OTHER INFORMATION: XBP1 peptide

<400> SEQUENCE: 280

Glu Val Arg Pro Val Ala Gly Ser Ala
1               5

<210> SEQ ID NO 281
<211> LENGTH: 11
<212> TYPE: PRT
<213> ORGANISM: Artificial Sequence
<220> FEATURE:
<223> OTHER INFORMATION: XBP1 peptide

<400> SEQUENCE: 281

Gln Ala Leu Pro Leu Met Val Pro Ala Gln Arg
1               5                   10

<210> SEQ ID NO 282
<211> LENGTH: 11
<212> TYPE: PRT
<213> ORGANISM: Artificial Sequence
<220> FEATURE:
<223> OTHER INFORMATION: XBP1 peptide

<400> SEQUENCE: 282

Glu Ala Ala Ser Gly Gly Leu Pro Gln Ala Arg
1               5                   10

<210> SEQ ID NO 283
<211> LENGTH: 11
<212> TYPE: PRT
<213> ORGANISM: Artificial Sequence
<220> FEATURE:
<223> OTHER INFORMATION: XBP1 peptide

<400> SEQUENCE: 283

Val Ala Gly Ser Ala Glu Ser Ala Ala Leu Arg
1               5                   10

<210> SEQ ID NO 284
<211> LENGTH: 11
<212> TYPE: PRT
<213> ORGANISM: Artificial Sequence
<220> FEATURE:
<223> OTHER INFORMATION: XBP1 peptide

<400> SEQUENCE: 284

Asn Ala Leu Pro Gln Ser Leu Pro Ala Trp Arg
1               5                   10

<210> SEQ ID NO 285
<211> LENGTH: 9
<212> TYPE: PRT
<213> ORGANISM: Artificial Sequence
<220> FEATURE:
<223> OTHER INFORMATION: XBP1 peptide

<400> SEQUENCE: 285

Ala Pro Ala Gly Gln Ala Leu Pro Leu
1               5

-continued

```
<210> SEQ ID NO 286
<211> LENGTH: 10
<212> TYPE: PRT
<213> ORGANISM: Artificial Sequence
<220> FEATURE:
<223> OTHER INFORMATION: XBP1 peptide

<400> SEQUENCE: 286

Ala Pro Leu Gln Gln Val Gln Ala Gln Leu
1               5                   10

<210> SEQ ID NO 287
<211> LENGTH: 10
<212> TYPE: PRT
<213> ORGANISM: Artificial Sequence
<220> FEATURE:
<223> OTHER INFORMATION: XBP1 peptide

<400> SEQUENCE: 287

Ser Pro Trp Ile Leu Ala Val Leu Thr Leu
1               5                   10

<210> SEQ ID NO 288
<211> LENGTH: 10
<212> TYPE: PRT
<213> ORGANISM: Artificial Sequence
<220> FEATURE:
<223> OTHER INFORMATION: XBP1 peptide

<400> SEQUENCE: 288

Asp Pro Val Pro Tyr Gln Pro Pro Phe Leu
1               5                   10

<210> SEQ ID NO 289
<211> LENGTH: 9
<212> TYPE: PRT
<213> ORGANISM: Artificial Sequence
<220> FEATURE:
<223> OTHER INFORMATION: XBP1 peptide

<400> SEQUENCE: 289

Leu Leu Arg Glu Lys Thr His Gly Leu
1               5

<210> SEQ ID NO 290
<211> LENGTH: 8
<212> TYPE: PRT
<213> ORGANISM: Artificial Sequence
<220> FEATURE:
<223> OTHER INFORMATION: XBP1 peptide

<400> SEQUENCE: 290

Ala Leu Arg Leu Arg Ala Pro Leu
1               5

<210> SEQ ID NO 291
<211> LENGTH: 9
<212> TYPE: PRT
<213> ORGANISM: Artificial Sequence
<220> FEATURE:
<223> OTHER INFORMATION: XBP1 peptide

<400> SEQUENCE: 291

Arg Lys Lys Ala Arg Met Ser Glu Leu
1               5
```

<210> SEQ ID NO 292
<211> LENGTH: 8
<212> TYPE: PRT
<213> ORGANISM: Artificial Sequence
<220> FEATURE:
<223> OTHER INFORMATION: XBP1 peptide

<400> SEQUENCE: 292

Gln Ala Arg Lys Arg Gln Arg Leu
1               5

<210> SEQ ID NO 293
<211> LENGTH: 10
<212> TYPE: PRT
<213> ORGANISM: Artificial Sequence
<220> FEATURE:
<223> OTHER INFORMATION: XBP1 peptide

<400> SEQUENCE: 293

Ile Gln Ser Leu Ile Ser Cys Trp Ala Phe
1               5                   10

<210> SEQ ID NO 294
<211> LENGTH: 10
<212> TYPE: PRT
<213> ORGANISM: Artificial Sequence
<220> FEATURE:
<223> OTHER INFORMATION: XBP1 peptide

<400> SEQUENCE: 294

Arg Leu Gly Met Asp Ala Leu Val Ala Glu
1               5                   10

<210> SEQ ID NO 295
<211> LENGTH: 10
<212> TYPE: PRT
<213> ORGANISM: Artificial Sequence
<220> FEATURE:
<223> OTHER INFORMATION: XBP1 peptide

<400> SEQUENCE: 295

Ala Gln Arg Gly Ala Ser Pro Glu Ala Ala
1               5                   10

<210> SEQ ID NO 296
<211> LENGTH: 10
<212> TYPE: PRT
<213> ORGANISM: Artificial Sequence
<220> FEATURE:
<223> OTHER INFORMATION: XBP1 peptide

<400> SEQUENCE: 296

Arg Leu Arg Ala Pro Leu Gln Gln Val Gln
1               5                   10

<210> SEQ ID NO 297
<211> LENGTH: 9
<212> TYPE: PRT
<213> ORGANISM: Artificial Sequence
<220> FEATURE:
<223> OTHER INFORMATION: XBP1 peptide

<400> SEQUENCE: 297

Ser Pro Glu Ala Ala Ser Gly Gly Leu
1               5

<210> SEQ ID NO 298

-continued

```
<211> LENGTH: 10
<212> TYPE: PRT
<213> ORGANISM: Artificial Sequence
<220> FEATURE:
<223> OTHER INFORMATION: XBP1 peptide

<400> SEQUENCE: 298

Asn Pro Ala Asp Gly Thr Pro Lys Val Leu
1               5                   10

<210> SEQ ID NO 299
<211> LENGTH: 10
<212> TYPE: PRT
<213> ORGANISM: Artificial Sequence
<220> FEATURE:
<223> OTHER INFORMATION: XBP1 peptide

<400> SEQUENCE: 299

Leu Pro Gln Ala Arg Lys Arg Gln Arg Leu
1               5                   10

<210> SEQ ID NO 300
<211> LENGTH: 10
<212> TYPE: PRT
<213> ORGANISM: Artificial Sequence
<220> FEATURE:
<223> OTHER INFORMATION: XBP1 peptide

<400> SEQUENCE: 300

Ala Pro Leu Gln Gln Val Gln Ala Gln Leu
1               5                   10

<210> SEQ ID NO 301
<211> LENGTH: 10
<212> TYPE: PRT
<213> ORGANISM: Artificial Sequence
<220> FEATURE:
<223> OTHER INFORMATION: XBP1 peptide

<400> SEQUENCE: 301

Arg Ser Thr Gln Lys Asp Pro Val Pro Tyr
1               5                   10

<210> SEQ ID NO 302
<211> LENGTH: 10
<212> TYPE: PRT
<213> ORGANISM: Artificial Sequence
<220> FEATURE:
<223> OTHER INFORMATION: XBP1 peptide

<400> SEQUENCE: 302

Gly Ser Ala Glu Ser Ala Ala Leu Arg Leu
1               5                   10

<210> SEQ ID NO 303
<211> LENGTH: 10
<212> TYPE: PRT
<213> ORGANISM: Artificial Sequence
<220> FEATURE:
<223> OTHER INFORMATION: XBP1 peptide

<400> SEQUENCE: 303

Ile Ser Cys Trp Ala Phe Trp Thr Thr Trp
1               5                   10

<210> SEQ ID NO 304
<211> LENGTH: 10
```

-continued

```
<212> TYPE: PRT
<213> ORGANISM: Artificial Sequence
<220> FEATURE:
<223> OTHER INFORMATION: XBP1 peptide

<400> SEQUENCE: 304

Ala Ser Pro Glu Ala Ala Ser Gly Gly Leu
1               5                   10

<210> SEQ ID NO 305
<211> LENGTH: 15
<212> TYPE: PRT
<213> ORGANISM: Artificial Sequence
<220> FEATURE:
<223> OTHER INFORMATION: XBP1 peptide

<400> SEQUENCE: 305

Thr Pro Lys Val Leu Leu Leu Ser Gly Gln Pro Ala Ser Ala Ala
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: XBP1 peptide

<400> SEQUENCE: 306

Val Leu Leu Leu Ser Gly Gln Pro Ala Ser Ala Ala Gly Ala Pro
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: XBP1 peptide

<400> SEQUENCE: 307

Pro Leu Met Val Pro Ala Gln Arg Gly Ala Ser Pro Glu Ala Ala
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: XBP1 peptide

<400> SEQUENCE: 308

Arg Ala Pro Leu Gln Gln Val Gln Ala Gln Leu Ser Pro Leu Gln
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: XBP1 peptide

<400> SEQUENCE: 309

Val Val Asp Leu Glu Glu Glu Asn Gln Lys Leu Leu Leu Glu Asn
1               5                   10                  15

<210> SEQ ID NO 310
<211> LENGTH: 15
<212> TYPE: PRT
```

-continued

```
<213> ORGANISM: Artificial Sequence
<220> FEATURE:
<223> OTHER INFORMATION: XBP1 peptide

<400> SEQUENCE: 310

Arg Gln Arg Leu Gly Met Asp Ala Leu Val Ala Glu Glu Glu Ala
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: XBP1 peptide

<400> SEQUENCE: 311

Pro Lys Val Leu Leu Leu Ser Gly Gln Pro Ala Ser Ala Ala Gly
1               5                   10                  15

<210> SEQ ID NO 312
<211> LENGTH: 15
<212> TYPE: PRT
<213> ORGANISM: Artificial Sequence
<220> FEATURE:
<223> OTHER INFORMATION: XBP1 peptide

<400> SEQUENCE: 312

Asn Gln Lys Leu Leu Leu Glu Asn Gln Leu Leu Arg Glu Lys Thr
1               5                   10                  15

<210> SEQ ID NO 313
<211> LENGTH: 15
<212> TYPE: PRT
<213> ORGANISM: Artificial Sequence
<220> FEATURE:
<223> OTHER INFORMATION: XBP1 peptide

<400> SEQUENCE: 313

Trp Thr Thr Trp Thr Gln Ser Cys Ser Ser Asn Ala Leu Pro Gln
1               5                   10                  15

<210> SEQ ID NO 314
<211> LENGTH: 15
<212> TYPE: PRT
<213> ORGANISM: Artificial Sequence
<220> FEATURE:
<223> OTHER INFORMATION: XBP1 peptide

<400> SEQUENCE: 314

Cys Trp Ala Phe Trp Thr Thr Trp Thr Gln Ser Cys Ser Ser Asn
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: XBP1 peptide

<400> SEQUENCE: 315

Glu Asn Gln Leu Leu Arg Glu Lys Thr His Gly Leu Val Val Glu
1               5                   10                  15

<210> SEQ ID NO 316
<211> LENGTH: 15
<212> TYPE: PRT
<213> ORGANISM: Artificial Sequence
```

-continued

```
<220> FEATURE:
<223> OTHER INFORMATION: XBP1 peptide

<400> SEQUENCE: 316

Val Arg Pro Val Ala Gly Ser Ala Glu Ser Ala Ala Leu Arg Leu
1               5                   10                  15

<210> SEQ ID NO 317
<211> LENGTH: 15
<212> TYPE: PRT
<213> ORGANISM: Artificial Sequence
<220> FEATURE:
<223> OTHER INFORMATION: XBP1 peptide

<400> SEQUENCE: 317

Leu Pro Leu Met Val Pro Ala Gln Arg Gly Ala Ser Pro Glu Ala
1               5                   10                  15

<210> SEQ ID NO 318
<211> LENGTH: 15
<212> TYPE: PRT
<213> ORGANISM: Artificial Sequence
<220> FEATURE:
<223> OTHER INFORMATION: XBP1 peptide

<400> SEQUENCE: 318

Ala Arg Lys Arg Gln Arg Leu Thr His Leu Ser Pro Glu Glu Lys
1               5                   10                  15

<210> SEQ ID NO 319
<211> LENGTH: 15
<212> TYPE: PRT
<213> ORGANISM: Artificial Sequence
<220> FEATURE:
<223> OTHER INFORMATION: XBP1 peptide

<400> SEQUENCE: 319

Pro Pro Phe Leu Cys Gln Trp Gly Arg His Gln Pro Ser Trp Lys
1               5                   10                  15

<210> SEQ ID NO 320
<211> LENGTH: 15
<212> TYPE: PRT
<213> ORGANISM: Artificial Sequence
<220> FEATURE:
<223> OTHER INFORMATION: XBP1 peptide

<400> SEQUENCE: 320

Arg Ala Pro Leu Gln Gln Val Gln Ala Gln Leu Ser Pro Leu Gln
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: XBP1 peptide

<400> SEQUENCE: 321

Pro Gln Ser Leu Pro Ala Trp Arg Ser Ser Gln Arg Ser Thr Gln
1               5                   10                  15

<210> SEQ ID NO 322
<211> LENGTH: 15
<212> TYPE: PRT
<213> ORGANISM: Artificial Sequence
<220> FEATURE:
```

<223> OTHER INFORMATION: XBP1 peptide

<400> SEQUENCE: 322

Asn Gln Glu Leu Arg Gln Arg Leu Gly Met Asp Ala Leu Val Ala
1               5                   10                  15

<210> SEQ ID NO 323
<211> LENGTH: 15
<212> TYPE: PRT
<213> ORGANISM: Artificial Sequence
<220> FEATURE:
<223> OTHER INFORMATION: XBP1 peptide

<400> SEQUENCE: 323

Ser Ala Ala Leu Arg Leu Arg Ala Pro Leu Gln Gln Val Gln Ala
1               5                   10                  15

<210> SEQ ID NO 324
<211> LENGTH: 15
<212> TYPE: PRT
<213> ORGANISM: Artificial Sequence
<220> FEATURE:
<223> OTHER INFORMATION: XBP1 peptide

<400> SEQUENCE: 324

Gln Ala Gln Leu Ser Pro Leu Gln Asn Ile Ser Pro Trp Ile Leu
1               5                   10                  15

<210> SEQ ID NO 325
<211> LENGTH: 335
<212> TYPE: PRT
<213> ORGANISM: Homo sapiens

<400> SEQUENCE: 325

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
                20                  25                  30

Val Gly Gly Ala Val Thr Phe Pro Leu Lys Ser Lys Val Lys Gln Val
            35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
                100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
            195                 200                 205

-continued

```
Ile Leu Ala Arg Lys Leu Cys Glu Gly Ala Ala Asp Asp Pro Asp Ser
    210             215             220

Ser Met Val Leu Leu Cys Leu Leu Leu Val Pro Leu Leu Leu Ser Leu
225             230             235             240

Phe Val Leu Gly Leu Phe Leu Trp Phe Leu Lys Arg Glu Arg Gln Glu
            245             250             255

Glu Tyr Ile Glu Glu Lys Lys Arg Val Asp Ile Cys Arg Glu Thr Pro
            260             265             270

Asn Ile Cys Pro His Ser Gly Glu Asn Thr Glu Tyr Asp Thr Ile Pro
        275             280             285

His Thr Asn Arg Thr Ile Leu Lys Glu Asp Pro Ala Asn Thr Val Tyr
    290             295             300

Ser Thr Val Glu Ile Pro Lys Lys Met Glu Asn Pro His Ser Leu Leu
305             310             315             320

Thr Met Pro Asp Thr Pro Arg Leu Phe Ala Tyr Glu Asn Val Ile
            325             330             335
```

```
<210> SEQ ID NO 326
<211> LENGTH: 10
<212> TYPE: PRT
<213> ORGANISM: Artificial Sequence
<220> FEATURE:
<223> OTHER INFORMATION: CS1 peptide

<400> SEQUENCE: 326

Leu Leu Leu Ser Leu Phe Val Leu Gly Leu
1               5               10
```

```
<210> SEQ ID NO 327
<211> LENGTH: 9
<212> TYPE: PRT
<213> ORGANISM: Artificial Sequence
<220> FEATURE:
<223> OTHER INFORMATION: CS1 peptide

<400> SEQUENCE: 327

Ser Leu Phe Val Leu Gly Leu Phe Leu
1               5
```

```
<210> SEQ ID NO 328
<211> LENGTH: 9
<212> TYPE: PRT
<213> ORGANISM: Artificial Sequence
<220> FEATURE:
<223> OTHER INFORMATION: CS1 peptide

<400> SEQUENCE: 328

Leu Leu Val Pro Leu Leu Leu Ser Leu
1               5
```

```
<210> SEQ ID NO 329
<211> LENGTH: 9
<212> TYPE: PRT
<213> ORGANISM: Artificial Sequence
<220> FEATURE:
<223> OTHER INFORMATION: CS1 peptide

<400> SEQUENCE: 329

Thr Leu Ile Tyr Ile Leu Trp Gln Leu
1               5
```

```
<210> SEQ ID NO 330
```

```
<211> LENGTH: 9
<212> TYPE: PRT
<213> ORGANISM: Artificial Sequence
<220> FEATURE:
<223> OTHER INFORMATION: CS1 peptide

<400> SEQUENCE: 330

Gly Tyr Ser Leu Lys Leu Ser Lys Leu
1               5

<210> SEQ ID NO 331
<211> LENGTH: 9
<212> TYPE: PRT
<213> ORGANISM: Artificial Sequence
<220> FEATURE:
<223> OTHER INFORMATION: CS1 peptide

<400> SEQUENCE: 331

Asp Phe Pro Asp Gly Gly Tyr Ser Leu
1               5

<210> SEQ ID NO 332
<211> LENGTH: 9
<212> TYPE: PRT
<213> ORGANISM: Artificial Sequence
<220> FEATURE:
<223> OTHER INFORMATION: CS1 peptide

<400> SEQUENCE: 332

Thr Met Pro Asp Thr Pro Arg Leu Phe
1               5

<210> SEQ ID NO 333
<211> LENGTH: 9
<212> TYPE: PRT
<213> ORGANISM: Artificial Sequence
<220> FEATURE:
<223> OTHER INFORMATION: CS1 peptide

<400> SEQUENCE: 333

Arg Trp Gly Glu Ser Asp Met Thr Phe
1               5

<210> SEQ ID NO 334
<211> LENGTH: 9
<212> TYPE: PRT
<213> ORGANISM: Artificial Sequence
<220> FEATURE:
<223> OTHER INFORMATION: CS1 peptide

<400> SEQUENCE: 334

Leu Phe Val Leu Gly Leu Phe Leu Trp
1               5

<210> SEQ ID NO 335
<211> LENGTH: 9
<212> TYPE: PRT
<213> ORGANISM: Artificial Sequence
<220> FEATURE:
<223> OTHER INFORMATION: CS1 peptide

<400> SEQUENCE: 335

Lys Met Glu Asn Pro His Ser Leu Leu
1               5

<210> SEQ ID NO 336
<211> LENGTH: 16
```

-continued

```
<212> TYPE: PRT
<213> ORGANISM: Artificial Sequence
<220> FEATURE:
<223> OTHER INFORMATION: CS1 peptide

<400> SEQUENCE: 336

Val Leu Leu Cys Leu Leu Leu Val Pro Leu Leu Leu Ser Leu Phe Val
1               5                   10                  15

<210> SEQ ID NO 337
<211> LENGTH: 17
<212> TYPE: PRT
<213> ORGANISM: Artificial Sequence
<220> FEATURE:
<223> OTHER INFORMATION: CS1 peptide

<400> SEQUENCE: 337

Val Leu Leu Cys Leu Leu Leu Val Pro Leu Leu Leu Ser Leu Phe Val
1               5                   10                  15

Leu

<210> SEQ ID NO 338
<211> LENGTH: 18
<212> TYPE: PRT
<213> ORGANISM: Artificial Sequence
<220> FEATURE:
<223> OTHER INFORMATION: CS1 peptide

<400> SEQUENCE: 338

Val Leu Leu Cys Leu Leu Leu Val Pro Leu Leu Leu Ser Leu Phe Val
1               5                   10                  15

Leu Gly

<210> SEQ ID NO 339
<211> LENGTH: 19
<212> TYPE: PRT
<213> ORGANISM: Artificial Sequence
<220> FEATURE:
<223> OTHER INFORMATION: CS1 peptide

<400> SEQUENCE: 339

Val Leu Leu Cys Leu Leu Leu Val Pro Leu Leu Leu Ser Leu Phe Val
1               5                   10                  15

Leu Gly Leu

<210> SEQ ID NO 340
<211> LENGTH: 20
<212> TYPE: PRT
<213> ORGANISM: Artificial Sequence
<220> FEATURE:
<223> OTHER INFORMATION: CS1 peptide

<400> SEQUENCE: 340

Val Leu Leu Cys Leu Leu Leu Val Pro Leu Leu Leu Ser Leu Phe Val
1               5                   10                  15

Leu Gly Leu Phe
            20

<210> SEQ ID NO 341
<211> LENGTH: 21
<212> TYPE: PRT
<213> ORGANISM: Artificial Sequence
<220> FEATURE:
<223> OTHER INFORMATION: CS1 peptide
```

-continued

<400> SEQUENCE: 341

Val Leu Leu Cys Leu Leu Leu Val Pro Leu Leu Leu Ser Leu Phe Val
1               5                   10                  15

Leu Gly Leu Phe Leu
            20

<210> SEQ ID NO 342
<211> LENGTH: 22
<212> TYPE: PRT
<213> ORGANISM: Artificial Sequence
<220> FEATURE:
<223> OTHER INFORMATION: CS1 peptide

<400> SEQUENCE: 342

Val Leu Leu Cys Leu Leu Leu Val Pro Leu Leu Leu Ser Leu Phe Val
1               5                   10                  15

Leu Gly Leu Phe Leu Trp
            20

<210> SEQ ID NO 343
<211> LENGTH: 23
<212> TYPE: PRT
<213> ORGANISM: Artificial Sequence
<220> FEATURE:
<223> OTHER INFORMATION: CS1 peptide

<400> SEQUENCE: 343

Val Leu Leu Cys Leu Leu Leu Val Pro Leu Leu Leu Ser Leu Phe Val
1               5                   10                  15

Leu Gly Leu Phe Leu Trp Phe
            20

<210> SEQ ID NO 344
<211> LENGTH: 24
<212> TYPE: PRT
<213> ORGANISM: Artificial Sequence
<220> FEATURE:
<223> OTHER INFORMATION: CS1 peptide

<400> SEQUENCE: 344

Val Leu Leu Cys Leu Leu Leu Val Pro Leu Leu Leu Ser Leu Phe Val
1               5                   10                  15

Leu Gly Leu Phe Leu Trp Phe Leu
            20

<210> SEQ ID NO 345
<211> LENGTH: 25
<212> TYPE: PRT
<213> ORGANISM: Artificial Sequence
<220> FEATURE:
<223> OTHER INFORMATION: CS1 peptide

<400> SEQUENCE: 345

Val Leu Leu Cys Leu Leu Leu Val Pro Leu Leu Leu Ser Leu Phe Val
1               5                   10                  15

Leu Gly Leu Phe Leu Trp Phe Leu Lys
            20                  25

<210> SEQ ID NO 346
<211> LENGTH: 26
<212> TYPE: PRT
<213> ORGANISM: Artificial Sequence
<220> FEATURE:
<223> OTHER INFORMATION: CS1 peptide

<400> SEQUENCE: 346

Val Leu Leu Cys Leu Leu Leu Val Pro Leu Leu Leu Ser Leu Phe Val
1               5                   10                  15

Leu Gly Leu Phe Leu Trp Phe Leu Lys Arg
            20                  25

<210> SEQ ID NO 347
<211> LENGTH: 27
<212> TYPE: PRT
<213> ORGANISM: Artificial Sequence
<220> FEATURE:
<223> OTHER INFORMATION: CS1 peptide

<400> SEQUENCE: 347

Val Leu Leu Cys Leu Leu Leu Val Pro Leu Leu Leu Ser Leu Phe Val
1               5                   10                  15

Leu Gly Leu Phe Leu Trp Phe Leu Lys Arg Glu
            20                  25

<210> SEQ ID NO 348
<211> LENGTH: 15
<212> TYPE: PRT
<213> ORGANISM: Artificial Sequence
<220> FEATURE:
<223> OTHER INFORMATION: CS1 peptide

<400> SEQUENCE: 348

Leu Leu Cys Leu Leu Leu Val Pro Leu Leu Leu Ser Leu Phe Val
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: CS1 peptide

<400> SEQUENCE: 349

Leu Leu Cys Leu Leu Leu Val Pro Leu Leu Leu Ser Leu Phe Val Leu
1               5                   10                  15

<210> SEQ ID NO 350
<211> LENGTH: 17
<212> TYPE: PRT
<213> ORGANISM: Artificial Sequence
<220> FEATURE:
<223> OTHER INFORMATION: CS1 peptide

<400> SEQUENCE: 350

Leu Leu Cys Leu Leu Leu Val Pro Leu Leu Leu Ser Leu Phe Val Leu
1               5                   10                  15

Gly

<210> SEQ ID NO 351
<211> LENGTH: 18
<212> TYPE: PRT
<213> ORGANISM: Artificial Sequence
<220> FEATURE:
<223> OTHER INFORMATION: CS1 peptide

<400> SEQUENCE: 351

Leu Leu Cys Leu Leu Leu Val Pro Leu Leu Leu Ser Leu Phe Val Leu
1               5                   10                  15

Gly Leu

<210> SEQ ID NO 352
<211> LENGTH: 19
<212> TYPE: PRT
<213> ORGANISM: Artificial Sequence
<220> FEATURE:
<223> OTHER INFORMATION: CS1 peptide

<400> SEQUENCE: 352

Leu Leu Cys Leu Leu Leu Val Pro Leu Leu Leu Ser Leu Phe Val Leu
1               5                   10                  15

Gly Leu Phe

<210> SEQ ID NO 353
<211> LENGTH: 20
<212> TYPE: PRT
<213> ORGANISM: Artificial Sequence
<220> FEATURE:
<223> OTHER INFORMATION: CS1 peptide

<400> SEQUENCE: 353

Leu Leu Cys Leu Leu Leu Val Pro Leu Leu Leu Ser Leu Phe Val Leu
1               5                   10                  15

Gly Leu Phe Leu
            20

<210> SEQ ID NO 354
<211> LENGTH: 21
<212> TYPE: PRT
<213> ORGANISM: Artificial Sequence
<220> FEATURE:
<223> OTHER INFORMATION: CS1 peptide

<400> SEQUENCE: 354

Leu Leu Cys Leu Leu Leu Val Pro Leu Leu Leu Ser Leu Phe Val Leu
1               5                   10                  15

Gly Leu Phe Leu Trp
            20

<210> SEQ ID NO 355
<211> LENGTH: 22
<212> TYPE: PRT
<213> ORGANISM: Artificial Sequence
<220> FEATURE:
<223> OTHER INFORMATION: CS1 peptide

<400> SEQUENCE: 355

Leu Leu Cys Leu Leu Leu Val Pro Leu Leu Leu Ser Leu Phe Val Leu
1               5                   10                  15

Gly Leu Phe Leu Trp Phe
            20

<210> SEQ ID NO 356
<211> LENGTH: 23
<212> TYPE: PRT
<213> ORGANISM: Artificial Sequence
<220> FEATURE:
<223> OTHER INFORMATION: CS1 peptide

<400> SEQUENCE: 356

Leu Leu Cys Leu Leu Leu Val Pro Leu Leu Leu Ser Leu Phe Val Leu
1               5                   10                  15

Gly Leu Phe Leu Trp Phe Leu

```
                20

<210> SEQ ID NO 357
<211> LENGTH: 24
<212> TYPE: PRT
<213> ORGANISM: Artificial Sequence
<220> FEATURE:
<223> OTHER INFORMATION: CS1 peptide

<400> SEQUENCE: 357

Leu Leu Cys Leu Leu Leu Val Pro Leu Leu Leu Ser Leu Phe Val Leu
1               5                   10                  15

Gly Leu Phe Leu Trp Phe Leu Lys
            20

<210> SEQ ID NO 358
<211> LENGTH: 25
<212> TYPE: PRT
<213> ORGANISM: Artificial Sequence
<220> FEATURE:
<223> OTHER INFORMATION: CS1 peptide

<400> SEQUENCE: 358

Leu Leu Cys Leu Leu Leu Val Pro Leu Leu Leu Ser Leu Phe Val Leu
1               5                   10                  15

Gly Leu Phe Leu Trp Phe Leu Lys Arg
            20                  25

<210> SEQ ID NO 359
<211> LENGTH: 26
<212> TYPE: PRT
<213> ORGANISM: Artificial Sequence
<220> FEATURE:
<223> OTHER INFORMATION: CS1 peptide

<400> SEQUENCE: 359

Leu Leu Cys Leu Leu Leu Val Pro Leu Leu Leu Ser Leu Phe Val Leu
1               5                   10                  15

Gly Leu Phe Leu Trp Phe Leu Lys Arg Glu
            20                  25

<210> SEQ ID NO 360
<211> LENGTH: 14
<212> TYPE: PRT
<213> ORGANISM: Artificial Sequence
<220> FEATURE:
<223> OTHER INFORMATION: CS1 peptide

<400> SEQUENCE: 360

Leu Cys Leu Leu Leu Val Pro Leu Leu Leu Ser Leu Phe Val
1               5                   10

<210> SEQ ID NO 361
<211> LENGTH: 15
<212> TYPE: PRT
<213> ORGANISM: Artificial Sequence
<220> FEATURE:
<223> OTHER INFORMATION: CS1 peptide

<400> SEQUENCE: 361

Leu Cys Leu Leu Leu Val Pro Leu Leu Leu Ser Leu Phe Val Leu
1               5                   10                  15

<210> SEQ ID NO 362
<211> LENGTH: 16
```

<212> TYPE: PRT
<213> ORGANISM: Artificial Sequence
<220> FEATURE:
<223> OTHER INFORMATION: CS1 peptide

<400> SEQUENCE: 362

Leu Cys Leu Leu Leu Val Pro Leu Leu Leu Ser Leu Phe Val Leu Gly
1               5                   10                  15

<210> SEQ ID NO 363
<211> LENGTH: 17
<212> TYPE: PRT
<213> ORGANISM: Artificial Sequence
<220> FEATURE:
<223> OTHER INFORMATION: CS1 peptide

<400> SEQUENCE: 363

Leu Cys Leu Leu Leu Val Pro Leu Leu Leu Ser Leu Phe Val Leu Gly
1               5                   10                  15

Leu

<210> SEQ ID NO 364
<211> LENGTH: 18
<212> TYPE: PRT
<213> ORGANISM: Artificial Sequence
<220> FEATURE:
<223> OTHER INFORMATION: CS1 peptide

<400> SEQUENCE: 364

Leu Cys Leu Leu Leu Val Pro Leu Leu Leu Ser Leu Phe Val Leu Gly
1               5                   10                  15

Leu Phe

<210> SEQ ID NO 365
<211> LENGTH: 19
<212> TYPE: PRT
<213> ORGANISM: Artificial Sequence
<220> FEATURE:
<223> OTHER INFORMATION: CS1 peptide

<400> SEQUENCE: 365

Leu Cys Leu Leu Leu Val Pro Leu Leu Leu Ser Leu Phe Val Leu Gly
1               5                   10                  15

Leu Phe Leu

<210> SEQ ID NO 366
<211> LENGTH: 20
<212> TYPE: PRT
<213> ORGANISM: Artificial Sequence
<220> FEATURE:
<223> OTHER INFORMATION: CS1 peptide

<400> SEQUENCE: 366

Leu Cys Leu Leu Leu Val Pro Leu Leu Leu Ser Leu Phe Val Leu Gly
1               5                   10                  15

Leu Phe Leu Trp
            20

<210> SEQ ID NO 367
<211> LENGTH: 21
<212> TYPE: PRT
<213> ORGANISM: Artificial Sequence
<220> FEATURE:
<223> OTHER INFORMATION: CS1 peptide

```
<400> SEQUENCE: 367

Leu Cys Leu Leu Leu Val Pro Leu Leu Leu Ser Leu Phe Val Leu Gly
1               5                   10                  15

Leu Phe Leu Trp Phe
            20

<210> SEQ ID NO 368
<211> LENGTH: 22
<212> TYPE: PRT
<213> ORGANISM: Artificial Sequence
<220> FEATURE:
<223> OTHER INFORMATION: CS1 peptide

<400> SEQUENCE: 368

Leu Cys Leu Leu Leu Val Pro Leu Leu Leu Ser Leu Phe Val Leu Gly
1               5                   10                  15

Leu Phe Leu Trp Phe Leu
            20

<210> SEQ ID NO 369
<211> LENGTH: 23
<212> TYPE: PRT
<213> ORGANISM: Artificial Sequence
<220> FEATURE:
<223> OTHER INFORMATION: CS1 peptide

<400> SEQUENCE: 369

Leu Cys Leu Leu Leu Val Pro Leu Leu Leu Ser Leu Phe Val Leu Gly
1               5                   10                  15

Leu Phe Leu Trp Phe Leu Lys
            20

<210> SEQ ID NO 370
<211> LENGTH: 24
<212> TYPE: PRT
<213> ORGANISM: Artificial Sequence
<220> FEATURE:
<223> OTHER INFORMATION: CS1 peptide

<400> SEQUENCE: 370

Leu Cys Leu Leu Leu Val Pro Leu Leu Leu Ser Leu Phe Val Leu Gly
1               5                   10                  15

Leu Phe Leu Trp Phe Leu Lys Arg
            20

<210> SEQ ID NO 371
<211> LENGTH: 25
<212> TYPE: PRT
<213> ORGANISM: Artificial Sequence
<220> FEATURE:
<223> OTHER INFORMATION: CS1 peptide

<400> SEQUENCE: 371

Leu Cys Leu Leu Leu Val Pro Leu Leu Leu Ser Leu Phe Val Leu Gly
1               5                   10                  15

Leu Phe Leu Trp Phe Leu Lys Arg Glu
            20                  25

<210> SEQ ID NO 372
<211> LENGTH: 13
<212> TYPE: PRT
<213> ORGANISM: Artificial Sequence
<220> FEATURE:
<223> OTHER INFORMATION: CS1 peptide
```

<400> SEQUENCE: 372

Cys Leu Leu Leu Val Pro Leu Leu Leu Ser Leu Phe Val
1               5                   10

<210> SEQ ID NO 373
<211> LENGTH: 14
<212> TYPE: PRT
<213> ORGANISM: Artificial Sequence
<220> FEATURE:
<223> OTHER INFORMATION: CS1 peptide

<400> SEQUENCE: 373

Cys Leu Leu Leu Val Pro Leu Leu Leu Ser Leu Phe Val Leu
1               5                   10

<210> SEQ ID NO 374
<211> LENGTH: 15
<212> TYPE: PRT
<213> ORGANISM: Artificial Sequence
<220> FEATURE:
<223> OTHER INFORMATION: CS1 peptide

<400> SEQUENCE: 374

Cys Leu Leu Leu Val Pro Leu Leu Leu Ser Leu Phe Val Leu Gly
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: CS1 peptide

<400> SEQUENCE: 375

Cys Leu Leu Leu Val Pro Leu Leu Leu Ser Leu Phe Val Leu Gly Leu
1               5                   10                  15

<210> SEQ ID NO 376
<211> LENGTH: 17
<212> TYPE: PRT
<213> ORGANISM: Artificial Sequence
<220> FEATURE:
<223> OTHER INFORMATION: CS1 peptide

<400> SEQUENCE: 376

Cys Leu Leu Leu Val Pro Leu Leu Leu Ser Leu Phe Val Leu Gly Leu
1               5                   10                  15

Phe

<210> SEQ ID NO 377
<211> LENGTH: 19
<212> TYPE: PRT
<213> ORGANISM: Artificial Sequence
<220> FEATURE:
<223> OTHER INFORMATION: CS1 peptide

<400> SEQUENCE: 377

Cys Leu Leu Leu Val Pro Leu Leu Leu Ser Leu Phe Val Leu Gly Leu
1               5                   10                  15

Phe Leu Trp

<210> SEQ ID NO 378
<211> LENGTH: 19
<212> TYPE: PRT

<213> ORGANISM: Artificial Sequence
<220> FEATURE:
<223> OTHER INFORMATION: CS1 peptide

<400> SEQUENCE: 378

Cys Leu Leu Leu Val Pro Leu Leu Leu Ser Leu Phe Val Leu Gly Leu
1               5                   10                  15

Phe Leu Trp

<210> SEQ ID NO 379
<211> LENGTH: 20
<212> TYPE: PRT
<213> ORGANISM: Artificial Sequence
<220> FEATURE:
<223> OTHER INFORMATION: CS1 peptide

<400> SEQUENCE: 379

Cys Leu Leu Leu Val Pro Leu Leu Leu Ser Leu Phe Val Leu Gly Leu
1               5                   10                  15

Phe Leu Trp Phe
            20

<210> SEQ ID NO 380
<211> LENGTH: 21
<212> TYPE: PRT
<213> ORGANISM: Artificial Sequence
<220> FEATURE:
<223> OTHER INFORMATION: CS1 peptide

<400> SEQUENCE: 380

Cys Leu Leu Leu Val Pro Leu Leu Leu Ser Leu Phe Val Leu Gly Leu
1               5                   10                  15

Phe Leu Trp Phe Leu
            20

<210> SEQ ID NO 381
<211> LENGTH: 22
<212> TYPE: PRT
<213> ORGANISM: Artificial Sequence
<220> FEATURE:
<223> OTHER INFORMATION: CS1 peptide

<400> SEQUENCE: 381

Cys Leu Leu Leu Val Pro Leu Leu Leu Ser Leu Phe Val Leu Gly Leu
1               5                   10                  15

Phe Leu Trp Phe Leu Lys
            20

<210> SEQ ID NO 382
<211> LENGTH: 23
<212> TYPE: PRT
<213> ORGANISM: Artificial Sequence
<220> FEATURE:
<223> OTHER INFORMATION: CS1 peptide

<400> SEQUENCE: 382

Cys Leu Leu Leu Val Pro Leu Leu Leu Ser Leu Phe Val Leu Gly Leu
1               5                   10                  15

Phe Leu Trp Phe Leu Lys Arg
            20

<210> SEQ ID NO 383
<211> LENGTH: 24
<212> TYPE: PRT

```
<213> ORGANISM: Artificial Sequence
<220> FEATURE:
<223> OTHER INFORMATION: CS1 peptide

<400> SEQUENCE: 383

Cys Leu Leu Leu Val Pro Leu Leu Leu Ser Leu Phe Val Leu Gly Leu
1               5                   10                  15

Phe Leu Trp Phe Leu Lys Arg Glu
            20

<210> SEQ ID NO 384
<211> LENGTH: 12
<212> TYPE: PRT
<213> ORGANISM: Artificial Sequence
<220> FEATURE:
<223> OTHER INFORMATION: CS1 peptide

<400> SEQUENCE: 384

Leu Leu Leu Val Pro Leu Leu Leu Ser Leu Phe Val
1               5                   10

<210> SEQ ID NO 385
<211> LENGTH: 13
<212> TYPE: PRT
<213> ORGANISM: Artificial Sequence
<220> FEATURE:
<223> OTHER INFORMATION: CS1 peptide

<400> SEQUENCE: 385

Leu Leu Leu Val Pro Leu Leu Leu Ser Leu Phe Val Leu
1               5                   10

<210> SEQ ID NO 386
<211> LENGTH: 14
<212> TYPE: PRT
<213> ORGANISM: Artificial Sequence
<220> FEATURE:
<223> OTHER INFORMATION: CS1 peptide

<400> SEQUENCE: 386

Leu Leu Leu Val Pro Leu Leu Leu Ser Leu Phe Val Leu Gly
1               5                   10

<210> SEQ ID NO 387
<211> LENGTH: 15
<212> TYPE: PRT
<213> ORGANISM: Artificial Sequence
<220> FEATURE:
<223> OTHER INFORMATION: CS1 peptide

<400> SEQUENCE: 387

Leu Leu Leu Val Pro Leu Leu Leu Ser Leu Phe Val Leu Gly Leu
1               5                   10                  15

<210> SEQ ID NO 388
<211> LENGTH: 16
<212> TYPE: PRT
<213> ORGANISM: Artificial Sequence
<220> FEATURE:
<223> OTHER INFORMATION: CS1 peptide

<400> SEQUENCE: 388

Leu Leu Leu Val Pro Leu Leu Leu Ser Leu Phe Val Leu Gly Leu Phe
1               5                   10                  15

<210> SEQ ID NO 389
```

-continued

```
<211> LENGTH: 17
<212> TYPE: PRT
<213> ORGANISM: Artificial Sequence
<220> FEATURE:
<223> OTHER INFORMATION: CS1 peptide

<400> SEQUENCE: 389

Leu Leu Leu Val Pro Leu Leu Leu Ser Leu Phe Val Leu Gly Leu Phe
1               5                   10                  15

Leu

<210> SEQ ID NO 390
<211> LENGTH: 18
<212> TYPE: PRT
<213> ORGANISM: Artificial Sequence
<220> FEATURE:
<223> OTHER INFORMATION: CS1 peptide

<400> SEQUENCE: 390

Leu Leu Leu Val Pro Leu Leu Leu Ser Leu Phe Val Leu Gly Leu Phe
1               5                   10                  15

Leu Trp

<210> SEQ ID NO 391
<211> LENGTH: 19
<212> TYPE: PRT
<213> ORGANISM: Artificial Sequence
<220> FEATURE:
<223> OTHER INFORMATION: CS1 peptide

<400> SEQUENCE: 391

Leu Leu Leu Val Pro Leu Leu Leu Ser Leu Phe Val Leu Gly Leu Phe
1               5                   10                  15

Leu Trp Phe

<210> SEQ ID NO 392
<211> LENGTH: 20
<212> TYPE: PRT
<213> ORGANISM: Artificial Sequence
<220> FEATURE:
<223> OTHER INFORMATION: CS1 peptide

<400> SEQUENCE: 392

Leu Leu Leu Val Pro Leu Leu Leu Ser Leu Phe Val Leu Gly Leu Phe
1               5                   10                  15

Leu Trp Phe Leu
            20

<210> SEQ ID NO 393
<211> LENGTH: 21
<212> TYPE: PRT
<213> ORGANISM: Artificial Sequence
<220> FEATURE:
<223> OTHER INFORMATION: CS1 peptide

<400> SEQUENCE: 393

Leu Leu Leu Val Pro Leu Leu Leu Ser Leu Phe Val Leu Gly Leu Phe
1               5                   10                  15

Leu Trp Phe Leu Lys
            20

<210> SEQ ID NO 394
<211> LENGTH: 22
<212> TYPE: PRT
```

-continued

<210> ORGANISM: Artificial Sequence
<220> FEATURE:
<223> OTHER INFORMATION: CS1 peptide

<400> SEQUENCE: 394

Leu Leu Leu Val Pro Leu Leu Leu Ser Leu Phe Val Leu Gly Leu Phe
1               5                   10                  15

Leu Trp Phe Leu Lys Arg
            20

<210> SEQ ID NO 395
<211> LENGTH: 23
<212> TYPE: PRT
<213> ORGANISM: Artificial Sequence
<220> FEATURE:
<223> OTHER INFORMATION: CS1 peptide

<400> SEQUENCE: 395

Leu Leu Leu Val Pro Leu Leu Leu Ser Leu Phe Val Leu Gly Leu Phe
1               5                   10                  15

Leu Trp Phe Leu Lys Arg Glu
            20

<210> SEQ ID NO 396
<211> LENGTH: 11
<212> TYPE: PRT
<213> ORGANISM: Artificial Sequence
<220> FEATURE:
<223> OTHER INFORMATION: CS1 peptide

<400> SEQUENCE: 396

Leu Leu Val Pro Leu Leu Leu Ser Leu Phe Val
1               5                   10

<210> SEQ ID NO 397
<211> LENGTH: 12
<212> TYPE: PRT
<213> ORGANISM: Artificial Sequence
<220> FEATURE:
<223> OTHER INFORMATION: CS1 peptide

<400> SEQUENCE: 397

Leu Leu Val Pro Leu Leu Leu Ser Leu Phe Val Leu
1               5                   10

<210> SEQ ID NO 398
<211> LENGTH: 13
<212> TYPE: PRT
<213> ORGANISM: Artificial Sequence
<220> FEATURE:
<223> OTHER INFORMATION: CS1 peptide

<400> SEQUENCE: 398

Leu Leu Val Pro Leu Leu Leu Ser Leu Phe Val Leu Gly
1               5                   10

<210> SEQ ID NO 399
<211> LENGTH: 14
<212> TYPE: PRT
<213> ORGANISM: Artificial Sequence
<220> FEATURE:
<223> OTHER INFORMATION: CS1 peptide

<400> SEQUENCE: 399

Leu Leu Val Pro Leu Leu Leu Ser Leu Phe Val Leu Gly Leu
1               5                   10

<210> SEQ ID NO 400
<211> LENGTH: 15
<212> TYPE: PRT
<213> ORGANISM: Artificial Sequence
<220> FEATURE:
<223> OTHER INFORMATION: CS1 peptide

<400> SEQUENCE: 400

Leu Leu Val Pro Leu Leu Leu Ser Leu Phe Val Leu Gly Leu Phe
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: CS1 peptide

<400> SEQUENCE: 401

Leu Leu Val Pro Leu Leu Leu Ser Leu Phe Val Leu Gly Leu Phe Leu
1               5                   10                  15

<210> SEQ ID NO 402
<211> LENGTH: 17
<212> TYPE: PRT
<213> ORGANISM: Artificial Sequence
<220> FEATURE:
<223> OTHER INFORMATION: CS1 peptide

<400> SEQUENCE: 402

Leu Leu Val Pro Leu Leu Leu Ser Leu Phe Val Leu Gly Leu Phe Leu
1               5                   10                  15

Trp

<210> SEQ ID NO 403
<211> LENGTH: 18
<212> TYPE: PRT
<213> ORGANISM: Artificial Sequence
<220> FEATURE:
<223> OTHER INFORMATION: CS1 peptide

<400> SEQUENCE: 403

Leu Leu Val Pro Leu Leu Leu Ser Leu Phe Val Leu Gly Leu Phe Leu
1               5                   10                  15

Trp Phe

<210> SEQ ID NO 404
<211> LENGTH: 19
<212> TYPE: PRT
<213> ORGANISM: Artificial Sequence
<220> FEATURE:
<223> OTHER INFORMATION: CS1 peptide

<400> SEQUENCE: 404

Leu Leu Val Pro Leu Leu Leu Ser Leu Phe Val Leu Gly Leu Phe Leu
1               5                   10                  15

Trp Phe Leu

<210> SEQ ID NO 405
<211> LENGTH: 20
<212> TYPE: PRT
<213> ORGANISM: Artificial Sequence
<220> FEATURE:
<223> OTHER INFORMATION: CS1 peptide

<400> SEQUENCE: 405

Leu Leu Val Pro Leu Leu Leu Ser Leu Phe Val Leu Gly Leu Phe Leu
1               5                   10                  15

Trp Phe Leu Lys
            20

<210> SEQ ID NO 406
<211> LENGTH: 21
<212> TYPE: PRT
<213> ORGANISM: Artificial Sequence
<220> FEATURE:
<223> OTHER INFORMATION: CS1 peptide

<400> SEQUENCE: 406

Leu Leu Val Pro Leu Leu Leu Ser Leu Phe Val Leu Gly Leu Phe Leu
1               5                   10                  15

Trp Phe Leu Lys Arg
            20

<210> SEQ ID NO 407
<211> LENGTH: 22
<212> TYPE: PRT
<213> ORGANISM: Artificial Sequence
<220> FEATURE:
<223> OTHER INFORMATION: CS1 peptide

<400> SEQUENCE: 407

Leu Leu Val Pro Leu Leu Leu Ser Leu Phe Val Leu Gly Leu Phe Leu
1               5                   10                  15

Trp Phe Leu Lys Arg Glu
            20

<210> SEQ ID NO 408
<211> LENGTH: 10
<212> TYPE: PRT
<213> ORGANISM: Artificial Sequence
<220> FEATURE:
<223> OTHER INFORMATION: CS1 peptide

<400> SEQUENCE: 408

Leu Val Pro Leu Leu Leu Ser Leu Phe Val
1               5                   10

<210> SEQ ID NO 409
<211> LENGTH: 11
<212> TYPE: PRT
<213> ORGANISM: Artificial Sequence
<220> FEATURE:
<223> OTHER INFORMATION: CS1 peptide

<400> SEQUENCE: 409

Leu Val Pro Leu Leu Leu Ser Leu Phe Val Leu
1               5                   10

<210> SEQ ID NO 410
<211> LENGTH: 12
<212> TYPE: PRT
<213> ORGANISM: Artificial Sequence
<220> FEATURE:
<223> OTHER INFORMATION: CS1 peptide

<400> SEQUENCE: 410

Leu Val Pro Leu Leu Leu Ser Leu Phe Val Leu Gly
1               5                   10

```
<210> SEQ ID NO 411
<211> LENGTH: 13
<212> TYPE: PRT
<213> ORGANISM: Artificial Sequence
<220> FEATURE:
<223> OTHER INFORMATION: CS1 peptide

<400> SEQUENCE: 411

Leu Val Pro Leu Leu Leu Ser Leu Phe Val Leu Gly Leu
1               5                   10

<210> SEQ ID NO 412
<211> LENGTH: 14
<212> TYPE: PRT
<213> ORGANISM: Artificial Sequence
<220> FEATURE:
<223> OTHER INFORMATION: CS1 peptide

<400> SEQUENCE: 412

Leu Val Pro Leu Leu Leu Ser Leu Phe Val Leu Gly Leu Phe
1               5                   10

<210> SEQ ID NO 413
<211> LENGTH: 15
<212> TYPE: PRT
<213> ORGANISM: Artificial Sequence
<220> FEATURE:
<223> OTHER INFORMATION: CS1 peptide

<400> SEQUENCE: 413

Leu Val Pro Leu Leu Leu Ser Leu Phe Val Leu Gly Leu Phe Leu
1               5                   10                  15

<210> SEQ ID NO 414
<211> LENGTH: 16
<212> TYPE: PRT
<213> ORGANISM: Artificial Sequence
<220> FEATURE:
<223> OTHER INFORMATION: CS1 peptide

<400> SEQUENCE: 414

Leu Val Pro Leu Leu Leu Ser Leu Phe Val Leu Gly Leu Phe Leu Trp
1               5                   10                  15

<210> SEQ ID NO 415
<211> LENGTH: 17
<212> TYPE: PRT
<213> ORGANISM: Artificial Sequence
<220> FEATURE:
<223> OTHER INFORMATION: CS1 peptide

<400> SEQUENCE: 415

Leu Val Pro Leu Leu Leu Ser Leu Phe Val Leu Gly Leu Phe Leu Trp
1               5                   10                  15

Phe

<210> SEQ ID NO 416
<211> LENGTH: 18
<212> TYPE: PRT
<213> ORGANISM: Artificial Sequence
<220> FEATURE:
<223> OTHER INFORMATION: CS1 peptide

<400> SEQUENCE: 416

Leu Val Pro Leu Leu Leu Ser Leu Phe Val Leu Gly Leu Phe Leu Trp
```

-continued

```
1               5              10             15

Phe Leu

<210> SEQ ID NO 417
<211> LENGTH: 19
<212> TYPE: PRT
<213> ORGANISM: Artificial Sequence
<220> FEATURE:
<223> OTHER INFORMATION: CS1 peptide

<400> SEQUENCE: 417

Leu Val Pro Leu Leu Leu Ser Leu Phe Val Leu Gly Leu Phe Leu Trp
1               5              10             15

Phe Leu Lys

<210> SEQ ID NO 418
<211> LENGTH: 20
<212> TYPE: PRT
<213> ORGANISM: Artificial Sequence
<220> FEATURE:
<223> OTHER INFORMATION: CS1 peptide

<400> SEQUENCE: 418

Leu Val Pro Leu Leu Leu Ser Leu Phe Val Leu Gly Leu Phe Leu Trp
1               5              10             15

Phe Leu Lys Arg
          20

<210> SEQ ID NO 419
<211> LENGTH: 21
<212> TYPE: PRT
<213> ORGANISM: Artificial Sequence
<220> FEATURE:
<223> OTHER INFORMATION: CS1 peptide

<400> SEQUENCE: 419

Leu Val Pro Leu Leu Leu Ser Leu Phe Val Leu Gly Leu Phe Leu Trp
1               5              10             15

Phe Leu Lys Arg Glu
          20

<210> SEQ ID NO 420
<211> LENGTH: 9
<212> TYPE: PRT
<213> ORGANISM: Artificial Sequence
<220> FEATURE:
<223> OTHER INFORMATION: CS1 peptide

<400> SEQUENCE: 420

Val Pro Leu Leu Leu Ser Leu Phe Val
1               5

<210> SEQ ID NO 421
<211> LENGTH: 10
<212> TYPE: PRT
<213> ORGANISM: Artificial Sequence
<220> FEATURE:
<223> OTHER INFORMATION: CS1 peptide

<400> SEQUENCE: 421

Val Pro Leu Leu Leu Ser Leu Phe Val Leu
1               5              10

<210> SEQ ID NO 422
```

<211> LENGTH: 11
<212> TYPE: PRT
<213> ORGANISM: Artificial Sequence
<220> FEATURE:
<223> OTHER INFORMATION: CS1 peptide

<400> SEQUENCE: 422

Val Pro Leu Leu Leu Ser Leu Phe Val Leu Gly
1               5                   10

<210> SEQ ID NO 423
<211> LENGTH: 12
<212> TYPE: PRT
<213> ORGANISM: Artificial Sequence
<220> FEATURE:
<223> OTHER INFORMATION: CS1 peptide

<400> SEQUENCE: 423

Val Pro Leu Leu Leu Ser Leu Phe Val Leu Gly Leu
1               5                   10

<210> SEQ ID NO 424
<211> LENGTH: 13
<212> TYPE: PRT
<213> ORGANISM: Artificial Sequence
<220> FEATURE:
<223> OTHER INFORMATION: CS1 peptide

<400> SEQUENCE: 424

Val Pro Leu Leu Leu Ser Leu Phe Val Leu Gly Leu Phe
1               5                   10

<210> SEQ ID NO 425
<211> LENGTH: 14
<212> TYPE: PRT
<213> ORGANISM: Artificial Sequence
<220> FEATURE:
<223> OTHER INFORMATION: CS1 peptide

<400> SEQUENCE: 425

Val Pro Leu Leu Leu Ser Leu Phe Val Leu Gly Leu Phe Leu
1               5                   10

<210> SEQ ID NO 426
<211> LENGTH: 15
<212> TYPE: PRT
<213> ORGANISM: Artificial Sequence
<220> FEATURE:
<223> OTHER INFORMATION: CS1 peptide

<400> SEQUENCE: 426

Val Pro Leu Leu Leu Ser Leu Phe Val Leu Gly Leu Phe Leu Trp
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: CS1 peptide

<400> SEQUENCE: 427

Val Pro Leu Leu Leu Ser Leu Phe Val Leu Gly Leu Phe Leu Trp Phe
1               5                   10                  15

<210> SEQ ID NO 428
<211> LENGTH: 17

-continued

```
<212> TYPE: PRT
<213> ORGANISM: Artificial Sequence
<220> FEATURE:
<223> OTHER INFORMATION: CS1 peptide

<400> SEQUENCE: 428

Val Pro Leu Leu Leu Ser Leu Phe Val Leu Gly Leu Phe Leu Trp Phe
1               5                   10                  15

Leu

<210> SEQ ID NO 429
<211> LENGTH: 18
<212> TYPE: PRT
<213> ORGANISM: Artificial Sequence
<220> FEATURE:
<223> OTHER INFORMATION: CS1 peptide

<400> SEQUENCE: 429

Val Pro Leu Leu Leu Ser Leu Phe Val Leu Gly Leu Phe Leu Trp Phe
1               5                   10                  15

Leu Lys

<210> SEQ ID NO 430
<211> LENGTH: 19
<212> TYPE: PRT
<213> ORGANISM: Artificial Sequence
<220> FEATURE:
<223> OTHER INFORMATION: CS1 peptide

<400> SEQUENCE: 430

Val Pro Leu Leu Leu Ser Leu Phe Val Leu Gly Leu Phe Leu Trp Phe
1               5                   10                  15

Leu Lys Arg

<210> SEQ ID NO 431
<211> LENGTH: 20
<212> TYPE: PRT
<213> ORGANISM: Artificial Sequence
<220> FEATURE:
<223> OTHER INFORMATION: CS1 peptide

<400> SEQUENCE: 431

Val Pro Leu Leu Leu Ser Leu Phe Val Leu Gly Leu Phe Leu Trp Phe
1               5                   10                  15

Leu Lys Arg Glu
            20

<210> SEQ ID NO 432
<211> LENGTH: 8
<212> TYPE: PRT
<213> ORGANISM: Artificial Sequence
<220> FEATURE:
<223> OTHER INFORMATION: CS1 peptide

<400> SEQUENCE: 432

Pro Leu Leu Leu Ser Leu Phe Val
1               5

<210> SEQ ID NO 433
<211> LENGTH: 9
<212> TYPE: PRT
<213> ORGANISM: Artificial Sequence
<220> FEATURE:
<223> OTHER INFORMATION: CS1 peptide
```

<400> SEQUENCE: 433

Pro Leu Leu Leu Ser Leu Phe Val Leu
1               5

<210> SEQ ID NO 434
<211> LENGTH: 10
<212> TYPE: PRT
<213> ORGANISM: Artificial Sequence
<220> FEATURE:
<223> OTHER INFORMATION: CS1 peptide

<400> SEQUENCE: 434

Pro Leu Leu Leu Ser Leu Phe Val Leu Gly
1               5                   10

<210> SEQ ID NO 435
<211> LENGTH: 11
<212> TYPE: PRT
<213> ORGANISM: Artificial Sequence
<220> FEATURE:
<223> OTHER INFORMATION: CS1 peptide

<400> SEQUENCE: 435

Pro Leu Leu Leu Ser Leu Phe Val Leu Gly Leu
1               5                   10

<210> SEQ ID NO 436
<211> LENGTH: 12
<212> TYPE: PRT
<213> ORGANISM: Artificial Sequence
<220> FEATURE:
<223> OTHER INFORMATION: CS1 peptide

<400> SEQUENCE: 436

Pro Leu Leu Leu Ser Leu Phe Val Leu Gly Leu Phe
1               5                   10

<210> SEQ ID NO 437
<211> LENGTH: 13
<212> TYPE: PRT
<213> ORGANISM: Artificial Sequence
<220> FEATURE:
<223> OTHER INFORMATION: CS1 peptide

<400> SEQUENCE: 437

Pro Leu Leu Leu Ser Leu Phe Val Leu Gly Leu Phe Leu
1               5                   10

<210> SEQ ID NO 438
<211> LENGTH: 14
<212> TYPE: PRT
<213> ORGANISM: Artificial Sequence
<220> FEATURE:
<223> OTHER INFORMATION: CS1 peptide

<400> SEQUENCE: 438

Pro Leu Leu Leu Ser Leu Phe Val Leu Gly Leu Phe Leu Trp
1               5                   10

<210> SEQ ID NO 439
<211> LENGTH: 15
<212> TYPE: PRT
<213> ORGANISM: Artificial Sequence
<220> FEATURE:
<223> OTHER INFORMATION: CS1 peptide

<400> SEQUENCE: 439

```
Pro Leu Leu Leu Ser Leu Phe Val Leu Gly Leu Phe Leu Trp Phe
1               5                   10                  15

<210> SEQ ID NO 440
<211> LENGTH: 16
<212> TYPE: PRT
<213> ORGANISM: Artificial Sequence
<220> FEATURE:
<223> OTHER INFORMATION: CS1 peptide

<400> SEQUENCE: 440

Pro Leu Leu Leu Ser Leu Phe Val Leu Gly Leu Phe Leu Trp Phe Leu
1               5                   10                  15

<210> SEQ ID NO 441
<211> LENGTH: 17
<212> TYPE: PRT
<213> ORGANISM: Artificial Sequence
<220> FEATURE:
<223> OTHER INFORMATION: CS1 peptide

<400> SEQUENCE: 441

Pro Leu Leu Leu Ser Leu Phe Val Leu Gly Leu Phe Leu Trp Phe Leu
1               5                   10                  15

Lys

<210> SEQ ID NO 442
<211> LENGTH: 18
<212> TYPE: PRT
<213> ORGANISM: Artificial Sequence
<220> FEATURE:
<223> OTHER INFORMATION: CS1 peptide

<400> SEQUENCE: 442

Pro Leu Leu Leu Ser Leu Phe Val Leu Gly Leu Phe Leu Trp Phe Leu
1               5                   10                  15

Lys Arg

<210> SEQ ID NO 443
<211> LENGTH: 19
<212> TYPE: PRT
<213> ORGANISM: Artificial Sequence
<220> FEATURE:
<223> OTHER INFORMATION: CS1 peptide

<400> SEQUENCE: 443

Pro Leu Leu Leu Ser Leu Phe Val Leu Gly Leu Phe Leu Trp Phe Leu
1               5                   10                  15

Lys Arg Glu

<210> SEQ ID NO 444
<211> LENGTH: 7
<212> TYPE: PRT
<213> ORGANISM: Artificial Sequence
<220> FEATURE:
<223> OTHER INFORMATION: CS1 peptide

<400> SEQUENCE: 444

Leu Leu Leu Ser Leu Phe Val
1               5

<210> SEQ ID NO 445
<211> LENGTH: 8
<212> TYPE: PRT
```

-continued

<213> ORGANISM: Artificial Sequence
<220> FEATURE:
<223> OTHER INFORMATION: CS1 peptide

<400> SEQUENCE: 445

Leu Leu Leu Ser Leu Phe Val Leu
1               5

<210> SEQ ID NO 446
<211> LENGTH: 9
<212> TYPE: PRT
<213> ORGANISM: Artificial Sequence
<220> FEATURE:
<223> OTHER INFORMATION: CS1 peptide

<400> SEQUENCE: 446

Leu Leu Leu Ser Leu Phe Val Leu Gly
1               5

<210> SEQ ID NO 447
<211> LENGTH: 10
<212> TYPE: PRT
<213> ORGANISM: Artificial Sequence
<220> FEATURE:
<223> OTHER INFORMATION: CS1 peptide

<400> SEQUENCE: 447

Leu Leu Leu Ser Leu Phe Val Leu Gly Leu
1               5                   10

<210> SEQ ID NO 448
<211> LENGTH: 11
<212> TYPE: PRT
<213> ORGANISM: Artificial Sequence
<220> FEATURE:
<223> OTHER INFORMATION: CS1 peptide

<400> SEQUENCE: 448

Leu Leu Leu Ser Leu Phe Val Leu Gly Leu Phe
1               5                   10

<210> SEQ ID NO 449
<211> LENGTH: 12
<212> TYPE: PRT
<213> ORGANISM: Artificial Sequence
<220> FEATURE:
<223> OTHER INFORMATION: CS1 peptide

<400> SEQUENCE: 449

Leu Leu Leu Ser Leu Phe Val Leu Gly Leu Phe Leu
1               5                   10

<210> SEQ ID NO 450
<211> LENGTH: 13
<212> TYPE: PRT
<213> ORGANISM: Artificial Sequence
<220> FEATURE:
<223> OTHER INFORMATION: CS1 peptide

<400> SEQUENCE: 450

Leu Leu Leu Ser Leu Phe Val Leu Gly Leu Phe Leu Trp
1               5                   10

<210> SEQ ID NO 451
<211> LENGTH: 14
<212> TYPE: PRT
<213> ORGANISM: Artificial Sequence
<220> FEATURE:
<223> OTHER INFORMATION: CS1 peptide

<400> SEQUENCE: 451

Leu Leu Leu Ser Leu Phe Val Leu Gly Leu Phe Leu Trp Phe
1               5                   10

<210> SEQ ID NO 452
<211> LENGTH: 15
<212> TYPE: PRT
<213> ORGANISM: Artificial Sequence
<220> FEATURE:
<223> OTHER INFORMATION: CS1 peptide

<400> SEQUENCE: 452

Leu Leu Leu Ser Leu Phe Val Leu Gly Leu Phe Leu Trp Phe Leu
1               5                   10                  15

<210> SEQ ID NO 453
<211> LENGTH: 16
<212> TYPE: PRT
<213> ORGANISM: Artificial Sequence
<220> FEATURE:
<223> OTHER INFORMATION: CS1 peptide

<400> SEQUENCE: 453

Leu Leu Leu Ser Leu Phe Val Leu Gly Leu Phe Leu Trp Phe Leu Lys
1               5                   10                  15

<210> SEQ ID NO 454
<211> LENGTH: 17
<212> TYPE: PRT
<213> ORGANISM: Artificial Sequence
<220> FEATURE:
<223> OTHER INFORMATION: CS1 peptide

<400> SEQUENCE: 454

Leu Leu Leu Ser Leu Phe Val Leu Gly Leu Phe Leu Trp Phe Leu Lys
1               5                   10                  15

Arg

<210> SEQ ID NO 455
<211> LENGTH: 18
<212> TYPE: PRT
<213> ORGANISM: Artificial Sequence
<220> FEATURE:
<223> OTHER INFORMATION: CS1 peptide

<400> SEQUENCE: 455

Leu Leu Leu Ser Leu Phe Val Leu Gly Leu Phe Leu Trp Phe Leu Lys
1               5                   10                  15

Arg Glu

<210> SEQ ID NO 456
<211> LENGTH: 6
<212> TYPE: PRT
<213> ORGANISM: Artificial Sequence
<220> FEATURE:
<223> OTHER INFORMATION: CS1 peptide

<400> SEQUENCE: 456

Leu Leu Ser Leu Phe Val
1               5

<210> SEQ ID NO 457

```
<211> LENGTH: 7
<212> TYPE: PRT
<213> ORGANISM: Artificial Sequence
<220> FEATURE:
<223> OTHER INFORMATION: CS1 peptide

<400> SEQUENCE: 457

Leu Leu Ser Leu Phe Val Leu
1               5

<210> SEQ ID NO 458
<211> LENGTH: 8
<212> TYPE: PRT
<213> ORGANISM: Artificial Sequence
<220> FEATURE:
<223> OTHER INFORMATION: CS1 peptide

<400> SEQUENCE: 458

Leu Leu Ser Leu Phe Val Leu Gly
1               5

<210> SEQ ID NO 459
<211> LENGTH: 9
<212> TYPE: PRT
<213> ORGANISM: Artificial Sequence
<220> FEATURE:
<223> OTHER INFORMATION: CS1 peptide

<400> SEQUENCE: 459

Leu Leu Ser Leu Phe Val Leu Gly Leu
1               5

<210> SEQ ID NO 460
<211> LENGTH: 10
<212> TYPE: PRT
<213> ORGANISM: Artificial Sequence
<220> FEATURE:
<223> OTHER INFORMATION: CS1 peptide

<400> SEQUENCE: 460

Leu Leu Ser Leu Phe Val Leu Gly Leu Phe
1               5                   10

<210> SEQ ID NO 461
<211> LENGTH: 11
<212> TYPE: PRT
<213> ORGANISM: Artificial Sequence
<220> FEATURE:
<223> OTHER INFORMATION: CS1 peptide

<400> SEQUENCE: 461

Leu Leu Ser Leu Phe Val Leu Gly Leu Phe Leu
1               5                   10

<210> SEQ ID NO 462
<211> LENGTH: 12
<212> TYPE: PRT
<213> ORGANISM: Artificial Sequence
<220> FEATURE:
<223> OTHER INFORMATION: CS1 peptide

<400> SEQUENCE: 462

Leu Leu Ser Leu Phe Val Leu Gly Leu Phe Leu Trp
1               5                   10

<210> SEQ ID NO 463
<211> LENGTH: 13
```

-continued

```
<212> TYPE: PRT
<213> ORGANISM: Artificial Sequence
<220> FEATURE:
<223> OTHER INFORMATION: CS1 peptide

<400> SEQUENCE: 463

Leu Leu Ser Leu Phe Val Leu Gly Leu Phe Leu Trp Phe
1               5                   10

<210> SEQ ID NO 464
<211> LENGTH: 14
<212> TYPE: PRT
<213> ORGANISM: Artificial Sequence
<220> FEATURE:
<223> OTHER INFORMATION: CS1 peptide

<400> SEQUENCE: 464

Leu Leu Ser Leu Phe Val Leu Gly Leu Phe Leu Trp Phe Leu
1               5                   10

<210> SEQ ID NO 465
<211> LENGTH: 15
<212> TYPE: PRT
<213> ORGANISM: Artificial Sequence
<220> FEATURE:
<223> OTHER INFORMATION: CS1 peptide

<400> SEQUENCE: 465

Leu Leu Ser Leu Phe Val Leu Gly Leu Phe Leu Trp Phe Leu Lys
1               5                   10                  15

<210> SEQ ID NO 466
<211> LENGTH: 16
<212> TYPE: PRT
<213> ORGANISM: Artificial Sequence
<220> FEATURE:
<223> OTHER INFORMATION: CS1 peptide

<400> SEQUENCE: 466

Leu Leu Ser Leu Phe Val Leu Gly Leu Phe Leu Trp Phe Leu Lys Arg
1               5                   10                  15

<210> SEQ ID NO 467
<211> LENGTH: 17
<212> TYPE: PRT
<213> ORGANISM: Artificial Sequence
<220> FEATURE:
<223> OTHER INFORMATION: CS1 peptide

<400> SEQUENCE: 467

Leu Leu Ser Leu Phe Val Leu Gly Leu Phe Leu Trp Phe Leu Lys Arg
1               5                   10                  15

Glu

<210> SEQ ID NO 468
<211> LENGTH: 5
<212> TYPE: PRT
<213> ORGANISM: Artificial Sequence
<220> FEATURE:
<223> OTHER INFORMATION: CS1 peptide

<400> SEQUENCE: 468

Leu Ser Leu Phe Val
1               5

<210> SEQ ID NO 469
```

```
<211> LENGTH: 6
<212> TYPE: PRT
<213> ORGANISM: Artificial Sequence
<220> FEATURE:
<223> OTHER INFORMATION: CS1 peptide

<400> SEQUENCE: 469

Leu Ser Leu Phe Val Leu
1               5

<210> SEQ ID NO 470
<211> LENGTH: 7
<212> TYPE: PRT
<213> ORGANISM: Artificial Sequence
<220> FEATURE:
<223> OTHER INFORMATION: CS1 peptide

<400> SEQUENCE: 470

Leu Ser Leu Phe Val Leu Gly
1               5

<210> SEQ ID NO 471
<211> LENGTH: 8
<212> TYPE: PRT
<213> ORGANISM: Artificial Sequence
<220> FEATURE:
<223> OTHER INFORMATION: CS1 peptide

<400> SEQUENCE: 471

Leu Ser Leu Phe Val Leu Gly Leu
1               5

<210> SEQ ID NO 472
<211> LENGTH: 9
<212> TYPE: PRT
<213> ORGANISM: Artificial Sequence
<220> FEATURE:
<223> OTHER INFORMATION: CS1 peptide

<400> SEQUENCE: 472

Leu Ser Leu Phe Val Leu Gly Leu Phe
1               5

<210> SEQ ID NO 473
<211> LENGTH: 10
<212> TYPE: PRT
<213> ORGANISM: Artificial Sequence
<220> FEATURE:
<223> OTHER INFORMATION: CS1 peptide

<400> SEQUENCE: 473

Leu Ser Leu Phe Val Leu Gly Leu Phe Leu
1               5                   10

<210> SEQ ID NO 474
<211> LENGTH: 11
<212> TYPE: PRT
<213> ORGANISM: Artificial Sequence
<220> FEATURE:
<223> OTHER INFORMATION: CS1 peptide

<400> SEQUENCE: 474

Leu Ser Leu Phe Val Leu Gly Leu Phe Leu Trp
1               5                   10

<210> SEQ ID NO 475
<211> LENGTH: 12
```

-continued

```
<212> TYPE: PRT
<213> ORGANISM: Artificial Sequence
<220> FEATURE:
<223> OTHER INFORMATION: CS1 peptide

<400> SEQUENCE: 475

Leu Ser Leu Phe Val Leu Gly Leu Phe Leu Trp Phe
1               5                   10

<210> SEQ ID NO 476
<211> LENGTH: 13
<212> TYPE: PRT
<213> ORGANISM: Artificial Sequence
<220> FEATURE:
<223> OTHER INFORMATION: CS1 peptide

<400> SEQUENCE: 476

Leu Ser Leu Phe Val Leu Gly Leu Phe Leu Trp Phe Leu
1               5                   10

<210> SEQ ID NO 477
<211> LENGTH: 14
<212> TYPE: PRT
<213> ORGANISM: Artificial Sequence
<220> FEATURE:
<223> OTHER INFORMATION: CS1 peptide

<400> SEQUENCE: 477

Leu Ser Leu Phe Val Leu Gly Leu Phe Leu Trp Phe Leu Lys
1               5                   10

<210> SEQ ID NO 478
<211> LENGTH: 15
<212> TYPE: PRT
<213> ORGANISM: Artificial Sequence
<220> FEATURE:
<223> OTHER INFORMATION: CS1 peptide

<400> SEQUENCE: 478

Leu Ser Leu Phe Val Leu Gly Leu Phe Leu Trp Phe Leu Lys Arg
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: CS1 peptide

<400> SEQUENCE: 479

Leu Ser Leu Phe Val Leu Gly Leu Phe Leu Trp Phe Leu Lys Arg Glu
1               5                   10                  15

<210> SEQ ID NO 480
<211> LENGTH: 5
<212> TYPE: PRT
<213> ORGANISM: Artificial Sequence
<220> FEATURE:
<223> OTHER INFORMATION: CS1 peptide

<400> SEQUENCE: 480

Ser Leu Phe Val Leu
1               5

<210> SEQ ID NO 481
<211> LENGTH: 6
<212> TYPE: PRT
```

-continued

```
<213> ORGANISM: Artificial Sequence
<220> FEATURE:
<223> OTHER INFORMATION: CS1 peptide

<400> SEQUENCE: 481

Ser Leu Phe Val Leu Gly
1               5

<210> SEQ ID NO 482
<211> LENGTH: 7
<212> TYPE: PRT
<213> ORGANISM: Artificial Sequence
<220> FEATURE:
<223> OTHER INFORMATION: CS1 peptide

<400> SEQUENCE: 482

Ser Leu Phe Val Leu Gly Leu
1               5

<210> SEQ ID NO 483
<211> LENGTH: 8
<212> TYPE: PRT
<213> ORGANISM: Artificial Sequence
<220> FEATURE:
<223> OTHER INFORMATION: CS1 peptide

<400> SEQUENCE: 483

Ser Leu Phe Val Leu Gly Leu Phe
1               5

<210> SEQ ID NO 484
<211> LENGTH: 9
<212> TYPE: PRT
<213> ORGANISM: Artificial Sequence
<220> FEATURE:
<223> OTHER INFORMATION: CS1 peptide

<400> SEQUENCE: 484

Ser Leu Phe Val Leu Gly Leu Phe Leu
1               5

<210> SEQ ID NO 485
<211> LENGTH: 10
<212> TYPE: PRT
<213> ORGANISM: Artificial Sequence
<220> FEATURE:
<223> OTHER INFORMATION: CS1 peptide

<400> SEQUENCE: 485

Ser Leu Phe Val Leu Gly Leu Phe Leu Trp
1               5                   10

<210> SEQ ID NO 486
<211> LENGTH: 11
<212> TYPE: PRT
<213> ORGANISM: Artificial Sequence
<220> FEATURE:
<223> OTHER INFORMATION: CS1 peptide

<400> SEQUENCE: 486

Ser Leu Phe Val Leu Gly Leu Phe Leu Trp Phe
1               5                   10

<210> SEQ ID NO 487
<211> LENGTH: 12
<212> TYPE: PRT
<213> ORGANISM: Artificial Sequence
```

<220> FEATURE:
<223> OTHER INFORMATION: CS1 peptide

<400> SEQUENCE: 487

Ser Leu Phe Val Leu Gly Leu Phe Leu Trp Phe Leu
1               5                   10

<210> SEQ ID NO 488
<211> LENGTH: 13
<212> TYPE: PRT
<213> ORGANISM: Artificial Sequence
<220> FEATURE:
<223> OTHER INFORMATION: CS1 peptide

<400> SEQUENCE: 488

Ser Leu Phe Val Leu Gly Leu Phe Leu Trp Phe Leu Lys
1               5                   10

<210> SEQ ID NO 489
<211> LENGTH: 14
<212> TYPE: PRT
<213> ORGANISM: Artificial Sequence
<220> FEATURE:
<223> OTHER INFORMATION: CS1 peptide

<400> SEQUENCE: 489

Ser Leu Phe Val Leu Gly Leu Phe Leu Trp Phe Leu Lys Arg
1               5                   10

<210> SEQ ID NO 490
<211> LENGTH: 15
<212> TYPE: PRT
<213> ORGANISM: Artificial Sequence
<220> FEATURE:
<223> OTHER INFORMATION: CS1 peptide

<400> SEQUENCE: 490

Ser Leu Phe Val Leu Gly Leu Phe Leu Trp Phe Leu Lys Arg Glu
1               5                       10                  15

<210> SEQ ID NO 491
<211> LENGTH: 5
<212> TYPE: PRT
<213> ORGANISM: Artificial Sequence
<220> FEATURE:
<223> OTHER INFORMATION: CS1 peptide

<400> SEQUENCE: 491

Leu Phe Val Leu Gly
1               5

<210> SEQ ID NO 492
<211> LENGTH: 6
<212> TYPE: PRT
<213> ORGANISM: Artificial Sequence
<220> FEATURE:
<223> OTHER INFORMATION: CS1 peptide

<400> SEQUENCE: 492

Leu Phe Val Leu Gly Leu
1               5

<210> SEQ ID NO 493
<211> LENGTH: 7
<212> TYPE: PRT
<213> ORGANISM: Artificial Sequence
<220> FEATURE:

-continued

```
<223> OTHER INFORMATION: CS1 peptide

<400> SEQUENCE: 493

Leu Phe Val Leu Gly Leu Phe
1               5

<210> SEQ ID NO 494
<211> LENGTH: 8
<212> TYPE: PRT
<213> ORGANISM: Artificial Sequence
<220> FEATURE:
<223> OTHER INFORMATION: CS1 peptide

<400> SEQUENCE: 494

Leu Phe Val Leu Gly Leu Phe Leu
1               5

<210> SEQ ID NO 495
<211> LENGTH: 9
<212> TYPE: PRT
<213> ORGANISM: Artificial Sequence
<220> FEATURE:
<223> OTHER INFORMATION: CS1 peptide

<400> SEQUENCE: 495

Leu Phe Val Leu Gly Leu Phe Leu Trp
1               5

<210> SEQ ID NO 496
<211> LENGTH: 11
<212> TYPE: PRT
<213> ORGANISM: Artificial Sequence
<220> FEATURE:
<223> OTHER INFORMATION: CS1 peptide

<400> SEQUENCE: 496

Leu Phe Val Leu Gly Leu Phe Leu Trp Phe Leu
1               5                   10

<210> SEQ ID NO 497
<211> LENGTH: 11
<212> TYPE: PRT
<213> ORGANISM: Artificial Sequence
<220> FEATURE:
<223> OTHER INFORMATION: CS1 peptide

<400> SEQUENCE: 497

Leu Phe Val Leu Gly Leu Phe Leu Trp Phe Leu
1               5                   10

<210> SEQ ID NO 498
<211> LENGTH: 12
<212> TYPE: PRT
<213> ORGANISM: Artificial Sequence
<220> FEATURE:
<223> OTHER INFORMATION: CS1 peptide

<400> SEQUENCE: 498

Leu Phe Val Leu Gly Leu Phe Leu Trp Phe Leu Lys
1               5                   10

<210> SEQ ID NO 499
<211> LENGTH: 13
<212> TYPE: PRT
<213> ORGANISM: Artificial Sequence
<220> FEATURE:
<223> OTHER INFORMATION: CS1 peptide
```

<400> SEQUENCE: 499

Leu Phe Val Leu Gly Leu Phe Leu Trp Phe Leu Lys Arg
1               5                   10

<210> SEQ ID NO 500
<211> LENGTH: 14
<212> TYPE: PRT
<213> ORGANISM: Artificial Sequence
<220> FEATURE:
<223> OTHER INFORMATION: CS1 peptide

<400> SEQUENCE: 500

Leu Phe Val Leu Gly Leu Phe Leu Trp Phe Leu Lys Arg Glu
1               5                   10

<210> SEQ ID NO 501
<211> LENGTH: 9
<212> TYPE: PRT
<213> ORGANISM: Artificial Sequence
<220> FEATURE:
<223> OTHER INFORMATION: CS1 peptide

<400> SEQUENCE: 501

Lys Glu Asp Pro Ala Asn Thr Val Tyr
1               5

<210> SEQ ID NO 502
<211> LENGTH: 10
<212> TYPE: PRT
<213> ORGANISM: Artificial Sequence
<220> FEATURE:
<223> OTHER INFORMATION: CS1 peptide

<400> SEQUENCE: 502

Met Pro Asp Thr Pro Arg Leu Phe Ala Tyr
1               5                   10

<210> SEQ ID NO 503
<211> LENGTH: 10
<212> TYPE: PRT
<213> ORGANISM: Artificial Sequence
<220> FEATURE:
<223> OTHER INFORMATION: CS1 peptide

<400> SEQUENCE: 503

Ser Thr Gln Glu Tyr Val Leu His Val Tyr
1               5                   10

<210> SEQ ID NO 504
<211> LENGTH: 9
<212> TYPE: PRT
<213> ORGANISM: Artificial Sequence
<220> FEATURE:
<223> OTHER INFORMATION: CS1 peptide

<400> SEQUENCE: 504

Arg Val Asp Phe Pro Asp Gly Gly Tyr
1               5

<210> SEQ ID NO 505
<211> LENGTH: 9
<212> TYPE: PRT
<213> ORGANISM: Artificial Sequence
<220> FEATURE:
<223> OTHER INFORMATION: CS1 peptide

```
<400> SEQUENCE: 505

Leu Leu Val Pro Leu Leu Leu Ser Leu
1               5

<210> SEQ ID NO 506
<211> LENGTH: 10
<212> TYPE: PRT
<213> ORGANISM: Artificial Sequence
<220> FEATURE:
<223> OTHER INFORMATION: CS1 peptide

<400> SEQUENCE: 506

Leu Leu Leu Val Pro Leu Leu Leu Ser Leu
1               5                   10

<210> SEQ ID NO 507
<211> LENGTH: 10
<212> TYPE: PRT
<213> ORGANISM: Artificial Sequence
<220> FEATURE:
<223> OTHER INFORMATION: CS1 peptide

<400> SEQUENCE: 507

Leu Leu Leu Ser Leu Phe Val Leu Gly Leu
1               5                   10

<210> SEQ ID NO 508
<211> LENGTH: 10
<212> TYPE: PRT
<213> ORGANISM: Artificial Sequence
<220> FEATURE:
<223> OTHER INFORMATION: CS1 peptide

<400> SEQUENCE: 508

Val Leu Leu Cys Leu Leu Leu Val Pro Leu
1               5                   10

<210> SEQ ID NO 509
<211> LENGTH: 9
<212> TYPE: PRT
<213> ORGANISM: Artificial Sequence
<220> FEATURE:
<223> OTHER INFORMATION: CS1 peptide

<400> SEQUENCE: 509

Ser Leu Lys Leu Ser Lys Leu Lys Lys
1               5

<210> SEQ ID NO 510
<211> LENGTH: 10
<212> TYPE: PRT
<213> ORGANISM: Artificial Sequence
<220> FEATURE:
<223> OTHER INFORMATION: CS1 peptide

<400> SEQUENCE: 510

Lys Val Thr Met Gly Leu Gln Ser Asn Lys
1               5                   10

<210> SEQ ID NO 511
<211> LENGTH: 10
<212> TYPE: PRT
<213> ORGANISM: Artificial Sequence
<220> FEATURE:
<223> OTHER INFORMATION: CS1 peptide

<400> SEQUENCE: 511
```

-continued

Val Leu His Val Tyr Glu His Leu Ser Lys
1               5                   10

<210> SEQ ID NO 512
<211> LENGTH: 10
<212> TYPE: PRT
<213> ORGANISM: Artificial Sequence
<220> FEATURE:
<223> OTHER INFORMATION: CS1 peptide

<400> SEQUENCE: 512

His Val Tyr Glu His Leu Ser Lys Pro Lys
1               5                   10

<210> SEQ ID NO 513
<211> LENGTH: 9
<212> TYPE: PRT
<213> ORGANISM: Artificial Sequence
<220> FEATURE:
<223> OTHER INFORMATION: CS1 peptide

<400> SEQUENCE: 513

Gly Ser Ala Ala Ser Gly Pro Val Lys
1               5

<210> SEQ ID NO 514
<211> LENGTH: 10
<212> TYPE: PRT
<213> ORGANISM: Artificial Sequence
<220> FEATURE:
<223> OTHER INFORMATION: CS1 peptide

<400> SEQUENCE: 514

Tyr Ser Leu Lys Leu Ser Lys Leu Lys Lys
1               5                   10

<210> SEQ ID NO 515
<211> LENGTH: 10
<212> TYPE: PRT
<213> ORGANISM: Artificial Sequence
<220> FEATURE:
<223> OTHER INFORMATION: CS1 peptide

<400> SEQUENCE: 515

Thr Val Tyr Ser Thr Val Glu Ile Pro Lys
1               5                   10

<210> SEQ ID NO 516
<211> LENGTH: 9
<212> TYPE: PRT
<213> ORGANISM: Artificial Sequence
<220> FEATURE:
<223> OTHER INFORMATION: CS1 peptide

<400> SEQUENCE: 516

Cys Val Ala Arg Asn Pro Val Ser Arg
1               5

<210> SEQ ID NO 517
<211> LENGTH: 9
<212> TYPE: PRT
<213> ORGANISM: Artificial Sequence
<220> FEATURE:
<223> OTHER INFORMATION: CS1 peptide

<400> SEQUENCE: 517

-continued

```
Gly Tyr Ser Leu Lys Leu Ser Lys Leu
1               5

<210> SEQ ID NO 518
<211> LENGTH: 10
<212> TYPE: PRT
<213> ORGANISM: Artificial Sequence
<220> FEATURE:
<223> OTHER INFORMATION: CS1 peptide

<400> SEQUENCE: 518

Glu Tyr Val Leu His Val Tyr Glu His Leu
1               5                   10

<210> SEQ ID NO 519
<211> LENGTH: 10
<212> TYPE: PRT
<213> ORGANISM: Artificial Sequence
<220> FEATURE:
<223> OTHER INFORMATION: CS1 peptide

<400> SEQUENCE: 519

Tyr Tyr Val Gly Ile Tyr Ser Ser Ser Leu
1               5                   10

<210> SEQ ID NO 520
<211> LENGTH: 9
<212> TYPE: PRT
<213> ORGANISM: Artificial Sequence
<220> FEATURE:
<223> OTHER INFORMATION: CS1 peptide

<400> SEQUENCE: 520

Asp Phe Pro Asp Gly Gly Tyr Ser Leu
1               5

<210> SEQ ID NO 521
<211> LENGTH: 9
<212> TYPE: PRT
<213> ORGANISM: Artificial Sequence
<220> FEATURE:
<223> OTHER INFORMATION: CS1 peptide

<400> SEQUENCE: 521

Asp Val Ile Tyr Thr Trp Lys Ala Leu
1               5

<210> SEQ ID NO 522
<211> LENGTH: 9
<212> TYPE: PRT
<213> ORGANISM: Artificial Sequence
<220> FEATURE:
<223> OTHER INFORMATION: CS1 peptide

<400> SEQUENCE: 522

Gln Val Asp Ser Ile Val Trp Thr Phe
1               5

<210> SEQ ID NO 523
<211> LENGTH: 10
<212> TYPE: PRT
<213> ORGANISM: Artificial Sequence
<220> FEATURE:
<223> OTHER INFORMATION: CS1 peptide

<400> SEQUENCE: 523

Glu Arg Val Asp Phe Pro Asp Gly Gly Tyr
```

-continued

```
1                5                10
```

<210> SEQ ID NO 524
<211> LENGTH: 10
<212> TYPE: PRT
<213> ORGANISM: Artificial Sequence
<220> FEATURE:
<223> OTHER INFORMATION: CS1 peptide

<400> SEQUENCE: 524

```
Ser Thr Gln Glu Tyr Val Leu His Val Tyr
1                5                10
```

<210> SEQ ID NO 525
<211> LENGTH: 9
<212> TYPE: PRT
<213> ORGANISM: Artificial Sequence
<220> FEATURE:
<223> OTHER INFORMATION: CS1 peptide

<400> SEQUENCE: 525

```
Cys Val Ala Arg Asn Pro Val Ser Arg
1                5
```

<210> SEQ ID NO 526
<211> LENGTH: 9
<212> TYPE: PRT
<213> ORGANISM: Artificial Sequence
<220> FEATURE:
<223> OTHER INFORMATION: CS1 peptide

<400> SEQUENCE: 526

```
Phe Ser Ser Pro Ile Leu Ala Arg Lys
1                5
```

<210> SEQ ID NO 527
<211> LENGTH: 10
<212> TYPE: PRT
<213> ORGANISM: Artificial Sequence
<220> FEATURE:
<223> OTHER INFORMATION: CS1 peptide

<400> SEQUENCE: 527

```
Thr Val Tyr Ser Thr Val Glu Ile Pro Lys
1                5                10
```

<210> SEQ ID NO 528
<211> LENGTH: 11
<212> TYPE: PRT
<213> ORGANISM: Artificial Sequence
<220> FEATURE:
<223> OTHER INFORMATION: CS1 peptide

<400> SEQUENCE: 528

```
Glu Ser Asp Met Thr Phe Ile Cys Val Ala Arg
1                5                10
```

<210> SEQ ID NO 529
<211> LENGTH: 10
<212> TYPE: PRT
<213> ORGANISM: Artificial Sequence
<220> FEATURE:
<223> OTHER INFORMATION: CS1 peptide

<400> SEQUENCE: 529

```
Phe Pro Asp Gly Gly Tyr Ser Leu Lys Leu
1                5                10
```

```
<210> SEQ ID NO 530
<211> LENGTH: 9
<212> TYPE: PRT
<213> ORGANISM: Artificial Sequence
<220> FEATURE:
<223> OTHER INFORMATION: CS1 peptide

<400> SEQUENCE: 530

Met Pro Asp Thr Pro Arg Leu Phe Ala
1               5

<210> SEQ ID NO 531
<211> LENGTH: 9
<212> TYPE: PRT
<213> ORGANISM: Artificial Sequence
<220> FEATURE:
<223> OTHER INFORMATION: CS1 peptide

<400> SEQUENCE: 531

Gln Pro Ser Thr Gln Glu Tyr Val Leu
1               5

<210> SEQ ID NO 532
<211> LENGTH: 9
<212> TYPE: PRT
<213> ORGANISM: Artificial Sequence
<220> FEATURE:
<223> OTHER INFORMATION: CS1 peptide

<400> SEQUENCE: 532

Asp Pro Asp Ser Ser Met Val Leu Leu
1               5

<210> SEQ ID NO 533
<211> LENGTH: 9
<212> TYPE: PRT
<213> ORGANISM: Artificial Sequence
<220> FEATURE:
<223> OTHER INFORMATION: CS1 peptide

<400> SEQUENCE: 533

Pro Leu Lys Ser Lys Val Lys Gln Val
1               5

<210> SEQ ID NO 534
<211> LENGTH: 8
<212> TYPE: PRT
<213> ORGANISM: Artificial Sequence
<220> FEATURE:
<223> OTHER INFORMATION: CS1 peptide

<400> SEQUENCE: 534

Lys Pro Lys Val Thr Met Gly Leu
1               5

<210> SEQ ID NO 535
<211> LENGTH: 8
<212> TYPE: PRT
<213> ORGANISM: Artificial Sequence
<220> FEATURE:
<223> OTHER INFORMATION: CS1 peptide

<400> SEQUENCE: 535

Pro Leu Lys Ser Lys Val Lys Gln
1               5
```

<210> SEQ ID NO 536
<211> LENGTH: 8
<212> TYPE: PRT
<213> ORGANISM: Artificial Sequence
<220> FEATURE:
<223> OTHER INFORMATION: CS1 peptide

<400> SEQUENCE: 536

Glu Glu Lys Lys Arg Val Asp Ile
1               5

<210> SEQ ID NO 537
<211> LENGTH: 10
<212> TYPE: PRT
<213> ORGANISM: Artificial Sequence
<220> FEATURE:
<223> OTHER INFORMATION: CS1 peptide

<400> SEQUENCE: 537

Lys Gln Val Asp Ser Ile Val Trp Thr Phe
1               5                   10

<210> SEQ ID NO 538
<211> LENGTH: 10
<212> TYPE: PRT
<213> ORGANISM: Artificial Sequence
<220> FEATURE:
<223> OTHER INFORMATION: CS1 peptide

<400> SEQUENCE: 538

Leu Leu Val Pro Leu Leu Leu Ser Leu Phe
1               5                   10

<210> SEQ ID NO 539
<211> LENGTH: 9
<212> TYPE: PRT
<213> ORGANISM: Artificial Sequence
<220> FEATURE:
<223> OTHER INFORMATION: CS1 peptide

<400> SEQUENCE: 539

Leu Gln Gln Pro Ser Thr Gln Glu Tyr
1               5

<210> SEQ ID NO 540
<211> LENGTH: 9
<212> TYPE: PRT
<213> ORGANISM: Artificial Sequence
<220> FEATURE:
<223> OTHER INFORMATION: CS1 peptide

<400> SEQUENCE: 540

Thr Gln Glu Tyr Val Leu His Val Tyr
1               5

<210> SEQ ID NO 541
<211> LENGTH: 10
<212> TYPE: PRT
<213> ORGANISM: Artificial Sequence
<220> FEATURE:
<223> OTHER INFORMATION: CS1 peptide

<400> SEQUENCE: 541

Met Pro Asp Thr Pro Arg Leu Phe Ala Tyr
1               5                   10

-continued

```
<210> SEQ ID NO 542
<211> LENGTH: 10
<212> TYPE: PRT
<213> ORGANISM: Artificial Sequence
<220> FEATURE:
<223> OTHER INFORMATION: CS1 peptide

<400> SEQUENCE: 542

Val Pro Leu Leu Leu Ser Leu Phe Val Leu
1               5                   10

<210> SEQ ID NO 543
<211> LENGTH: 9
<212> TYPE: PRT
<213> ORGANISM: Artificial Sequence
<220> FEATURE:
<223> OTHER INFORMATION: CS1 peptide

<400> SEQUENCE: 543

Asp Pro Asp Ser Ser Met Val Leu Leu
1               5

<210> SEQ ID NO 544
<211> LENGTH: 10
<212> TYPE: PRT
<213> ORGANISM: Artificial Sequence
<220> FEATURE:
<223> OTHER INFORMATION: CS1 peptide

<400> SEQUENCE: 544

Phe Pro Asp Gly Gly Tyr Ser Leu Lys Leu
1               5                   10

<210> SEQ ID NO 545
<211> LENGTH: 10
<212> TYPE: PRT
<213> ORGANISM: Artificial Sequence
<220> FEATURE:
<223> OTHER INFORMATION: CS1 peptide

<400> SEQUENCE: 545

Lys Ser Lys Val Lys Gln Val Asp Ser Ile
1               5                   10

<210> SEQ ID NO 546
<211> LENGTH: 10
<212> TYPE: PRT
<213> ORGANISM: Artificial Sequence
<220> FEATURE:
<223> OTHER INFORMATION: CS1 peptide

<400> SEQUENCE: 546

Phe Ser Ser Pro Ile Leu Ala Arg Lys Leu
1               5                   10

<210> SEQ ID NO 547
<211> LENGTH: 10
<212> TYPE: PRT
<213> ORGANISM: Artificial Sequence
<220> FEATURE:
<223> OTHER INFORMATION: CS1 peptide

<400> SEQUENCE: 547

Asp Thr Ile Pro His Thr Asn Arg Thr Ile
1               5                   10

<210> SEQ ID NO 548
```

<211> LENGTH: 9
<212> TYPE: PRT
<213> ORGANISM: Artificial Sequence
<220> FEATURE:
<223> OTHER INFORMATION: CS1 peptide

<400> SEQUENCE: 548

Ser Ser Pro Ile Leu Ala Arg Lys Leu
1               5

<210> SEQ ID NO 549
<211> LENGTH: 15
<212> TYPE: PRT
<213> ORGANISM: Artificial Sequence
<220> FEATURE:
<223> OTHER INFORMATION: CS1 peptide

<400> SEQUENCE: 549

Ile Tyr Ile Leu Trp Gln Leu Thr Gly Ser Ala Ala Ser Gly Pro
1               5                   10                  15

<210> SEQ ID NO 550
<211> LENGTH: 15
<212> TYPE: PRT
<213> ORGANISM: Artificial Sequence
<220> FEATURE:
<223> OTHER INFORMATION: CS1 peptide

<400> SEQUENCE: 550

Gly Ile Tyr Tyr Val Gly Ile Tyr Ser Ser Ser Leu Gln Gln Pro
1               5                   10                  15

<210> SEQ ID NO 551
<211> LENGTH: 15
<212> TYPE: PRT
<213> ORGANISM: Artificial Sequence
<220> FEATURE:
<223> OTHER INFORMATION: CS1 peptide

<400> SEQUENCE: 551

Leu Ile Tyr Ile Leu Trp Gln Leu Thr Gly Ser Ala Ala Ser Gly
1               5                   10                  15

<210> SEQ ID NO 552
<211> LENGTH: 15
<212> TYPE: PRT
<213> ORGANISM: Artificial Sequence
<220> FEATURE:
<223> OTHER INFORMATION: CS1 peptide

<400> SEQUENCE: 552

Leu Ile Tyr Ile Leu Trp Gln Leu Thr Gly Ser Ala Ala Ser Gly
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: CS1 peptide

<400> SEQUENCE: 553

Leu Trp Phe Leu Lys Arg Glu Arg Gln Glu Glu Tyr Ile Glu Glu
1               5                   10                  15

<210> SEQ ID NO 554
<211> LENGTH: 15

-continued

```
<212> TYPE: PRT
<213> ORGANISM: Artificial Sequence
<220> FEATURE:
<223> OTHER INFORMATION: CS1 peptide

<400> SEQUENCE: 554

Tyr Asp Thr Ile Pro His Thr Asn Arg Thr Ile Leu Lys Glu Asp
1               5                   10                  15

<210> SEQ ID NO 555
<211> LENGTH: 15
<212> TYPE: PRT
<213> ORGANISM: Artificial Sequence
<220> FEATURE:
<223> OTHER INFORMATION: CS1 peptide

<400> SEQUENCE: 555

Arg Thr Ile Leu Lys Glu Asp Pro Ala Asn Thr Val Tyr Ser Thr
1               5                   10                  15

<210> SEQ ID NO 556
<211> LENGTH: 15
<212> TYPE: PRT
<213> ORGANISM: Artificial Sequence
<220> FEATURE:
<223> OTHER INFORMATION: CS1 peptide

<400> SEQUENCE: 556

Ser Met Val Leu Leu Cys Leu Leu Leu Val Pro Leu Leu Leu Ser
1               5                   10                  15

<210> SEQ ID NO 557
<211> LENGTH: 15
<212> TYPE: PRT
<213> ORGANISM: Artificial Sequence
<220> FEATURE:
<223> OTHER INFORMATION: CS1 peptide

<400> SEQUENCE: 557

Gly Ile Tyr Tyr Val Gly Ile Tyr Ser Ser Ser Leu Gln Gln Pro
1               5                   10                  15

<210> SEQ ID NO 558
<211> LENGTH: 15
<212> TYPE: PRT
<213> ORGANISM: Artificial Sequence
<220> FEATURE:
<223> OTHER INFORMATION: CS1 peptide

<400> SEQUENCE: 558

Val Gly Ser Val Gly Gly Ala Val Thr Phe Pro Leu Lys Ser Lys
1               5                   10                  15

<210> SEQ ID NO 559
<211> LENGTH: 15
<212> TYPE: PRT
<213> ORGANISM: Artificial Sequence
<220> FEATURE:
<223> OTHER INFORMATION: CS1 peptide

<400> SEQUENCE: 559

Tyr Ile Leu Trp Gln Leu Thr Gly Ser Ala Ala Ser Gly Pro Val
1               5                   10                  15

<210> SEQ ID NO 560
<211> LENGTH: 15
<212> TYPE: PRT
```

-continued

```
<213> ORGANISM: Artificial Sequence
<220> FEATURE:
<223> OTHER INFORMATION: CS1 peptide

<400> SEQUENCE: 560

Ser Ile Val Trp Thr Phe Asn Thr Thr Pro Leu Val Thr Ile Gln
1               5                   10                  15

<210> SEQ ID NO 561
<211> LENGTH: 15
<212> TYPE: PRT
<213> ORGANISM: Artificial Sequence
<220> FEATURE:
<223> OTHER INFORMATION: CS1 peptide

<400> SEQUENCE: 561

Ser Leu Lys Leu Ser Lys Leu Lys Lys Asn Asp Ser Gly Ile Tyr
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: CS1 peptide

<400> SEQUENCE: 562

Leu His Val Tyr Glu His Leu Ser Lys Pro Lys Val Thr Met Gly
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: CS1 peptide

<400> SEQUENCE: 563

Asp Met Thr Phe Ile Cys Val Ala Arg Asn Pro Val Ser Arg Asn
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: CS1 peptide

<400> SEQUENCE: 564

Asn Thr Glu Tyr Asp Thr Ile Pro His Thr Asn Arg Thr Ile Leu
1               5                   10                  15

<210> SEQ ID NO 565
<211> LENGTH: 15
<212> TYPE: PRT
<213> ORGANISM: Artificial Sequence
<220> FEATURE:
<223> OTHER INFORMATION: CS1 peptide

<400> SEQUENCE: 565

Glu Asp Val Ile Tyr Thr Trp Lys Ala Leu Gly Gln Ala Ala Asn
1               5                   10                  15

<210> SEQ ID NO 566
<211> LENGTH: 15
<212> TYPE: PRT
<213> ORGANISM: Artificial Sequence
```

```
<220> FEATURE:
<223> OTHER INFORMATION: CS1 peptide

<400> SEQUENCE: 566

Glu Tyr Val Leu His Val Tyr Glu His Leu Ser Lys Pro Lys Val
1               5                   10                  15

<210> SEQ ID NO 567
<211> LENGTH: 15
<212> TYPE: PRT
<213> ORGANISM: Artificial Sequence
<220> FEATURE:
<223> OTHER INFORMATION: CS1 peptide

<400> SEQUENCE: 567

Leu Phe Val Leu Gly Leu Phe Leu Trp Phe Leu Lys Arg Glu Arg
1               5                   10                  15

<210> SEQ ID NO 568
<211> LENGTH: 15
<212> TYPE: PRT
<213> ORGANISM: Artificial Sequence
<220> FEATURE:
<223> OTHER INFORMATION: CS1 peptide

<400> SEQUENCE: 568

Asp Ser Ile Val Trp Thr Phe Asn Thr Thr Pro Leu Val Thr Ile
1               5                   10                  15

<210> SEQ ID NO 569
<211> LENGTH: 310
<212> TYPE: PRT
<213> ORGANISM: Homo sapiens

<400> SEQUENCE: 569

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
```

-continued

```
        195               200               205
Gln Asp Phe Thr Phe Glu Thr Ser Gly Glu Asn Thr Ala Val Val Ala
    210               215               220

Val Glu Pro Asp Arg Arg Asn Gln Ser Pro Val Asp Gln Gly Ala Thr
225               230               235               240

Gly Ala Ser Gln Gly Leu Leu Asp Arg Lys Glu Val Leu Gly Gly Val
                245               250               255

Ile Ala Gly Gly Leu Val Gly Leu Ile Phe Ala Val Cys Leu Val Gly
        260               265               270

Phe Met Leu Tyr Arg Met Lys Lys Lys Asp Glu Gly Ser Tyr Ser Leu
        275               280               285

Glu Glu Pro Lys Gln Ala Asn Gly Gly Ala Tyr Gln Lys Pro Thr Lys
    290               295               300

Gln Glu Glu Phe Tyr Ala
305               310

<210> SEQ ID NO 570
<211> LENGTH: 9
<212> TYPE: PRT
<213> ORGANISM: Artificial Sequence
<220> FEATURE:
<223> OTHER INFORMATION: CD138 peptide

<400> SEQUENCE: 570

Val Ile Ala Gly Gly Leu Val Gly Leu
1               5

<210> SEQ ID NO 571
<211> LENGTH: 9
<212> TYPE: PRT
<213> ORGANISM: Artificial Sequence
<220> FEATURE:
<223> OTHER INFORMATION: CD138 peptide

<400> SEQUENCE: 571

Gly Leu Val Gly Leu Ile Phe Ala Val
1               5

<210> SEQ ID NO 572
<211> LENGTH: 9
<212> TYPE: PRT
<213> ORGANISM: Artificial Sequence
<220> FEATURE:
<223> OTHER INFORMATION: CD138 peptide

<400> SEQUENCE: 572

Ala Leu Trp Leu Trp Leu Cys Ala Leu
1               5

<210> SEQ ID NO 573
<211> LENGTH: 9
<212> TYPE: PRT
<213> ORGANISM: Artificial Sequence
<220> FEATURE:
<223> OTHER INFORMATION: CD138 peptide

<400> SEQUENCE: 573

Trp Leu Trp Leu Cys Ala Leu Ala Leu
1               5

<210> SEQ ID NO 574
<211> LENGTH: 9
<212> TYPE: PRT
```

<213> ORGANISM: Artificial Sequence
<220> FEATURE:
<223> OTHER INFORMATION: CD138 peptide

<400> SEQUENCE: 574

Ile Phe Ala Val Cys Leu Val Gly Phe
1               5

<210> SEQ ID NO 575
<211> LENGTH: 9
<212> TYPE: PRT
<213> ORGANISM: Artificial Sequence
<220> FEATURE:
<223> OTHER INFORMATION: CD138 peptide

<400> SEQUENCE: 575

Val Leu Pro Glu Val Glu Pro Gly Leu
1               5

<210> SEQ ID NO 576
<211> LENGTH: 9
<212> TYPE: PRT
<213> ORGANISM: Artificial Sequence
<220> FEATURE:
<223> OTHER INFORMATION: CD138 peptide

<400> SEQUENCE: 576

Leu Pro Gln Ile Val Ala Thr Asn Leu
1               5

<210> SEQ ID NO 577
<211> LENGTH: 9
<212> TYPE: PRT
<213> ORGANISM: Artificial Sequence
<220> FEATURE:
<223> OTHER INFORMATION: CD138 peptide

<400> SEQUENCE: 577

Leu Ala Leu Ser Leu Gln Pro Ala Leu
1               5

<210> SEQ ID NO 578
<211> LENGTH: 9
<212> TYPE: PRT
<213> ORGANISM: Artificial Sequence
<220> FEATURE:
<223> OTHER INFORMATION: CD138 peptide

<400> SEQUENCE: 578

Gly Leu Leu Asp Arg Lys Glu Val Leu
1               5

<210> SEQ ID NO 579
<211> LENGTH: 9
<212> TYPE: PRT
<213> ORGANISM: Artificial Sequence
<220> FEATURE:
<223> OTHER INFORMATION: CD138 peptide

<400> SEQUENCE: 579

Val Gly Leu Ile Phe Ala Val Cys Leu
1               5

<210> SEQ ID NO 580
<211> LENGTH: 9
<212> TYPE: PRT
<213> ORGANISM: Artificial Sequence -continued

```
<220> FEATURE:
<223> OTHER INFORMATION: CD138 peptide

<400> SEQUENCE: 580

Ser Leu Gln Pro Ala Leu Pro Gln Ile
1               5

<210> SEQ ID NO 581
<211> LENGTH: 18
<212> TYPE: PRT
<213> ORGANISM: Artificial Sequence
<220> FEATURE:
<223> OTHER INFORMATION: CD138 peptide

<400> SEQUENCE: 581

Glu Val Leu Gly Gly Val Ile Ala Gly Gly Leu Val Gly Leu Ile Phe
1               5                   10                  15

Ala Val

<210> SEQ ID NO 582
<211> LENGTH: 19
<212> TYPE: PRT
<213> ORGANISM: Artificial Sequence
<220> FEATURE:
<223> OTHER INFORMATION: CD138 peptide

<400> SEQUENCE: 582

Glu Val Leu Gly Gly Val Ile Ala Gly Gly Leu Val Gly Leu Ile Phe
1               5                   10                  15

Ala Val Cys

<210> SEQ ID NO 583
<211> LENGTH: 20
<212> TYPE: PRT
<213> ORGANISM: Artificial Sequence
<220> FEATURE:
<223> OTHER INFORMATION: CD138 peptide

<400> SEQUENCE: 583

Glu Val Leu Gly Gly Val Ile Ala Gly Gly Leu Val Gly Leu Ile Phe
1               5                   10                  15

Ala Val Cys Leu
            20

<210> SEQ ID NO 584
<211> LENGTH: 21
<212> TYPE: PRT
<213> ORGANISM: Artificial Sequence
<220> FEATURE:
<223> OTHER INFORMATION: CD138 peptide

<400> SEQUENCE: 584

Glu Val Leu Gly Gly Val Ile Ala Gly Gly Leu Val Gly Leu Ile Phe
1               5                   10                  15

Ala Val Cys Leu Val
            20

<210> SEQ ID NO 585
<211> LENGTH: 22
<212> TYPE: PRT
<213> ORGANISM: Artificial Sequence
<220> FEATURE:
<223> OTHER INFORMATION: CD138 peptide

<400> SEQUENCE: 585
```

Glu Val Leu Gly Gly Val Ile Ala Gly Gly Leu Val Gly Leu Ile Phe
1               5                   10                  15

Ala Val Cys Leu Val Gly
          20

<210> SEQ ID NO 586
<211> LENGTH: 24
<212> TYPE: PRT
<213> ORGANISM: Artificial Sequence
<220> FEATURE:
<223> OTHER INFORMATION: CD138 peptide

<400> SEQUENCE: 586

Glu Val Leu Gly Gly Val Ile Ala Gly Gly Leu Val Gly Leu Ile Phe
1               5                   10                  15

Ala Val Cys Leu Val Gly Phe Met
          20

<210> SEQ ID NO 587
<211> LENGTH: 24
<212> TYPE: PRT
<213> ORGANISM: Artificial Sequence
<220> FEATURE:
<223> OTHER INFORMATION: CD138 peptide

<400> SEQUENCE: 587

Glu Val Leu Gly Gly Val Ile Ala Gly Gly Leu Val Gly Leu Ile Phe
1               5                   10                  15

Ala Val Cys Leu Val Gly Phe Met
          20

<210> SEQ ID NO 588
<211> LENGTH: 25
<212> TYPE: PRT
<213> ORGANISM: Artificial Sequence
<220> FEATURE:
<223> OTHER INFORMATION: CD138 peptide

<400> SEQUENCE: 588

Glu Val Leu Gly Gly Val Ile Ala Gly Gly Leu Val Gly Leu Ile Phe
1               5                   10                  15

Ala Val Cys Leu Val Gly Phe Met Leu
          20                  25

<210> SEQ ID NO 589
<211> LENGTH: 26
<212> TYPE: PRT
<213> ORGANISM: Artificial Sequence
<220> FEATURE:
<223> OTHER INFORMATION: CD138 peptide

<400> SEQUENCE: 589

Glu Val Leu Gly Gly Val Ile Ala Gly Gly Leu Val Gly Leu Ile Phe
1               5                   10                  15

Ala Val Cys Leu Val Gly Phe Met Leu Tyr
          20                  25

<210> SEQ ID NO 590
<211> LENGTH: 27
<212> TYPE: PRT
<213> ORGANISM: Artificial Sequence
<220> FEATURE:
<223> OTHER INFORMATION: CD138 peptide -continued

```
<400> SEQUENCE: 590

Glu Val Leu Gly Gly Val Ile Ala Gly Gly Leu Val Gly Leu Ile Phe
1               5                   10                  15

Ala Val Cys Leu Val Gly Phe Met Leu Tyr Arg
            20                  25

<210> SEQ ID NO 591
<211> LENGTH: 28
<212> TYPE: PRT
<213> ORGANISM: Artificial Sequence
<220> FEATURE:
<223> OTHER INFORMATION: CD138 peptide

<400> SEQUENCE: 591

Glu Val Leu Gly Gly Val Ile Ala Gly Gly Leu Val Gly Leu Ile Phe
1               5                   10                  15

Ala Val Cys Leu Val Gly Phe Met Leu Tyr Arg Met
            20                  25

<210> SEQ ID NO 592
<211> LENGTH: 17
<212> TYPE: PRT
<213> ORGANISM: Artificial Sequence
<220> FEATURE:
<223> OTHER INFORMATION: CD138 peptide

<400> SEQUENCE: 592

Val Leu Gly Gly Val Ile Ala Gly Gly Leu Val Gly Leu Ile Phe Ala
1               5                   10                  15

Val

<210> SEQ ID NO 593
<211> LENGTH: 18
<212> TYPE: PRT
<213> ORGANISM: Artificial Sequence
<220> FEATURE:
<223> OTHER INFORMATION: CD138 peptide

<400> SEQUENCE: 593

Val Leu Gly Gly Val Ile Ala Gly Gly Leu Val Gly Leu Ile Phe Ala
1               5                   10                  15

Val Cys

<210> SEQ ID NO 594
<211> LENGTH: 19
<212> TYPE: PRT
<213> ORGANISM: Artificial Sequence
<220> FEATURE:
<223> OTHER INFORMATION: CD138 peptide

<400> SEQUENCE: 594

Val Leu Gly Gly Val Ile Ala Gly Gly Leu Val Gly Leu Ile Phe Ala
1               5                   10                  15

Val Cys Leu

<210> SEQ ID NO 595
<211> LENGTH: 20
<212> TYPE: PRT
<213> ORGANISM: Artificial Sequence
<220> FEATURE:
<223> OTHER INFORMATION: CD138 peptide

<400> SEQUENCE: 595
```

```
Val Leu Gly Gly Val Ile Ala Gly Gly Leu Val Gly Leu Ile Phe Ala
1               5                   10                  15

Val Cys Leu Val
            20

<210> SEQ ID NO 596
<211> LENGTH: 21
<212> TYPE: PRT
<213> ORGANISM: Artificial Sequence
<220> FEATURE:
<223> OTHER INFORMATION: CD138 peptide

<400> SEQUENCE: 596

Val Leu Gly Gly Val Ile Ala Gly Gly Leu Val Gly Leu Ile Phe Ala
1               5                   10                  15

Val Cys Leu Val Gly
            20

<210> SEQ ID NO 597
<211> LENGTH: 22
<212> TYPE: PRT
<213> ORGANISM: Artificial Sequence
<220> FEATURE:
<223> OTHER INFORMATION: CD138 peptide

<400> SEQUENCE: 597

Val Leu Gly Gly Val Ile Ala Gly Gly Leu Val Gly Leu Ile Phe Ala
1               5                   10                  15

Val Cys Leu Val Gly Phe
            20

<210> SEQ ID NO 598
<211> LENGTH: 23
<212> TYPE: PRT
<213> ORGANISM: Artificial Sequence
<220> FEATURE:
<223> OTHER INFORMATION: CD138 peptide

<400> SEQUENCE: 598

Val Leu Gly Gly Val Ile Ala Gly Gly Leu Val Gly Leu Ile Phe Ala
1               5                   10                  15

Val Cys Leu Val Gly Phe Met
            20

<210> SEQ ID NO 599
<211> LENGTH: 24
<212> TYPE: PRT
<213> ORGANISM: Artificial Sequence
<220> FEATURE:
<223> OTHER INFORMATION: CD138 peptide

<400> SEQUENCE: 599

Val Leu Gly Gly Val Ile Ala Gly Gly Leu Val Gly Leu Ile Phe Ala
1               5                   10                  15

Val Cys Leu Val Gly Phe Met Leu
            20

<210> SEQ ID NO 600
<211> LENGTH: 25
<212> TYPE: PRT
<213> ORGANISM: Artificial Sequence
<220> FEATURE:
<223> OTHER INFORMATION: CD138 peptide

<400> SEQUENCE: 600
```

-continued

```
Val Leu Gly Gly Val Ile Ala Gly Gly Leu Val Gly Leu Ile Phe Ala
1               5                   10                  15

Val Cys Leu Val Gly Phe Met Leu Tyr
            20                  25

<210> SEQ ID NO 601
<211> LENGTH: 26
<212> TYPE: PRT
<213> ORGANISM: Artificial Sequence
<220> FEATURE:
<223> OTHER INFORMATION: CD138 peptide

<400> SEQUENCE: 601

Val Leu Gly Gly Val Ile Ala Gly Gly Leu Val Gly Leu Ile Phe Ala
1               5                   10                  15

Val Cys Leu Val Gly Phe Met Leu Tyr Arg
            20                  25

<210> SEQ ID NO 602
<211> LENGTH: 27
<212> TYPE: PRT
<213> ORGANISM: Artificial Sequence
<220> FEATURE:
<223> OTHER INFORMATION: CD138 peptide

<400> SEQUENCE: 602

Val Leu Gly Gly Val Ile Ala Gly Gly Leu Val Gly Leu Ile Phe Ala
1               5                   10                  15

Val Cys Leu Val Gly Phe Met Leu Tyr Arg Met
            20                  25

<210> SEQ ID NO 603
<211> LENGTH: 16
<212> TYPE: PRT
<213> ORGANISM: Artificial Sequence
<220> FEATURE:
<223> OTHER INFORMATION: CD138 peptide

<400> SEQUENCE: 603

Leu Gly Gly Val Ile Ala Gly Gly Leu Val Gly Leu Ile Phe Ala Val
1               5                   10                  15

<210> SEQ ID NO 604
<211> LENGTH: 17
<212> TYPE: PRT
<213> ORGANISM: Artificial Sequence
<220> FEATURE:
<223> OTHER INFORMATION: CD138 peptide

<400> SEQUENCE: 604

Leu Gly Gly Val Ile Ala Gly Gly Leu Val Gly Leu Ile Phe Ala Val
1               5                   10                  15

Cys

<210> SEQ ID NO 605
<211> LENGTH: 18
<212> TYPE: PRT
<213> ORGANISM: Artificial Sequence
<220> FEATURE:
<223> OTHER INFORMATION: CD138 peptide

<400> SEQUENCE: 605

Leu Gly Gly Val Ile Ala Gly Gly Leu Val Gly Leu Ile Phe Ala Val
1               5                   10                  15
```

-continued

```
Cys Leu

<210> SEQ ID NO 606
<211> LENGTH: 19
<212> TYPE: PRT
<213> ORGANISM: Artificial Sequence
<220> FEATURE:
<223> OTHER INFORMATION: CD138 peptide

<400> SEQUENCE: 606

Leu Gly Gly Val Ile Ala Gly Gly Leu Val Gly Leu Ile Phe Ala Val
1               5                   10                  15

Cys Leu Val

<210> SEQ ID NO 607
<211> LENGTH: 20
<212> TYPE: PRT
<213> ORGANISM: Artificial Sequence
<220> FEATURE:
<223> OTHER INFORMATION: CD138 peptide

<400> SEQUENCE: 607

Leu Gly Gly Val Ile Ala Gly Gly Leu Val Gly Leu Ile Phe Ala Val
1               5                   10                  15

Cys Leu Val Gly
            20

<210> SEQ ID NO 608
<211> LENGTH: 21
<212> TYPE: PRT
<213> ORGANISM: Artificial Sequence
<220> FEATURE:
<223> OTHER INFORMATION: CD138 peptide

<400> SEQUENCE: 608

Leu Gly Gly Val Ile Ala Gly Gly Leu Val Gly Leu Ile Phe Ala Val
1               5                   10                  15

Cys Leu Val Gly Phe
            20

<210> SEQ ID NO 609
<211> LENGTH: 22
<212> TYPE: PRT
<213> ORGANISM: Artificial Sequence
<220> FEATURE:
<223> OTHER INFORMATION: CD138 peptide

<400> SEQUENCE: 609

Leu Gly Gly Val Ile Ala Gly Gly Leu Val Gly Leu Ile Phe Ala Val
1               5                   10                  15

Cys Leu Val Gly Phe Met
            20

<210> SEQ ID NO 610
<211> LENGTH: 23
<212> TYPE: PRT
<213> ORGANISM: Artificial Sequence
<220> FEATURE:
<223> OTHER INFORMATION: CD138 peptide

<400> SEQUENCE: 610

Leu Gly Gly Val Ile Ala Gly Gly Leu Val Gly Leu Ile Phe Ala Val
1               5                   10                  15
```

-continued

Cys Leu Val Gly Phe Met Leu
        20

<210> SEQ ID NO 611
<211> LENGTH: 24
<212> TYPE: PRT
<213> ORGANISM: Artificial Sequence
<220> FEATURE:
<223> OTHER INFORMATION: CD138 peptide

<400> SEQUENCE: 611

Leu Gly Gly Val Ile Ala Gly Gly Leu Val Gly Leu Ile Phe Ala Val
1               5                   10                  15

Cys Leu Val Gly Phe Met Leu Tyr
        20

<210> SEQ ID NO 612
<211> LENGTH: 25
<212> TYPE: PRT
<213> ORGANISM: Artificial Sequence
<220> FEATURE:
<223> OTHER INFORMATION: CD138 peptide

<400> SEQUENCE: 612

Leu Gly Gly Val Ile Ala Gly Gly Leu Val Gly Leu Ile Phe Ala Val
1               5                   10                  15

Cys Leu Val Gly Phe Met Leu Tyr Arg
        20                  25

<210> SEQ ID NO 613
<211> LENGTH: 26
<212> TYPE: PRT
<213> ORGANISM: Artificial Sequence
<220> FEATURE:
<223> OTHER INFORMATION: CD138 peptide

<400> SEQUENCE: 613

Leu Gly Gly Val Ile Ala Gly Gly Leu Val Gly Leu Ile Phe Ala Val
1               5                   10                  15

Cys Leu Val Gly Phe Met Leu Tyr Arg Met
        20                  25

<210> SEQ ID NO 614
<211> LENGTH: 15
<212> TYPE: PRT
<213> ORGANISM: Artificial Sequence
<220> FEATURE:
<223> OTHER INFORMATION: CD138 peptide

<400> SEQUENCE: 614

Gly Gly Val Ile Ala Gly Gly Leu Val Gly Leu Ile Phe Ala Val
1               5                   10                  15

<210> SEQ ID NO 615
<211> LENGTH: 16
<212> TYPE: PRT
<213> ORGANISM: Artificial Sequence
<220> FEATURE:
<223> OTHER INFORMATION: CD138 peptide

<400> SEQUENCE: 615

Gly Gly Val Ile Ala Gly Gly Leu Val Gly Leu Ile Phe Ala Val Cys
1               5                   10                  15

<210> SEQ ID NO 616

```
<211> LENGTH: 17
<212> TYPE: PRT
<213> ORGANISM: Artificial Sequence
<220> FEATURE:
<223> OTHER INFORMATION: CD138 peptide

<400> SEQUENCE: 616

Gly Gly Val Ile Ala Gly Gly Leu Val Gly Leu Ile Phe Ala Val Cys
1               5                   10                  15

Leu

<210> SEQ ID NO 617
<211> LENGTH: 18
<212> TYPE: PRT
<213> ORGANISM: Artificial Sequence
<220> FEATURE:
<223> OTHER INFORMATION: CD138 peptide

<400> SEQUENCE: 617

Gly Gly Val Ile Ala Gly Gly Leu Val Gly Leu Ile Phe Ala Val Cys
1               5                   10                  15

Leu Val

<210> SEQ ID NO 618
<211> LENGTH: 19
<212> TYPE: PRT
<213> ORGANISM: Artificial Sequence
<220> FEATURE:
<223> OTHER INFORMATION: CD138 peptide

<400> SEQUENCE: 618

Gly Gly Val Ile Ala Gly Gly Leu Val Gly Leu Ile Phe Ala Val Cys
1               5                   10                  15

Leu Val Gly

<210> SEQ ID NO 619
<211> LENGTH: 20
<212> TYPE: PRT
<213> ORGANISM: Artificial Sequence
<220> FEATURE:
<223> OTHER INFORMATION: CD138 peptide

<400> SEQUENCE: 619

Gly Gly Val Ile Ala Gly Gly Leu Val Gly Leu Ile Phe Ala Val Cys
1               5                   10                  15

Leu Val Gly Phe
            20

<210> SEQ ID NO 620
<211> LENGTH: 21
<212> TYPE: PRT
<213> ORGANISM: Artificial Sequence
<220> FEATURE:
<223> OTHER INFORMATION: CD138 peptide

<400> SEQUENCE: 620

Gly Gly Val Ile Ala Gly Gly Leu Val Gly Leu Ile Phe Ala Val Cys
1               5                   10                  15

Leu Val Gly Phe Met
            20

<210> SEQ ID NO 621
<211> LENGTH: 22
<212> TYPE: PRT
```

<213> ORGANISM: Artificial Sequence
<220> FEATURE:
<223> OTHER INFORMATION: CD138 peptide

<400> SEQUENCE: 621

Gly Gly Val Ile Ala Gly Gly Leu Val Gly Leu Ile Phe Ala Val Cys
1               5                   10                  15

Leu Val Gly Phe Met Leu
            20

<210> SEQ ID NO 622
<211> LENGTH: 23
<212> TYPE: PRT
<213> ORGANISM: Artificial Sequence
<220> FEATURE:
<223> OTHER INFORMATION: CD138 peptide

<400> SEQUENCE: 622

Gly Gly Val Ile Ala Gly Gly Leu Val Gly Leu Ile Phe Ala Val Cys
1               5                   10                  15

Leu Val Gly Phe Met Leu Tyr
            20

<210> SEQ ID NO 623
<211> LENGTH: 24
<212> TYPE: PRT
<213> ORGANISM: Artificial Sequence
<220> FEATURE:
<223> OTHER INFORMATION: CD138 peptide

<400> SEQUENCE: 623

Gly Gly Val Ile Ala Gly Gly Leu Val Gly Leu Ile Phe Ala Val Cys
1               5                   10                  15

Leu Val Gly Phe Met Leu Tyr Arg
            20

<210> SEQ ID NO 624
<211> LENGTH: 25
<212> TYPE: PRT
<213> ORGANISM: Artificial Sequence
<220> FEATURE:
<223> OTHER INFORMATION: CD138 peptide

<400> SEQUENCE: 624

Gly Gly Val Ile Ala Gly Gly Leu Val Gly Leu Ile Phe Ala Val Cys
1               5                   10                  15

Leu Val Gly Phe Met Leu Tyr Arg Met
            20              25

<210> SEQ ID NO 625
<211> LENGTH: 14
<212> TYPE: PRT
<213> ORGANISM: Artificial Sequence
<220> FEATURE:
<223> OTHER INFORMATION: CD138 peptide

<400> SEQUENCE: 625

Gly Val Ile Ala Gly Gly Leu Val Gly Leu Ile Phe Ala Val
1               5                   10

<210> SEQ ID NO 626
<211> LENGTH: 15
<212> TYPE: PRT
<213> ORGANISM: Artificial Sequence
<220> FEATURE:

<223> OTHER INFORMATION: CD138 peptide

<400> SEQUENCE: 626

Gly Val Ile Ala Gly Gly Leu Val Gly Leu Ile Phe Ala Val Cys
1               5                   10                  15

<210> SEQ ID NO 627
<211> LENGTH: 16
<212> TYPE: PRT
<213> ORGANISM: Artificial Sequence
<220> FEATURE:
<223> OTHER INFORMATION: CD138 peptide

<400> SEQUENCE: 627

Gly Val Ile Ala Gly Gly Leu Val Gly Leu Ile Phe Ala Val Cys Leu
1               5                   10                  15

<210> SEQ ID NO 628
<211> LENGTH: 17
<212> TYPE: PRT
<213> ORGANISM: Artificial Sequence
<220> FEATURE:
<223> OTHER INFORMATION: CD138 peptide

<400> SEQUENCE: 628

Gly Val Ile Ala Gly Gly Leu Val Gly Leu Ile Phe Ala Val Cys Leu
1               5                   10                  15

Val

<210> SEQ ID NO 629
<211> LENGTH: 18
<212> TYPE: PRT
<213> ORGANISM: Artificial Sequence
<220> FEATURE:
<223> OTHER INFORMATION: CD138 peptide

<400> SEQUENCE: 629

Gly Val Ile Ala Gly Gly Leu Val Gly Leu Ile Phe Ala Val Cys Leu
1               5                   10                  15

Val Gly

<210> SEQ ID NO 630
<211> LENGTH: 19
<212> TYPE: PRT
<213> ORGANISM: Artificial Sequence
<220> FEATURE:
<223> OTHER INFORMATION: CD138 peptide

<400> SEQUENCE: 630

Gly Val Ile Ala Gly Gly Leu Val Gly Leu Ile Phe Ala Val Cys Leu
1               5                   10                  15

Val Gly Phe

<210> SEQ ID NO 631
<211> LENGTH: 20
<212> TYPE: PRT
<213> ORGANISM: Artificial Sequence
<220> FEATURE:
<223> OTHER INFORMATION: CD138 peptide

<400> SEQUENCE: 631

Gly Val Ile Ala Gly Gly Leu Val Gly Leu Ile Phe Ala Val Cys Leu
1               5                   10                  15

Val Gly Phe Met

-continued

```
          20

<210> SEQ ID NO 632
<211> LENGTH: 21
<212> TYPE: PRT
<213> ORGANISM: Artificial Sequence
<220> FEATURE:
<223> OTHER INFORMATION: CD138 peptide

<400> SEQUENCE: 632

Gly Val Ile Ala Gly Gly Leu Val Gly Leu Ile Phe Ala Val Cys Leu
1               5                   10                  15

Val Gly Phe Met Leu
          20

<210> SEQ ID NO 633
<211> LENGTH: 22
<212> TYPE: PRT
<213> ORGANISM: Artificial Sequence
<220> FEATURE:
<223> OTHER INFORMATION: CD138 peptide

<400> SEQUENCE: 633

Gly Val Ile Ala Gly Gly Leu Val Gly Leu Ile Phe Ala Val Cys Leu
1               5                   10                  15

Val Gly Phe Met Leu Tyr
          20

<210> SEQ ID NO 634
<211> LENGTH: 23
<212> TYPE: PRT
<213> ORGANISM: Artificial Sequence
<220> FEATURE:
<223> OTHER INFORMATION: CD138 peptide

<400> SEQUENCE: 634

Gly Val Ile Ala Gly Gly Leu Val Gly Leu Ile Phe Ala Val Cys Leu
1               5                   10                  15

Val Gly Phe Met Leu Tyr Arg
          20

<210> SEQ ID NO 635
<211> LENGTH: 24
<212> TYPE: PRT
<213> ORGANISM: Artificial Sequence
<220> FEATURE:
<223> OTHER INFORMATION: CD138 peptide

<400> SEQUENCE: 635

Gly Val Ile Ala Gly Gly Leu Val Gly Leu Ile Phe Ala Val Cys Leu
1               5                   10                  15

Val Gly Phe Met Leu Tyr Arg Met
          20

<210> SEQ ID NO 636
<211> LENGTH: 13
<212> TYPE: PRT
<213> ORGANISM: Artificial Sequence
<220> FEATURE:
<223> OTHER INFORMATION: CD138 peptide

<400> SEQUENCE: 636

Val Ile Ala Gly Gly Leu Val Gly Leu Ile Phe Ala Val
1               5                   10
```

-continued

```
<210> SEQ ID NO 637
<211> LENGTH: 14
<212> TYPE: PRT
<213> ORGANISM: Artificial Sequence
<220> FEATURE:
<223> OTHER INFORMATION: CD138 peptide

<400> SEQUENCE: 637

Val Ile Ala Gly Gly Leu Val Gly Leu Ile Phe Ala Val Cys
1               5                   10

<210> SEQ ID NO 638
<211> LENGTH: 15
<212> TYPE: PRT
<213> ORGANISM: Artificial Sequence
<220> FEATURE:
<223> OTHER INFORMATION: CD138 peptide

<400> SEQUENCE: 638

Val Ile Ala Gly Gly Leu Val Gly Leu Ile Phe Ala Val Cys Leu
1               5                   10                  15

<210> SEQ ID NO 639
<211> LENGTH: 16
<212> TYPE: PRT
<213> ORGANISM: Artificial Sequence
<220> FEATURE:
<223> OTHER INFORMATION: CD138 peptide

<400> SEQUENCE: 639

Val Ile Ala Gly Gly Leu Val Gly Leu Ile Phe Ala Val Cys Leu Val
1               5                   10                  15

<210> SEQ ID NO 640
<211> LENGTH: 17
<212> TYPE: PRT
<213> ORGANISM: Artificial Sequence
<220> FEATURE:
<223> OTHER INFORMATION: CD138 peptide

<400> SEQUENCE: 640

Val Ile Ala Gly Gly Leu Val Gly Leu Ile Phe Ala Val Cys Leu Val
1               5                   10                  15

Gly

<210> SEQ ID NO 641
<211> LENGTH: 18
<212> TYPE: PRT
<213> ORGANISM: Artificial Sequence
<220> FEATURE:
<223> OTHER INFORMATION: CD138 peptide

<400> SEQUENCE: 641

Val Ile Ala Gly Gly Leu Val Gly Leu Ile Phe Ala Val Cys Leu Val
1               5                   10                  15

Gly Phe

<210> SEQ ID NO 642
<211> LENGTH: 19
<212> TYPE: PRT
<213> ORGANISM: Artificial Sequence
<220> FEATURE:
<223> OTHER INFORMATION: CD138 peptide

<400> SEQUENCE: 642
```

-continued

```
Val Ile Ala Gly Gly Leu Val Gly Leu Ile Phe Ala Val Cys Leu Val
1               5                   10                  15

Gly Phe Met

<210> SEQ ID NO 643
<211> LENGTH: 20
<212> TYPE: PRT
<213> ORGANISM: Artificial Sequence
<220> FEATURE:
<223> OTHER INFORMATION: CD138 peptide

<400> SEQUENCE: 643

Val Ile Ala Gly Gly Leu Val Gly Leu Ile Phe Ala Val Cys Leu Val
1               5                   10                  15

Gly Phe Met Leu
            20

<210> SEQ ID NO 644
<211> LENGTH: 21
<212> TYPE: PRT
<213> ORGANISM: Artificial Sequence
<220> FEATURE:
<223> OTHER INFORMATION: CD138 peptide

<400> SEQUENCE: 644

Val Ile Ala Gly Gly Leu Val Gly Leu Ile Phe Ala Val Cys Leu Val
1               5                   10                  15

Gly Phe Met Leu Tyr
            20

<210> SEQ ID NO 645
<211> LENGTH: 22
<212> TYPE: PRT
<213> ORGANISM: Artificial Sequence
<220> FEATURE:
<223> OTHER INFORMATION: CD138 peptide

<400> SEQUENCE: 645

Val Ile Ala Gly Gly Leu Val Gly Leu Ile Phe Ala Val Cys Leu Val
1               5                   10                  15

Gly Phe Met Leu Tyr Arg
            20

<210> SEQ ID NO 646
<211> LENGTH: 23
<212> TYPE: PRT
<213> ORGANISM: Artificial Sequence
<220> FEATURE:
<223> OTHER INFORMATION: CD138 peptide

<400> SEQUENCE: 646

Val Ile Ala Gly Gly Leu Val Gly Leu Ile Phe Ala Val Cys Leu Val
1               5                   10                  15

Gly Phe Met Leu Tyr Arg Met
            20

<210> SEQ ID NO 647
<211> LENGTH: 12
<212> TYPE: PRT
<213> ORGANISM: Artificial Sequence
<220> FEATURE:
<223> OTHER INFORMATION: CD138 peptide

<400> SEQUENCE: 647
```

```
Ile Ala Gly Gly Leu Val Gly Leu Ile Phe Ala Val
1               5                   10
```

<210> SEQ ID NO 648
<211> LENGTH: 13
<212> TYPE: PRT
<213> ORGANISM: Artificial Sequence
<220> FEATURE:
<223> OTHER INFORMATION: CD138 peptide

<400> SEQUENCE: 648

```
Ile Ala Gly Gly Leu Val Gly Leu Ile Phe Ala Val Cys
1               5                   10
```

<210> SEQ ID NO 649
<211> LENGTH: 14
<212> TYPE: PRT
<213> ORGANISM: Artificial Sequence
<220> FEATURE:
<223> OTHER INFORMATION: CD138 peptide

<400> SEQUENCE: 649

```
Ile Ala Gly Gly Leu Val Gly Leu Ile Phe Ala Val Cys Leu
1               5                   10
```

<210> SEQ ID NO 650
<211> LENGTH: 15
<212> TYPE: PRT
<213> ORGANISM: Artificial Sequence
<220> FEATURE:
<223> OTHER INFORMATION: CD138 peptide

<400> SEQUENCE: 650

```
Ile Ala Gly Gly Leu Val Gly Leu Ile Phe Ala Val Cys Leu Val
1               5                   10                  15
```

<210> SEQ ID NO 651
<211> LENGTH: 16
<212> TYPE: PRT
<213> ORGANISM: Artificial Sequence
<220> FEATURE:
<223> OTHER INFORMATION: CD138 peptide

<400> SEQUENCE: 651

```
Ile Ala Gly Gly Leu Val Gly Leu Ile Phe Ala Val Cys Leu Val Gly
1               5                   10                  15
```

<210> SEQ ID NO 652
<211> LENGTH: 17
<212> TYPE: PRT
<213> ORGANISM: Artificial Sequence
<220> FEATURE:
<223> OTHER INFORMATION: CD138 peptide

<400> SEQUENCE: 652

```
Ile Ala Gly Gly Leu Val Gly Leu Ile Phe Ala Val Cys Leu Val Gly
1               5                   10                  15

Phe
```

<210> SEQ ID NO 653
<211> LENGTH: 18
<212> TYPE: PRT
<213> ORGANISM: Artificial Sequence
<220> FEATURE:
<223> OTHER INFORMATION: CD138 peptide

<400> SEQUENCE: 653

-continued

```
Ile Ala Gly Gly Leu Val Gly Leu Ile Phe Ala Val Cys Leu Val Gly
1               5                   10                  15

Phe Met

<210> SEQ ID NO 654
<211> LENGTH: 19
<212> TYPE: PRT
<213> ORGANISM: Artificial Sequence
<220> FEATURE:
<223> OTHER INFORMATION: CD138 peptide

<400> SEQUENCE: 654

Ile Ala Gly Gly Leu Val Gly Leu Ile Phe Ala Val Cys Leu Val Gly
1               5                   10                  15

Phe Met Leu

<210> SEQ ID NO 655
<211> LENGTH: 20
<212> TYPE: PRT
<213> ORGANISM: Artificial Sequence
<220> FEATURE:
<223> OTHER INFORMATION: CD138 peptide

<400> SEQUENCE: 655

Ile Ala Gly Gly Leu Val Gly Leu Ile Phe Ala Val Cys Leu Val Gly
1               5                   10                  15

Phe Met Leu Tyr
            20

<210> SEQ ID NO 656
<211> LENGTH: 21
<212> TYPE: PRT
<213> ORGANISM: Artificial Sequence
<220> FEATURE:
<223> OTHER INFORMATION: CD138 peptide

<400> SEQUENCE: 656

Ile Ala Gly Gly Leu Val Gly Leu Ile Phe Ala Val Cys Leu Val Gly
1               5                   10                  15

Phe Met Leu Tyr Arg
            20

<210> SEQ ID NO 657
<211> LENGTH: 22
<212> TYPE: PRT
<213> ORGANISM: Artificial Sequence
<220> FEATURE:
<223> OTHER INFORMATION: CD138 peptide

<400> SEQUENCE: 657

Ile Ala Gly Gly Leu Val Gly Leu Ile Phe Ala Val Cys Leu Val Gly
1               5                   10                  15

Phe Met Leu Tyr Arg Met
            20

<210> SEQ ID NO 658
<211> LENGTH: 11
<212> TYPE: PRT
<213> ORGANISM: Artificial Sequence
<220> FEATURE:
<223> OTHER INFORMATION: CD138 peptide

<400> SEQUENCE: 658
```

-continued

```
Ala Gly Gly Leu Val Gly Leu Ile Phe Ala Val
1               5                   10

<210> SEQ ID NO 659
<211> LENGTH: 12
<212> TYPE: PRT
<213> ORGANISM: Artificial Sequence
<220> FEATURE:
<223> OTHER INFORMATION: CD138 peptide

<400> SEQUENCE: 659

Ala Gly Gly Leu Val Gly Leu Ile Phe Ala Val Cys
1               5                   10

<210> SEQ ID NO 660
<211> LENGTH: 13
<212> TYPE: PRT
<213> ORGANISM: Artificial Sequence
<220> FEATURE:
<223> OTHER INFORMATION: CD138 peptide

<400> SEQUENCE: 660

Ala Gly Gly Leu Val Gly Leu Ile Phe Ala Val Cys Leu
1               5                   10

<210> SEQ ID NO 661
<211> LENGTH: 14
<212> TYPE: PRT
<213> ORGANISM: Artificial Sequence
<220> FEATURE:
<223> OTHER INFORMATION: CD138 peptide

<400> SEQUENCE: 661

Ala Gly Gly Leu Val Gly Leu Ile Phe Ala Val Cys Leu Val
1               5                   10

<210> SEQ ID NO 662
<211> LENGTH: 15
<212> TYPE: PRT
<213> ORGANISM: Artificial Sequence
<220> FEATURE:
<223> OTHER INFORMATION: CD138 peptide

<400> SEQUENCE: 662

Ala Gly Gly Leu Val Gly Leu Ile Phe Ala Val Cys Leu Val Gly
1               5                   10                  15

<210> SEQ ID NO 663
<211> LENGTH: 16
<212> TYPE: PRT
<213> ORGANISM: Artificial Sequence
<220> FEATURE:
<223> OTHER INFORMATION: CD138 peptide

<400> SEQUENCE: 663

Ala Gly Gly Leu Val Gly Leu Ile Phe Ala Val Cys Leu Val Gly Phe
1               5                   10                  15

<210> SEQ ID NO 664
<211> LENGTH: 17
<212> TYPE: PRT
<213> ORGANISM: Artificial Sequence
<220> FEATURE:
<223> OTHER INFORMATION: CD138 peptide

<400> SEQUENCE: 664

Ala Gly Gly Leu Val Gly Leu Ile Phe Ala Val Cys Leu Val Gly Phe
```

-continued

```
1               5                10               15

Met

<210> SEQ ID NO 665
<211> LENGTH: 18
<212> TYPE: PRT
<213> ORGANISM: Artificial Sequence
<220> FEATURE:
<223> OTHER INFORMATION: CD138 peptide

<400> SEQUENCE: 665

Ala Gly Gly Leu Val Gly Leu Ile Phe Ala Val Cys Leu Val Gly Phe
1               5                10               15

Met Leu

<210> SEQ ID NO 666
<211> LENGTH: 19
<212> TYPE: PRT
<213> ORGANISM: Artificial Sequence
<220> FEATURE:
<223> OTHER INFORMATION: CD138 peptide

<400> SEQUENCE: 666

Ala Gly Gly Leu Val Gly Leu Ile Phe Ala Val Cys Leu Val Gly Phe
1               5                10               15

Met Leu Tyr

<210> SEQ ID NO 667
<211> LENGTH: 20
<212> TYPE: PRT
<213> ORGANISM: Artificial Sequence
<220> FEATURE:
<223> OTHER INFORMATION: CD138 peptide

<400> SEQUENCE: 667

Ala Gly Gly Leu Val Gly Leu Ile Phe Ala Val Cys Leu Val Gly Phe
1               5                10               15

Met Leu Tyr Arg
            20

<210> SEQ ID NO 668
<211> LENGTH: 21
<212> TYPE: PRT
<213> ORGANISM: Artificial Sequence
<220> FEATURE:
<223> OTHER INFORMATION: CD138 peptide

<400> SEQUENCE: 668

Ala Gly Gly Leu Val Gly Leu Ile Phe Ala Val Cys Leu Val Gly Phe
1               5                10               15

Met Leu Tyr Arg Met
            20

<210> SEQ ID NO 669
<211> LENGTH: 10
<212> TYPE: PRT
<213> ORGANISM: Artificial Sequence
<220> FEATURE:
<223> OTHER INFORMATION: CD138 peptide

<400> SEQUENCE: 669

Gly Gly Leu Val Gly Leu Ile Phe Ala Val
1               5                10
```

-continued

<210> SEQ ID NO 670
<211> LENGTH: 11
<212> TYPE: PRT
<213> ORGANISM: Artificial Sequence
<220> FEATURE:
<223> OTHER INFORMATION: CD138 peptide

<400> SEQUENCE: 670

Gly Gly Leu Val Gly Leu Ile Phe Ala Val Cys
1               5                   10

<210> SEQ ID NO 671
<211> LENGTH: 12
<212> TYPE: PRT
<213> ORGANISM: Artificial Sequence
<220> FEATURE:
<223> OTHER INFORMATION: CD138 peptide

<400> SEQUENCE: 671

Gly Gly Leu Val Gly Leu Ile Phe Ala Val Cys Leu
1               5                   10

<210> SEQ ID NO 672
<211> LENGTH: 13
<212> TYPE: PRT
<213> ORGANISM: Artificial Sequence
<220> FEATURE:
<223> OTHER INFORMATION: CD138 peptide

<400> SEQUENCE: 672

Gly Gly Leu Val Gly Leu Ile Phe Ala Val Cys Leu Val
1               5                   10

<210> SEQ ID NO 673
<211> LENGTH: 14
<212> TYPE: PRT
<213> ORGANISM: Artificial Sequence
<220> FEATURE:
<223> OTHER INFORMATION: CD138 peptide

<400> SEQUENCE: 673

Gly Gly Leu Val Gly Leu Ile Phe Ala Val Cys Leu Val Gly
1               5                   10

<210> SEQ ID NO 674
<211> LENGTH: 15
<212> TYPE: PRT
<213> ORGANISM: Artificial Sequence
<220> FEATURE:
<223> OTHER INFORMATION: CD138 peptide

<400> SEQUENCE: 674

Gly Gly Leu Val Gly Leu Ile Phe Ala Val Cys Leu Val Gly Phe
1               5                   10                  15

<210> SEQ ID NO 675
<211> LENGTH: 16
<212> TYPE: PRT
<213> ORGANISM: Artificial Sequence
<220> FEATURE:
<223> OTHER INFORMATION: CD138 peptide

<400> SEQUENCE: 675

Gly Gly Leu Val Gly Leu Ile Phe Ala Val Cys Leu Val Gly Phe Met
1               5                   10                  15

```
<210> SEQ ID NO 676
<211> LENGTH: 17
<212> TYPE: PRT
<213> ORGANISM: Artificial Sequence
<220> FEATURE:
<223> OTHER INFORMATION: CD138 peptide

<400> SEQUENCE: 676

Gly Gly Leu Val Gly Leu Ile Phe Ala Val Cys Leu Val Gly Phe Met
1               5                   10                  15

Leu

<210> SEQ ID NO 677
<211> LENGTH: 18
<212> TYPE: PRT
<213> ORGANISM: Artificial Sequence
<220> FEATURE:
<223> OTHER INFORMATION: CD138 peptide

<400> SEQUENCE: 677

Gly Gly Leu Val Gly Leu Ile Phe Ala Val Cys Leu Val Gly Phe Met
1               5                   10                  15

Leu Tyr

<210> SEQ ID NO 678
<211> LENGTH: 19
<212> TYPE: PRT
<213> ORGANISM: Artificial Sequence
<220> FEATURE:
<223> OTHER INFORMATION: CD138 peptide

<400> SEQUENCE: 678

Gly Gly Leu Val Gly Leu Ile Phe Ala Val Cys Leu Val Gly Phe Met
1               5                   10                  15

Leu Tyr Arg

<210> SEQ ID NO 679
<211> LENGTH: 20
<212> TYPE: PRT
<213> ORGANISM: Artificial Sequence
<220> FEATURE:
<223> OTHER INFORMATION: CD138 peptide

<400> SEQUENCE: 679

Gly Gly Leu Val Gly Leu Ile Phe Ala Val Cys Leu Val Gly Phe Met
1               5                   10                  15

Leu Tyr Arg Met
            20

<210> SEQ ID NO 680
<211> LENGTH: 9
<212> TYPE: PRT
<213> ORGANISM: Artificial Sequence
<220> FEATURE:
<223> OTHER INFORMATION: CD138 peptide

<400> SEQUENCE: 680

Gly Leu Val Gly Leu Ile Phe Ala Val
1               5

<210> SEQ ID NO 681
<211> LENGTH: 10
<212> TYPE: PRT
<213> ORGANISM: Artificial Sequence
<220> FEATURE:
```

<223> OTHER INFORMATION: CD138 peptide

<400> SEQUENCE: 681

Gly Leu Val Gly Leu Ile Phe Ala Val Cys
1               5                   10

<210> SEQ ID NO 682
<211> LENGTH: 11
<212> TYPE: PRT
<213> ORGANISM: Artificial Sequence
<220> FEATURE:
<223> OTHER INFORMATION: CD138 peptide

<400> SEQUENCE: 682

Gly Leu Val Gly Leu Ile Phe Ala Val Cys Leu
1               5                   10

<210> SEQ ID NO 683
<211> LENGTH: 12
<212> TYPE: PRT
<213> ORGANISM: Artificial Sequence
<220> FEATURE:
<223> OTHER INFORMATION: CD138 peptide

<400> SEQUENCE: 683

Gly Leu Val Gly Leu Ile Phe Ala Val Cys Leu Val
1               5                   10

<210> SEQ ID NO 684
<211> LENGTH: 13
<212> TYPE: PRT
<213> ORGANISM: Artificial Sequence
<220> FEATURE:
<223> OTHER INFORMATION: CD138 peptide

<400> SEQUENCE: 684

Gly Leu Val Gly Leu Ile Phe Ala Val Cys Leu Val Gly
1               5                   10

<210> SEQ ID NO 685
<211> LENGTH: 14
<212> TYPE: PRT
<213> ORGANISM: Artificial Sequence
<220> FEATURE:
<223> OTHER INFORMATION: CD138 peptide

<400> SEQUENCE: 685

Gly Leu Val Gly Leu Ile Phe Ala Val Cys Leu Val Gly Phe
1               5                   10

<210> SEQ ID NO 686
<211> LENGTH: 15
<212> TYPE: PRT
<213> ORGANISM: Artificial Sequence
<220> FEATURE:
<223> OTHER INFORMATION: CD138 peptide

<400> SEQUENCE: 686

Gly Leu Val Gly Leu Ile Phe Ala Val Cys Leu Val Gly Phe Met
1               5                   10                  15

<210> SEQ ID NO 687
<211> LENGTH: 16
<212> TYPE: PRT
<213> ORGANISM: Artificial Sequence
<220> FEATURE:
<223> OTHER INFORMATION: CD138 peptide

<400> SEQUENCE: 687

Gly Leu Val Gly Leu Ile Phe Ala Val Cys Leu Val Gly Phe Met Leu
1               5                   10                  15

<210> SEQ ID NO 688
<211> LENGTH: 17
<212> TYPE: PRT
<213> ORGANISM: Artificial Sequence
<220> FEATURE:
<223> OTHER INFORMATION: CD138 peptide

<400> SEQUENCE: 688

Gly Leu Val Gly Leu Ile Phe Ala Val Cys Leu Val Gly Phe Met Leu
1               5                   10                  15

Tyr

<210> SEQ ID NO 689
<211> LENGTH: 18
<212> TYPE: PRT
<213> ORGANISM: Artificial Sequence
<220> FEATURE:
<223> OTHER INFORMATION: CD138 peptide

<400> SEQUENCE: 689

Gly Leu Val Gly Leu Ile Phe Ala Val Cys Leu Val Gly Phe Met Leu
1               5                   10                  15

Tyr Arg

<210> SEQ ID NO 690
<211> LENGTH: 19
<212> TYPE: PRT
<213> ORGANISM: Artificial Sequence
<220> FEATURE:
<223> OTHER INFORMATION: CD138 peptide

<400> SEQUENCE: 690

Gly Leu Val Gly Leu Ile Phe Ala Val Cys Leu Val Gly Phe Met Leu
1               5                   10                  15

Tyr Arg Met

<210> SEQ ID NO 691
<211> LENGTH: 8
<212> TYPE: PRT
<213> ORGANISM: Artificial Sequence
<220> FEATURE:
<223> OTHER INFORMATION: CD138 peptide

<400> SEQUENCE: 691

Leu Val Gly Leu Ile Phe Ala Val
1               5

<210> SEQ ID NO 692
<211> LENGTH: 9
<212> TYPE: PRT
<213> ORGANISM: Artificial Sequence
<220> FEATURE:
<223> OTHER INFORMATION: CD138 peptide

<400> SEQUENCE: 692

Leu Val Gly Leu Ile Phe Ala Val Cys
1               5

<210> SEQ ID NO 693

```
<211> LENGTH: 10
<212> TYPE: PRT
<213> ORGANISM: Artificial Sequence
<220> FEATURE:
<223> OTHER INFORMATION: CD138 peptide

<400> SEQUENCE: 693

Leu Val Gly Leu Ile Phe Ala Val Cys Leu
1               5                   10

<210> SEQ ID NO 694
<211> LENGTH: 11
<212> TYPE: PRT
<213> ORGANISM: Artificial Sequence
<220> FEATURE:
<223> OTHER INFORMATION: CD138 peptide

<400> SEQUENCE: 694

Leu Val Gly Leu Ile Phe Ala Val Cys Leu Val
1               5                   10

<210> SEQ ID NO 695
<211> LENGTH: 12
<212> TYPE: PRT
<213> ORGANISM: Artificial Sequence
<220> FEATURE:
<223> OTHER INFORMATION: CD138 peptide

<400> SEQUENCE: 695

Leu Val Gly Leu Ile Phe Ala Val Cys Leu Val Gly
1               5                   10

<210> SEQ ID NO 696
<211> LENGTH: 13
<212> TYPE: PRT
<213> ORGANISM: Artificial Sequence
<220> FEATURE:
<223> OTHER INFORMATION: CD138 peptide

<400> SEQUENCE: 696

Leu Val Gly Leu Ile Phe Ala Val Cys Leu Val Gly Phe
1               5                   10

<210> SEQ ID NO 697
<211> LENGTH: 14
<212> TYPE: PRT
<213> ORGANISM: Artificial Sequence
<220> FEATURE:
<223> OTHER INFORMATION: CD138 peptide

<400> SEQUENCE: 697

Leu Val Gly Leu Ile Phe Ala Val Cys Leu Val Gly Phe Met
1               5                   10

<210> SEQ ID NO 698
<211> LENGTH: 15
<212> TYPE: PRT
<213> ORGANISM: Artificial Sequence
<220> FEATURE:
<223> OTHER INFORMATION: CD138 peptide

<400> SEQUENCE: 698

Leu Val Gly Leu Ile Phe Ala Val Cys Leu Val Gly Phe Met Leu
1               5                   10                  15

<210> SEQ ID NO 699
<211> LENGTH: 16
```

-continued

```
<212> TYPE: PRT
<213> ORGANISM: Artificial Sequence
<220> FEATURE:
<223> OTHER INFORMATION: CD138 peptide

<400> SEQUENCE: 699

Leu Val Gly Leu Ile Phe Ala Val Cys Leu Val Gly Phe Met Leu Tyr
1               5                   10                  15

<210> SEQ ID NO 700
<211> LENGTH: 17
<212> TYPE: PRT
<213> ORGANISM: Artificial Sequence
<220> FEATURE:
<223> OTHER INFORMATION: CD138 peptide

<400> SEQUENCE: 700

Leu Val Gly Leu Ile Phe Ala Val Cys Leu Val Gly Phe Met Leu Tyr
1               5                   10                  15

Arg

<210> SEQ ID NO 701
<211> LENGTH: 18
<212> TYPE: PRT
<213> ORGANISM: Artificial Sequence
<220> FEATURE:
<223> OTHER INFORMATION: CD138 peptide

<400> SEQUENCE: 701

Leu Val Gly Leu Ile Phe Ala Val Cys Leu Val Gly Phe Met Leu Tyr
1               5                   10                  15

Arg Met

<210> SEQ ID NO 702
<211> LENGTH: 7
<212> TYPE: PRT
<213> ORGANISM: Artificial Sequence
<220> FEATURE:
<223> OTHER INFORMATION: CD138 peptide

<400> SEQUENCE: 702

Val Gly Leu Ile Phe Ala Val
1               5

<210> SEQ ID NO 703
<211> LENGTH: 8
<212> TYPE: PRT
<213> ORGANISM: Artificial Sequence
<220> FEATURE:
<223> OTHER INFORMATION: CD138 peptide

<400> SEQUENCE: 703

Val Gly Leu Ile Phe Ala Val Cys
1               5

<210> SEQ ID NO 704
<211> LENGTH: 9
<212> TYPE: PRT
<213> ORGANISM: Artificial Sequence
<220> FEATURE:
<223> OTHER INFORMATION: CD138 peptide

<400> SEQUENCE: 704

Val Gly Leu Ile Phe Ala Val Cys Leu
1               5
```

```
<210> SEQ ID NO 705
<211> LENGTH: 10
<212> TYPE: PRT
<213> ORGANISM: Artificial Sequence
<220> FEATURE:
<223> OTHER INFORMATION: CD138 peptide

<400> SEQUENCE: 705

Val Gly Leu Ile Phe Ala Val Cys Leu Val
1               5                   10

<210> SEQ ID NO 706
<211> LENGTH: 11
<212> TYPE: PRT
<213> ORGANISM: Artificial Sequence
<220> FEATURE:
<223> OTHER INFORMATION: CD138 peptide

<400> SEQUENCE: 706

Val Gly Leu Ile Phe Ala Val Cys Leu Val Gly
1               5                   10

<210> SEQ ID NO 707
<211> LENGTH: 12
<212> TYPE: PRT
<213> ORGANISM: Artificial Sequence
<220> FEATURE:
<223> OTHER INFORMATION: CD138 peptide

<400> SEQUENCE: 707

Val Gly Leu Ile Phe Ala Val Cys Leu Val Gly Phe
1               5                   10

<210> SEQ ID NO 708
<211> LENGTH: 13
<212> TYPE: PRT
<213> ORGANISM: Artificial Sequence
<220> FEATURE:
<223> OTHER INFORMATION: CD138 peptide

<400> SEQUENCE: 708

Val Gly Leu Ile Phe Ala Val Cys Leu Val Gly Phe Met
1               5                   10

<210> SEQ ID NO 709
<211> LENGTH: 14
<212> TYPE: PRT
<213> ORGANISM: Artificial Sequence
<220> FEATURE:
<223> OTHER INFORMATION: CD138 peptide

<400> SEQUENCE: 709

Val Gly Leu Ile Phe Ala Val Cys Leu Val Gly Phe Met Leu
1               5                   10

<210> SEQ ID NO 710
<211> LENGTH: 15
<212> TYPE: PRT
<213> ORGANISM: Artificial Sequence
<220> FEATURE:
<223> OTHER INFORMATION: CD138 peptide

<400> SEQUENCE: 710

Val Gly Leu Ile Phe Ala Val Cys Leu Val Gly Phe Met Leu Tyr
1               5                   10                  15
```

<210> SEQ ID NO 711
<211> LENGTH: 16
<212> TYPE: PRT
<213> ORGANISM: Artificial Sequence
<220> FEATURE:
<223> OTHER INFORMATION: CD138 peptide

<400> SEQUENCE: 711

Val Gly Leu Ile Phe Ala Val Cys Leu Val Gly Phe Met Leu Tyr Arg
1               5                   10                  15

<210> SEQ ID NO 712
<211> LENGTH: 17
<212> TYPE: PRT
<213> ORGANISM: Artificial Sequence
<220> FEATURE:
<223> OTHER INFORMATION: CD138 peptide

<400> SEQUENCE: 712

Val Gly Leu Ile Phe Ala Val Cys Leu Val Gly Phe Met Leu Tyr Arg
1               5                   10                  15

Met

<210> SEQ ID NO 713
<211> LENGTH: 6
<212> TYPE: PRT
<213> ORGANISM: Artificial Sequence
<220> FEATURE:
<223> OTHER INFORMATION: CD138 peptide

<400> SEQUENCE: 713

Gly Leu Ile Phe Ala Val
1               5

<210> SEQ ID NO 714
<211> LENGTH: 7
<212> TYPE: PRT
<213> ORGANISM: Artificial Sequence
<220> FEATURE:
<223> OTHER INFORMATION: CD138 peptide

<400> SEQUENCE: 714

Gly Leu Ile Phe Ala Val Cys
1               5

<210> SEQ ID NO 715
<211> LENGTH: 8
<212> TYPE: PRT
<213> ORGANISM: Artificial Sequence
<220> FEATURE:
<223> OTHER INFORMATION: CD138 peptide

<400> SEQUENCE: 715

Gly Leu Ile Phe Ala Val Cys Leu
1               5

<210> SEQ ID NO 716
<211> LENGTH: 9
<212> TYPE: PRT
<213> ORGANISM: Artificial Sequence
<220> FEATURE:
<223> OTHER INFORMATION: CD138 peptide

<400> SEQUENCE: 716

Gly Leu Ile Phe Ala Val Cys Leu Val
1               5

```
<210> SEQ ID NO 717
<211> LENGTH: 10
<212> TYPE: PRT
<213> ORGANISM: Artificial Sequence
<220> FEATURE:
<223> OTHER INFORMATION: CD138 peptide

<400> SEQUENCE: 717

Gly Leu Ile Phe Ala Val Cys Leu Val Gly
1               5                   10

<210> SEQ ID NO 718
<211> LENGTH: 11
<212> TYPE: PRT
<213> ORGANISM: Artificial Sequence
<220> FEATURE:
<223> OTHER INFORMATION: CD138 peptide

<400> SEQUENCE: 718

Gly Leu Ile Phe Ala Val Cys Leu Val Gly Phe
1               5                   10

<210> SEQ ID NO 719
<211> LENGTH: 12
<212> TYPE: PRT
<213> ORGANISM: Artificial Sequence
<220> FEATURE:
<223> OTHER INFORMATION: CD138 peptide

<400> SEQUENCE: 719

Gly Leu Ile Phe Ala Val Cys Leu Val Gly Phe Met
1               5                   10

<210> SEQ ID NO 720
<211> LENGTH: 13
<212> TYPE: PRT
<213> ORGANISM: Artificial Sequence
<220> FEATURE:
<223> OTHER INFORMATION: CD138 peptide

<400> SEQUENCE: 720

Gly Leu Ile Phe Ala Val Cys Leu Val Gly Phe Met Leu
1               5                   10

<210> SEQ ID NO 721
<211> LENGTH: 14
<212> TYPE: PRT
<213> ORGANISM: Artificial Sequence
<220> FEATURE:
<223> OTHER INFORMATION: CD138 peptide

<400> SEQUENCE: 721

Gly Leu Ile Phe Ala Val Cys Leu Val Gly Phe Met Leu Tyr
1               5                   10

<210> SEQ ID NO 722
<211> LENGTH: 15
<212> TYPE: PRT
<213> ORGANISM: Artificial Sequence
<220> FEATURE:
<223> OTHER INFORMATION: CD138 peptide

<400> SEQUENCE: 722

Gly Leu Ile Phe Ala Val Cys Leu Val Gly Phe Met Leu Tyr Arg
1               5                   10                  15
```

<210> SEQ ID NO 723
<211> LENGTH: 16
<212> TYPE: PRT
<213> ORGANISM: Artificial Sequence
<220> FEATURE:
<223> OTHER INFORMATION: CD138 peptide

<400> SEQUENCE: 723

Gly Leu Ile Phe Ala Val Cys Leu Val Gly Phe Met Leu Tyr Arg Met
1               5                   10                  15

<210> SEQ ID NO 724
<211> LENGTH: 5
<212> TYPE: PRT
<213> ORGANISM: Artificial Sequence
<220> FEATURE:
<223> OTHER INFORMATION: CD138 peptide

<400> SEQUENCE: 724

Leu Ile Phe Ala Val
1               5

<210> SEQ ID NO 725
<211> LENGTH: 6
<212> TYPE: PRT
<213> ORGANISM: Artificial Sequence
<220> FEATURE:
<223> OTHER INFORMATION: CD138 peptide

<400> SEQUENCE: 725

Leu Ile Phe Ala Val Cys
1               5

<210> SEQ ID NO 726
<211> LENGTH: 7
<212> TYPE: PRT
<213> ORGANISM: Artificial Sequence
<220> FEATURE:
<223> OTHER INFORMATION: CD138 peptide

<400> SEQUENCE: 726

Leu Ile Phe Ala Val Cys Leu
1               5

<210> SEQ ID NO 727
<211> LENGTH: 8
<212> TYPE: PRT
<213> ORGANISM: Artificial Sequence
<220> FEATURE:
<223> OTHER INFORMATION: CD138 peptide

<400> SEQUENCE: 727

Leu Ile Phe Ala Val Cys Leu Val
1               5

<210> SEQ ID NO 728
<211> LENGTH: 9
<212> TYPE: PRT
<213> ORGANISM: Artificial Sequence
<220> FEATURE:
<223> OTHER INFORMATION: CD138 peptide

<400> SEQUENCE: 728

Leu Ile Phe Ala Val Cys Leu Val Gly
1               5

<210> SEQ ID NO 729

```
<211> LENGTH: 10
<212> TYPE: PRT
<213> ORGANISM: Artificial Sequence
<220> FEATURE:
<223> OTHER INFORMATION: CD138 peptide

<400> SEQUENCE: 729

Leu Ile Phe Ala Val Cys Leu Val Gly Phe
1               5                   10

<210> SEQ ID NO 730
<211> LENGTH: 11
<212> TYPE: PRT
<213> ORGANISM: Artificial Sequence
<220> FEATURE:
<223> OTHER INFORMATION: CD138 peptide

<400> SEQUENCE: 730

Leu Ile Phe Ala Val Cys Leu Val Gly Phe Met
1               5                   10

<210> SEQ ID NO 731
<211> LENGTH: 12
<212> TYPE: PRT
<213> ORGANISM: Artificial Sequence
<220> FEATURE:
<223> OTHER INFORMATION: CD138 peptide

<400> SEQUENCE: 731

Leu Ile Phe Ala Val Cys Leu Val Gly Phe Met Leu
1               5                   10

<210> SEQ ID NO 732
<211> LENGTH: 13
<212> TYPE: PRT
<213> ORGANISM: Artificial Sequence
<220> FEATURE:
<223> OTHER INFORMATION: CD138 peptide

<400> SEQUENCE: 732

Leu Ile Phe Ala Val Cys Leu Val Gly Phe Met Leu Tyr
1               5                   10

<210> SEQ ID NO 733
<211> LENGTH: 14
<212> TYPE: PRT
<213> ORGANISM: Artificial Sequence
<220> FEATURE:
<223> OTHER INFORMATION: CD138 peptide

<400> SEQUENCE: 733

Leu Ile Phe Ala Val Cys Leu Val Gly Phe Met Leu Tyr Arg
1               5                   10

<210> SEQ ID NO 734
<211> LENGTH: 15
<212> TYPE: PRT
<213> ORGANISM: Artificial Sequence
<220> FEATURE:
<223> OTHER INFORMATION: CD138 peptide

<400> SEQUENCE: 734

Leu Ile Phe Ala Val Cys Leu Val Gly Phe Met Leu Tyr Arg Met
1               5                   10                  15

<210> SEQ ID NO 735
<211> LENGTH: 4
```

```
<212> TYPE: PRT
<213> ORGANISM: Artificial Sequence
<220> FEATURE:
<223> OTHER INFORMATION: CD138 peptide

<400> SEQUENCE: 735

Ile Phe Ala Val
1

<210> SEQ ID NO 736
<211> LENGTH: 5
<212> TYPE: PRT
<213> ORGANISM: Artificial Sequence
<220> FEATURE:
<223> OTHER INFORMATION: CD138 peptide

<400> SEQUENCE: 736

Ile Phe Ala Val Cys
1               5

<210> SEQ ID NO 737
<211> LENGTH: 6
<212> TYPE: PRT
<213> ORGANISM: Artificial Sequence
<220> FEATURE:
<223> OTHER INFORMATION: CD138 peptide

<400> SEQUENCE: 737

Ile Phe Ala Val Cys Leu
1               5

<210> SEQ ID NO 738
<211> LENGTH: 7
<212> TYPE: PRT
<213> ORGANISM: Artificial Sequence
<220> FEATURE:
<223> OTHER INFORMATION: CD138 peptide

<400> SEQUENCE: 738

Ile Phe Ala Val Cys Leu Val
1               5

<210> SEQ ID NO 739
<211> LENGTH: 8
<212> TYPE: PRT
<213> ORGANISM: Artificial Sequence
<220> FEATURE:
<223> OTHER INFORMATION: CD138 peptide

<400> SEQUENCE: 739

Ile Phe Ala Val Cys Leu Val Gly
1               5

<210> SEQ ID NO 740
<211> LENGTH: 9
<212> TYPE: PRT
<213> ORGANISM: Artificial Sequence
<220> FEATURE:
<223> OTHER INFORMATION: CD138 peptide

<400> SEQUENCE: 740

Ile Phe Ala Val Cys Leu Val Gly Phe
1               5

<210> SEQ ID NO 741
<211> LENGTH: 10
<212> TYPE: PRT
```

```
<213> ORGANISM: Artificial Sequence
<220> FEATURE:
<223> OTHER INFORMATION: CD138 peptide

<400> SEQUENCE: 741

Ile Phe Ala Val Cys Leu Val Gly Phe Met
1               5                   10

<210> SEQ ID NO 742
<211> LENGTH: 11
<212> TYPE: PRT
<213> ORGANISM: Artificial Sequence
<220> FEATURE:
<223> OTHER INFORMATION: CD138 peptide

<400> SEQUENCE: 742

Ile Phe Ala Val Cys Leu Val Gly Phe Met Leu
1               5                   10

<210> SEQ ID NO 743
<211> LENGTH: 12
<212> TYPE: PRT
<213> ORGANISM: Artificial Sequence
<220> FEATURE:
<223> OTHER INFORMATION: CD138 peptide

<400> SEQUENCE: 743

Ile Phe Ala Val Cys Leu Val Gly Phe Met Leu Tyr
1               5                   10

<210> SEQ ID NO 744
<211> LENGTH: 13
<212> TYPE: PRT
<213> ORGANISM: Artificial Sequence
<220> FEATURE:
<223> OTHER INFORMATION: CD138 peptide

<400> SEQUENCE: 744

Ile Phe Ala Val Cys Leu Val Gly Phe Met Leu Tyr Arg
1               5                   10

<210> SEQ ID NO 745
<211> LENGTH: 14
<212> TYPE: PRT
<213> ORGANISM: Artificial Sequence
<220> FEATURE:
<223> OTHER INFORMATION: CD138 peptide

<400> SEQUENCE: 745

Ile Phe Ala Val Cys Leu Val Gly Phe Met Leu Tyr Arg Met
1               5                   10

<210> SEQ ID NO 746
<211> LENGTH: 9
<212> TYPE: PRT
<213> ORGANISM: Artificial Sequence
<220> FEATURE:
<223> OTHER INFORMATION: CD138 peptide

<400> SEQUENCE: 746

Val Cys Leu Val Gly Phe Met Leu Tyr
1               5

<210> SEQ ID NO 747
<211> LENGTH: 10
<212> TYPE: PRT
<213> ORGANISM: Artificial Sequence
```

```
<220> FEATURE:
<223> OTHER INFORMATION: CD138 peptide

<400> SEQUENCE: 747

Ala Val Cys Leu Val Gly Phe Met Leu Tyr
1               5                   10

<210> SEQ ID NO 748
<211> LENGTH: 11
<212> TYPE: PRT
<213> ORGANISM: Artificial Sequence
<220> FEATURE:
<223> OTHER INFORMATION: CD138 peptide

<400> SEQUENCE: 748

Tyr Arg Met Lys Lys Lys Asp Glu Gly Ser Tyr
1               5                   10

<210> SEQ ID NO 749
<211> LENGTH: 11
<212> TYPE: PRT
<213> ORGANISM: Artificial Sequence
<220> FEATURE:
<223> OTHER INFORMATION: CD138 peptide

<400> SEQUENCE: 749

Tyr Gln Lys Pro Thr Lys Gln Glu Glu Phe Tyr
1               5                   10

<210> SEQ ID NO 750
<211> LENGTH: 9
<212> TYPE: PRT
<213> ORGANISM: Artificial Sequence
<220> FEATURE:
<223> OTHER INFORMATION: CD138 peptide

<400> SEQUENCE: 750

Val Ile Ala Gly Gly Leu Val Gly Leu
1               5

<210> SEQ ID NO 751
<211> LENGTH: 9
<212> TYPE: PRT
<213> ORGANISM: Artificial Sequence
<220> FEATURE:
<223> OTHER INFORMATION: CD138 peptide

<400> SEQUENCE: 751

Gly Leu Val Gly Leu Ile Phe Ala Val
1               5

<210> SEQ ID NO 752
<211> LENGTH: 9
<212> TYPE: PRT
<213> ORGANISM: Artificial Sequence
<220> FEATURE:
<223> OTHER INFORMATION: CD138 peptide

<400> SEQUENCE: 752

Ala Leu Trp Leu Trp Leu Cys Ala Leu
1               5

<210> SEQ ID NO 753
<211> LENGTH: 9
<212> TYPE: PRT
<213> ORGANISM: Artificial Sequence
<220> FEATURE:
```

<223> OTHER INFORMATION: CD138 peptide

<400> SEQUENCE: 753

Ser Leu Gln Pro Ala Leu Pro Gln Ile
1               5

<210> SEQ ID NO 754
<211> LENGTH: 9
<212> TYPE: PRT
<213> ORGANISM: Artificial Sequence
<220> FEATURE:
<223> OTHER INFORMATION: CD138 peptide

<400> SEQUENCE: 754

Gly Val Ile Ala Gly Gly Leu Val Gly
1               5

<210> SEQ ID NO 755
<211> LENGTH: 9
<212> TYPE: PRT
<213> ORGANISM: Artificial Sequence
<220> FEATURE:
<223> OTHER INFORMATION: CD138 peptide

<400> SEQUENCE: 755

Thr Leu Pro Ala Gly Glu Gly Pro Lys
1               5

<210> SEQ ID NO 756
<211> LENGTH: 9
<212> TYPE: PRT
<213> ORGANISM: Artificial Sequence
<220> FEATURE:
<223> OTHER INFORMATION: CD138 peptide

<400> SEQUENCE: 756

Gln Ala Asn Gly Gly Ala Tyr Gln Lys
1               5

<210> SEQ ID NO 757
<211> LENGTH: 10
<212> TYPE: PRT
<213> ORGANISM: Artificial Sequence
<220> FEATURE:
<223> OTHER INFORMATION: CD138 peptide

<400> SEQUENCE: 757

Gly Leu Glu Ala Thr Ala Ala Ser Thr Ser
1               5                   10

<210> SEQ ID NO 758
<211> LENGTH: 10
<212> TYPE: PRT
<213> ORGANISM: Artificial Sequence
<220> FEATURE:
<223> OTHER INFORMATION: CD138 peptide

<400> SEQUENCE: 758

Ser Thr Leu Pro Ala Gly Glu Gly Pro Lys
1               5                   10

<210> SEQ ID NO 759
<211> LENGTH: 9
<212> TYPE: PRT
<213> ORGANISM: Artificial Sequence
<220> FEATURE:
<223> OTHER INFORMATION: CD138 peptide

<400> SEQUENCE: 759

Ala Ser Gln Gly Leu Leu Asp Arg Lys
1               5

<210> SEQ ID NO 760
<211> LENGTH: 9
<212> TYPE: PRT
<213> ORGANISM: Artificial Sequence
<220> FEATURE:
<223> OTHER INFORMATION: CD138 peptide

<400> SEQUENCE: 760

Gly Ser Tyr Ser Leu Glu Glu Pro Lys
1               5

<210> SEQ ID NO 761
<211> LENGTH: 10
<212> TYPE: PRT
<213> ORGANISM: Artificial Sequence
<220> FEATURE:
<223> OTHER INFORMATION: CD138 peptide

<400> SEQUENCE: 761

Ala Val Val Ala Val Glu Pro Asp Arg Arg
1               5                   10

<210> SEQ ID NO 762
<211> LENGTH: 9
<212> TYPE: PRT
<213> ORGANISM: Artificial Sequence
<220> FEATURE:
<223> OTHER INFORMATION: CD138 peptide

<400> SEQUENCE: 762

Val Leu Pro Glu Val Glu Pro Gly Leu
1               5

<210> SEQ ID NO 763
<211> LENGTH: 9
<212> TYPE: PRT
<213> ORGANISM: Artificial Sequence
<220> FEATURE:
<223> OTHER INFORMATION: CD138 peptide

<400> SEQUENCE: 763

Ile Phe Ala Val Cys Leu Val Gly Phe
1               5

<210> SEQ ID NO 764
<211> LENGTH: 10
<212> TYPE: PRT
<213> ORGANISM: Artificial Sequence
<220> FEATURE:
<223> OTHER INFORMATION: CD138 peptide

<400> SEQUENCE: 764

Asn Phe Ser Gly Ser Gly Ala Gly Ala Leu
1               5                   10

<210> SEQ ID NO 765
<211> LENGTH: 10
<212> TYPE: PRT
<213> ORGANISM: Artificial Sequence
<220> FEATURE:
<223> OTHER INFORMATION: CD138 peptide

<400> SEQUENCE: 765

Val Val Leu Pro Glu Val Glu Pro Gly Leu
1               5                   10

<210> SEQ ID NO 766
<211> LENGTH: 9
<212> TYPE: PRT
<213> ORGANISM: Artificial Sequence
<220> FEATURE:
<223> OTHER INFORMATION: CD138 peptide

<400> SEQUENCE: 766

Glu Val Glu Pro Gly Leu Thr Ala Arg
1               5

<210> SEQ ID NO 767
<211> LENGTH: 9
<212> TYPE: PRT
<213> ORGANISM: Artificial Sequence
<220> FEATURE:
<223> OTHER INFORMATION: CD138 peptide

<400> SEQUENCE: 767

Glu Val Leu Gly Gly Val Ile Ala Gly
1               5

<210> SEQ ID NO 768
<211> LENGTH: 10
<212> TYPE: PRT
<213> ORGANISM: Artificial Sequence
<220> FEATURE:
<223> OTHER INFORMATION: CD138 peptide

<400> SEQUENCE: 768

Gly Val Ile Ala Gly Gly Leu Val Gly Leu
1               5                   10

<210> SEQ ID NO 769
<211> LENGTH: 10
<212> TYPE: PRT
<213> ORGANISM: Artificial Sequence
<220> FEATURE:
<223> OTHER INFORMATION: CD138 peptide

<400> SEQUENCE: 769

Glu Val Leu Gly Gly Val Ile Ala Gly Gly
1               5                   10

<210> SEQ ID NO 770
<211> LENGTH: 9
<212> TYPE: PRT
<213> ORGANISM: Artificial Sequence
<220> FEATURE:
<223> OTHER INFORMATION: CD138 peptide

<400> SEQUENCE: 770

Glu Val Glu Pro Gly Leu Thr Ala Arg
1               5

<210> SEQ ID NO 771
<211> LENGTH: 11
<212> TYPE: PRT
<213> ORGANISM: Artificial Sequence
<220> FEATURE:
<223> OTHER INFORMATION: CD138 peptide

<400> SEQUENCE: 771

```
Leu Thr Ala Arg Glu Gln Glu Ala Thr Pro Arg
1               5                   10

<210> SEQ ID NO 772
<211> LENGTH: 9
<212> TYPE: PRT
<213> ORGANISM: Artificial Sequence
<220> FEATURE:
<223> OTHER INFORMATION: CD138 peptide

<400> SEQUENCE: 772

Gly Ala Ser Gln Gly Leu Leu Asp Arg
1               5

<210> SEQ ID NO 773
<211> LENGTH: 9
<212> TYPE: PRT
<213> ORGANISM: Artificial Sequence
<220> FEATURE:
<223> OTHER INFORMATION: CD138 peptide

<400> SEQUENCE: 773

Glu Val Leu Gly Gly Val Ile Ala Gly
1               5

<210> SEQ ID NO 774
<211> LENGTH: 10
<212> TYPE: PRT
<213> ORGANISM: Artificial Sequence
<220> FEATURE:
<223> OTHER INFORMATION: CD138 peptide

<400> SEQUENCE: 774

Thr Pro Arg Pro Arg Glu Thr Thr Gln Leu
1               5                   10

<210> SEQ ID NO 775
<211> LENGTH: 10
<212> TYPE: PRT
<213> ORGANISM: Artificial Sequence
<220> FEATURE:
<223> OTHER INFORMATION: CD138 peptide

<400> SEQUENCE: 775

Thr Pro Ala Gly Pro Ser Gln Ala Asp Leu
1               5                   10

<210> SEQ ID NO 776
<211> LENGTH: 10
<212> TYPE: PRT
<213> ORGANISM: Artificial Sequence
<220> FEATURE:
<223> OTHER INFORMATION: CD138 peptide

<400> SEQUENCE: 776

Thr Pro Ser Thr Trp Lys Asp Thr Gln Leu
1               5                   10

<210> SEQ ID NO 777
<211> LENGTH: 10
<212> TYPE: PRT
<213> ORGANISM: Artificial Sequence
<220> FEATURE:
<223> OTHER INFORMATION: CD138 peptide

<400> SEQUENCE: 777
```

-continued

```
Gly Pro Lys Glu Gly Glu Ala Val Val Leu
1               5               10

<210> SEQ ID NO 778
<211> LENGTH: 8
<212> TYPE: PRT
<213> ORGANISM: Artificial Sequence
<220> FEATURE:
<223> OTHER INFORMATION: CD138 peptide

<400> SEQUENCE: 778

Leu Leu Asp Arg Lys Glu Val Leu
1               5

<210> SEQ ID NO 779
<211> LENGTH: 9
<212> TYPE: PRT
<213> ORGANISM: Artificial Sequence
<220> FEATURE:
<223> OTHER INFORMATION: CD138 peptide

<400> SEQUENCE: 779

Gly Leu Leu Asp Arg Lys Glu Val Leu
1               5

<210> SEQ ID NO 780
<211> LENGTH: 8
<212> TYPE: PRT
<213> ORGANISM: Artificial Sequence
<220> FEATURE:
<223> OTHER INFORMATION: CD138 peptide

<400> SEQUENCE: 780

Arg Pro Arg Glu Thr Thr Gln Leu
1               5

<210> SEQ ID NO 781
<211> LENGTH: 8
<212> TYPE: PRT
<213> ORGANISM: Artificial Sequence
<220> FEATURE:
<223> OTHER INFORMATION: CD138 peptide

<400> SEQUENCE: 781

Thr Trp Lys Asp Thr Gln Leu Leu
1               5

<210> SEQ ID NO 782
<211> LENGTH: 10
<212> TYPE: PRT
<213> ORGANISM: Artificial Sequence
<220> FEATURE:
<223> OTHER INFORMATION: CD138 peptide

<400> SEQUENCE: 782

Ala Val Cys Leu Val Gly Phe Met Leu Tyr
1               5               10

<210> SEQ ID NO 783
<211> LENGTH: 10
<212> TYPE: PRT
<213> ORGANISM: Artificial Sequence
<220> FEATURE:
<223> OTHER INFORMATION: CD138 peptide

<400> SEQUENCE: 783

Tyr Gln Lys Pro Thr Lys Gln Glu Glu Phe
```

```
1               5                   10
```

<210> SEQ ID NO 784
<211> LENGTH: 9
<212> TYPE: PRT
<213> ORGANISM: Artificial Sequence
<220> FEATURE:
<223> OTHER INFORMATION: CD138 peptide

<400> SEQUENCE: 784

Ala Leu Gln Asp Ile Thr Leu Ser Gln
1               5

<210> SEQ ID NO 785
<211> LENGTH: 10
<212> TYPE: PRT
<213> ORGANISM: Artificial Sequence
<220> FEATURE:
<223> OTHER INFORMATION: CD138 peptide

<400> SEQUENCE: 785

Gly Val Ile Ala Gly Gly Leu Val Gly Leu
1               5                   10

<210> SEQ ID NO 786
<211> LENGTH: 10
<212> TYPE: PRT
<213> ORGANISM: Artificial Sequence
<220> FEATURE:
<223> OTHER INFORMATION: CD138 peptide

<400> SEQUENCE: 786

Gly Pro Lys Glu Gly Glu Ala Val Val Leu
1               5                   10

<210> SEQ ID NO 787
<211> LENGTH: 9
<212> TYPE: PRT
<213> ORGANISM: Artificial Sequence
<220> FEATURE:
<223> OTHER INFORMATION: CD138 peptide

<400> SEQUENCE: 787

Leu Pro Gln Ile Val Ala Thr Asn Leu
1               5

<210> SEQ ID NO 788
<211> LENGTH: 9
<212> TYPE: PRT
<213> ORGANISM: Artificial Sequence
<220> FEATURE:
<223> OTHER INFORMATION: CD138 peptide

<400> SEQUENCE: 788

Lys Pro Thr Lys Gln Glu Glu Phe Tyr
1               5

<210> SEQ ID NO 789
<211> LENGTH: 10
<212> TYPE: PRT
<213> ORGANISM: Artificial Sequence
<220> FEATURE:
<223> OTHER INFORMATION: CD138 peptide

<400> SEQUENCE: 789

Thr Pro Ser Thr Trp Lys Asp Thr Gln Leu
1               5                   10

```
<210> SEQ ID NO 790
<211> LENGTH: 9
<212> TYPE: PRT
<213> ORGANISM: Artificial Sequence
<220> FEATURE:
<223> OTHER INFORMATION: CD138 peptide

<400> SEQUENCE: 790

Gly Ser Gly Glu Gln Asp Phe Thr Phe
1               5

<210> SEQ ID NO 791
<211> LENGTH: 9
<212> TYPE: PRT
<213> ORGANISM: Artificial Sequence
<220> FEATURE:
<223> OTHER INFORMATION: CD138 peptide

<400> SEQUENCE: 791

Leu Ser Gln Gln Thr Pro Ser Thr Trp
1               5

<210> SEQ ID NO 792
<211> LENGTH: 9
<212> TYPE: PRT
<213> ORGANISM: Artificial Sequence
<220> FEATURE:
<223> OTHER INFORMATION: CD138 peptide

<400> SEQUENCE: 792

Ala Thr Ser His Pro His Arg Asp Met
1               5

<210> SEQ ID NO 793
<211> LENGTH: 10
<212> TYPE: PRT
<213> ORGANISM: Artificial Sequence
<220> FEATURE:
<223> OTHER INFORMATION: CD138 peptide

<400> SEQUENCE: 793

Pro Ala Thr Ser His Pro His Arg Asp Met
1               5                   10

<210> SEQ ID NO 794
<211> LENGTH: 15
<212> TYPE: PRT
<213> ORGANISM: Artificial Sequence
<220> FEATURE:
<223> OTHER INFORMATION: CD138 peptide

<400> SEQUENCE: 794

Ala Ala Leu Trp Leu Trp Leu Cys Ala Leu Ala Leu Ser Leu Gln
1               5                   10                  15

<210> SEQ ID NO 795
<211> LENGTH: 15
<212> TYPE: PRT
<213> ORGANISM: Artificial Sequence
<220> FEATURE:
<223> OTHER INFORMATION: CD138 peptide

<400> SEQUENCE: 795

Lys Glu Val Leu Gly Gly Val Ile Ala Gly Gly Leu Val Gly Leu
1               5                   10                  15
```

<210> SEQ ID NO 796
<211> LENGTH: 15
<212> TYPE: PRT
<213> ORGANISM: Artificial Sequence
<220> FEATURE:
<223> OTHER INFORMATION: CD138 peptide

<400> SEQUENCE: 796

Gln Pro Ala Leu Pro Gln Ile Val Ala Thr Asn Leu Pro Pro Glu
1               5                   10                  15

<210> SEQ ID NO 797
<211> LENGTH: 15
<212> TYPE: PRT
<213> ORGANISM: Artificial Sequence
<220> FEATURE:
<223> OTHER INFORMATION: CD138 peptide

<400> SEQUENCE: 797

Gly Gly Leu Val Gly Leu Ile Phe Ala Val Cys Leu Val Gly Phe
1               5                   10                  15

<210> SEQ ID NO 798
<211> LENGTH: 15
<212> TYPE: PRT
<213> ORGANISM: Artificial Sequence
<220> FEATURE:
<223> OTHER INFORMATION: CD138 peptide

<400> SEQUENCE: 798

Val Val Ala Val Glu Pro Asp Arg Arg Asn Gln Ser Pro Val Asp
1               5                   10                  15

<210> SEQ ID NO 799
<211> LENGTH: 15
<212> TYPE: PRT
<213> ORGANISM: Artificial Sequence
<220> FEATURE:
<223> OTHER INFORMATION: CD138 peptide

<400> SEQUENCE: 799

Leu Cys Ala Leu Ala Leu Ser Leu Gln Pro Ala Leu Pro Gln Ile
1               5                   10                  15

<210> SEQ ID NO 800
<211> LENGTH: 15
<212> TYPE: PRT
<213> ORGANISM: Artificial Sequence
<220> FEATURE:
<223> OTHER INFORMATION: CD138 peptide

<400> SEQUENCE: 800

Glu Ala Val Val Leu Pro Glu Val Glu Pro Gly Leu Thr Ala Arg
1               5                   10                  15

<210> SEQ ID NO 801
<211> LENGTH: 15
<212> TYPE: PRT
<213> ORGANISM: Artificial Sequence
<220> FEATURE:
<223> OTHER INFORMATION: CD138 peptide

<400> SEQUENCE: 801

Ala Ser Gln Gly Leu Leu Asp Arg Lys Glu Val Leu Gly Gly Val
1               5                   10                  15

<210> SEQ ID NO 802
<211> LENGTH: 15
<212> TYPE: PRT
<213> ORGANISM: Artificial Sequence
<220> FEATURE:
<223> OTHER INFORMATION: CD138 peptide

<400> SEQUENCE: 802

Asp Phe Thr Phe Glu Thr Ser Gly Glu Asn Thr Ala Val Val Ala
1               5                   10                  15

<210> SEQ ID NO 803
<211> LENGTH: 15
<212> TYPE: PRT
<213> ORGANISM: Artificial Sequence
<220> FEATURE:
<223> OTHER INFORMATION: CD138 peptide

<400> SEQUENCE: 803

Leu Trp Leu Trp Leu Cys Ala Leu Ala Leu Ser Leu Gln Pro Ala
1               5                   10                  15

<210> SEQ ID NO 804
<211> LENGTH: 15
<212> TYPE: PRT
<213> ORGANISM: Artificial Sequence
<220> FEATURE:
<223> OTHER INFORMATION: CD138 peptide

<400> SEQUENCE: 804

Ser Asp Asn Phe Ser Gly Ser Gly Ala Gly Ala Leu Gln Asp Ile
1               5                   10                  15

<210> SEQ ID NO 805
<211> LENGTH: 15
<212> TYPE: PRT
<213> ORGANISM: Artificial Sequence
<220> FEATURE:
<223> OTHER INFORMATION: CD138 peptide

<400> SEQUENCE: 805

Leu Cys Ala Leu Ala Leu Ser Leu Gln Pro Ala Leu Pro Gln Ile
1               5                   10                  15

<210> SEQ ID NO 806
<211> LENGTH: 15
<212> TYPE: PRT
<213> ORGANISM: Artificial Sequence
<220> FEATURE:
<223> OTHER INFORMATION: CD138 peptide

<400> SEQUENCE: 806

Phe Met Leu Tyr Arg Met Lys Lys Lys Asp Glu Gly Ser Tyr Ser
1               5                   10                  15

<210> SEQ ID NO 807
<211> LENGTH: 15
<212> TYPE: PRT
<213> ORGANISM: Artificial Sequence
<220> FEATURE:
<223> OTHER INFORMATION: CD138 peptide

<400> SEQUENCE: 807

His Arg Asp Met Gln Pro Gly His His Glu Thr Ser Thr Pro Ala
1               5                   10                  15

<210> SEQ ID NO 808

US 12,590,292 B2

359                  360

-continued

```
<211> LENGTH: 15
<212> TYPE: PRT
<213> ORGANISM: Artificial Sequence
<220> FEATURE:
<223> OTHER INFORMATION: CD138 peptide

<400> SEQUENCE: 808

Val Val Ala Val Glu Pro Asp Arg Arg Asn Gln Ser Pro Val Asp
1               5                   10                  15

<210> SEQ ID NO 809
<211> LENGTH: 15
<212> TYPE: PRT
<213> ORGANISM: Artificial Sequence
<220> FEATURE:
<223> OTHER INFORMATION: CD138 peptide

<400> SEQUENCE: 809

Gly Phe Met Leu Tyr Arg Met Lys Lys Lys Asp Glu Gly Ser Tyr
1               5                   10                  15

<210> SEQ ID NO 810
<211> LENGTH: 15
<212> TYPE: PRT
<213> ORGANISM: Artificial Sequence
<220> FEATURE:
<223> OTHER INFORMATION: CD138 peptide

<400> SEQUENCE: 810

Arg Ala Ala Leu Trp Leu Trp Leu Cys Ala Leu Ala Leu Ser Leu
1               5                   10                  15

<210> SEQ ID NO 811
<211> LENGTH: 15
<212> TYPE: PRT
<213> ORGANISM: Artificial Sequence
<220> FEATURE:
<223> OTHER INFORMATION: CD138 peptide

<400> SEQUENCE: 811

Ala Leu Ala Leu Ser Leu Gln Pro Ala Leu Pro Gln Ile Val Ala
1               5                   10                  15

<210> SEQ ID NO 812
<211> LENGTH: 15
<212> TYPE: PRT
<213> ORGANISM: Artificial Sequence
<220> FEATURE:
<223> OTHER INFORMATION: CD138 peptide

<400> SEQUENCE: 812

Gly Gly Leu Val Gly Leu Ile Phe Ala Val Cys Leu Val Gly Phe
1               5                   10                  15

<210> SEQ ID NO 813
<211> LENGTH: 15
<212> TYPE: PRT
<213> ORGANISM: Artificial Sequence
<220> FEATURE:
<223> OTHER INFORMATION: CD138 peptide

<400> SEQUENCE: 813

Ala Val Cys Leu Val Gly Phe Met Leu Tyr Arg Met Lys Lys Lys
1               5                   10                  15

<210> SEQ ID NO 814
<211> LENGTH: 509
```

<212> TYPE: PRT
<213> ORGANISM: Homo sapiens

<400> SEQUENCE: 814

```
Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
        290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
        370                 375                 380

Phe Asp Glu Cys Gly Ile Thr Asp Asp Gln Leu Leu Ala Leu Leu Pro
385                 390                 395                 400
```

-continued

```
Ser Leu Ser His Cys Ser Gln Leu Thr Thr Leu Ser Phe Tyr Gly Asn
            405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
            485                 490                 495

Asp Pro Glu Pro Ile Leu Cys Pro Cys Phe Met Pro Asn
            500                 505
```

```
<210> SEQ ID NO 815
<211> LENGTH: 10
<212> TYPE: PRT
<213> ORGANISM: Artificial Sequence
<220> FEATURE:
<223> OTHER INFORMATION: PRAME peptide

<400> SEQUENCE: 815

Gly Thr Leu His Leu Glu Arg Leu Ala Tyr
1               5                   10

<210> SEQ ID NO 816
<211> LENGTH: 9
<212> TYPE: PRT
<213> ORGANISM: Artificial Sequence
<220> FEATURE:
<223> OTHER INFORMATION: PRAME peptide

<400> SEQUENCE: 816

Pro Thr Leu Ala Lys Phe Ser Pro Tyr
1               5

<210> SEQ ID NO 817
<211> LENGTH: 10
<212> TYPE: PRT
<213> ORGANISM: Artificial Sequence
<220> FEATURE:
<223> OTHER INFORMATION: PRAME peptide

<400> SEQUENCE: 817

Cys Ser Gln Leu Thr Thr Leu Ser Phe Tyr
1               5                   10

<210> SEQ ID NO 818
<211> LENGTH: 9
<212> TYPE: PRT
<213> ORGANISM: Artificial Sequence
<220> FEATURE:
<223> OTHER INFORMATION: PRAME peptide

<400> SEQUENCE: 818

Leu Ser Asn Leu Thr His Val Leu Tyr
1               5

<210> SEQ ID NO 819
<211> LENGTH: 10
<212> TYPE: PRT
<213> ORGANISM: Artificial Sequence
```

-continued

```
<220> FEATURE:
<223> OTHER INFORMATION: PRAME peptide

<400> SEQUENCE: 819

Ala Leu Leu Glu Arg Ala Ser Ala Thr Leu
1               5                   10

<210> SEQ ID NO 820
<211> LENGTH: 9
<212> TYPE: PRT
<213> ORGANISM: Artificial Sequence
<220> FEATURE:
<223> OTHER INFORMATION: PRAME peptide

<400> SEQUENCE: 820

Gln Leu Leu Ala Leu Leu Pro Ser Leu
1               5

<210> SEQ ID NO 821
<211> LENGTH: 9
<212> TYPE: PRT
<213> ORGANISM: Artificial Sequence
<220> FEATURE:
<223> OTHER INFORMATION: PRAME peptide

<400> SEQUENCE: 821

Ser Leu Leu Gln His Leu Ile Gly Leu
1               5

<210> SEQ ID NO 822
<211> LENGTH: 9
<212> TYPE: PRT
<213> ORGANISM: Artificial Sequence
<220> FEATURE:
<223> OTHER INFORMATION: PRAME peptide

<400> SEQUENCE: 822

Arg Leu Arg Glu Leu Leu Cys Glu Leu
1               5

<210> SEQ ID NO 823
<211> LENGTH: 9
<212> TYPE: PRT
<213> ORGANISM: Artificial Sequence
<220> FEATURE:
<223> OTHER INFORMATION: PRAME peptide

<400> SEQUENCE: 823

Cys Leu Pro Leu Gly Val Leu Met Lys
1               5

<210> SEQ ID NO 824
<211> LENGTH: 9
<212> TYPE: PRT
<213> ORGANISM: Artificial Sequence
<220> FEATURE:
<223> OTHER INFORMATION: PRAME peptide

<400> SEQUENCE: 824

Glu Leu Ala Gly Gln Ser Leu Leu Lys
1               5

<210> SEQ ID NO 825
<211> LENGTH: 9
<212> TYPE: PRT
<213> ORGANISM: Artificial Sequence
<220> FEATURE:
```

-continued

```
<223> OTHER INFORMATION: PRAME peptide

<400> SEQUENCE: 825

Lys Leu Gln Val Leu Asp Leu Arg Lys
1               5

<210> SEQ ID NO 826
<211> LENGTH: 9
<212> TYPE: PRT
<213> ORGANISM: Artificial Sequence
<220> FEATURE:
<223> OTHER INFORMATION: PRAME peptide

<400> SEQUENCE: 826

Arg Leu Ser Glu Gly Asp Val Met His
1               5

<210> SEQ ID NO 827
<211> LENGTH: 10
<212> TYPE: PRT
<213> ORGANISM: Artificial Sequence
<220> FEATURE:
<223> OTHER INFORMATION: PRAME peptide

<400> SEQUENCE: 827

Lys Val Lys Arg Lys Lys Asn Val Leu Arg
1               5                   10

<210> SEQ ID NO 828
<211> LENGTH: 10
<212> TYPE: PRT
<213> ORGANISM: Artificial Sequence
<220> FEATURE:
<223> OTHER INFORMATION: PRAME peptide

<400> SEQUENCE: 828

Pro Met Gln Asp Ile Lys Met Ile Leu Lys
1               5                   10

<210> SEQ ID NO 829
<211> LENGTH: 10
<212> TYPE: PRT
<213> ORGANISM: Artificial Sequence
<220> FEATURE:
<223> OTHER INFORMATION: PRAME peptide

<400> SEQUENCE: 829

Cys Thr Trp Lys Leu Pro Thr Leu Ala Lys
1               5                   10

<210> SEQ ID NO 830
<211> LENGTH: 10
<212> TYPE: PRT
<213> ORGANISM: Artificial Sequence
<220> FEATURE:
<223> OTHER INFORMATION: PRAME peptide

<400> SEQUENCE: 830

Ala Ile Ala Ala Leu Glu Leu Leu Pro Arg
1               5                   10

<210> SEQ ID NO 831
<211> LENGTH: 9
<212> TYPE: PRT
<213> ORGANISM: Artificial Sequence
<220> FEATURE:
<223> OTHER INFORMATION: PRAME peptide
```

-continued

<400> SEQUENCE: 831

Ser Tyr Glu Asp Ile His Gly Thr Leu
1               5

<210> SEQ ID NO 832
<211> LENGTH: 9
<212> TYPE: PRT
<213> ORGANISM: Artificial Sequence
<220> FEATURE:
<223> OTHER INFORMATION: PRAME peptide

<400> SEQUENCE: 832

Pro Tyr Leu Gly Gln Met Ile Asn Leu
1               5

<210> SEQ ID NO 833
<211> LENGTH: 9
<212> TYPE: PRT
<213> ORGANISM: Artificial Sequence
<220> FEATURE:
<223> OTHER INFORMATION: PRAME peptide

<400> SEQUENCE: 833

Leu Tyr Val Asp Ser Leu Phe Phe Leu
1               5

<210> SEQ ID NO 834
<211> LENGTH: 10
<212> TYPE: PRT
<213> ORGANISM: Artificial Sequence
<220> FEATURE:
<223> OTHER INFORMATION: PRAME peptide

<400> SEQUENCE: 834

Gln Tyr Ile Ala Gln Phe Thr Ser Gln Phe
1               5                   10

<210> SEQ ID NO 835
<211> LENGTH: 10
<212> TYPE: PRT
<213> ORGANISM: Artificial Sequence
<220> FEATURE:
<223> OTHER INFORMATION: PRAME peptide

<400> SEQUENCE: 835

Glu Thr Phe Lys Ala Val Leu Asp Gly Leu
1               5                   10

<210> SEQ ID NO 836
<211> LENGTH: 10
<212> TYPE: PRT
<213> ORGANISM: Artificial Sequence
<220> FEATURE:
<223> OTHER INFORMATION: PRAME peptide

<400> SEQUENCE: 836

Asp Val Ser Pro Glu Pro Leu Gln Ala Leu
1               5                   10

<210> SEQ ID NO 837
<211> LENGTH: 9
<212> TYPE: PRT
<213> ORGANISM: Artificial Sequence
<220> FEATURE:
<223> OTHER INFORMATION: PRAME peptide -continued

```
<400> SEQUENCE: 837

Glu Val Arg Pro Arg Arg Trp Lys Leu
1               5

<210> SEQ ID NO 838
<211> LENGTH: 9
<212> TYPE: PRT
<213> ORGANISM: Artificial Sequence
<220> FEATURE:
<223> OTHER INFORMATION: PRAME peptide

<400> SEQUENCE: 838

Glu Thr Phe Lys Ala Val Leu Asp Gly
1               5

<210> SEQ ID NO 839
<211> LENGTH: 9
<212> TYPE: PRT
<213> ORGANISM: Artificial Sequence
<220> FEATURE:
<223> OTHER INFORMATION: PRAME peptide

<400> SEQUENCE: 839

Glu Ala Ala Gln Pro Met Thr Lys Lys
1               5

<210> SEQ ID NO 840
<211> LENGTH: 9
<212> TYPE: PRT
<213> ORGANISM: Artificial Sequence
<220> FEATURE:
<223> OTHER INFORMATION: PRAME peptide

<400> SEQUENCE: 840

Glu Val Leu Val Asp Leu Phe Leu Lys
1               5

<210> SEQ ID NO 841
<211> LENGTH: 9
<212> TYPE: PRT
<213> ORGANISM: Artificial Sequence
<220> FEATURE:
<223> OTHER INFORMATION: PRAME peptide

<400> SEQUENCE: 841

Glu Leu Phe Ser Tyr Leu Ile Glu Lys
1               5

<210> SEQ ID NO 842
<211> LENGTH: 9
<212> TYPE: PRT
<213> ORGANISM: Artificial Sequence
<220> FEATURE:
<223> OTHER INFORMATION: PRAME peptide

<400> SEQUENCE: 842

Glu Thr Leu Ser Ile Thr Asn Cys Arg
1               5

<210> SEQ ID NO 843
<211> LENGTH: 9
<212> TYPE: PRT
<213> ORGANISM: Artificial Sequence
<220> FEATURE:
<223> OTHER INFORMATION: PRAME peptide

<400> SEQUENCE: 843
```

Leu Pro Arg Glu Leu Phe Pro Pro Leu
1               5

<210> SEQ ID NO 844
<211> LENGTH: 9
<212> TYPE: PRT
<213> ORGANISM: Artificial Sequence
<220> FEATURE:
<223> OTHER INFORMATION: PRAME peptide

<400> SEQUENCE: 844

Gln Pro Phe Ile Pro Val Glu Val Leu
1               5

<210> SEQ ID NO 845
<211> LENGTH: 10
<212> TYPE: PRT
<213> ORGANISM: Artificial Sequence
<220> FEATURE:
<223> OTHER INFORMATION: PRAME peptide

<400> SEQUENCE: 845

Arg Pro Arg Arg Trp Lys Leu Gln Val Leu
1               5                   10

<210> SEQ ID NO 846
<211> LENGTH: 10
<212> TYPE: PRT
<213> ORGANISM: Artificial Sequence
<220> FEATURE:
<223> OTHER INFORMATION: PRAME peptide

<400> SEQUENCE: 846

Ser Pro Ser Val Ser Gln Leu Ser Val Leu
1               5                   10

<210> SEQ ID NO 847
<211> LENGTH: 9
<212> TYPE: PRT
<213> ORGANISM: Artificial Sequence
<220> FEATURE:
<223> OTHER INFORMATION: PRAME peptide

<400> SEQUENCE: 847

Thr Lys Lys Arg Lys Val Asp Gly Leu
1               5

<210> SEQ ID NO 848
<211> LENGTH: 9
<212> TYPE: PRT
<213> ORGANISM: Artificial Sequence
<220> FEATURE:
<223> OTHER INFORMATION: PRAME peptide

<400> SEQUENCE: 848

Phe Leu Arg Gly Arg Leu Asp Gln Leu
1               5

<210> SEQ ID NO 849
<211> LENGTH: 9
<212> TYPE: PRT
<213> ORGANISM: Artificial Sequence
<220> FEATURE:
<223> OTHER INFORMATION: PRAME peptide

<400> SEQUENCE: 849

-continued

```
Lys Val Lys Arg Lys Lys Asn Val Leu
1               5

<210> SEQ ID NO 850
<211> LENGTH: 8
<212> TYPE: PRT
<213> ORGANISM: Artificial Sequence
<220> FEATURE:
<223> OTHER INFORMATION: PRAME peptide

<400> SEQUENCE: 850

His Ala Arg Leu Arg Glu Leu Leu
1               5

<210> SEQ ID NO 851
<211> LENGTH: 10
<212> TYPE: PRT
<213> ORGANISM: Artificial Sequence
<220> FEATURE:
<223> OTHER INFORMATION: PRAME peptide

<400> SEQUENCE: 851

Val Leu Tyr Pro Val Pro Leu Glu Ser Tyr
1               5                   10

<210> SEQ ID NO 852
<211> LENGTH: 10
<212> TYPE: PRT
<213> ORGANISM: Artificial Sequence
<220> FEATURE:
<223> OTHER INFORMATION: PRAME peptide

<400> SEQUENCE: 852

Arg Leu Trp Gly Ser Ile Gln Ser Arg Tyr
1               5                   10

<210> SEQ ID NO 853
<211> LENGTH: 10
<212> TYPE: PRT
<213> ORGANISM: Artificial Sequence
<220> FEATURE:
<223> OTHER INFORMATION: PRAME peptide

<400> SEQUENCE: 853

Gly Leu Ser Asn Leu Thr His Val Leu Tyr
1               5                   10

<210> SEQ ID NO 854
<211> LENGTH: 10
<212> TYPE: PRT
<213> ORGANISM: Artificial Sequence
<220> FEATURE:
<223> OTHER INFORMATION: PRAME peptide

<400> SEQUENCE: 854

Arg Leu Cys Cys Lys Lys Leu Lys Ile Phe
1               5                   10

<210> SEQ ID NO 855
<211> LENGTH: 9
<212> TYPE: PRT
<213> ORGANISM: Artificial Sequence
<220> FEATURE:
<223> OTHER INFORMATION: PRAME peptide

<400> SEQUENCE: 855

Ile Pro Val Glu Val Leu Val Asp Leu
```

```
1               5

<210> SEQ ID NO 856
<211> LENGTH: 9
<212> TYPE: PRT
<213> ORGANISM: Artificial Sequence
<220> FEATURE:
<223> OTHER INFORMATION: PRAME peptide

<400> SEQUENCE: 856

Leu Pro Arg Glu Leu Phe Pro Pro Leu
1               5

<210> SEQ ID NO 857
<211> LENGTH: 9
<212> TYPE: PRT
<213> ORGANISM: Artificial Sequence
<220> FEATURE:
<223> OTHER INFORMATION: PRAME peptide

<400> SEQUENCE: 857

Ser Pro Glu Pro Leu Gln Ala Leu Leu
1               5

<210> SEQ ID NO 858
<211> LENGTH: 10
<212> TYPE: PRT
<213> ORGANISM: Artificial Sequence
<220> FEATURE:
<223> OTHER INFORMATION: PRAME peptide

<400> SEQUENCE: 858

Arg Pro Arg Arg Trp Lys Leu Gln Val Leu
1               5                   10

<210> SEQ ID NO 859
<211> LENGTH: 9
<212> TYPE: PRT
<213> ORGANISM: Artificial Sequence
<220> FEATURE:
<223> OTHER INFORMATION: PRAME peptide

<400> SEQUENCE: 859

Lys Ala Met Val Gln Ala Trp Pro Phe
1               5

<210> SEQ ID NO 860
<211> LENGTH: 10
<212> TYPE: PRT
<213> ORGANISM: Artificial Sequence
<220> FEATURE:
<223> OTHER INFORMATION: PRAME peptide

<400> SEQUENCE: 860

Met Ser Val Trp Thr Ser Pro Arg Arg Leu
1               5                   10

<210> SEQ ID NO 861
<211> LENGTH: 10
<212> TYPE: PRT
<213> ORGANISM: Artificial Sequence
<220> FEATURE:
<223> OTHER INFORMATION: PRAME peptide

<400> SEQUENCE: 861

Ala Ala Leu Glu Leu Leu Pro Arg Glu Leu
1               5                   10
```

<210> SEQ ID NO 862
<211> LENGTH: 10
<212> TYPE: PRT
<213> ORGANISM: Artificial Sequence
<220> FEATURE:
<223> OTHER INFORMATION: PRAME peptide

<400> SEQUENCE: 862

Lys Ala Val Leu Asp Gly Leu Asp Val Leu
1               5                   10

<210> SEQ ID NO 863
<211> LENGTH: 15
<212> TYPE: PRT
<213> ORGANISM: Artificial Sequence
<220> FEATURE:
<223> OTHER INFORMATION: PRAME peptide

<400> SEQUENCE: 863

Pro Arg Arg Leu Val Glu Leu Ala Gly Gln Ser Leu Leu Lys Asp
1               5                   10                  15

<210> SEQ ID NO 864
<211> LENGTH: 15
<212> TYPE: PRT
<213> ORGANISM: Artificial Sequence
<220> FEATURE:
<223> OTHER INFORMATION: PRAME peptide

<400> SEQUENCE: 864

Leu Asp Gly Leu Asp Val Leu Leu Ala Gln Glu Val Arg Pro Arg
1               5                   10                  15

<210> SEQ ID NO 865
<211> LENGTH: 15
<212> TYPE: PRT
<213> ORGANISM: Artificial Sequence
<220> FEATURE:
<223> OTHER INFORMATION: PRAME peptide

<400> SEQUENCE: 865

Phe Leu Ser Leu Gln Cys Leu Gln Ala Leu Tyr Val Asp Ser Leu
1               5                   10                  15

<210> SEQ ID NO 866
<211> LENGTH: 15
<212> TYPE: PRT
<213> ORGANISM: Artificial Sequence
<220> FEATURE:
<223> OTHER INFORMATION: PRAME peptide

<400> SEQUENCE: 866

Arg His Val Met Asn Pro Leu Glu Thr Leu Ser Ile Thr Asn Cys
1               5                   10                  15

<210> SEQ ID NO 867
<211> LENGTH: 15
<212> TYPE: PRT
<213> ORGANISM: Artificial Sequence
<220> FEATURE:
<223> OTHER INFORMATION: PRAME peptide

<400> SEQUENCE: 867

Glu Cys Gly Ile Thr Asp Asp Gln Leu Leu Ala Leu Leu Pro Ser
1               5                   10                  15

-continued

```
<210> SEQ ID NO 868
<211> LENGTH: 15
<212> TYPE: PRT
<213> ORGANISM: Artificial Sequence
<220> FEATURE:
<223> OTHER INFORMATION: PRAME peptide

<400> SEQUENCE: 868

Leu Lys Met Val Gln Leu Asp Ser Ile Glu Asp Leu Glu Val Thr
1               5                   10                  15

<210> SEQ ID NO 869
<211> LENGTH: 15
<212> TYPE: PRT
<213> ORGANISM: Artificial Sequence
<220> FEATURE:
<223> OTHER INFORMATION: PRAME peptide

<400> SEQUENCE: 869

Leu Gln Ala Leu Tyr Val Asp Ser Leu Phe Phe Leu Arg Gly Arg
1               5                   10                  15

<210> SEQ ID NO 870
<211> LENGTH: 15
<212> TYPE: PRT
<213> ORGANISM: Artificial Sequence
<220> FEATURE:
<223> OTHER INFORMATION: PRAME peptide

<400> SEQUENCE: 870

Arg Arg Leu Val Glu Leu Ala Gly Gln Ser Leu Leu Lys Asp Glu
1               5                   10                  15

<210> SEQ ID NO 871
<211> LENGTH: 15
<212> TYPE: PRT
<213> ORGANISM: Artificial Sequence
<220> FEATURE:
<223> OTHER INFORMATION: PRAME peptide

<400> SEQUENCE: 871

Arg Arg Leu Trp Gly Ser Ile Gln Ser Arg Tyr Ile Ser Met Ser
1               5                   10                  15

<210> SEQ ID NO 872
<211> LENGTH: 15
<212> TYPE: PRT
<213> ORGANISM: Artificial Sequence
<220> FEATURE:
<223> OTHER INFORMATION: PRAME peptide

<400> SEQUENCE: 872

Ile Glu Asp Leu Glu Val Thr Cys Thr Trp Lys Leu Pro Thr Leu
1               5                   10                  15

<210> SEQ ID NO 873
<211> LENGTH: 15
<212> TYPE: PRT
<213> ORGANISM: Artificial Sequence
<220> FEATURE:
<223> OTHER INFORMATION: PRAME peptide

<400> SEQUENCE: 873

Gly Asp Val Met His Leu Ser Gln Ser Pro Ser Val Ser Gln Leu
1               5                   10                  15
```

-continued

<210> SEQ ID NO 874
<211> LENGTH: 15
<212> TYPE: PRT
<213> ORGANISM: Artificial Sequence
<220> FEATURE:
<223> OTHER INFORMATION: PRAME peptide

<400> SEQUENCE: 874

Met Val Gln Leu Asp Ser Ile Glu Asp Leu Glu Val Thr Cys Thr
1               5                   10                  15

<210> SEQ ID NO 875
<211> LENGTH: 15
<212> TYPE: PRT
<213> ORGANISM: Artificial Sequence
<220> FEATURE:
<223> OTHER INFORMATION: PRAME peptide

<400> SEQUENCE: 875

Thr Trp Lys Leu Pro Thr Leu Ala Lys Phe Ser Pro Tyr Leu Gly
1               5                   10                  15

<210> SEQ ID NO 876
<211> LENGTH: 15
<212> TYPE: PRT
<213> ORGANISM: Artificial Sequence
<220> FEATURE:
<223> OTHER INFORMATION: PRAME peptide

<400> SEQUENCE: 876

Gln Ser Arg Tyr Ile Ser Met Ser Val Trp Thr Ser Pro Arg Arg
1               5                   10                  15

<210> SEQ ID NO 877
<211> LENGTH: 15
<212> TYPE: PRT
<213> ORGANISM: Artificial Sequence
<220> FEATURE:
<223> OTHER INFORMATION: PRAME peptide

<400> SEQUENCE: 877

Ala Gln Pro Met Thr Lys Lys Arg Lys Val Asp Gly Leu Ser Thr
1               5                   10                  15

<210> SEQ ID NO 878
<211> LENGTH: 15
<212> TYPE: PRT
<213> ORGANISM: Artificial Sequence
<220> FEATURE:
<223> OTHER INFORMATION: PRAME peptide

<400> SEQUENCE: 878

Thr Ser Gln Phe Leu Ser Leu Gln Cys Leu Gln Ala Leu Tyr Val
1               5                   10                  15

<210> SEQ ID NO 879
<211> LENGTH: 15
<212> TYPE: PRT
<213> ORGANISM: Artificial Sequence
<220> FEATURE:
<223> OTHER INFORMATION: PRAME peptide

<400> SEQUENCE: 879

His Leu His Leu Glu Thr Phe Lys Ala Val Leu Asp Gly Leu Asp
1               5                   10                  15

<210> SEQ ID NO 880

```
<211> LENGTH: 15
<212> TYPE: PRT
<213> ORGANISM: Artificial Sequence
<220> FEATURE:
<223> OTHER INFORMATION: PRAME peptide

<400> SEQUENCE: 880

Pro Val Pro Leu Glu Ser Tyr Glu Asp Ile His Gly Thr Leu His
1               5                   10                  15

<210> SEQ ID NO 881
<211> LENGTH: 15
<212> TYPE: PRT
<213> ORGANISM: Artificial Sequence
<220> FEATURE:
<223> OTHER INFORMATION: PRAME peptide

<400> SEQUENCE: 881

Tyr Ile Ser Met Ser Val Trp Thr Ser Pro Arg Arg Leu Val Glu
1               5                   10                  15

<210> SEQ ID NO 882
<211> LENGTH: 15
<212> TYPE: PRT
<213> ORGANISM: Artificial Sequence
<220> FEATURE:
<223> OTHER INFORMATION: PRAME peptide

<400> SEQUENCE: 882

Pro Leu Phe Met Ala Ala Phe Asp Gly Arg His Ser Gln Thr Leu
1               5                   10                  15

<210> SEQ ID NO 883
<211> LENGTH: 141
<212> TYPE: PRT
<213> ORGANISM: Homo sapiens

<400> SEQUENCE: 883

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Gln Cys Phe Phe Cys Phe Lys Glu Leu Glu
    50                  55                  60

Gly Trp Glu Pro Asp Asp Asp Pro Ile Glu Glu His Lys Lys His Ser
65                  70                  75                  80

Ser Gly Cys Ala Phe Leu Ser Val Lys Lys Gln Phe Glu Glu Leu Thr
                85                  90                  95

Leu Gly Glu Phe Leu Lys Leu Asp Arg Glu Arg Ala Lys Asn Lys Ile
            100                 105                 110

Ala Lys Glu Thr Asn Asn Lys Lys Lys Glu Phe Glu Glu Thr Ala Lys
        115                 120                 125

Lys Val Arg Arg Ala Ile Glu Gln Leu Ala Ala Met Asp
    130                 135                 140

<210> SEQ ID NO 884
<211> LENGTH: 10
<212> TYPE: PRT
<213> ORGANISM: Artificial Sequence
<220> FEATURE:
<223> OTHER INFORMATION: Survivin peptide
```

-continued

<400> SEQUENCE: 884

Pro Thr Glu Asn Glu Pro Asp Leu Gln Cys
1               5                   10

<210> SEQ ID NO 885
<211> LENGTH: 11
<212> TYPE: PRT
<213> ORGANISM: Artificial Sequence
<220> FEATURE:
<223> OTHER INFORMATION: Survivin peptide

<400> SEQUENCE: 885

Pro Thr Glu Asn Glu Pro Asp Leu Gln Cys Phe
1               5                   10

<210> SEQ ID NO 886
<211> LENGTH: 9
<212> TYPE: PRT
<213> ORGANISM: Artificial Sequence
<220> FEATURE:
<223> OTHER INFORMATION: Survivin peptide

<400> SEQUENCE: 886

Pro Thr Glu Asn Glu Pro Asp Leu Gln
1               5

<210> SEQ ID NO 887
<211> LENGTH: 9
<212> TYPE: PRT
<213> ORGANISM: Artificial Sequence
<220> FEATURE:
<223> OTHER INFORMATION: Survivin peptide

<400> SEQUENCE: 887

Leu Thr Leu Gly Glu Phe Leu Lys Leu
1               5

<210> SEQ ID NO 888
<211> LENGTH: 10
<212> TYPE: PRT
<213> ORGANISM: Artificial Sequence
<220> FEATURE:
<223> OTHER INFORMATION: Survivin peptide

<400> SEQUENCE: 888

Thr Leu Pro Pro Ala Trp Gln Pro Phe Leu
1               5                   10

<210> SEQ ID NO 889
<211> LENGTH: 9
<212> TYPE: PRT
<213> ORGANISM: Artificial Sequence
<220> FEATURE:
<223> OTHER INFORMATION: Survivin peptide

<400> SEQUENCE: 889

Leu Thr Leu Gly Glu Phe Leu Lys Leu
1               5

<210> SEQ ID NO 890
<211> LENGTH: 9
<212> TYPE: PRT
<213> ORGANISM: Artificial Sequence
<220> FEATURE:
<223> OTHER INFORMATION: Survivin peptide -continued

```
<400> SEQUENCE: 890

Lys Val Arg Arg Ala Ile Glu Gln Leu
1               5

<210> SEQ ID NO 891
<211> LENGTH: 9
<212> TYPE: PRT
<213> ORGANISM: Artificial Sequence
<220> FEATURE:
<223> OTHER INFORMATION: Survivin peptide

<400> SEQUENCE: 891

Arg Ala Ile Glu Gln Leu Ala Ala Met
1               5

<210> SEQ ID NO 892
<211> LENGTH: 10
<212> TYPE: PRT
<213> ORGANISM: Artificial Sequence
<220> FEATURE:
<223> OTHER INFORMATION: Survivin peptide

<400> SEQUENCE: 892

Lys Leu Asp Arg Glu Arg Ala Lys Asn Lys
1               5                   10

<210> SEQ ID NO 893
<211> LENGTH: 10
<212> TYPE: PRT
<213> ORGANISM: Artificial Sequence
<220> FEATURE:
<223> OTHER INFORMATION: Survivin peptide

<400> SEQUENCE: 893

Phe Leu Lys Asp His Arg Ile Ser Thr Phe
1               5                   10

<210> SEQ ID NO 894
<211> LENGTH: 10
<212> TYPE: PRT
<213> ORGANISM: Artificial Sequence
<220> FEATURE:
<223> OTHER INFORMATION: Survivin peptide

<400> SEQUENCE: 894

Phe Leu Lys Leu Asp Arg Glu Arg Ala Lys
1               5                   10

<210> SEQ ID NO 895
<211> LENGTH: 9
<212> TYPE: PRT
<213> ORGANISM: Artificial Sequence
<220> FEATURE:
<223> OTHER INFORMATION: Survivin peptide

<400> SEQUENCE: 895

Glu Leu Thr Leu Gly Glu Phe Leu Lys
1               5

<210> SEQ ID NO 896
<211> LENGTH: 10
<212> TYPE: PRT
<213> ORGANISM: Artificial Sequence
<220> FEATURE:
<223> OTHER INFORMATION: Survivin peptide

<400> SEQUENCE: 896
```

-continued

```
Ser Ser Gly Cys Ala Phe Leu Ser Val Lys
1               5                   10

<210> SEQ ID NO 897
<211> LENGTH: 10
<212> TYPE: PRT
<213> ORGANISM: Artificial Sequence
<220> FEATURE:
<223> OTHER INFORMATION: Survivin peptide

<400> SEQUENCE: 897

Ser Gly Cys Ala Phe Leu Ser Val Lys Lys
1               5                   10

<210> SEQ ID NO 898
<211> LENGTH: 10
<212> TYPE: PRT
<213> ORGANISM: Artificial Sequence
<220> FEATURE:
<223> OTHER INFORMATION: Survivin peptide

<400> SEQUENCE: 898

Thr Leu Gly Glu Phe Leu Lys Leu Asp Arg
1               5                   10

<210> SEQ ID NO 899
<211> LENGTH: 9
<212> TYPE: PRT
<213> ORGANISM: Artificial Sequence
<220> FEATURE:
<223> OTHER INFORMATION: Survivin peptide

<400> SEQUENCE: 899

Asp Leu Gln Cys Phe Phe Cys Phe Lys
1               5

<210> SEQ ID NO 900
<211> LENGTH: 9
<212> TYPE: PRT
<213> ORGANISM: Artificial Sequence
<220> FEATURE:
<223> OTHER INFORMATION: Survivin peptide

<400> SEQUENCE: 900

Ala Phe Leu Ser Val Lys Lys Gln Phe
1               5

<210> SEQ ID NO 901
<211> LENGTH: 10
<212> TYPE: PRT
<213> ORGANISM: Artificial Sequence
<220> FEATURE:
<223> OTHER INFORMATION: Survivin peptide

<400> SEQUENCE: 901

Gln Phe Glu Glu Leu Thr Leu Gly Glu Phe
1               5                   10

<210> SEQ ID NO 902
<211> LENGTH: 9
<212> TYPE: PRT
<213> ORGANISM: Artificial Sequence
<220> FEATURE:
<223> OTHER INFORMATION: Survivin peptide

<400> SEQUENCE: 902
```

-continued

Leu Thr Leu Gly Glu Phe Leu Lys Leu
1               5

<210> SEQ ID NO 903
<211> LENGTH: 9
<212> TYPE: PRT
<213> ORGANISM: Artificial Sequence
<220> FEATURE:
<223> OTHER INFORMATION: Survivin peptide

<400> SEQUENCE: 903

Thr Leu Pro Pro Ala Trp Gln Pro Phe
1               5

<210> SEQ ID NO 904
<211> LENGTH: 9
<212> TYPE: PRT
<213> ORGANISM: Artificial Sequence
<220> FEATURE:
<223> OTHER INFORMATION: Survivin peptide

<400> SEQUENCE: 904

Glu Thr Asn Asn Lys Lys Lys Glu Phe
1               5

<210> SEQ ID NO 905
<211> LENGTH: 9
<212> TYPE: PRT
<213> ORGANISM: Artificial Sequence
<220> FEATURE:
<223> OTHER INFORMATION: Survivin peptide

<400> SEQUENCE: 905

Glu Asn Glu Pro Asp Leu Gln Cys Phe
1               5

<210> SEQ ID NO 906
<211> LENGTH: 9
<212> TYPE: PRT
<213> ORGANISM: Artificial Sequence
<220> FEATURE:
<223> OTHER INFORMATION: Survivin peptide

<400> SEQUENCE: 906

Glu Thr Ala Lys Lys Val Arg Arg Ala
1               5

<210> SEQ ID NO 907
<211> LENGTH: 9
<212> TYPE: PRT
<213> ORGANISM: Artificial Sequence
<220> FEATURE:
<223> OTHER INFORMATION: Survivin peptide

<400> SEQUENCE: 907

Lys Val Arg Arg Ala Ile Glu Gln Leu
1               5

<210> SEQ ID NO 908
<211> LENGTH: 11
<212> TYPE: PRT
<213> ORGANISM: Artificial Sequence
<220> FEATURE:
<223> OTHER INFORMATION: Survivin peptide

<400> SEQUENCE: 908

Leu Thr Leu Gly Glu Phe Leu Lys Leu Asp Arg

-continued

```
1              5              10

<210> SEQ ID NO 909
<211> LENGTH: 11
<212> TYPE: PRT
<213> ORGANISM: Artificial Sequence
<220> FEATURE:
<223> OTHER INFORMATION: Survivin peptide

<400> SEQUENCE: 909

Pro Ala Trp Gln Pro Phe Leu Lys Asp His Arg
1              5              10

<210> SEQ ID NO 910
<211> LENGTH: 11
<212> TYPE: PRT
<213> ORGANISM: Artificial Sequence
<220> FEATURE:
<223> OTHER INFORMATION: Survivin peptide

<400> SEQUENCE: 910

Ser Ser Gly Cys Ala Phe Leu Ser Val Lys Lys
1              5              10

<210> SEQ ID NO 911
<211> LENGTH: 11
<212> TYPE: PRT
<213> ORGANISM: Artificial Sequence
<220> FEATURE:
<223> OTHER INFORMATION: Survivin peptide

<400> SEQUENCE: 911

Glu Phe Glu Glu Thr Ala Lys Lys Val Arg Arg
1              5              10

<210> SEQ ID NO 912
<211> LENGTH: 9
<212> TYPE: PRT
<213> ORGANISM: Artificial Sequence
<220> FEATURE:
<223> OTHER INFORMATION: Survivin peptide

<400> SEQUENCE: 912

Leu Pro Pro Ala Trp Gln Pro Phe Leu
1              5

<210> SEQ ID NO 913
<211> LENGTH: 9
<212> TYPE: PRT
<213> ORGANISM: Artificial Sequence
<220> FEATURE:
<223> OTHER INFORMATION: Survivin peptide

<400> SEQUENCE: 913

Cys Pro Thr Glu Asn Glu Pro Asp Leu
1              5

<210> SEQ ID NO 914
<211> LENGTH: 10
<212> TYPE: PRT
<213> ORGANISM: Artificial Sequence
<220> FEATURE:
<223> OTHER INFORMATION: Survivin peptide

<400> SEQUENCE: 914

Glu Pro Asp Leu Gln Cys Phe Phe Cys Phe
1              5              10
```

```
<210> SEQ ID NO 915
<211> LENGTH: 10
<212> TYPE: PRT
<213> ORGANISM: Artificial Sequence
<220> FEATURE:
<223> OTHER INFORMATION: Survivin peptide

<400> SEQUENCE: 915

Trp Pro Phe Leu Glu Gly Cys Ala Cys Thr
1               5                   10

<210> SEQ ID NO 916
<211> LENGTH: 9
<212> TYPE: PRT
<213> ORGANISM: Artificial Sequence
<220> FEATURE:
<223> OTHER INFORMATION: Survivin peptide

<400> SEQUENCE: 916

Arg Ala Lys Asn Lys Ile Ala Lys Glu
1               5

<210> SEQ ID NO 917
<211> LENGTH: 8
<212> TYPE: PRT
<213> ORGANISM: Artificial Sequence
<220> FEATURE:
<223> OTHER INFORMATION: Survivin peptide

<400> SEQUENCE: 917

Ala Lys Lys Val Arg Arg Ala Ile
1               5

<210> SEQ ID NO 918
<211> LENGTH: 8
<212> TYPE: PRT
<213> ORGANISM: Artificial Sequence
<220> FEATURE:
<223> OTHER INFORMATION: Survivin peptide

<400> SEQUENCE: 918

Phe Leu Ser Val Lys Lys Gln Phe
1               5

<210> SEQ ID NO 919
<211> LENGTH: 8
<212> TYPE: PRT
<213> ORGANISM: Artificial Sequence
<220> FEATURE:
<223> OTHER INFORMATION: Survivin peptide

<400> SEQUENCE: 919

Arg Ala Lys Asn Lys Ile Ala Lys
1               5

<210> SEQ ID NO 920
<211> LENGTH: 9
<212> TYPE: PRT
<213> ORGANISM: Artificial Sequence
<220> FEATURE:
<223> OTHER INFORMATION: Survivin peptide

<400> SEQUENCE: 920

Thr Leu Pro Pro Ala Trp Gln Pro Phe
1               5
```

```
<210> SEQ ID NO 921
<211> LENGTH: 10
<212> TYPE: PRT
<213> ORGANISM: Artificial Sequence
<220> FEATURE:
<223> OTHER INFORMATION: Survivin peptide

<400> SEQUENCE: 921

Phe Leu Lys Asp His Arg Ile Ser Thr Phe
1               5                   10

<210> SEQ ID NO 922
<211> LENGTH: 10
<212> TYPE: PRT
<213> ORGANISM: Artificial Sequence
<220> FEATURE:
<223> OTHER INFORMATION: Survivin peptide

<400> SEQUENCE: 922

Lys Gln Phe Glu Glu Leu Thr Leu Gly Glu
1               5                   10

<210> SEQ ID NO 923
<211> LENGTH: 9
<212> TYPE: PRT
<213> ORGANISM: Artificial Sequence
<220> FEATURE:
<223> OTHER INFORMATION: Survivin peptide

<400> SEQUENCE: 923

Lys Gln Phe Glu Glu Leu Thr Leu Gly
1               5

<210> SEQ ID NO 924
<211> LENGTH: 9
<212> TYPE: PRT
<213> ORGANISM: Artificial Sequence
<220> FEATURE:
<223> OTHER INFORMATION: Survivin peptide

<400> SEQUENCE: 924

Leu Pro Pro Ala Trp Gln Pro Phe Leu
1               5

<210> SEQ ID NO 925
<211> LENGTH: 9
<212> TYPE: PRT
<213> ORGANISM: Artificial Sequence
<220> FEATURE:
<223> OTHER INFORMATION: Survivin peptide

<400> SEQUENCE: 925

Cys Pro Thr Glu Asn Glu Pro Asp Leu
1               5

<210> SEQ ID NO 926
<211> LENGTH: 10
<212> TYPE: PRT
<213> ORGANISM: Artificial Sequence
<220> FEATURE:
<223> OTHER INFORMATION: Survivin peptide

<400> SEQUENCE: 926

Thr Pro Glu Arg Met Ala Glu Ala Gly Phe
1               5                   10
```

```
<210> SEQ ID NO 927
<211> LENGTH: 10
<212> TYPE: PRT
<213> ORGANISM: Artificial Sequence
<220> FEATURE:
<223> OTHER INFORMATION: Survivin peptide

<400> SEQUENCE: 927

Glu Pro Asp Leu Gln Cys Phe Phe Cys Phe
1               5               10

<210> SEQ ID NO 928
<211> LENGTH: 9
<212> TYPE: PRT
<213> ORGANISM: Artificial Sequence
<220> FEATURE:
<223> OTHER INFORMATION: Survivin peptide

<400> SEQUENCE: 928

Thr Ala Lys Lys Val Arg Arg Ala Ile
1               5

<210> SEQ ID NO 929
<211> LENGTH: 9
<212> TYPE: PRT
<213> ORGANISM: Artificial Sequence
<220> FEATURE:
<223> OTHER INFORMATION: Survivin peptide

<400> SEQUENCE: 929

Arg Ala Ile Glu Gln Leu Ala Ala Met
1               5

<210> SEQ ID NO 930
<211> LENGTH: 9
<212> TYPE: PRT
<213> ORGANISM: Artificial Sequence
<220> FEATURE:
<223> OTHER INFORMATION: Survivin peptide

<400> SEQUENCE: 930

Lys Val Arg Arg Ala Ile Glu Gln Leu
1               5

<210> SEQ ID NO 931
<211> LENGTH: 10
<212> TYPE: PRT
<213> ORGANISM: Artificial Sequence
<220> FEATURE:
<223> OTHER INFORMATION: Survivin peptide

<400> SEQUENCE: 931

Glu Thr Ala Lys Lys Val Arg Arg Ala Ile
1               5               10

<210> SEQ ID NO 932
<211> LENGTH: 15
<212> TYPE: PRT
<213> ORGANISM: Artificial Sequence
<220> FEATURE:
<223> OTHER INFORMATION: Survivin peptide

<400> SEQUENCE: 932

Phe Phe Cys Phe Lys Glu Leu Glu Gly Trp Glu Pro Asp Asp Asp
1               5               10              15

<210> SEQ ID NO 933
```

-continued

```
<211> LENGTH: 15
<212> TYPE: PRT
<213> ORGANISM: Artificial Sequence
<220> FEATURE:
<223> OTHER INFORMATION: Survivin peptide

<400> SEQUENCE: 933

Phe Lys Asn Trp Pro Phe Leu Glu Gly Cys Ala Cys Thr Pro Glu
1               5                   10                  15

<210> SEQ ID NO 934
<211> LENGTH: 15
<212> TYPE: PRT
<213> ORGANISM: Artificial Sequence
<220> FEATURE:
<223> OTHER INFORMATION: Survivin peptide

<400> SEQUENCE: 934

Leu Gly Glu Phe Leu Lys Leu Asp Arg Glu Arg Ala Lys Asn Lys
1               5                   10                  15

<210> SEQ ID NO 935
<211> LENGTH: 15
<212> TYPE: PRT
<213> ORGANISM: Artificial Sequence
<220> FEATURE:
<223> OTHER INFORMATION: Survivin peptide

<400> SEQUENCE: 935

Asn Trp Pro Phe Leu Glu Gly Cys Ala Cys Thr Pro Glu Arg Met
1               5                   10                  15

<210> SEQ ID NO 936
<211> LENGTH: 15
<212> TYPE: PRT
<213> ORGANISM: Artificial Sequence
<220> FEATURE:
<223> OTHER INFORMATION: Survivin peptide

<400> SEQUENCE: 936

Gly Glu Phe Leu Lys Leu Asp Arg Glu Arg Ala Lys Asn Lys Ile
1               5                   10                  15

<210> SEQ ID NO 937
<211> LENGTH: 15
<212> TYPE: PRT
<213> ORGANISM: Artificial Sequence
<220> FEATURE:
<223> OTHER INFORMATION: Survivin peptide

<400> SEQUENCE: 937

Trp Gln Pro Phe Leu Lys Asp His Arg Ile Ser Thr Phe Lys Asn
1               5                   10                  15

<210> SEQ ID NO 938
<211> LENGTH: 15
<212> TYPE: PRT
<213> ORGANISM: Artificial Sequence
<220> FEATURE:
<223> OTHER INFORMATION: Survivin peptide

<400> SEQUENCE: 938

Pro Thr Glu Asn Glu Pro Asp Leu Gln Cys Phe Phe Cys Phe Lys
1               5                   10                  15

<210> SEQ ID NO 939
<211> LENGTH: 15
```

-continued

```
<212> TYPE: PRT
<213> ORGANISM: Artificial Sequence
<220> FEATURE:
<223> OTHER INFORMATION: Survivin peptide

<400> SEQUENCE: 939

Ala Pro Thr Leu Pro Pro Ala Trp Gln Pro Phe Leu Lys Asp His
1               5                   10                  15

<210> SEQ ID NO 940
<211> LENGTH: 15
<212> TYPE: PRT
<213> ORGANISM: Artificial Sequence
<220> FEATURE:
<223> OTHER INFORMATION: Survivin peptide

<400> SEQUENCE: 940

Ala Lys Lys Val Arg Arg Ala Ile Glu Gln Leu Ala Ala Met Asp
1               5                   10                  15

<210> SEQ ID NO 941
<211> LENGTH: 15
<212> TYPE: PRT
<213> ORGANISM: Artificial Sequence
<220> FEATURE:
<223> OTHER INFORMATION: Survivin peptide

<400> SEQUENCE: 941

Ala Pro Thr Leu Pro Pro Ala Trp Gln Pro Phe Leu Lys Asp His
1               5                   10                  15

<210> SEQ ID NO 942
<211> LENGTH: 15
<212> TYPE: PRT
<213> ORGANISM: Artificial Sequence
<220> FEATURE:
<223> OTHER INFORMATION: Survivin peptide

<400> SEQUENCE: 942

Asp His Arg Ile Ser Thr Phe Lys Asn Trp Pro Phe Leu Glu Gly
1               5                   10                  15

<210> SEQ ID NO 943
<211> LENGTH: 15
<212> TYPE: PRT
<213> ORGANISM: Artificial Sequence
<220> FEATURE:
<223> OTHER INFORMATION: Survivin peptide

<400> SEQUENCE: 943

Leu Glu Gly Cys Ala Cys Thr Pro Glu Arg Met Ala Glu Ala Gly
1               5                   10                  15

<210> SEQ ID NO 944
<211> LENGTH: 15
<212> TYPE: PRT
<213> ORGANISM: Artificial Sequence
<220> FEATURE:
<223> OTHER INFORMATION: Survivin peptide

<400> SEQUENCE: 944

Leu Gly Glu Phe Leu Lys Leu Asp Arg Glu Arg Ala Lys Asn Lys
1               5                   10                  15

<210> SEQ ID NO 945
<211> LENGTH: 15
<212> TYPE: PRT
```

<213> ORGANISM: Artificial Sequence
<220> FEATURE:
<223> OTHER INFORMATION: Survivin peptide

<400> SEQUENCE: 945

Gly Cys Ala Phe Leu Ser Val Lys Lys Gln Phe Glu Glu Leu Thr
1               5                   10                  15

<210> SEQ ID NO 946
<211> LENGTH: 15
<212> TYPE: PRT
<213> ORGANISM: Artificial Sequence
<220> FEATURE:
<223> OTHER INFORMATION: Survivin peptide

<400> SEQUENCE: 946

Phe Phe Cys Phe Lys Glu Leu Glu Gly Trp Glu Pro Asp Asp Asp
1               5                   10                  15

<210> SEQ ID NO 947
<211> LENGTH: 15
<212> TYPE: PRT
<213> ORGANISM: Artificial Sequence
<220> FEATURE:
<223> OTHER INFORMATION: Survivin peptide

<400> SEQUENCE: 947

Asp Asp Pro Ile Glu Glu His Lys Lys His Ser Ser Gly Cys Ala
1               5                   10                  15

<210> SEQ ID NO 948
<211> LENGTH: 15
<212> TYPE: PRT
<213> ORGANISM: Artificial Sequence
<220> FEATURE:
<223> OTHER INFORMATION: Survivin peptide

<400> SEQUENCE: 948

Glu Leu Thr Leu Gly Glu Phe Leu Lys Leu Asp Arg Glu Arg Ala
1               5                   10                  15

<210> SEQ ID NO 949
<211> LENGTH: 15
<212> TYPE: PRT
<213> ORGANISM: Artificial Sequence
<220> FEATURE:
<223> OTHER INFORMATION: Survivin peptide

<400> SEQUENCE: 949

Ile Ser Thr Phe Lys Asn Trp Pro Phe Leu Glu Gly Cys Ala Cys
1               5                   10                  15

<210> SEQ ID NO 950
<211> LENGTH: 15
<212> TYPE: PRT
<213> ORGANISM: Artificial Sequence
<220> FEATURE:
<223> OTHER INFORMATION: Survivin peptide

<400> SEQUENCE: 950

Leu Gln Cys Phe Phe Cys Phe Lys Glu Leu Glu Gly Trp Glu Pro
1               5                   10                  15

<210> SEQ ID NO 951
<211> LENGTH: 15
<212> TYPE: PRT
<213> ORGANISM: Artificial Sequence -continued

```
<220> FEATURE:
<223> OTHER INFORMATION: Survivin peptide

<400> SEQUENCE: 951

Glu Pro Asp Leu Gln Cys Phe Phe Cys Phe Lys Glu Leu Glu Gly
1               5                   10                  15

<210> SEQ ID NO 952
<211> LENGTH: 449
<212> TYPE: PRT
<213> ORGANISM: Homo sapiens

<400> SEQUENCE: 952

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
                100                 105                 110

Gly Pro Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Ala Ile
        130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
                195                 200                 205

Cys Thr Gly Ser Gln Ala Leu Leu Leu Arg Thr Pro Tyr Ser Ser Asp
        210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335
```

```
Leu Ser His Leu Gln Met His Ser Arg Lys His Thr Gly Glu Lys Pro
            340             345             350

Tyr Gln Cys Asp Phe Lys Asp Cys Glu Arg Arg Phe Ser Arg Ser Asp
            355             360             365

Gln Leu Lys Arg His Gln Arg Arg His Thr Gly Val Lys Pro Phe Gln
            370             375             380

Cys Lys Thr Cys Gln Arg Lys Phe Ser Arg Ser Asp His Leu Lys Thr
385             390             395             400

His Thr Arg Thr His Thr Gly Lys Thr Ser Glu Lys Pro Phe Ser Cys
                405             410             415

Arg Trp Pro Ser Cys Gln Lys Lys Phe Ala Arg Ser Asp Glu Leu Val
            420             425             430

Arg His His Asn Met His Gln Arg Asn Met Thr Lys Leu Gln Leu Ala
            435             440             445

Leu

<210> SEQ ID NO 953
<211> LENGTH: 15
<212> TYPE: PRT
<213> ORGANISM: Artificial Sequence
<220> FEATURE:
<223> OTHER INFORMATION: WT1 peptide

<400> SEQUENCE: 953

Ser Arg Gln Arg Pro His Pro Gly Ala Leu Arg Asn Pro Thr Ala
1               5               10              15

<210> SEQ ID NO 954
<211> LENGTH: 15
<212> TYPE: PRT
<213> ORGANISM: Artificial Sequence
<220> FEATURE:
<223> OTHER INFORMATION: WT1 peptide

<400> SEQUENCE: 954

Pro His Pro Gly Ala Leu Arg Asn Pro Thr Ala Cys Pro Leu Pro
1               5               10              15

<210> SEQ ID NO 955
<211> LENGTH: 15
<212> TYPE: PRT
<213> ORGANISM: Artificial Sequence
<220> FEATURE:
<223> OTHER INFORMATION: WT1 peptide

<400> SEQUENCE: 955

Ala Leu Arg Asn Pro Thr Ala Cys Pro Leu Pro His Phe Pro Pro
1               5               10              15

<210> SEQ ID NO 956
<211> LENGTH: 15
<212> TYPE: PRT
<213> ORGANISM: Artificial Sequence
<220> FEATURE:
<223> OTHER INFORMATION: WT1 peptide

<400> SEQUENCE: 956

Pro Thr Ala Cys Pro Leu Pro His Phe Pro Pro Ser Leu Pro Pro
1               5               10              15

<210> SEQ ID NO 957
<211> LENGTH: 15
<212> TYPE: PRT
```

<213> ORGANISM: Artificial Sequence
<220> FEATURE:
<223> OTHER INFORMATION: WT1 peptide

<400> SEQUENCE: 957

Pro Leu Pro His Phe Pro Pro Ser Leu Pro Pro Thr His Ser Pro
1               5                   10                  15

<210> SEQ ID NO 958
<211> LENGTH: 15
<212> TYPE: PRT
<213> ORGANISM: Artificial Sequence
<220> FEATURE:
<223> OTHER INFORMATION: WT1 peptide

<400> SEQUENCE: 958

Phe Pro Pro Ser Leu Pro Pro Thr His Ser Pro Thr His Pro Pro
1               5                   10                  15

<210> SEQ ID NO 959
<211> LENGTH: 15
<212> TYPE: PRT
<213> ORGANISM: Artificial Sequence
<220> FEATURE:
<223> OTHER INFORMATION: WT1 peptide

<400> SEQUENCE: 959

Leu Pro Pro Thr His Ser Pro Thr His Pro Pro Arg Ala Gly Thr
1               5                   10                  15

<210> SEQ ID NO 960
<211> LENGTH: 15
<212> TYPE: PRT
<213> ORGANISM: Artificial Sequence
<220> FEATURE:
<223> OTHER INFORMATION: WT1 peptide

<400> SEQUENCE: 960

His Ser Pro Thr His Pro Pro Arg Ala Gly Thr Ala Ala Gln Ala
1               5                   10                  15

<210> SEQ ID NO 961
<211> LENGTH: 15
<212> TYPE: PRT
<213> ORGANISM: Artificial Sequence
<220> FEATURE:
<223> OTHER INFORMATION: WT1 peptide

<400> SEQUENCE: 961

His Pro Pro Arg Ala Gly Thr Ala Ala Gln Ala Pro Gly Pro Arg
1               5                   10                  15

<210> SEQ ID NO 962
<211> LENGTH: 15
<212> TYPE: PRT
<213> ORGANISM: Artificial Sequence
<220> FEATURE:
<223> OTHER INFORMATION: WT1 peptide

<400> SEQUENCE: 962

Ala Gly Thr Ala Ala Gln Ala Pro Gly Pro Arg Arg Leu Leu Ala
1               5                   10                  15

<210> SEQ ID NO 963
<211> LENGTH: 15
<212> TYPE: PRT
<213> ORGANISM: Artificial Sequence
<220> FEATURE:
<223> OTHER INFORMATION: WT1 peptide

<400> SEQUENCE: 963

Ala Gln Ala Pro Gly Pro Arg Arg Leu Leu Ala Ala Ile Leu Asp
1               5                   10                  15

<210> SEQ ID NO 964
<211> LENGTH: 15
<212> TYPE: PRT
<213> ORGANISM: Artificial Sequence
<220> FEATURE:
<223> OTHER INFORMATION: WT1 peptide

<400> SEQUENCE: 964

Gly Pro Arg Arg Leu Leu Ala Ala Ile Leu Asp Phe Leu Leu Leu
1               5                   10                  15

<210> SEQ ID NO 965
<211> LENGTH: 15
<212> TYPE: PRT
<213> ORGANISM: Artificial Sequence
<220> FEATURE:
<223> OTHER INFORMATION: WT1 peptide

<400> SEQUENCE: 965

Leu Leu Ala Ala Ile Leu Asp Phe Leu Leu Leu Gln Asp Pro Ala
1               5                   10                  15

<210> SEQ ID NO 966
<211> LENGTH: 15
<212> TYPE: PRT
<213> ORGANISM: Artificial Sequence
<220> FEATURE:
<223> OTHER INFORMATION: WT1 peptide

<400> SEQUENCE: 966

Ile Leu Asp Phe Leu Leu Leu Gln Asp Pro Ala Ser Thr Cys Val
1               5                   10                  15

<210> SEQ ID NO 967
<211> LENGTH: 15
<212> TYPE: PRT
<213> ORGANISM: Artificial Sequence
<220> FEATURE:
<223> OTHER INFORMATION: WT1 peptide

<400> SEQUENCE: 967

Leu Leu Leu Gln Asp Pro Ala Ser Thr Cys Val Pro Glu Pro Ala
1               5                   10                  15

<210> SEQ ID NO 968
<211> LENGTH: 15
<212> TYPE: PRT
<213> ORGANISM: Artificial Sequence
<220> FEATURE:
<223> OTHER INFORMATION: WT1 peptide

<400> SEQUENCE: 968

Asp Pro Ala Ser Thr Cys Val Pro Glu Pro Ala Ser Gln His Thr
1               5                   10                  15

<210> SEQ ID NO 969
<211> LENGTH: 15
<212> TYPE: PRT
<213> ORGANISM: Artificial Sequence
<220> FEATURE:

-continued

<223> OTHER INFORMATION: WT1 peptide

<400> SEQUENCE: 969

Thr Cys Val Pro Glu Pro Ala Ser Gln His Thr Leu Arg Ser Gly
1               5                   10                  15

<210> SEQ ID NO 970
<211> LENGTH: 15
<212> TYPE: PRT
<213> ORGANISM: Artificial Sequence
<220> FEATURE:
<223> OTHER INFORMATION: WT1 peptide

<400> SEQUENCE: 970

Glu Pro Ala Ser Gln His Thr Leu Arg Ser Gly Pro Gly Cys Leu
1               5                   10                  15

<210> SEQ ID NO 971
<211> LENGTH: 15
<212> TYPE: PRT
<213> ORGANISM: Artificial Sequence
<220> FEATURE:
<223> OTHER INFORMATION: WT1 peptide

<400> SEQUENCE: 971

Gln His Thr Leu Arg Ser Gly Pro Gly Cys Leu Gln Gln Pro Glu
1               5                   10                  15

<210> SEQ ID NO 972
<211> LENGTH: 15
<212> TYPE: PRT
<213> ORGANISM: Artificial Sequence
<220> FEATURE:
<223> OTHER INFORMATION: WT1 peptide

<400> SEQUENCE: 972

Arg Ser Gly Pro Gly Cys Leu Gln Gln Pro Glu Gln Gln Gly Val
1               5                   10                  15

<210> SEQ ID NO 973
<211> LENGTH: 15
<212> TYPE: PRT
<213> ORGANISM: Artificial Sequence
<220> FEATURE:
<223> OTHER INFORMATION: WT1 peptide

<400> SEQUENCE: 973

Gly Cys Leu Gln Gln Pro Glu Gln Gln Gly Val Arg Asp Pro Gly
1               5                   10                  15

<210> SEQ ID NO 974
<211> LENGTH: 15
<212> TYPE: PRT
<213> ORGANISM: Artificial Sequence
<220> FEATURE:
<223> OTHER INFORMATION: WT1 peptide

<400> SEQUENCE: 974

Gln Pro Glu Gln Gln Gly Val Arg Asp Pro Gly Gly Ile Trp Ala
1               5                   10                  15

<210> SEQ ID NO 975
<211> LENGTH: 15
<212> TYPE: PRT
<213> ORGANISM: Artificial Sequence
<220> FEATURE:
<223> OTHER INFORMATION: WT1 peptide

<400> SEQUENCE: 975

Gln Gly Val Arg Asp Pro Gly Gly Ile Trp Ala Lys Leu Gly Ala
1               5                   10                  15

<210> SEQ ID NO 976
<211> LENGTH: 15
<212> TYPE: PRT
<213> ORGANISM: Artificial Sequence
<220> FEATURE:
<223> OTHER INFORMATION: WT1 peptide

<400> SEQUENCE: 976

Asp Pro Gly Gly Ile Trp Ala Lys Leu Gly Ala Ala Glu Ala Ser
1               5                   10                  15

<210> SEQ ID NO 977
<211> LENGTH: 15
<212> TYPE: PRT
<213> ORGANISM: Artificial Sequence
<220> FEATURE:
<223> OTHER INFORMATION: WT1 peptide

<400> SEQUENCE: 977

Ile Trp Ala Lys Leu Gly Ala Ala Glu Ala Ser Ala Glu Arg Leu
1               5                   10                  15

<210> SEQ ID NO 978
<211> LENGTH: 15
<212> TYPE: PRT
<213> ORGANISM: Artificial Sequence
<220> FEATURE:
<223> OTHER INFORMATION: WT1 peptide

<400> SEQUENCE: 978

Leu Gly Ala Ala Glu Ala Ser Ala Glu Arg Leu Gln Gly Arg Arg
1               5                   10                  15

<210> SEQ ID NO 979
<211> LENGTH: 15
<212> TYPE: PRT
<213> ORGANISM: Artificial Sequence
<220> FEATURE:
<223> OTHER INFORMATION: WT1 peptide

<400> SEQUENCE: 979

Glu Ala Ser Ala Glu Arg Leu Gln Gly Arg Arg Ser Arg Gly Ala
1               5                   10                  15

<210> SEQ ID NO 980
<211> LENGTH: 15
<212> TYPE: PRT
<213> ORGANISM: Artificial Sequence
<220> FEATURE:
<223> OTHER INFORMATION: WT1 peptide

<400> SEQUENCE: 980

Glu Arg Leu Gln Gly Arg Arg Ser Arg Gly Ala Ser Gly Ser Glu
1               5                   10                  15

<210> SEQ ID NO 981
<211> LENGTH: 15
<212> TYPE: PRT
<213> ORGANISM: Artificial Sequence
<220> FEATURE:
<223> OTHER INFORMATION: WT1 peptide

<400> SEQUENCE: 981

Gly Arg Arg Ser Arg Gly Ala Ser Gly Ser Glu Pro Gln Gln Met
1               5                   10                  15

<210> SEQ ID NO 982
<211> LENGTH: 15
<212> TYPE: PRT
<213> ORGANISM: Artificial Sequence
<220> FEATURE:
<223> OTHER INFORMATION: WT1 peptide

<400> SEQUENCE: 982

Arg Gly Ala Ser Gly Ser Glu Pro Gln Gln Met Gly Ser Asp Val
1               5                   10                  15

<210> SEQ ID NO 983
<211> LENGTH: 15
<212> TYPE: PRT
<213> ORGANISM: Artificial Sequence
<220> FEATURE:
<223> OTHER INFORMATION: WT1 peptide

<400> SEQUENCE: 983

Gly Ser Glu Pro Gln Gln Met Gly Ser Asp Val Arg Asp Leu Asn
1               5                   10                  15

<210> SEQ ID NO 984
<211> LENGTH: 15
<212> TYPE: PRT
<213> ORGANISM: Artificial Sequence
<220> FEATURE:
<223> OTHER INFORMATION: WT1 peptide

<400> SEQUENCE: 984

Gln Gln Met Gly Ser Asp Val Arg Asp Leu Asn Ala Leu Leu Pro
1               5                   10                  15

<210> SEQ ID NO 985
<211> LENGTH: 15
<212> TYPE: PRT
<213> ORGANISM: Artificial Sequence
<220> FEATURE:
<223> OTHER INFORMATION: WT1 peptide

<400> SEQUENCE: 985

Ser Asp Val Arg Asp Leu Asn Ala Leu Leu Pro Ala Val Pro Ser
1               5                   10                  15

<210> SEQ ID NO 986
<211> LENGTH: 15
<212> TYPE: PRT
<213> ORGANISM: Artificial Sequence
<220> FEATURE:
<223> OTHER INFORMATION: WT1 peptide

<400> SEQUENCE: 986

Asp Leu Asn Ala Leu Leu Pro Ala Val Pro Ser Leu Gly Gly Gly
1               5                   10                  15

<210> SEQ ID NO 987
<211> LENGTH: 15
<212> TYPE: PRT
<213> ORGANISM: Artificial Sequence
<220> FEATURE:
<223> OTHER INFORMATION: WT1 peptide

<400> SEQUENCE: 987

```
Leu Leu Pro Ala Val Pro Ser Leu Gly Gly Gly Gly Gly Cys Ala
1               5                   10                  15

<210> SEQ ID NO 988
<211> LENGTH: 15
<212> TYPE: PRT
<213> ORGANISM: Artificial Sequence
<220> FEATURE:
<223> OTHER INFORMATION: WT1 peptide

<400> SEQUENCE: 988

Val Pro Ser Leu Gly Gly Gly Gly Gly Cys Ala Leu Pro Val Ser
1               5                   10                  15

<210> SEQ ID NO 989
<211> LENGTH: 15
<212> TYPE: PRT
<213> ORGANISM: Artificial Sequence
<220> FEATURE:
<223> OTHER INFORMATION: WT1 peptide

<400> SEQUENCE: 989

Gly Gly Gly Gly Gly Cys Ala Leu Pro Val Ser Gly Ala Ala Gln
1               5                   10                  15

<210> SEQ ID NO 990
<211> LENGTH: 15
<212> TYPE: PRT
<213> ORGANISM: Artificial Sequence
<220> FEATURE:
<223> OTHER INFORMATION: WT1 peptide

<400> SEQUENCE: 990

Gly Cys Ala Leu Pro Val Ser Gly Ala Ala Gln Trp Ala Pro Val
1               5                   10                  15

<210> SEQ ID NO 991
<211> LENGTH: 15
<212> TYPE: PRT
<213> ORGANISM: Artificial Sequence
<220> FEATURE:
<223> OTHER INFORMATION: WT1 peptide

<400> SEQUENCE: 991

Pro Val Ser Gly Ala Ala Gln Trp Ala Pro Val Leu Asp Phe Ala
1               5                   10                  15

<210> SEQ ID NO 992
<211> LENGTH: 15
<212> TYPE: PRT
<213> ORGANISM: Artificial Sequence
<220> FEATURE:
<223> OTHER INFORMATION: WT1 peptide

<400> SEQUENCE: 992

Ala Ala Gln Trp Ala Pro Val Leu Asp Phe Ala Pro Pro Gly Ala
1               5                   10                  15

<210> SEQ ID NO 993
<211> LENGTH: 15
<212> TYPE: PRT
<213> ORGANISM: Artificial Sequence
<220> FEATURE:
<223> OTHER INFORMATION: WT1 peptide

<400> SEQUENCE: 993
```

Ala Pro Val Leu Asp Phe Ala Pro Pro Gly Ala Ser Ala Tyr Gly
1               5                   10                  15

<210> SEQ ID NO 994
<211> LENGTH: 15
<212> TYPE: PRT
<213> ORGANISM: Artificial Sequence
<220> FEATURE:
<223> OTHER INFORMATION: WT1 peptide

<400> SEQUENCE: 994

Asp Phe Ala Pro Pro Gly Ala Ser Ala Tyr Gly Ser Leu Gly Gly
1               5                   10                  15

<210> SEQ ID NO 995
<211> LENGTH: 15
<212> TYPE: PRT
<213> ORGANISM: Artificial Sequence
<220> FEATURE:
<223> OTHER INFORMATION: WT1 peptide

<400> SEQUENCE: 995

Pro Gly Ala Ser Ala Tyr Gly Ser Leu Gly Gly Pro Ala Pro Pro
1               5                   10                  15

<210> SEQ ID NO 996
<211> LENGTH: 15
<212> TYPE: PRT
<213> ORGANISM: Artificial Sequence
<220> FEATURE:
<223> OTHER INFORMATION: WT1 peptide

<400> SEQUENCE: 996

Ala Tyr Gly Ser Leu Gly Gly Pro Ala Pro Pro Pro Ala Pro Pro
1               5                   10                  15

<210> SEQ ID NO 997
<211> LENGTH: 15
<212> TYPE: PRT
<213> ORGANISM: Artificial Sequence
<220> FEATURE:
<223> OTHER INFORMATION: WT1 peptide

<400> SEQUENCE: 997

Leu Gly Gly Pro Ala Pro Pro Pro Ala Pro Pro Pro Pro Pro Pro
1               5                   10                  15

<210> SEQ ID NO 998
<211> LENGTH: 15
<212> TYPE: PRT
<213> ORGANISM: Artificial Sequence
<220> FEATURE:
<223> OTHER INFORMATION: WT1 peptide

<400> SEQUENCE: 998

Ala Pro Pro Pro Ala Pro Pro Pro Pro Pro Pro Pro Pro Pro His
1               5                   10                  15

<210> SEQ ID NO 999
<211> LENGTH: 15
<212> TYPE: PRT
<213> ORGANISM: Artificial Sequence
<220> FEATURE:
<223> OTHER INFORMATION: WT1 peptide

<400> SEQUENCE: 999

Ala Pro Pro Pro Pro Pro Pro Pro Pro Pro His Ser Phe Ile Lys

-continued

```
1               5               10              15

<210> SEQ ID NO 1000
<211> LENGTH: 15
<212> TYPE: PRT
<213> ORGANISM: Artificial Sequence
<220> FEATURE:
<223> OTHER INFORMATION: WT1 peptide

<400> SEQUENCE: 1000

Pro Pro Pro Pro Pro Pro His Ser Phe Ile Lys Gln Glu Pro Ser
1               5               10              15

<210> SEQ ID NO 1001
<211> LENGTH: 15
<212> TYPE: PRT
<213> ORGANISM: Artificial Sequence
<220> FEATURE:
<223> OTHER INFORMATION: WT1 peptide

<400> SEQUENCE: 1001

Pro Pro His Ser Phe Ile Lys Gln Glu Pro Ser Trp Gly Gly Ala
1               5               10              15

<210> SEQ ID NO 1002
<211> LENGTH: 15
<212> TYPE: PRT
<213> ORGANISM: Artificial Sequence
<220> FEATURE:
<223> OTHER INFORMATION: WT1 peptide

<400> SEQUENCE: 1002

Phe Ile Lys Gln Glu Pro Ser Trp Gly Gly Ala Glu Pro His Glu
1               5               10              15

<210> SEQ ID NO 1003
<211> LENGTH: 15
<212> TYPE: PRT
<213> ORGANISM: Artificial Sequence
<220> FEATURE:
<223> OTHER INFORMATION: WT1 peptide

<400> SEQUENCE: 1003

Glu Pro Ser Trp Gly Gly Ala Glu Pro His Glu Glu Gln Cys Leu
1               5               10              15

<210> SEQ ID NO 1004
<211> LENGTH: 15
<212> TYPE: PRT
<213> ORGANISM: Artificial Sequence
<220> FEATURE:
<223> OTHER INFORMATION: WT1 peptide

<400> SEQUENCE: 1004

Gly Gly Ala Glu Pro His Glu Glu Gln Cys Leu Ser Ala Phe Thr
1               5               10              15

<210> SEQ ID NO 1005
<211> LENGTH: 15
<212> TYPE: PRT
<213> ORGANISM: Artificial Sequence
<220> FEATURE:
<223> OTHER INFORMATION: WT1 peptide

<400> SEQUENCE: 1005

Pro His Glu Glu Gln Cys Leu Ser Ala Phe Thr Val His Phe Ser
1               5               10              15
```

```
<210> SEQ ID NO 1006
<211> LENGTH: 15
<212> TYPE: PRT
<213> ORGANISM: Artificial Sequence
<220> FEATURE:
<223> OTHER INFORMATION: WT1 peptide

<400> SEQUENCE: 1006

Gln Cys Leu Ser Ala Phe Thr Val His Phe Ser Gly Gln Phe Thr
1               5                   10                  15

<210> SEQ ID NO 1007
<211> LENGTH: 15
<212> TYPE: PRT
<213> ORGANISM: Artificial Sequence
<220> FEATURE:
<223> OTHER INFORMATION: WT1 peptide

<400> SEQUENCE: 1007

Ala Phe Thr Val His Phe Ser Gly Gln Phe Thr Gly Thr Ala Gly
1               5                   10                  15

<210> SEQ ID NO 1008
<211> LENGTH: 15
<212> TYPE: PRT
<213> ORGANISM: Artificial Sequence
<220> FEATURE:
<223> OTHER INFORMATION: WT1 peptide

<400> SEQUENCE: 1008

His Phe Ser Gly Gln Phe Thr Gly Thr Ala Gly Ala Cys Arg Tyr
1               5                   10                  15

<210> SEQ ID NO 1009
<211> LENGTH: 15
<212> TYPE: PRT
<213> ORGANISM: Artificial Sequence
<220> FEATURE:
<223> OTHER INFORMATION: WT1 peptide

<400> SEQUENCE: 1009

Gln Phe Thr Gly Thr Ala Gly Ala Cys Arg Tyr Gly Pro Phe Gly
1               5                   10                  15

<210> SEQ ID NO 1010
<211> LENGTH: 15
<212> TYPE: PRT
<213> ORGANISM: Artificial Sequence
<220> FEATURE:
<223> OTHER INFORMATION: WT1 peptide

<400> SEQUENCE: 1010

Thr Ala Gly Ala Cys Arg Tyr Gly Pro Phe Gly Pro Pro Pro Pro
1               5                   10                  15

<210> SEQ ID NO 1011
<211> LENGTH: 15
<212> TYPE: PRT
<213> ORGANISM: Artificial Sequence
<220> FEATURE:
<223> OTHER INFORMATION: WT1 peptide

<400> SEQUENCE: 1011

Cys Arg Tyr Gly Pro Phe Gly Pro Pro Pro Pro Ser Gln Ala Ser
1               5                   10                  15
```

<210> SEQ ID NO 1012
<211> LENGTH: 15
<212> TYPE: PRT
<213> ORGANISM: Artificial Sequence
<220> FEATURE:
<223> OTHER INFORMATION: WT1 peptide

<400> SEQUENCE: 1012

Pro Phe Gly Pro Pro Pro Pro Ser Gln Ala Ser Ser Gly Gln Ala
1               5                   10                  15

<210> SEQ ID NO 1013
<211> LENGTH: 15
<212> TYPE: PRT
<213> ORGANISM: Artificial Sequence
<220> FEATURE:
<223> OTHER INFORMATION: WT1 peptide

<400> SEQUENCE: 1013

Pro Pro Pro Ser Gln Ala Ser Ser Gly Gln Ala Arg Met Phe Pro
1               5                   10                  15

<210> SEQ ID NO 1014
<211> LENGTH: 15
<212> TYPE: PRT
<213> ORGANISM: Artificial Sequence
<220> FEATURE:
<223> OTHER INFORMATION: WT1 peptide

<400> SEQUENCE: 1014

Gln Ala Ser Ser Gly Gln Ala Arg Met Phe Pro Asn Ala Pro Tyr
1               5                   10                  15

<210> SEQ ID NO 1015
<211> LENGTH: 15
<212> TYPE: PRT
<213> ORGANISM: Artificial Sequence
<220> FEATURE:
<223> OTHER INFORMATION: WT1 peptide

<400> SEQUENCE: 1015

Gly Gln Ala Arg Met Phe Pro Asn Ala Pro Tyr Leu Pro Ser Cys
1               5                   10                  15

<210> SEQ ID NO 1016
<211> LENGTH: 15
<212> TYPE: PRT
<213> ORGANISM: Artificial Sequence
<220> FEATURE:
<223> OTHER INFORMATION: WT1 peptide

<400> SEQUENCE: 1016

Met Phe Pro Asn Ala Pro Tyr Leu Pro Ser Cys Leu Glu Ser Gln
1               5                   10                  15

<210> SEQ ID NO 1017
<211> LENGTH: 15
<212> TYPE: PRT
<213> ORGANISM: Artificial Sequence
<220> FEATURE:
<223> OTHER INFORMATION: WT1 peptide

<400> SEQUENCE: 1017

Ala Pro Tyr Leu Pro Ser Cys Leu Glu Ser Gln Pro Ala Ile Arg
1               5                   10                  15

```
<210> SEQ ID NO 1018
<211> LENGTH: 15
<212> TYPE: PRT
<213> ORGANISM: Artificial Sequence
<220> FEATURE:
<223> OTHER INFORMATION: WT1 peptide

<400> SEQUENCE: 1018

Pro Ser Cys Leu Glu Ser Gln Pro Ala Ile Arg Asn Gln Gly Tyr
1               5                   10                  15

<210> SEQ ID NO 1019
<211> LENGTH: 15
<212> TYPE: PRT
<213> ORGANISM: Artificial Sequence
<220> FEATURE:
<223> OTHER INFORMATION: WT1 peptide

<400> SEQUENCE: 1019

Glu Ser Gln Pro Ala Ile Arg Asn Gln Gly Tyr Ser Thr Val Thr
1               5                   10                  15

<210> SEQ ID NO 1020
<211> LENGTH: 15
<212> TYPE: PRT
<213> ORGANISM: Artificial Sequence
<220> FEATURE:
<223> OTHER INFORMATION: WT1 peptide

<400> SEQUENCE: 1020

Ala Ile Arg Asn Gln Gly Tyr Ser Thr Val Thr Phe Asp Gly Thr
1               5                   10                  15

<210> SEQ ID NO 1021
<211> LENGTH: 15
<212> TYPE: PRT
<213> ORGANISM: Artificial Sequence
<220> FEATURE:
<223> OTHER INFORMATION: WT1 peptide

<400> SEQUENCE: 1021

Gln Gly Tyr Ser Thr Val Thr Phe Asp Gly Thr Pro Ser Tyr Gly
1               5                   10                  15

<210> SEQ ID NO 1022
<211> LENGTH: 15
<212> TYPE: PRT
<213> ORGANISM: Artificial Sequence
<220> FEATURE:
<223> OTHER INFORMATION: WT1 peptide

<400> SEQUENCE: 1022

Thr Val Thr Phe Asp Gly Thr Pro Ser Tyr Gly His Thr Pro Ser
1               5                   10                  15

<210> SEQ ID NO 1023
<211> LENGTH: 15
<212> TYPE: PRT
<213> ORGANISM: Artificial Sequence
<220> FEATURE:
<223> OTHER INFORMATION: WT1 peptide

<400> SEQUENCE: 1023

Asp Gly Thr Pro Ser Tyr Gly His Thr Pro Ser His His Ala Ala
1               5                   10                  15

<210> SEQ ID NO 1024
```

-continued

<211> LENGTH: 15
<212> TYPE: PRT
<213> ORGANISM: Artificial Sequence
<220> FEATURE:
<223> OTHER INFORMATION: WT1 peptide

<400> SEQUENCE: 1024

Ser Tyr Gly His Thr Pro Ser His His Ala Ala Gln Phe Pro Asn
1               5                   10                  15

<210> SEQ ID NO 1025
<211> LENGTH: 15
<212> TYPE: PRT
<213> ORGANISM: Artificial Sequence
<220> FEATURE:
<223> OTHER INFORMATION: WT1 peptide

<400> SEQUENCE: 1025

Thr Pro Ser His His Ala Ala Gln Phe Pro Asn His Ser Phe Lys
1               5                   10                  15

<210> SEQ ID NO 1026
<211> LENGTH: 15
<212> TYPE: PRT
<213> ORGANISM: Artificial Sequence
<220> FEATURE:
<223> OTHER INFORMATION: WT1 peptide

<400> SEQUENCE: 1026

His Ala Ala Gln Phe Pro Asn His Ser Phe Lys His Glu Asp Pro
1               5                   10                  15

<210> SEQ ID NO 1027
<211> LENGTH: 15
<212> TYPE: PRT
<213> ORGANISM: Artificial Sequence
<220> FEATURE:
<223> OTHER INFORMATION: WT1 peptide

<400> SEQUENCE: 1027

Phe Pro Asn His Ser Phe Lys His Glu Asp Pro Met Gly Gln Gln
1               5                   10                  15

<210> SEQ ID NO 1028
<211> LENGTH: 15
<212> TYPE: PRT
<213> ORGANISM: Artificial Sequence
<220> FEATURE:
<223> OTHER INFORMATION: WT1 peptide

<400> SEQUENCE: 1028

Ser Phe Lys His Glu Asp Pro Met Gly Gln Gln Gly Ser Leu Gly
1               5                   10                  15

<210> SEQ ID NO 1029
<211> LENGTH: 15
<212> TYPE: PRT
<213> ORGANISM: Artificial Sequence
<220> FEATURE:
<223> OTHER INFORMATION: WT1 peptide

<400> SEQUENCE: 1029

Glu Asp Pro Met Gly Gln Gln Gly Ser Leu Gly Glu Gln Gln Tyr
1               5                   10                  15

<210> SEQ ID NO 1030
<211> LENGTH: 15

```
<212> TYPE: PRT
<213> ORGANISM: Artificial Sequence
<220> FEATURE:
<223> OTHER INFORMATION: WT1 peptide

<400> SEQUENCE: 1030

Gly Gln Gln Gly Ser Leu Gly Glu Gln Gln Tyr Ser Val Pro Pro
1               5                   10                  15

<210> SEQ ID NO 1031
<211> LENGTH: 15
<212> TYPE: PRT
<213> ORGANISM: Artificial Sequence
<220> FEATURE:
<223> OTHER INFORMATION: WT1 peptide

<400> SEQUENCE: 1031

Ser Leu Gly Glu Gln Gln Tyr Ser Val Pro Pro Val Tyr Gly
1               5                   10                  15

<210> SEQ ID NO 1032
<211> LENGTH: 15
<212> TYPE: PRT
<213> ORGANISM: Artificial Sequence
<220> FEATURE:
<223> OTHER INFORMATION: WT1 peptide

<400> SEQUENCE: 1032

Gln Gln Tyr Ser Val Pro Pro Pro Val Tyr Gly Cys His Thr Pro
1               5                   10                  15

<210> SEQ ID NO 1033
<211> LENGTH: 15
<212> TYPE: PRT
<213> ORGANISM: Artificial Sequence
<220> FEATURE:
<223> OTHER INFORMATION: WT1 peptide

<400> SEQUENCE: 1033

Val Pro Pro Pro Val Tyr Gly Cys His Thr Pro Thr Asp Ser Cys
1               5                   10                  15

<210> SEQ ID NO 1034
<211> LENGTH: 15
<212> TYPE: PRT
<213> ORGANISM: Artificial Sequence
<220> FEATURE:
<223> OTHER INFORMATION: WT1 peptide

<400> SEQUENCE: 1034

Val Tyr Gly Cys His Thr Pro Thr Asp Ser Cys Thr Gly Ser Gln
1               5                   10                  15

<210> SEQ ID NO 1035
<211> LENGTH: 15
<212> TYPE: PRT
<213> ORGANISM: Artificial Sequence
<220> FEATURE:
<223> OTHER INFORMATION: WT1 peptide

<400> SEQUENCE: 1035

His Thr Pro Thr Asp Ser Cys Thr Gly Ser Gln Ala Leu Leu Leu
1               5                   10                  15

<210> SEQ ID NO 1036
<211> LENGTH: 15
<212> TYPE: PRT
```

-continued

```
<213> ORGANISM: Artificial Sequence
<220> FEATURE:
<223> OTHER INFORMATION: WT1 peptide

<400> SEQUENCE: 1036

Asp Ser Cys Thr Gly Ser Gln Ala Leu Leu Leu Arg Thr Pro Tyr
1               5                   10                  15

<210> SEQ ID NO 1037
<211> LENGTH: 15
<212> TYPE: PRT
<213> ORGANISM: Artificial Sequence
<220> FEATURE:
<223> OTHER INFORMATION: WT1 peptide

<400> SEQUENCE: 1037

Gly Ser Gln Ala Leu Leu Leu Arg Thr Pro Tyr Ser Ser Asp Asn
1               5                   10                  15

<210> SEQ ID NO 1038
<211> LENGTH: 15
<212> TYPE: PRT
<213> ORGANISM: Artificial Sequence
<220> FEATURE:
<223> OTHER INFORMATION: WT1 peptide

<400> SEQUENCE: 1038

Leu Leu Leu Arg Thr Pro Tyr Ser Ser Asp Asn Leu Tyr Gln Met
1               5                   10                  15

<210> SEQ ID NO 1039
<211> LENGTH: 15
<212> TYPE: PRT
<213> ORGANISM: Artificial Sequence
<220> FEATURE:
<223> OTHER INFORMATION: WT1 peptide

<400> SEQUENCE: 1039

Thr Pro Tyr Ser Ser Asp Asn Leu Tyr Gln Met Thr Ser Gln Leu
1               5                   10                  15

<210> SEQ ID NO 1040
<211> LENGTH: 15
<212> TYPE: PRT
<213> ORGANISM: Artificial Sequence
<220> FEATURE:
<223> OTHER INFORMATION: WT1 peptide

<400> SEQUENCE: 1040

Ser Asp Asn Leu Tyr Gln Met Thr Ser Gln Leu Glu Cys Met Thr
1               5                   10                  15

<210> SEQ ID NO 1041
<211> LENGTH: 15
<212> TYPE: PRT
<213> ORGANISM: Artificial Sequence
<220> FEATURE:
<223> OTHER INFORMATION: WT1 peptide

<400> SEQUENCE: 1041

Tyr Gln Met Thr Ser Gln Leu Glu Cys Met Thr Trp Asn Gln Met
1               5                   10                  15

<210> SEQ ID NO 1042
<211> LENGTH: 15
<212> TYPE: PRT
<213> ORGANISM: Artificial Sequence
```

-continued

```
<220> FEATURE:
<223> OTHER INFORMATION: WT1 peptide

<400> SEQUENCE: 1042

Ser Gln Leu Glu Cys Met Thr Trp Asn Gln Met Asn Leu Gly Ala
1               5                   10                  15

<210> SEQ ID NO 1043
<211> LENGTH: 15
<212> TYPE: PRT
<213> ORGANISM: Artificial Sequence
<220> FEATURE:
<223> OTHER INFORMATION: WT1 peptide

<400> SEQUENCE: 1043

Cys Met Thr Trp Asn Gln Met Asn Leu Gly Ala Thr Leu Lys Gly
1               5                   10                  15

<210> SEQ ID NO 1044
<211> LENGTH: 15
<212> TYPE: PRT
<213> ORGANISM: Artificial Sequence
<220> FEATURE:
<223> OTHER INFORMATION: WT1 peptide

<400> SEQUENCE: 1044

Asn Gln Met Asn Leu Gly Ala Thr Leu Lys Gly Val Ala Ala Gly
1               5                   10                  15

<210> SEQ ID NO 1045
<211> LENGTH: 15
<212> TYPE: PRT
<213> ORGANISM: Artificial Sequence
<220> FEATURE:
<223> OTHER INFORMATION: WT1 peptide

<400> SEQUENCE: 1045

Leu Gly Ala Thr Leu Lys Gly Val Ala Ala Gly Ser Ser Ser Ser
1               5                   10                  15

<210> SEQ ID NO 1046
<211> LENGTH: 15
<212> TYPE: PRT
<213> ORGANISM: Artificial Sequence
<220> FEATURE:
<223> OTHER INFORMATION: WT1 peptide

<400> SEQUENCE: 1046

Leu Lys Gly Val Ala Ala Gly Ser Ser Ser Ser Val Lys Trp Thr
1               5                   10                  15

<210> SEQ ID NO 1047
<211> LENGTH: 15
<212> TYPE: PRT
<213> ORGANISM: Artificial Sequence
<220> FEATURE:
<223> OTHER INFORMATION: WT1 peptide

<400> SEQUENCE: 1047

Ala Ala Gly Ser Ser Ser Ser Val Lys Trp Thr Glu Gly Gln Ser
1               5                   10                  15

<210> SEQ ID NO 1048
<211> LENGTH: 15
<212> TYPE: PRT
<213> ORGANISM: Artificial Sequence
<220> FEATURE:
```

<223> OTHER INFORMATION: WT1 peptide

<400> SEQUENCE: 1048

Ser Ser Ser Val Lys Trp Thr Glu Gly Gln Ser Asn His Ser Thr
1               5                   10                  15

<210> SEQ ID NO 1049
<211> LENGTH: 15
<212> TYPE: PRT
<213> ORGANISM: Artificial Sequence
<220> FEATURE:
<223> OTHER INFORMATION: WT1 peptide

<400> SEQUENCE: 1049

Lys Trp Thr Glu Gly Gln Ser Asn His Ser Thr Gly Tyr Glu Ser
1               5                   10                  15

<210> SEQ ID NO 1050
<211> LENGTH: 15
<212> TYPE: PRT
<213> ORGANISM: Artificial Sequence
<220> FEATURE:
<223> OTHER INFORMATION: WT1 peptide

<400> SEQUENCE: 1050

Gly Gln Ser Asn His Ser Thr Gly Tyr Glu Ser Asp Asn His Thr
1               5                   10                  15

<210> SEQ ID NO 1051
<211> LENGTH: 15
<212> TYPE: PRT
<213> ORGANISM: Artificial Sequence
<220> FEATURE:
<223> OTHER INFORMATION: WT1 peptide

<400> SEQUENCE: 1051

His Ser Thr Gly Tyr Glu Ser Asp Asn His Thr Thr Pro Ile Leu
1               5                   10                  15

<210> SEQ ID NO 1052
<211> LENGTH: 15
<212> TYPE: PRT
<213> ORGANISM: Artificial Sequence
<220> FEATURE:
<223> OTHER INFORMATION: WT1 peptide

<400> SEQUENCE: 1052

Tyr Glu Ser Asp Asn His Thr Thr Pro Ile Leu Cys Gly Ala Gln
1               5                   10                  15

<210> SEQ ID NO 1053
<211> LENGTH: 15
<212> TYPE: PRT
<213> ORGANISM: Artificial Sequence
<220> FEATURE:
<223> OTHER INFORMATION: WT1 peptide

<400> SEQUENCE: 1053

Asn His Thr Thr Pro Ile Leu Cys Gly Ala Gln Tyr Arg Ile His
1               5                   10                  15

<210> SEQ ID NO 1054
<211> LENGTH: 15
<212> TYPE: PRT
<213> ORGANISM: Artificial Sequence
<220> FEATURE:
<223> OTHER INFORMATION: WT1 peptide -continued

```
<400> SEQUENCE: 1054

Pro Ile Leu Cys Gly Ala Gln Tyr Arg Ile His Thr His Gly Val
1               5                   10                  15

<210> SEQ ID NO 1055
<211> LENGTH: 15
<212> TYPE: PRT
<213> ORGANISM: Artificial Sequence
<220> FEATURE:
<223> OTHER INFORMATION: WT1 peptide

<400> SEQUENCE: 1055

Gly Ala Gln Tyr Arg Ile His Thr His Gly Val Phe Arg Gly Ile
1               5                   10                  15

<210> SEQ ID NO 1056
<211> LENGTH: 15
<212> TYPE: PRT
<213> ORGANISM: Artificial Sequence
<220> FEATURE:
<223> OTHER INFORMATION: WT1 peptide

<400> SEQUENCE: 1056

Arg Ile His Thr His Gly Val Phe Arg Gly Ile Gln Asp Val Arg
1               5                   10                  15

<210> SEQ ID NO 1057
<211> LENGTH: 15
<212> TYPE: PRT
<213> ORGANISM: Artificial Sequence
<220> FEATURE:
<223> OTHER INFORMATION: WT1 peptide

<400> SEQUENCE: 1057

His Gly Val Phe Arg Gly Ile Gln Asp Val Arg Arg Val Pro Gly
1               5                   10                  15

<210> SEQ ID NO 1058
<211> LENGTH: 15
<212> TYPE: PRT
<213> ORGANISM: Artificial Sequence
<220> FEATURE:
<223> OTHER INFORMATION: WT1 peptide

<400> SEQUENCE: 1058

Arg Gly Ile Gln Asp Val Arg Arg Val Pro Gly Val Ala Pro Thr
1               5                   10                  15

<210> SEQ ID NO 1059
<211> LENGTH: 15
<212> TYPE: PRT
<213> ORGANISM: Artificial Sequence
<220> FEATURE:
<223> OTHER INFORMATION: WT1 peptide

<400> SEQUENCE: 1059

Asp Val Arg Arg Val Pro Gly Val Ala Pro Thr Leu Val Arg Ser
1               5                   10                  15

<210> SEQ ID NO 1060
<211> LENGTH: 15
<212> TYPE: PRT
<213> ORGANISM: Artificial Sequence
<220> FEATURE:
<223> OTHER INFORMATION: WT1 peptide
```

<400> SEQUENCE: 1060

Val Pro Gly Val Ala Pro Thr Leu Val Arg Ser Ala Ser Glu Thr
1               5                   10                  15

<210> SEQ ID NO 1061
<211> LENGTH: 15
<212> TYPE: PRT
<213> ORGANISM: Artificial Sequence
<220> FEATURE:
<223> OTHER INFORMATION: WT1 peptide

<400> SEQUENCE: 1061

Ala Pro Thr Leu Val Arg Ser Ala Ser Glu Thr Ser Glu Lys Arg
1               5                   10                  15

<210> SEQ ID NO 1062
<211> LENGTH: 15
<212> TYPE: PRT
<213> ORGANISM: Artificial Sequence
<220> FEATURE:
<223> OTHER INFORMATION: WT1 peptide

<400> SEQUENCE: 1062

Val Arg Ser Ala Ser Glu Thr Ser Glu Lys Arg Pro Phe Met Cys
1               5                   10                  15

<210> SEQ ID NO 1063
<211> LENGTH: 15
<212> TYPE: PRT
<213> ORGANISM: Artificial Sequence
<220> FEATURE:
<223> OTHER INFORMATION: WT1 peptide

<400> SEQUENCE: 1063

Ser Glu Thr Ser Glu Lys Arg Pro Phe Met Cys Ala Tyr Pro Gly
1               5                   10                  15

<210> SEQ ID NO 1064
<211> LENGTH: 15
<212> TYPE: PRT
<213> ORGANISM: Artificial Sequence
<220> FEATURE:
<223> OTHER INFORMATION: WT1 peptide

<400> SEQUENCE: 1064

Glu Lys Arg Pro Phe Met Cys Ala Tyr Pro Gly Cys Asn Lys Arg
1               5                   10                  15

<210> SEQ ID NO 1065
<211> LENGTH: 15
<212> TYPE: PRT
<213> ORGANISM: Artificial Sequence
<220> FEATURE:
<223> OTHER INFORMATION: WT1 peptide

<400> SEQUENCE: 1065

Phe Met Cys Ala Tyr Pro Gly Cys Asn Lys Arg Tyr Phe Lys Leu
1               5                   10                  15

<210> SEQ ID NO 1066
<211> LENGTH: 15
<212> TYPE: PRT
<213> ORGANISM: Artificial Sequence
<220> FEATURE:
<223> OTHER INFORMATION: WT1 peptide

<400> SEQUENCE: 1066

Tyr Pro Gly Cys Asn Lys Arg Tyr Phe Lys Leu Ser His Leu Gln
1                   5                       10                      15

<210> SEQ ID NO 1067
<211> LENGTH: 15
<212> TYPE: PRT
<213> ORGANISM: Artificial Sequence
<220> FEATURE:
<223> OTHER INFORMATION: WT1 peptide

<400> SEQUENCE: 1067

Phe Lys Leu Ser His Leu Gln Met His Ser Arg Lys His Thr Gly
1                   5                       10                      15

<210> SEQ ID NO 1068
<211> LENGTH: 15
<212> TYPE: PRT
<213> ORGANISM: Artificial Sequence
<220> FEATURE:
<223> OTHER INFORMATION: WT1 peptide

<400> SEQUENCE: 1068

Phe Lys Leu Ser His Leu Gln Met His Ser Arg Lys His Thr Gly
1                   5                       10                      15

<210> SEQ ID NO 1069
<211> LENGTH: 15
<212> TYPE: PRT
<213> ORGANISM: Artificial Sequence
<220> FEATURE:
<223> OTHER INFORMATION: WT1 peptide

<400> SEQUENCE: 1069

His Leu Gln Met His Ser Arg Lys His Thr Gly Glu Lys Pro Tyr
1                   5                       10                      15

<210> SEQ ID NO 1070
<211> LENGTH: 15
<212> TYPE: PRT
<213> ORGANISM: Artificial Sequence
<220> FEATURE:
<223> OTHER INFORMATION: WT1 peptide

<400> SEQUENCE: 1070

His Ser Arg Lys His Thr Gly Glu Lys Pro Tyr Gln Cys Asp Phe
1                   5                       10                      15

<210> SEQ ID NO 1071
<211> LENGTH: 15
<212> TYPE: PRT
<213> ORGANISM: Artificial Sequence
<220> FEATURE:
<223> OTHER INFORMATION: WT1 peptide

<400> SEQUENCE: 1071

His Thr Gly Glu Lys Pro Tyr Gln Cys Asp Phe Lys Asp Cys Glu
1                   5                       10                      15

<210> SEQ ID NO 1072
<211> LENGTH: 15
<212> TYPE: PRT
<213> ORGANISM: Artificial Sequence
<220> FEATURE:
<223> OTHER INFORMATION: WT1 peptide

<400> SEQUENCE: 1072

```
Lys Pro Tyr Gln Cys Asp Phe Lys Asp Cys Glu Arg Arg Phe Ser
1               5                   10                  15

<210> SEQ ID NO 1073
<211> LENGTH: 15
<212> TYPE: PRT
<213> ORGANISM: Artificial Sequence
<220> FEATURE:
<223> OTHER INFORMATION: WT1 peptide

<400> SEQUENCE: 1073

Cys Asp Phe Lys Asp Cys Glu Arg Arg Phe Ser Arg Ser Asp Gln
1               5                   10                  15

<210> SEQ ID NO 1074
<211> LENGTH: 15
<212> TYPE: PRT
<213> ORGANISM: Artificial Sequence
<220> FEATURE:
<223> OTHER INFORMATION: WT1 peptide

<400> SEQUENCE: 1074

Asp Cys Glu Arg Arg Phe Ser Arg Ser Asp Gln Leu Lys Arg His
1               5                   10                  15

<210> SEQ ID NO 1075
<211> LENGTH: 15
<212> TYPE: PRT
<213> ORGANISM: Artificial Sequence
<220> FEATURE:
<223> OTHER INFORMATION: WT1 peptide

<400> SEQUENCE: 1075

Arg Phe Ser Arg Ser Asp Gln Leu Lys Arg His Gln Arg Arg His
1               5                   10                  15

<210> SEQ ID NO 1076
<211> LENGTH: 15
<212> TYPE: PRT
<213> ORGANISM: Artificial Sequence
<220> FEATURE:
<223> OTHER INFORMATION: WT1 peptide

<400> SEQUENCE: 1076

Ser Asp Gln Leu Lys Arg His Gln Arg Arg His Thr Gly Val Lys
1               5                   10                  15

<210> SEQ ID NO 1077
<211> LENGTH: 15
<212> TYPE: PRT
<213> ORGANISM: Artificial Sequence
<220> FEATURE:
<223> OTHER INFORMATION: WT1 peptide

<400> SEQUENCE: 1077

Lys Arg His Gln Arg Arg His Thr Gly Val Lys Pro Phe Gln Cys
1               5                   10                  15

<210> SEQ ID NO 1078
<211> LENGTH: 15
<212> TYPE: PRT
<213> ORGANISM: Artificial Sequence
<220> FEATURE:
<223> OTHER INFORMATION: WT1 peptide

<400> SEQUENCE: 1078

Arg Arg His Thr Gly Val Lys Pro Phe Gln Cys Lys Thr Cys Gln
```

```
1               5              10             15

<210> SEQ ID NO 1079
<211> LENGTH: 15
<212> TYPE: PRT
<213> ORGANISM: Artificial Sequence
<220> FEATURE:
<223> OTHER INFORMATION: WT1 peptide

<400> SEQUENCE: 1079

Gly Val Lys Pro Phe Gln Cys Lys Thr Cys Gln Arg Lys Phe Ser
1               5              10             15

<210> SEQ ID NO 1080
<211> LENGTH: 15
<212> TYPE: PRT
<213> ORGANISM: Artificial Sequence
<220> FEATURE:
<223> OTHER INFORMATION: WT1 peptide

<400> SEQUENCE: 1080

Phe Gln Cys Lys Thr Cys Gln Arg Lys Phe Ser Arg Ser Asp His
1               5              10             15

<210> SEQ ID NO 1081
<211> LENGTH: 15
<212> TYPE: PRT
<213> ORGANISM: Artificial Sequence
<220> FEATURE:
<223> OTHER INFORMATION: WT1 peptide

<400> SEQUENCE: 1081

Thr Cys Gln Arg Lys Phe Ser Arg Ser Asp His Leu Lys Thr His
1               5              10             15

<210> SEQ ID NO 1082
<211> LENGTH: 15
<212> TYPE: PRT
<213> ORGANISM: Artificial Sequence
<220> FEATURE:
<223> OTHER INFORMATION: WT1 peptide

<400> SEQUENCE: 1082

Lys Phe Ser Arg Ser Asp His Leu Lys Thr His Thr Arg Thr His
1               5              10             15

<210> SEQ ID NO 1083
<211> LENGTH: 15
<212> TYPE: PRT
<213> ORGANISM: Artificial Sequence
<220> FEATURE:
<223> OTHER INFORMATION: WT1 peptide

<400> SEQUENCE: 1083

Ser Asp His Leu Lys Thr His Thr Arg Thr His Thr Gly Lys Thr
1               5              10             15

<210> SEQ ID NO 1084
<211> LENGTH: 15
<212> TYPE: PRT
<213> ORGANISM: Artificial Sequence
<220> FEATURE:
<223> OTHER INFORMATION: WT1 peptide

<400> SEQUENCE: 1084

Lys Thr His Thr Arg Thr His Thr Gly Lys Thr Ser Glu Lys Pro
1               5              10             15
```

<210> SEQ ID NO 1085
<211> LENGTH: 15
<212> TYPE: PRT
<213> ORGANISM: Artificial Sequence
<220> FEATURE:
<223> OTHER INFORMATION: WT1 peptide

<400> SEQUENCE: 1085

Arg Thr His Thr Gly Lys Thr Ser Glu Lys Pro Phe Ser Cys Arg
1               5                   10                  15

<210> SEQ ID NO 1086
<211> LENGTH: 15
<212> TYPE: PRT
<213> ORGANISM: Artificial Sequence
<220> FEATURE:
<223> OTHER INFORMATION: WT1 peptide

<400> SEQUENCE: 1086

Gly Lys Thr Ser Glu Lys Pro Phe Ser Cys Arg Trp Pro Ser Cys
1               5                   10                  15

<210> SEQ ID NO 1087
<211> LENGTH: 15
<212> TYPE: PRT
<213> ORGANISM: Artificial Sequence
<220> FEATURE:
<223> OTHER INFORMATION: WT1 peptide

<400> SEQUENCE: 1087

Glu Lys Pro Phe Ser Cys Arg Trp Pro Ser Cys Gln Lys Lys Phe
1               5                   10                  15

<210> SEQ ID NO 1088
<211> LENGTH: 15
<212> TYPE: PRT
<213> ORGANISM: Artificial Sequence
<220> FEATURE:
<223> OTHER INFORMATION: WT1 peptide

<400> SEQUENCE: 1088

Ser Cys Arg Trp Pro Ser Cys Gln Lys Lys Phe Ala Arg Ser Asp
1               5                   10                  15

<210> SEQ ID NO 1089
<211> LENGTH: 15
<212> TYPE: PRT
<213> ORGANISM: Artificial Sequence
<220> FEATURE:
<223> OTHER INFORMATION: WT1 peptide

<400> SEQUENCE: 1089

Pro Ser Cys Gln Lys Lys Phe Ala Arg Ser Asp Glu Leu Val Arg
1               5                   10                  15

<210> SEQ ID NO 1090
<211> LENGTH: 15
<212> TYPE: PRT
<213> ORGANISM: Artificial Sequence
<220> FEATURE:
<223> OTHER INFORMATION: WT1 peptide

<400> SEQUENCE: 1090

Lys Lys Phe Ala Arg Ser Asp Glu Leu Val Arg His His Asn Met
1               5                   10                  15

```
<210> SEQ ID NO 1091
<211> LENGTH: 15
<212> TYPE: PRT
<213> ORGANISM: Artificial Sequence
<220> FEATURE:
<223> OTHER INFORMATION: WT1 peptide

<400> SEQUENCE: 1091

Arg Ser Asp Glu Leu Val Arg His His Asn Met His Gln Arg Asn
1               5               10              15

<210> SEQ ID NO 1092
<211> LENGTH: 15
<212> TYPE: PRT
<213> ORGANISM: Artificial Sequence
<220> FEATURE:
<223> OTHER INFORMATION: WT1 peptide

<400> SEQUENCE: 1092

Leu Val Arg His His Asn Met His Gln Arg Asn Met Thr Lys Leu
1               5               10              15

<210> SEQ ID NO 1093
<211> LENGTH: 15
<212> TYPE: PRT
<213> ORGANISM: Artificial Sequence
<220> FEATURE:
<223> OTHER INFORMATION: WT1 peptide

<400> SEQUENCE: 1093

His Asn Met His Gln Arg Asn Met Thr Lys Leu Gln Leu Ala Leu
1               5               10              15

<210> SEQ ID NO 1094
<211> LENGTH: 9
<212> TYPE: PRT
<213> ORGANISM: Artificial Sequence
<220> FEATURE:
<223> OTHER INFORMATION: WT1 peptide

<400> SEQUENCE: 1094

Arg Gln Arg Pro His Pro Gly Ala Leu
1               5

<210> SEQ ID NO 1095
<211> LENGTH: 9
<212> TYPE: PRT
<213> ORGANISM: Artificial Sequence
<220> FEATURE:
<223> OTHER INFORMATION: WT1 peptide

<400> SEQUENCE: 1095

Gly Ala Leu Arg Asn Pro Thr Ala Cys
1               5

<210> SEQ ID NO 1096
<211> LENGTH: 9
<212> TYPE: PRT
<213> ORGANISM: Artificial Sequence
<220> FEATURE:
<223> OTHER INFORMATION: WT1 peptide

<400> SEQUENCE: 1096

Pro Leu Pro His Phe Pro Pro Ser Leu
1               5
```

```
<210> SEQ ID NO 1097
<211> LENGTH: 9
<212> TYPE: PRT
<213> ORGANISM: Artificial Sequence
<220> FEATURE:
<223> OTHER INFORMATION: WT1 peptide

<400> SEQUENCE: 1097

His Phe Pro Pro Ser Leu Pro Pro Thr
1               5

<210> SEQ ID NO 1098
<211> LENGTH: 9
<212> TYPE: PRT
<213> ORGANISM: Artificial Sequence
<220> FEATURE:
<223> OTHER INFORMATION: WT1 peptide

<400> SEQUENCE: 1098

Thr His Ser Pro Thr His Pro Pro Arg
1               5

<210> SEQ ID NO 1099
<211> LENGTH: 9
<212> TYPE: PRT
<213> ORGANISM: Artificial Sequence
<220> FEATURE:
<223> OTHER INFORMATION: WT1 peptide

<400> SEQUENCE: 1099

Ala Ile Leu Asp Phe Leu Leu Leu Gln
1               5

<210> SEQ ID NO 1100
<211> LENGTH: 9
<212> TYPE: PRT
<213> ORGANISM: Artificial Sequence
<220> FEATURE:
<223> OTHER INFORMATION: WT1 peptide

<400> SEQUENCE: 1100

Pro Gly Cys Leu Gln Gln Pro Glu Gln
1               5

<210> SEQ ID NO 1101
<211> LENGTH: 11
<212> TYPE: PRT
<213> ORGANISM: Artificial Sequence
<220> FEATURE:
<223> OTHER INFORMATION: WT1 peptide

<400> SEQUENCE: 1101

Pro Gly Cys Leu Gln Gln Pro Glu Gln Gln Gly
1               5                   10

<210> SEQ ID NO 1102
<211> LENGTH: 9
<212> TYPE: PRT
<213> ORGANISM: Artificial Sequence
<220> FEATURE:
<223> OTHER INFORMATION: WT1 peptide

<400> SEQUENCE: 1102

Lys Leu Gly Ala Ala Glu Ala Ser Ala
1               5

<210> SEQ ID NO 1103
```

-continued

```
<211> LENGTH: 9
<212> TYPE: PRT
<213> ORGANISM: Artificial Sequence
<220> FEATURE:
<223> OTHER INFORMATION: WT1 peptide

<400> SEQUENCE: 1103

Ala Ser Gly Ser Glu Pro Gln Gln Met
1               5

<210> SEQ ID NO 1104
<211> LENGTH: 10
<212> TYPE: PRT
<213> ORGANISM: Artificial Sequence
<220> FEATURE:
<223> OTHER INFORMATION: WT1 peptide

<400> SEQUENCE: 1104

Arg Asp Leu Asn Ala Leu Leu Pro Ala Val
1               5                   10

<210> SEQ ID NO 1105
<211> LENGTH: 10
<212> TYPE: PRT
<213> ORGANISM: Artificial Sequence
<220> FEATURE:
<223> OTHER INFORMATION: WT1 peptide

<400> SEQUENCE: 1105

Gly Gly Cys Ala Leu Pro Val Ser Gly Ala
1               5                   10

<210> SEQ ID NO 1106
<211> LENGTH: 9
<212> TYPE: PRT
<213> ORGANISM: Artificial Sequence
<220> FEATURE:
<223> OTHER INFORMATION: WT1 peptide

<400> SEQUENCE: 1106

Gly Ala Ala Gln Trp Ala Pro Val Leu
1               5

<210> SEQ ID NO 1107
<211> LENGTH: 9
<212> TYPE: PRT
<213> ORGANISM: Artificial Sequence
<220> FEATURE:
<223> OTHER INFORMATION: WT1 peptide

<400> SEQUENCE: 1107

Leu Asp Phe Ala Pro Pro Gly Ala Ser
1               5

<210> SEQ ID NO 1108
<211> LENGTH: 11
<212> TYPE: PRT
<213> ORGANISM: Artificial Sequence
<220> FEATURE:
<223> OTHER INFORMATION: WT1 peptide

<400> SEQUENCE: 1108

Leu Asp Phe Ala Pro Pro Gly Ala Ser Ala Tyr
1               5                   10

<210> SEQ ID NO 1109
<211> LENGTH: 9
```

-continued

```
<212> TYPE: PRT
<213> ORGANISM: Artificial Sequence
<220> FEATURE:
<223> OTHER INFORMATION: WT1 peptide

<400> SEQUENCE: 1109

Ser Ala Tyr Gly Ser Leu Gly Gly Pro
1               5

<210> SEQ ID NO 1110
<211> LENGTH: 9
<212> TYPE: PRT
<213> ORGANISM: Artificial Sequence
<220> FEATURE:
<223> OTHER INFORMATION: WT1 peptide

<400> SEQUENCE: 1110

Pro Ala Pro Pro Pro Pro Pro Pro Pro
1               5

<210> SEQ ID NO 1111
<211> LENGTH: 9
<212> TYPE: PRT
<213> ORGANISM: Artificial Sequence
<220> FEATURE:
<223> OTHER INFORMATION: WT1 peptide

<400> SEQUENCE: 1111

Ala Cys Arg Tyr Gly Pro Phe Gly Pro
1               5

<210> SEQ ID NO 1112
<211> LENGTH: 9
<212> TYPE: PRT
<213> ORGANISM: Artificial Sequence
<220> FEATURE:
<223> OTHER INFORMATION: WT1 peptide

<400> SEQUENCE: 1112

Ser Gly Gln Ala Arg Met Phe Pro Asn
1               5

<210> SEQ ID NO 1113
<211> LENGTH: 9
<212> TYPE: PRT
<213> ORGANISM: Artificial Sequence
<220> FEATURE:
<223> OTHER INFORMATION: WT1 peptide

<400> SEQUENCE: 1113

Arg Met Phe Pro Asn Ala Pro Tyr Leu
1               5

<210> SEQ ID NO 1114
<211> LENGTH: 9
<212> TYPE: PRT
<213> ORGANISM: Artificial Sequence
<220> FEATURE:
<223> OTHER INFORMATION: WT1 peptide

<400> SEQUENCE: 1114

Pro Ser Cys Leu Glu Ser Gln Pro Ala
1               5

<210> SEQ ID NO 1115
<211> LENGTH: 9
<212> TYPE: PRT
```

```
<213> ORGANISM: Artificial Sequence
<220> FEATURE:
<223> OTHER INFORMATION: WT1 peptide

<400> SEQUENCE: 1115

Asn Gln Gly Tyr Ser Thr Val Thr Phe
1               5

<210> SEQ ID NO 1116
<211> LENGTH: 9
<212> TYPE: PRT
<213> ORGANISM: Artificial Sequence
<220> FEATURE:
<223> OTHER INFORMATION: WT1 peptide

<400> SEQUENCE: 1116

His His Ala Ala Gln Phe Pro Asn His
1               5

<210> SEQ ID NO 1117
<211> LENGTH: 9
<212> TYPE: PRT
<213> ORGANISM: Artificial Sequence
<220> FEATURE:
<223> OTHER INFORMATION: WT1 peptide

<400> SEQUENCE: 1117

His Ser Phe Lys His Glu Asp Pro Met
1               5

<210> SEQ ID NO 1118
<211> LENGTH: 9
<212> TYPE: PRT
<213> ORGANISM: Artificial Sequence
<220> FEATURE:
<223> OTHER INFORMATION: WT1 peptide

<400> SEQUENCE: 1118

Cys His Thr Pro Thr Asp Ser Cys Thr
1               5

<210> SEQ ID NO 1119
<211> LENGTH: 9
<212> TYPE: PRT
<213> ORGANISM: Artificial Sequence
<220> FEATURE:
<223> OTHER INFORMATION: WT1 peptide

<400> SEQUENCE: 1119

Cys Thr Gly Ser Gln Ala Leu Leu Leu
1               5

<210> SEQ ID NO 1120
<211> LENGTH: 9
<212> TYPE: PRT
<213> ORGANISM: Artificial Sequence
<220> FEATURE:
<223> OTHER INFORMATION: WT1 peptide

<400> SEQUENCE: 1120

Thr Asp Ser Cys Thr Gly Ser Gln Ala
1               5

<210> SEQ ID NO 1121
<211> LENGTH: 9
<212> TYPE: PRT
<213> ORGANISM: Artificial Sequence
```

-continued

```
<220> FEATURE:
<223> OTHER INFORMATION: WT1 peptide

<400> SEQUENCE: 1121

Arg Thr Pro Tyr Ser Ser Asp Asn Leu
1               5

<210> SEQ ID NO 1122
<211> LENGTH: 10
<212> TYPE: PRT
<213> ORGANISM: Artificial Sequence
<220> FEATURE:
<223> OTHER INFORMATION: WT1 peptide

<400> SEQUENCE: 1122

Asn Leu Tyr Gln Met Thr Ser Gln Leu Glu
1               5                   10

<210> SEQ ID NO 1123
<211> LENGTH: 9
<212> TYPE: PRT
<213> ORGANISM: Artificial Sequence
<220> FEATURE:
<223> OTHER INFORMATION: WT1 peptide

<400> SEQUENCE: 1123

Trp Asn Gln Met Asn Leu Gly Ala Thr
1               5

<210> SEQ ID NO 1124
<211> LENGTH: 9
<212> TYPE: PRT
<213> ORGANISM: Artificial Sequence
<220> FEATURE:
<223> OTHER INFORMATION: WT1 peptide

<400> SEQUENCE: 1124

Asn Gln Met Asn Leu Gly Ala Thr Leu
1               5

<210> SEQ ID NO 1125
<211> LENGTH: 11
<212> TYPE: PRT
<213> ORGANISM: Artificial Sequence
<220> FEATURE:
<223> OTHER INFORMATION: WT1 peptide

<400> SEQUENCE: 1125

Trp Asn Gln Met Asn Leu Gly Ala Thr Leu Lys
1               5                   10

<210> SEQ ID NO 1126
<211> LENGTH: 15
<212> TYPE: PRT
<213> ORGANISM: Artificial Sequence
<220> FEATURE:
<223> OTHER INFORMATION: WT1 peptide

<400> SEQUENCE: 1126

Cys Met Thr Trp Asn Gln Met Asn Leu Gly Ala Thr Leu Lys Gly
1               5                   10                  15

<210> SEQ ID NO 1127
<211> LENGTH: 9
<212> TYPE: PRT
<213> ORGANISM: Artificial Sequence
<220> FEATURE:
```

```
<223> OTHER INFORMATION: WT1 peptide

<400> SEQUENCE: 1127

Asn Leu Gly Ala Thr Leu Lys Gly Val
1               5

<210> SEQ ID NO 1128
<211> LENGTH: 10
<212> TYPE: PRT
<213> ORGANISM: Artificial Sequence
<220> FEATURE:
<223> OTHER INFORMATION: WT1 peptide

<400> SEQUENCE: 1128

Leu Gly Ala Thr Leu Lys Gly Val Ala Ala
1               5                   10

<210> SEQ ID NO 1129
<211> LENGTH: 8
<212> TYPE: PRT
<213> ORGANISM: Artificial Sequence
<220> FEATURE:
<223> OTHER INFORMATION: WT1 peptide

<400> SEQUENCE: 1129

Thr Leu Gly Val Ala Ala Gly Ser
1               5

<210> SEQ ID NO 1130
<211> LENGTH: 9
<212> TYPE: PRT
<213> ORGANISM: Artificial Sequence
<220> FEATURE:
<223> OTHER INFORMATION: WT1 peptide

<400> SEQUENCE: 1130

Gly Tyr Glu Ser Asp Asn His Thr Thr
1               5

<210> SEQ ID NO 1131
<211> LENGTH: 10
<212> TYPE: PRT
<213> ORGANISM: Artificial Sequence
<220> FEATURE:
<223> OTHER INFORMATION: WT1 peptide

<400> SEQUENCE: 1131

Phe Met Cys Ala Tyr Pro Gly Cys Asn Lys
1               5                   10

<210> SEQ ID NO 1132
<211> LENGTH: 11
<212> TYPE: PRT
<213> ORGANISM: Artificial Sequence
<220> FEATURE:
<223> OTHER INFORMATION: WT1 peptide

<400> SEQUENCE: 1132

Lys Arg Pro Phe Met Cys Ala Tyr Pro Gly Cys
1               5                   10

<210> SEQ ID NO 1133
<211> LENGTH: 9
<212> TYPE: PRT
<213> ORGANISM: Artificial Sequence
<220> FEATURE:
<223> OTHER INFORMATION: WT1 peptide
```

<400> SEQUENCE: 1133

Arg Lys Phe Ser Arg Ser Asp His Leu
1               5

<210> SEQ ID NO 1134
<211> LENGTH: 9
<212> TYPE: PRT
<213> ORGANISM: Artificial Sequence
<220> FEATURE:
<223> OTHER INFORMATION: WT1 peptide

<400> SEQUENCE: 1134

Leu Lys Thr His Thr Arg Thr His Thr
1               5

<210> SEQ ID NO 1135
<211> LENGTH: 10
<212> TYPE: PRT
<213> ORGANISM: Artificial Sequence
<220> FEATURE:
<223> OTHER INFORMATION: WT1 peptide

<400> SEQUENCE: 1135

Asn Met His Gln Arg Asn His Thr Lys Leu
1               5                   10

<210> SEQ ID NO 1136
<211> LENGTH: 9
<212> TYPE: PRT
<213> ORGANISM: Artificial Sequence
<220> FEATURE:
<223> OTHER INFORMATION: WT1 peptide

<400> SEQUENCE: 1136

Leu Leu Ala Ala Ile Leu Asp Phe Leu
1               5

<210> SEQ ID NO 1137
<211> LENGTH: 10
<212> TYPE: PRT
<213> ORGANISM: Artificial Sequence
<220> FEATURE:
<223> OTHER INFORMATION: WT1 peptide

<400> SEQUENCE: 1137

Cys Leu Gln Gln Pro Glu Gln Gln Gly Val
1               5                   10

<210> SEQ ID NO 1138
<211> LENGTH: 9
<212> TYPE: PRT
<213> ORGANISM: Artificial Sequence
<220> FEATURE:
<223> OTHER INFORMATION: WT1 peptide

<400> SEQUENCE: 1138

Asp Leu Asn Ala Leu Leu Pro Ala Val
1               5

<210> SEQ ID NO 1139
<211> LENGTH: 9
<212> TYPE: PRT
<213> ORGANISM: Artificial Sequence
<220> FEATURE:
<223> OTHER INFORMATION: WT1 peptide

```
<400> SEQUENCE: 1139

Ala Leu Leu Pro Ala Val Pro Ser Leu
1               5

<210> SEQ ID NO 1140
<211> LENGTH: 9
<212> TYPE: PRT
<213> ORGANISM: Artificial Sequence
<220> FEATURE:
<223> OTHER INFORMATION: WT1 peptide

<400> SEQUENCE: 1140

Val Leu Asp Phe Ala Pro Pro Gly Ala
1               5

<210> SEQ ID NO 1141
<211> LENGTH: 9
<212> TYPE: PRT
<213> ORGANISM: Artificial Sequence
<220> FEATURE:
<223> OTHER INFORMATION: WT1 peptide

<400> SEQUENCE: 1141

Cys Met Thr Trp Asn Gln Met Asn Leu
1               5

<210> SEQ ID NO 1142
<211> LENGTH: 10
<212> TYPE: PRT
<213> ORGANISM: Artificial Sequence
<220> FEATURE:
<223> OTHER INFORMATION: WT1 peptide

<400> SEQUENCE: 1142

Gln Ala Arg Met Phe Pro Asn Ala Pro Tyr
1               5                   10

<210> SEQ ID NO 1143
<211> LENGTH: 10
<212> TYPE: PRT
<213> ORGANISM: Artificial Sequence
<220> FEATURE:
<223> OTHER INFORMATION: WT1 peptide

<400> SEQUENCE: 1143

Ala Leu Arg Asn Pro Thr Ala Cys Pro Leu
1               5                   10

<210> SEQ ID NO 1144
<211> LENGTH: 9
<212> TYPE: PRT
<213> ORGANISM: Artificial Sequence
<220> FEATURE:
<223> OTHER INFORMATION: WT1 peptide

<400> SEQUENCE: 1144

Tyr Pro Gly Cys Asn Lys Arg Tyr Phe
1               5

<210> SEQ ID NO 1145
<211> LENGTH: 11
<212> TYPE: PRT
<213> ORGANISM: Artificial Sequence
<220> FEATURE:
<223> OTHER INFORMATION: WT1 peptide

<400> SEQUENCE: 1145
```

```
Thr Ser Glu Lys Arg Pro Phe Met Cys Ala Tyr
1               5                   10

<210> SEQ ID NO 1146
<211> LENGTH: 11
<212> TYPE: PRT
<213> ORGANISM: Artificial Sequence
<220> FEATURE:
<223> OTHER INFORMATION: WT1 peptide

<400> SEQUENCE: 1146

Ser Thr Val Thr Phe Asp Gly Thr Pro Ser Tyr
1               5                   10

<210> SEQ ID NO 1147
<211> LENGTH: 9
<212> TYPE: PRT
<213> ORGANISM: Artificial Sequence
<220> FEATURE:
<223> OTHER INFORMATION: WT1 peptide

<400> SEQUENCE: 1147

Val Thr Phe Asp Gly Thr Pro Ser Tyr
1               5

<210> SEQ ID NO 1148
<211> LENGTH: 11
<212> TYPE: PRT
<213> ORGANISM: Artificial Sequence
<220> FEATURE:
<223> OTHER INFORMATION: WT1 peptide

<400> SEQUENCE: 1148

His Thr Thr Pro Ile Leu Cys Gly Ala Gln Tyr
1               5                   10

<210> SEQ ID NO 1149
<211> LENGTH: 9
<212> TYPE: PRT
<213> ORGANISM: Artificial Sequence
<220> FEATURE:
<223> OTHER INFORMATION: WT1 peptide

<400> SEQUENCE: 1149

Ala Leu Leu Pro Ala Val Pro Ser Leu
1               5

<210> SEQ ID NO 1150
<211> LENGTH: 9
<212> TYPE: PRT
<213> ORGANISM: Artificial Sequence
<220> FEATURE:
<223> OTHER INFORMATION: WT1 peptide

<400> SEQUENCE: 1150

Asp Leu Asn Ala Leu Leu Pro Ala Val
1               5

<210> SEQ ID NO 1151
<211> LENGTH: 9
<212> TYPE: PRT
<213> ORGANISM: Artificial Sequence
<220> FEATURE:
<223> OTHER INFORMATION: WT1 peptide

<400> SEQUENCE: 1151
```

-continued

```
Ser Leu Gly Glu Gln Gln Tyr Ser Val
1               5

<210> SEQ ID NO 1152
<211> LENGTH: 10
<212> TYPE: PRT
<213> ORGANISM: Artificial Sequence
<220> FEATURE:
<223> OTHER INFORMATION: WT1 peptide

<400> SEQUENCE: 1152

Ser Leu Gly Gly Gly Gly Gly Cys Ala Leu
1               5                   10

<210> SEQ ID NO 1153
<211> LENGTH: 10
<212> TYPE: PRT
<213> ORGANISM: Artificial Sequence
<220> FEATURE:
<223> OTHER INFORMATION: WT1 peptide

<400> SEQUENCE: 1153

Asp Val Arg Arg Val Pro Gly Val Ala Pro
1               5                   10

<210> SEQ ID NO 1154
<211> LENGTH: 9
<212> TYPE: PRT
<213> ORGANISM: Artificial Sequence
<220> FEATURE:
<223> OTHER INFORMATION: WT1 peptide

<400> SEQUENCE: 1154

Arg Val Pro Gly Val Ala Pro Thr Leu
1               5

<210> SEQ ID NO 1155
<211> LENGTH: 9
<212> TYPE: PRT
<213> ORGANISM: Artificial Sequence
<220> FEATURE:
<223> OTHER INFORMATION: WT1 peptide

<400> SEQUENCE: 1155

Arg Ile His Thr His Gly Val Phe Arg
1               5

<210> SEQ ID NO 1156
<211> LENGTH: 9
<212> TYPE: PRT
<213> ORGANISM: Artificial Sequence
<220> FEATURE:
<223> OTHER INFORMATION: WT1 peptide

<400> SEQUENCE: 1156

Asp Val Arg Arg Val Pro Gly Val Ala
1               5

<210> SEQ ID NO 1157
<211> LENGTH: 10
<212> TYPE: PRT
<213> ORGANISM: Artificial Sequence
<220> FEATURE:
<223> OTHER INFORMATION: WT1 peptide

<400> SEQUENCE: 1157

Cys Thr Gly Ser Gln Ala Leu Leu Leu Arg
```

```
1               5                    10

<210> SEQ ID NO 1158
<211> LENGTH: 10
<212> TYPE: PRT
<213> ORGANISM: Artificial Sequence
<220> FEATURE:
<223> OTHER INFORMATION: WT1 peptide

<400> SEQUENCE: 1158

Gly Val Phe Arg Gly Ile Gln Asp Val Arg
1               5                    10

<210> SEQ ID NO 1159
<211> LENGTH: 9
<212> TYPE: PRT
<213> ORGANISM: Artificial Sequence
<220> FEATURE:
<223> OTHER INFORMATION: WT1 peptide

<400> SEQUENCE: 1159

Arg Ser Ala Ser Glu Thr Ser Glu Lys
1               5

<210> SEQ ID NO 1160
<211> LENGTH: 9
<212> TYPE: PRT
<213> ORGANISM: Artificial Sequence
<220> FEATURE:
<223> OTHER INFORMATION: WT1 peptide

<400> SEQUENCE: 1160

Phe Ser Arg Ser Asp Gln Leu Lys Arg
1               5

<210> SEQ ID NO 1161
<211> LENGTH: 10
<212> TYPE: PRT
<213> ORGANISM: Artificial Sequence
<220> FEATURE:
<223> OTHER INFORMATION: WT1 peptide

<400> SEQUENCE: 1161

Ala Tyr Pro Gly Cys Asn Lys Arg Tyr Phe
1               5                    10

<210> SEQ ID NO 1162
<211> LENGTH: 10
<212> TYPE: PRT
<213> ORGANISM: Artificial Sequence
<220> FEATURE:
<223> OTHER INFORMATION: WT1 peptide

<400> SEQUENCE: 1162

Gln Tyr Arg Ile His Thr His Gly Val Phe
1               5                    10

<210> SEQ ID NO 1163
<211> LENGTH: 10
<212> TYPE: PRT
<213> ORGANISM: Artificial Sequence
<220> FEATURE:
<223> OTHER INFORMATION: WT1 peptide

<400> SEQUENCE: 1163

Ala Phe Thr Val His Phe Ser Gly Gln Phe
1               5                    10
```

-continued

```
<210> SEQ ID NO 1164
<211> LENGTH: 9
<212> TYPE: PRT
<213> ORGANISM: Artificial Sequence
<220> FEATURE:
<223> OTHER INFORMATION: WT1 peptide

<400> SEQUENCE: 1164

Asp Phe Lys Asp Cys Glu Arg Arg Phe
1               5

<210> SEQ ID NO 1165
<211> LENGTH: 9
<212> TYPE: PRT
<213> ORGANISM: Artificial Sequence
<220> FEATURE:
<223> OTHER INFORMATION: WT1 peptide

<400> SEQUENCE: 1165

Asp Val Arg Asp Leu Asn Ala Leu Leu
1               5

<210> SEQ ID NO 1166
<211> LENGTH: 9
<212> TYPE: PRT
<213> ORGANISM: Artificial Sequence
<220> FEATURE:
<223> OTHER INFORMATION: WT1 peptide

<400> SEQUENCE: 1166

Val Thr Phe Asp Gly Thr Pro Ser Tyr
1               5

<210> SEQ ID NO 1167
<211> LENGTH: 10
<212> TYPE: PRT
<213> ORGANISM: Artificial Sequence
<220> FEATURE:
<223> OTHER INFORMATION: WT1 peptide

<400> SEQUENCE: 1167

Thr Val Thr Phe Asp Gly Thr Pro Ser Tyr
1               5                   10

<210> SEQ ID NO 1168
<211> LENGTH: 9
<212> TYPE: PRT
<213> ORGANISM: Artificial Sequence
<220> FEATURE:
<223> OTHER INFORMATION: WT1 peptide

<400> SEQUENCE: 1168

Phe Thr Val His Phe Ser Gly Gln Phe
1               5

<210> SEQ ID NO 1169
<211> LENGTH: 11
<212> TYPE: PRT
<213> ORGANISM: Artificial Sequence
<220> FEATURE:
<223> OTHER INFORMATION: WT1 peptide

<400> SEQUENCE: 1169

Gly Val Phe Arg Gly Ile Gln Asp Val Arg Arg
1               5                   10
```

```
<210> SEQ ID NO 1170
<211> LENGTH: 9
<212> TYPE: PRT
<213> ORGANISM: Artificial Sequence
<220> FEATURE:
<223> OTHER INFORMATION: WT1 peptide

<400> SEQUENCE: 1170

Phe Thr Gly Thr Ala Gly Ala Cys Arg
1               5

<210> SEQ ID NO 1171
<211> LENGTH: 11
<212> TYPE: PRT
<213> ORGANISM: Artificial Sequence
<220> FEATURE:
<223> OTHER INFORMATION: WT1 peptide

<400> SEQUENCE: 1171

Thr Thr Pro Ile Leu Cys Gly Ala Gln Tyr Arg
1               5                   10

<210> SEQ ID NO 1172
<211> LENGTH: 11
<212> TYPE: PRT
<213> ORGANISM: Artificial Sequence
<220> FEATURE:
<223> OTHER INFORMATION: WT1 peptide

<400> SEQUENCE: 1172

Glu Leu Val Arg His His Asn Met His Gln Arg
1               5                   10

<210> SEQ ID NO 1173
<211> LENGTH: 9
<212> TYPE: PRT
<213> ORGANISM: Artificial Sequence
<220> FEATURE:
<223> OTHER INFORMATION: WT1 peptide

<400> SEQUENCE: 1173

Asp Pro Met Gly Gln Gln Gly Ser Leu
1               5

<210> SEQ ID NO 1174
<211> LENGTH: 10
<212> TYPE: PRT
<213> ORGANISM: Artificial Sequence
<220> FEATURE:
<223> OTHER INFORMATION: WT1 peptide

<400> SEQUENCE: 1174

Pro Pro Gly Ala Ser Ala Tyr Gly Ser Leu
1               5                   10

<210> SEQ ID NO 1175
<211> LENGTH: 9
<212> TYPE: PRT
<213> ORGANISM: Artificial Sequence
<220> FEATURE:
<223> OTHER INFORMATION: WT1 peptide

<400> SEQUENCE: 1175

Pro Pro Pro Pro Pro His Ser Phe Ile
1               5
```

```
<210> SEQ ID NO 1176
<211> LENGTH: 9
<212> TYPE: PRT
<213> ORGANISM: Artificial Sequence
<220> FEATURE:
<223> OTHER INFORMATION: WT1 peptide

<400> SEQUENCE: 1176

Pro Pro Pro Pro Pro Pro His Ser Phe
1               5

<210> SEQ ID NO 1177
<211> LENGTH: 8
<212> TYPE: PRT
<213> ORGANISM: Artificial Sequence
<220> FEATURE:
<223> OTHER INFORMATION: WT1 peptide

<400> SEQUENCE: 1177

Met Thr Lys Leu Gln Leu Ala Leu
1               5

<210> SEQ ID NO 1178
<211> LENGTH: 8
<212> TYPE: PRT
<213> ORGANISM: Artificial Sequence
<220> FEATURE:
<223> OTHER INFORMATION: WT1 peptide

<400> SEQUENCE: 1178

Glu Pro His Glu Glu Gln Cys Leu
1               5

<210> SEQ ID NO 1179
<211> LENGTH: 8
<212> TYPE: PRT
<213> ORGANISM: Artificial Sequence
<220> FEATURE:
<223> OTHER INFORMATION: WT1 peptide

<400> SEQUENCE: 1179

Glu Thr Ser Glu Lys Arg Pro Phe
1               5

<210> SEQ ID NO 1180
<211> LENGTH: 8
<212> TYPE: PRT
<213> ORGANISM: Artificial Sequence
<220> FEATURE:
<223> OTHER INFORMATION: WT1 peptide

<400> SEQUENCE: 1180

Cys Asn Lys Arg Tyr Phe Lys Leu
1               5

<210> SEQ ID NO 1181
<211> LENGTH: 10
<212> TYPE: PRT
<213> ORGANISM: Artificial Sequence
<220> FEATURE:
<223> OTHER INFORMATION: WT1 peptide

<400> SEQUENCE: 1181

Gln Gln Tyr Ser Val Pro Pro Pro Val Tyr
1               5                   10

<210> SEQ ID NO 1182
```

```
<211> LENGTH: 10
<212> TYPE: PRT
<213> ORGANISM: Artificial Sequence
<220> FEATURE:
<223> OTHER INFORMATION: WT1 peptide

<400> SEQUENCE: 1182

Thr Val Thr Phe Asp Gly Thr Pro Ser Tyr
1               5                   10

<210> SEQ ID NO 1183
<211> LENGTH: 10
<212> TYPE: PRT
<213> ORGANISM: Artificial Sequence
<220> FEATURE:
<223> OTHER INFORMATION: WT1 peptide

<400> SEQUENCE: 1183

Gln Gln Gly Ser Leu Gly Glu Gln Gln Tyr
1               5                   10

<210> SEQ ID NO 1184
<211> LENGTH: 10
<212> TYPE: PRT
<213> ORGANISM: Artificial Sequence
<220> FEATURE:
<223> OTHER INFORMATION: WT1 peptide

<400> SEQUENCE: 1184

Ser Gln Ala Leu Leu Leu Arg Thr Pro Tyr
1               5                   10

<210> SEQ ID NO 1185
<211> LENGTH: 9
<212> TYPE: PRT
<213> ORGANISM: Artificial Sequence
<220> FEATURE:
<223> OTHER INFORMATION: WT1 peptide

<400> SEQUENCE: 1185

Thr Pro Tyr Ser Ser Asp Asn Leu Tyr
1               5

<210> SEQ ID NO 1186
<211> LENGTH: 10
<212> TYPE: PRT
<213> ORGANISM: Artificial Sequence
<220> FEATURE:
<223> OTHER INFORMATION: WT1 peptide

<400> SEQUENCE: 1186

Pro Pro Gly Ala Ser Ala Tyr Gly Ser Leu
1               5                   10

<210> SEQ ID NO 1187
<211> LENGTH: 9
<212> TYPE: PRT
<213> ORGANISM: Artificial Sequence
<220> FEATURE:
<223> OTHER INFORMATION: WT1 peptide

<400> SEQUENCE: 1187

Gln Pro Ala Ile Arg Asn Gln Gly Tyr
1               5

<210> SEQ ID NO 1188
<211> LENGTH: 9
```

```
<212> TYPE: PRT
<213> ORGANISM: Artificial Sequence
<220> FEATURE:
<223> OTHER INFORMATION: WT1 peptide

<400> SEQUENCE: 1188

Asp Pro Met Gly Gln Gln Gly Ser Leu
1               5

<210> SEQ ID NO 1189
<211> LENGTH: 9
<212> TYPE: PRT
<213> ORGANISM: Artificial Sequence
<220> FEATURE:
<223> OTHER INFORMATION: WT1 peptide

<400> SEQUENCE: 1189

Ala Ser Ser Gly Gln Ala Arg Met Phe
1               5

<210> SEQ ID NO 1190
<211> LENGTH: 9
<212> TYPE: PRT
<213> ORGANISM: Artificial Sequence
<220> FEATURE:
<223> OTHER INFORMATION: WT1 peptide

<400> SEQUENCE: 1190

Arg Val Pro Gly Val Ala Pro Thr Leu
1               5

<210> SEQ ID NO 1191
<211> LENGTH: 10
<212> TYPE: PRT
<213> ORGANISM: Artificial Sequence
<220> FEATURE:
<223> OTHER INFORMATION: WT1 peptide

<400> SEQUENCE: 1191

Ala Ser Glu Thr Ser Glu Lys Arg Pro Phe
1               5                   10

<210> SEQ ID NO 1192
<211> LENGTH: 10
<212> TYPE: PRT
<213> ORGANISM: Artificial Sequence
<220> FEATURE:
<223> OTHER INFORMATION: WT1 peptide

<400> SEQUENCE: 1192

Gln Ala Ser Ser Gly Gln Ala Arg Met Phe
1               5                   10

<210> SEQ ID NO 1193
<211> LENGTH: 15
<212> TYPE: PRT
<213> ORGANISM: Artificial Sequence
<220> FEATURE:
<223> OTHER INFORMATION: WT1 peptide

<400> SEQUENCE: 1193

Ala Ser Ala Tyr Gly Ser Leu Gly Gly Pro Ala Pro Pro Pro Ala
1               5                   10                  15

<210> SEQ ID NO 1194
<211> LENGTH: 15
<212> TYPE: PRT
```

-continued

```
<213> ORGANISM: Artificial Sequence
<220> FEATURE:
<223> OTHER INFORMATION: WT1 peptide

<400> SEQUENCE: 1194

Gly Ser Asp Val Arg Asp Leu Asn Ala Leu Leu Pro Ala Val Pro
1               5                   10                  15

<210> SEQ ID NO 1195
<211> LENGTH: 15
<212> TYPE: PRT
<213> ORGANISM: Artificial Sequence
<220> FEATURE:
<223> OTHER INFORMATION: WT1 peptide

<400> SEQUENCE: 1195

Ile Gln Asp Val Arg Arg Val Pro Gly Val Ala Pro Thr Leu Val
1               5                   10                  15

<210> SEQ ID NO 1196
<211> LENGTH: 15
<212> TYPE: PRT
<213> ORGANISM: Artificial Sequence
<220> FEATURE:
<223> OTHER INFORMATION: WT1 peptide

<400> SEQUENCE: 1196

Val Arg Asp Leu Asn Ala Leu Leu Pro Ala Val Pro Ser Leu Gly
1               5                   10                  15

<210> SEQ ID NO 1197
<211> LENGTH: 15
<212> TYPE: PRT
<213> ORGANISM: Artificial Sequence
<220> FEATURE:
<223> OTHER INFORMATION: WT1 peptide

<400> SEQUENCE: 1197

Tyr Ser Thr Val Thr Phe Asp Gly Thr Pro Ser Tyr Gly His Thr
1               5                   10                  15

<210> SEQ ID NO 1198
<211> LENGTH: 15
<212> TYPE: PRT
<213> ORGANISM: Artificial Sequence
<220> FEATURE:
<223> OTHER INFORMATION: WT1 peptide

<400> SEQUENCE: 1198

Met Gly Ser Asp Val Arg Asp Leu Asn Ala Leu Leu Pro Ala Val
1               5                   10                  15

<210> SEQ ID NO 1199
<211> LENGTH: 15
<212> TYPE: PRT
<213> ORGANISM: Artificial Sequence
<220> FEATURE:
<223> OTHER INFORMATION: WT1 peptide

<400> SEQUENCE: 1199

Tyr Gln Cys Asp Phe Lys Asp Cys Glu Arg Arg Phe Ser Arg Ser
1               5                   10                  15

<210> SEQ ID NO 1200
<211> LENGTH: 15
<212> TYPE: PRT
<213> ORGANISM: Artificial Sequence
```

```
<220> FEATURE:
<223> OTHER INFORMATION: WT1 peptide

<400> SEQUENCE: 1200

Val Pro Ser Leu Gly Gly Gly Gly Gly Cys Ala Leu Pro Val Ser
1               5                   10                  15

<210> SEQ ID NO 1201
<211> LENGTH: 15
<212> TYPE: PRT
<213> ORGANISM: Artificial Sequence
<220> FEATURE:
<223> OTHER INFORMATION: WT1 peptide

<400> SEQUENCE: 1201

Thr Pro Ser Tyr Gly His Thr Pro Ser His His Ala Ala Gln Phe
1               5                   10                  15

<210> SEQ ID NO 1202
<211> LENGTH: 15
<212> TYPE: PRT
<213> ORGANISM: Artificial Sequence
<220> FEATURE:
<223> OTHER INFORMATION: WT1 peptide

<400> SEQUENCE: 1202

Thr Val Thr Phe Asp Gly Thr Pro Ser Tyr Gly His Thr Pro Ser
1               5                   10                  15

<210> SEQ ID NO 1203
<211> LENGTH: 15
<212> TYPE: PRT
<213> ORGANISM: Artificial Sequence
<220> FEATURE:
<223> OTHER INFORMATION: WT1 peptide

<400> SEQUENCE: 1203

Leu Ser Ala Phe Thr Val His Phe Ser Gly Gln Phe Thr Gly Thr
1               5                   10                  15

<210> SEQ ID NO 1204
<211> LENGTH: 15
<212> TYPE: PRT
<213> ORGANISM: Artificial Sequence
<220> FEATURE:
<223> OTHER INFORMATION: WT1 peptide

<400> SEQUENCE: 1204

Thr Pro Thr Asp Ser Cys Thr Gly Ser Gln Ala Leu Leu Leu Arg
1               5                   10                  15

<210> SEQ ID NO 1205
<211> LENGTH: 15
<212> TYPE: PRT
<213> ORGANISM: Artificial Sequence
<220> FEATURE:
<223> OTHER INFORMATION: WT1 peptide

<400> SEQUENCE: 1205

Phe Arg Gly Ile Gln Asp Val Arg Arg Val Pro Gly Val Ala Pro
1               5                   10                  15

<210> SEQ ID NO 1206
<211> LENGTH: 15
<212> TYPE: PRT
<213> ORGANISM: Artificial Sequence
<220> FEATURE:
```

-continued

```
<223> OTHER INFORMATION: WT1 peptide

<400> SEQUENCE: 1206

Asn Lys Arg Tyr Phe Lys Leu Ser His Leu Gln Met His Ser Arg
1               5                   10                  15

<210> SEQ ID NO 1207
<211> LENGTH: 15
<212> TYPE: PRT
<213> ORGANISM: Artificial Sequence
<220> FEATURE:
<223> OTHER INFORMATION: WT1 peptide

<400> SEQUENCE: 1207

Gln Cys Asp Phe Lys Asp Cys Glu Arg Arg Phe Ser Arg Ser Asp
1               5                   10                  15

<210> SEQ ID NO 1208
<211> LENGTH: 15
<212> TYPE: PRT
<213> ORGANISM: Artificial Sequence
<220> FEATURE:
<223> OTHER INFORMATION: WT1 peptide

<400> SEQUENCE: 1208

Ser Thr Gly Tyr Glu Ser Asp Asn His Thr Thr Pro Ile Leu Cys
1               5                   10                  15

<210> SEQ ID NO 1209
<211> LENGTH: 15
<212> TYPE: PRT
<213> ORGANISM: Artificial Sequence
<220> FEATURE:
<223> OTHER INFORMATION: WT1 peptide

<400> SEQUENCE: 1209

Trp Ala Pro Val Leu Asp Phe Ala Pro Pro Gly Ala Ser Ala Tyr
1               5                   10                  15

<210> SEQ ID NO 1210
<211> LENGTH: 15
<212> TYPE: PRT
<213> ORGANISM: Artificial Sequence
<220> FEATURE:
<223> OTHER INFORMATION: WT1 peptide

<400> SEQUENCE: 1210

Arg Pro Phe Met Cys Ala Tyr Pro Gly Cys Asn Lys Arg Tyr Phe
1               5                   10                  15

<210> SEQ ID NO 1211
<211> LENGTH: 15
<212> TYPE: PRT
<213> ORGANISM: Artificial Sequence
<220> FEATURE:
<223> OTHER INFORMATION: WT1 peptide

<400> SEQUENCE: 1211

Gly Ser Asp Val Arg Asp Leu Asn Ala Leu Leu Pro Ala Val Pro
1               5                   10                  15

<210> SEQ ID NO 1212
<211> LENGTH: 15
<212> TYPE: PRT
<213> ORGANISM: Artificial Sequence
<220> FEATURE:
<223> OTHER INFORMATION: WT1 peptide
```

<400> SEQUENCE: 1212

```
Asn Ala Leu Leu Pro Ala Val Pro Ser Leu Gly Gly Gly Gly Gly
1               5                   10                  15
```

<210> SEQ ID NO 1213
<211> LENGTH: 140
<212> TYPE: PRT
<213> ORGANISM: Homo sapiens

<400> SEQUENCE: 1213

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
            115                 120                 125

Phe Asn Leu Leu Met Thr Leu Arg Leu Trp Ser Ser
        130                 135                 140
```

<210> SEQ ID NO 1214
<211> LENGTH: 176
<212> TYPE: PRT
<213> ORGANISM: Homo sapiens

<400> SEQUENCE: 1214

```
Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
            115                 120                 125
```

-continued

```
Asp Cys Gly Phe Thr Ser Val Ser Tyr Gln Gln Gly Val Leu Ser Ala
    130             135             140

Thr Ile Leu Tyr Glu Ile Leu Leu Gly Lys Ala Thr Leu Tyr Ala Val
145             150             155             160

Leu Val Ser Ala Leu Val Leu Met Ala Met Val Lys Arg Lys Asp Phe
                165             170             175
```